(12) United States Patent
Francischetti et al.

(10) Patent No.: US 7,078,508 B2
(45) Date of Patent: Jul. 18, 2006

(54) IXODES SCAPULARIS TISSUE FACTOR PATHWAY INHIBITOR

(75) Inventors: Ivo M. B. Francischetti, Bethesda, MD (US); Jesus G. Valenzuela, Gaithersburg, MD (US); José M. C. Ribeiro, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/408,166

(22) Filed: Apr. 4, 2003

(65) Prior Publication Data

US 2004/0018516 A1    Jan. 29, 2004

Related U.S. Application Data

(63) Continuation of application No. PCT/US01/42472, filed on Oct. 5, 2001.

(60) Provisional application No. 60/240,575, filed on Oct. 5, 2000.

(51) Int. Cl.
*C12N 15/11* (2006.01)
*C12N 15/85* (2006.01)
*C12N 15/63* (2006.01)
*C07H 21/02* (2006.01)
*C07H 21/04* (2006.01)

(52) U.S. Cl. ............... 536/23.1; 435/320.1; 435/325; 435/252.1; 435/254; 530/402; 530/350

(58) Field of Classification Search ............... 536/23.1, 536/23.4, 24.5, 23.5, 24.1; 435/325, 174, 435/252.1, 254; 530/402, 350; 436/536, 436/518
See application file for complete search history.

(56) References Cited

OTHER PUBLICATIONS

Cole et al. Science 1992; 258: 1650-54.*
Valenzuela e tal. JBC. Jun. 2000; 275:18717-23.*
Abendschein D.R. et al. 1995 *Maintenance of coronary patency after fibrinolysis with tissue factor pathway inhibitor.* Circulation 92(4):944-9.
Altschul S.F. et al. 1997 *Gapped Blast and PSI-Blast: a new generation of protein database search programs. Nucl Acids Res.* 25:3389-3402.
Anderson P.J. et al. 2000 *Characterization of proexosite I on prothrombin. J Biol Chem.* 275:16428-16434.
Bajaj M.S. & Bajaj S.P. 1997 *Tissue factor pathway inhibitor: potential therapeutic applications. Thromb Haemost.* 78:471-477.

(Continued)

*Primary Examiner*—David Guzo
*Assistant Examiner*—Ramin (Ray) Akhavan
(74) *Attorney, Agent, or Firm*—Knobbe, Martens, Olson & Bear, LLP

(57) ABSTRACT

Ixolaris, a novel protein with anticoagulant activity is described. Ixolaris can be isolated from the salivary glands of ticks or made by recombinant methods using various DNA expression techniques.

7 Claims, 29 Drawing Sheets

OTHER PUBLICATIONS

Baugh R.J. et al. 2000 *Exosite interactions determine the affinity of FX for the extrinsic Xase complex*. J Biol Chem. 275:28826-28833.

Belaaouaj A. et al. 1993 *Revised cDNA sequence of rabbit tissue factor pathway inhibitor*. Thromb Res. 69(6):547-53.

Belaaouaj A. et al. 1993 Database accession No. S61902 Database GenBank Aug. 25.

Bergun P.W. et al. 2001 *Role of zymogen and activated FX as scaffolds for the inhibition of the blood coagulation FVIIa-tissue factor complex by recombinant nematode anticoagulant protein c2*. J Biol Chem. 276:10063-10071.

Bromberg M.E. & Cappello M. 1999 *Cancer and blood coagulation: molecular aspects*. Cancer J Sci Am. 5(3):132-8.

Broze G.J. Jr. et al. 1995 *Regulation of coagulation by multivalent Kunitz-type inhibitor*. Biochemistry. 29:7539-7546.

Broze G.J. Jr. et al. 1988 *The lipoprotein-associated coagulation inhibitor that inhibits the FVII-tissue factor complex also inhibits FXa: insight into its possible mechanism of action*. Blood. 71:335-343.

Broze, G.J. Jr. *Tissue factor pathway inhbitor*. In: Loscalzo J. & Schafer A.I. eds. *Thrombosis and Hemorrhage*. 2nd ed. Baltimore, MD: Williams & Wilkins; 1998:77-104.

Broze G.J. & Miletich J.P. 1987 *Isolation of the tissue factor inhibitor produced by HepG2 hepatoma cells*. PNAS USA. 84:1886-1890.

Davie E.W. et al. 1991 *The coagulation cascade: initiation, maintenance, and regulation*. Biochemistry. 30:10363-10370.

Demchenko A.P. 2001 *Recognition between flexible protein molecules: induced and assisted folding*. J Mol Recognit. 14:42-61.

Dickinson C.D. et al. 1996 *Identification of surface residues mediating tissue factor binding and catalytic function of the serine protease FVIIa*. PNAS USA 93:14379-14384.

Francischetti I.M. et al. 2001 Database accession No. AF286029 Database EMBL Aug. 2.

Francischetti I.M. et al. 2002 *Ixolaris, a novel recombinant tissue factor pathway inhibitor (TFPI) from the salivary gland of the tick, Ixodes scapularis: identification of factor X and factor Xa as scaffolds for the inhibition of factor VIIa/tissue factor complex*. Blood. 99(10):3602-12.

Francischetti I.M. et al. 1999 *Anophelin: kinetics and mechanism of thrombin inhibition*. Biochemistry. 38:16674-16685.

Girard T.J. et al. 1990 *Inhibition of factor VIIa-tissue factor coagulation activity by a hybrid protein*. Science. 248:1421-1424.

Girard T.J. et al. 1989 *Functional significance of the Kunitz-type inhibitory domains of lipoprotein-associated coagulation inhibitor*. Nature. 338:518-520.

Hamamoto T. et al. 1993 *Inhibitory properties of full-length and truncated recombinant tissue factor pathway inhibitor (TFPI)*. J Biol Chem. 268:8704-8710.

Han X. et al. 1999 *Structural requirements for TFPI-mediated inhibition of neointimal thickening after balloon injury in the rat*. Arterioscler Thromb Vasc Biol. 19:2563-2567.

Harker L.A. et al. 1996 *Antithrombotic and antilesion benefits without hemorrhagic risks by inhibiting tissue factor pathway*. Haemostasis. 26:76-82.

Himber J. et al. 1997 *Dissociation of antithrombotic effect and bleeding time prolongation in rabbits by inhibiting tissue factor function*. Thromb Haemost. 78:1142-1149.

Ho G. et al. 2000 *Recombinant full-length tissue factor pathway inhibitor fails to bind to the cell surface: implications for catabolism in vitro and in vivo*. Blood 95:1973-1978.

Huang Z-F. et al. 1993 *Kinetics of FXa inhibition by tissue factor pathway inhibitor*. J Biol Chem. 268:26950-26955.

Huber R. et al. 1974 *Structure of the complex formed by bovine trypsin and bovine pancreatic trypsin inhibitor, II: crystallographic refinement at 1.9 A resolution*. J Mol Biol. 89:73-101.

Husten E.J. et al. 1987 *The active site of blood coagulation FXa. Its distance from the phospholipid surface and its conformational sensitivity to components of the prothrombinase complex*. J Biol Chem. 262:12953-12961.

Jenny N.S. & Mann K.G. 1998 *Coagulation cascade: an overview*. In: Loscalzo J. & Schafer A.I. eds. *Thrombosis and Hemorrhage*. 2nd ed. Baltimore, MD: Williams & Wilkins; 1998:3-27.

Jeske W. et al. 1996 *Pharmacological profiling of recombinant tissue factor pathway inhibitor*. Semin Thromb Hemost. 22:213-219.

Jonge E. et al. 1999 *Tissue factor pathway inhibitor dose-dependently inhibits coagulation activation without influencing the fibrinolytic and cytokine response during human endotoxemia*. Blood. 95:1124-1129.

Karczewski J. et al. 1994 *Disagregin is a fibrinogen receptor antagonist lacking the Arg-Gly-Asp sequence from the tick, Ornithodoros moubata*. J Biol Chem. 269:6702-6708.

Kirchhofer D. et al. 2001 *The tissue factor region that interacts with FXa in the activation of FVII*. Biochemistry. 40:675-682.

Kirchhofer D. et al. 2000 *The tissue factor region that interacts with substrates FIX and FX*. Biochemistry. 3:7380-7387.

Komiyama Y. et al. 1991 *Proteolytic activation of human factors IX and X by recombinant human FVIIa: effects of calcium, phospholipids, and tissue factor*. Biochemistry. 29:9418-9425.

Krishnaswamy S. & Betz A. 1997 *Exosites determine macromolecular substrate recognition by prothrombinase*. Biochemistry 36:12080-12086.

Lapatto R., et al. 1997 *X-ray structure of antistasin at 1.9 A resolution and its modeled complex with blood coagulation FXa*. EMBO J. 16:5151-5161.

Law L.H. et al. 1992 *Biochemical insights derived from insect diversity*. Annu Rev Biochem. 61:87-111.

Lee A. et al. 2001 *A dose-response study of recombinant FVIIa/TF inhibitor recombinant nematode anticoagulant protein c2 in prevention of postoperative venous thromboembolism in patients undergoing total knee replacement*. Circulation. 104:74-78.

Lee G.F. et al. 1997 *Potent bifunctional anticoagulants: Kunitz domain-tissue factor fusion proteins*. Biochemistry. 36:5608-5611.

Lindhout T. et al. 1995 *Kinetics of the inhibition of tissue factor-FVIIa by tissue factor pathway inhibitor*. Thromb Haemost. 74:910-915.

Locht A. et al. 1996 *The ornithodorin-thrombin crystal structure, a key to the TAP enigma?* EMBO J. 15:6011-6017.

Markwardt F. 1999 *Inhibitors of Factor Xa from Haematophagous Animals* Ann Haematol 78(suppl 1): A4.

Nielsen H. et al. 1997 *A neural network method for identification of prokaryotic and eukaryotic signal peptides and prediction of their cleavage sites*. Protein Eng. 10:1-6.

Orthner C. et al. 1995 *Pyrrolidine dithiocarbamate abrogates tissue factor (TF) expression by endothelial cells: evidence implicating nuclear factor-kB in TF induction by diverse agonists.* Blood. 86:436-443.

Pedersen A.H. et al. 1990 *Recombinant human extrinsic pathway inhibitor. Production, isolation, and characterization of its inhibitory activity on tissue factor-initiated coagulation reactions.* J Biol Chem. 254:16786-16793.

Petersen L.C. et al. 1996 *Inhibitory properties of separate recombinant Kunitz-type-protease-inhibitor domains from tissue-factor-pathway inhibitor.* Eur J Biochem. 235:310-316.

Rao L.V.M. & Rapaport S.I. 1987 *Studies of a mechanism inhibiting the intiation of the extrinsic pathway of coagulation.* Blood. 69:645-651.

Rao L.V.M. & Ruf W. 1995 *Tissue factor residues Lys165 and Lys166 are essential for rapid formation of the quaternary complex of tissue factor-VIIa with Xa-tissue factor pathway inhibitor.* Biochemistry. 34:10867-10871.

Rapaport S.I. 1989 *Inhibition of FVIIa/tissue factor-induced blood coagulation: with particular emphasis upon a FXa-dependent inhibitory mechanism.* Blood. 73:359-365.

Rezaie A.R. 2000 *Identification of basic residues in the heparin-binding exosite of FXa critical for heparin and factor Va binding.* J Biol Chem. 275:3320-3327.

Ribeiro J.M.C. et al. 1985 *Antihemostatic, anti-inflammatory, and immunosuppressive properties of the saliva of a tick, Ixodes dammini.* J Exp Med. 161:332-344.

Ribeiro J.M.C. et al. 1990 *Saliva of the tick Ixodes dammini inhibits neutrophil function.* Exp Parasitol. 70:382-388.

Ruf W. et al. 1999 *Importance of FVIIa Gla-domain residue Arg-36 for recognition of the macromolecular substrate FX Gla-domain.* Biochemistry. 38:1957-1966.

Sprecher C.A. et al. 1994 *Molecular cloning, expression, and partial characterization of a second human tissue-factor-pathway inhibitor.* PNAS USA 91(8):3353-7.

Stassens P. et al. 1996 *Anticoagulant repertoire of the hookworm Ancylostoma caninum.* PNAS USA 93:2149-2154.

Tatchell R.J. 1967 *A modified method for obtaining tick oral secretion.* J Parasitol. 53:1106-1107.

Thompson J.D. et al. 1994 *CLUSTAL W: improving the sensitivity of progressive multiple sequence alignment through sequence weighting, position-specific gap penalties and weight matrix choice.* Nucl Acids Res. 22:4673-4680.

Valenzuela J.G. et al. 2000 *Purification, cloning, and expression of a novel salivary anticomplement protein from the tick, Ixodes scapularis.* J Biol Chem 275:8717-8723.

Valenzuela J.G. et al. 1999 *Purification, cloning, and synthesis of a novel salivary anti-thrombin from the mosquito Anopheles albimanus.* Biochemistry. 38:11209-11215.

Warr T.A. et al. 1990 *Disseminated intravascular coagulation in rabbits induced by administration of endotoxin or tissue factor: effect of anti-tissue factor antibodies and measurement of plasma extrinsic pathway inhibitor activity.* Blood. 75:1481-1489.

Warshawsky I. et al. 1995 *The carboxy terminus of tissue factor pathway inhibitor is required for interacting with hepatoma cells in vitro and in vivo.* J Clin Invest. 95:1173-1181.

Waxman L. et al. 1990 *Tick anticoagulant peptide (TAP) is a novel inhibitor of blood coagulation FXa.* Science. 248:593-596.

Weitz J.I. & Hirsh J. 2001 *New anticoagulant drugs.* Chest. 119:95S-107S.

Wesselschmidt R. et al. 1992 *Tissue factor pathway inhibitor: the carboxy-terminus is required for optimal inhibition of FXa.* Blood. 79:2004-2010.

White G.C. et al. 1997 *Recombinant Factor IX.* Thrombos Hemost. 78:261-265.

Williams J.W. & Morrison J.F. 1979 *The kinetics of reversible tight-binding inhibition.* Methods Enzymol. 63:437-467.

Wun T.-C. et al. 1988 *Cloning and characterization of a cDNA coding for the lipoprotein-associated coagulation inhibitor shows that it consists of three tandem Kunitz-type inhibitory domains.* J Biol Chem. 263:6001-6004.

Zhang Y. et al. 1998 *Nitrophorin-2: a novel mixed-type reversible specific inhibitor of the intrinsic factor-X activating complex.* Biochemistry. 37:10681-10690.

* cited by examiner

FIG. 3A

```
Ixolaris   ---------AERVSEMDIYEFESWVSCLDPEQV-TCESQEGTHASYRKG      Q-K TE       60
TFPI       DSEEDEEHTIITDTELPPLKLMHSFCAFKADDGPCKAIMKRFF-NIFTRQ  EF IYG-G 61
Ixolaris   G GEN H  TL K NES N---------DAPK -P S EVDY VG ANIP WY  DTNN     120
TFPI       E NQ R  ES  EEKKM TRDNANRIIKTTLQQEK DF F EDP IC GYIT YF NNQT 121                                                    163
Ixolaris   AT EM T  I TG K N SE    ETK-K -  FSLLKKV VTIN
TFPI       KQ ER  K   L  M   TL  K NI ED PNGFQVD YG--
```

FIG. 3B

SEQUENCE LISTING

<160> NUMBER OF SEQ ID NOS: 475

<210> SEQ ID NO 1
<211> LENGTH: 3
<212> TYPE: PRT
<213> ORGANISM: Ixodes scapularis

<400> SEQUENCE: 1

Ala Glu Arg
 1

<210> SEQ ID NO 2
<211> LENGTH: 4
<212> TYPE: PRT
<213> ORGANISM: Ixodes scapularis

<400> SEQUENCE: 2

Ala Glu Arg Val
 1

<210> SEQ ID NO 3
<211> LENGTH: 5
<212> TYPE: PRT
<213> ORGANISM: Ixodes scapularis

<400> SEQUENCE: 3

Ala Glu Arg Val Ser
 1               5

<210> SEQ ID NO 4

```
<211> LENGTH: 6
<212> TYPE: PRT
<213> ORGANISM: Ixodes scapularis

<400> SEQUENCE: 4

Ala Glu Arg Val Ser Glu
 1               5

<210> SEQ ID NO 5
<211> LENGTH: 7
<212> TYPE: PRT
<213> ORGANISM: Ixodes scapularis

<400> SEQUENCE: 5

Ala Glu Arg Val Ser Glu Met
 1               5

<210> SEQ ID NO 6
<211> LENGTH: 8
<212> TYPE: PRT
<213> ORGANISM: Ixodes scapularis

<400> SEQUENCE: 6

Ala Glu Arg Val Ser Glu Met Asp
 1               5

<210> SEQ ID NO 7
<211> LENGTH: 9
<212> TYPE: PRT
<213> ORGANISM: Ixodes scapularis

<400> SEQUENCE: 7

Ala Glu Arg Val Ser Glu Met Asp Ile
 1               5

<210> SEQ ID NO 8
<211> LENGTH: 10
<212> TYPE: PRT
<213> ORGANISM: Ixodes scapularis

<400> SEQUENCE: 8

Ala Glu Arg Val Ser Glu Met Asp Ile Tyr
 1               5                  10

<210> SEQ ID NO 9
<211> LENGTH: 11
<212> TYPE: PRT
<213> ORGANISM: Ixodes scapularis

<400> SEQUENCE: 9

Ala Glu Arg Val Ser Glu Met Asp Ile Tyr Glu
 1               5                  10

<210> SEQ ID NO 10
<211> LENGTH: 12
<212> TYPE: PRT
<213> ORGANISM: Ixodes scapularis

<400> SEQUENCE: 10

Ala Glu Arg Val Ser Glu Met Asp Ile Tyr Glu Phe
 1               5                  10

<210> SEQ ID NO 11
<211> LENGTH: 13
<212> TYPE: PRT
```

-continued

<213> ORGANISM: Ixodes scapularis

<400> SEQUENCE: 11

Ala Glu Arg Val Ser Glu Met Asp Ile Tyr Glu Phe Glu
1               5                   10

<210> SEQ ID NO 12
<211> LENGTH: 14
<212> TYPE: PRT
<213> ORGANISM: Ixodes scapularis

<400> SEQUENCE: 12

Ala Glu Arg Val Ser Glu Met Asp Ile Tyr Glu Phe Glu Ser
1               5                   10

<210> SEQ ID NO 13
<211> LENGTH: 15
<212> TYPE: PRT
<213> ORGANISM: Ixodes scapularis

<400> SEQUENCE: 13

Ala Glu Arg Val Ser Glu Met Asp Ile Tyr Glu Phe Glu Ser Trp
1               5                   10                  15

<210> SEQ ID NO 14
<211> LENGTH: 16
<212> TYPE: PRT
<213> ORGANISM: Ixodes scapularis

<400> SEQUENCE: 14

Ala Glu Arg Val Ser Glu Met Asp Ile Tyr Glu Phe Glu Ser Trp Val
1               5                   10                  15

<210> SEQ ID NO 15
<211> LENGTH: 17
<212> TYPE: PRT
<213> ORGANISM: Ixodes scapularis

<400> SEQUENCE: 15

Ala Glu Arg Val Ser Glu Met Asp Ile Tyr Glu Phe Glu Ser Trp Val
1               5                   10                  15
Ser

<210> SEQ ID NO 16
<211> LENGTH: 18
<212> TYPE: PRT
<213> ORGANISM: Ixodes scapularis

<400> SEQUENCE: 16

Ala Glu Arg Val Ser Glu Met Asp Ile Tyr Glu Phe Glu Ser Trp Val
1               5                   10                  15
Ser Cys

<210> SEQ ID NO 17
<211> LENGTH: 19
<212> TYPE: PRT
<213> ORGANISM: Ixodes scapularis

SEQUENCE: 17

Ala Glu Arg Val Ser Glu Met Asp Ile Tyr Glu Phe Glu Ser Trp Val
1               5                   10                  15
Ser Cys Leu

```
<210> SEQ ID NO 18
<211> LENGTH: 20
<212> TYPE: PRT
<213> ORGANISM: Ixodes scapularis

<400> SEQUENCE: 18

Ala Glu Arg Val Ser Glu Met Asp Ile Tyr Glu Phe Glu Ser Trp Val
  1               5                  10                  15

Ser Cys Leu Asp
            20

<210> SEQ ID NO 19
<211> LENGTH: 21
<212> TYPE: PRT
<213> ORGANISM: Ixodes scapularis

<400> SEQUENCE: 19

Ala Glu Arg Val Ser Glu Met Asp Ile Tyr Glu Phe Glu Ser Trp Val
  1               5                  10                  15

Ser Cys Leu Asp Pro
            20

<210> SEQ ID NO 20
<211> LENGTH: 22
<212> TYPE: PRT
<213> ORGANISM: Ixodes scapularis

<400> SEQUENCE: 20

Ala Glu Arg Val Ser Glu Met Asp Ile Tyr Glu Phe Glu Ser Trp Val
  1               5                  10                  15

Ser Cys Leu Asp Pro Glu
            20

<210> SEQ ID NO 21
<211> LENGTH: 23
<212> TYPE: PRT
<213> ORGANISM: Ixodes scapularis

<400> SEQUENCE: 21

Ala Glu Arg Val Ser Glu Met Asp Ile Tyr Glu Phe Glu Ser Trp Val
  1               5                  10                  15

Ser Cys Leu Asp Pro Glu Gln
            20

<210> SEQ ID NO 22
<211> LENGTH: 24
<212> TYPE: PRT
<213> ORGANISM: Ixodes scapularis

<400> SEQUENCE: 22

Ala Glu Arg Val Ser Glu Met Asp Ile Tyr Glu Phe Glu Ser Trp Val
  1               5                  10                  15

Ser Cys Leu Asp Pro Glu Gln Val
            20

<210> SEQ ID NO 23
<211> LENGTH: 25
<212> TYPE: PRT
<213> ORGANISM: Ixodes scapularis

<400> SEQUENCE: 23

Ala Glu Arg Val Ser Glu Met Asp Ile Tyr Glu Phe Glu Ser Trp Val
```

```
                 1               5                  10                 15
Ser Cys Leu Asp Pro Glu Gln Val Thr
             20                  25

<210> SEQ ID NO 24
<211> LENGTH: 26
<212> TYPE: PRT
<213> ORGANISM: Ixodes scapularis

<400> SEQUENCE: 24

Ala Glu Arg Val Ser Glu Met Asp Ile Tyr Glu Phe Glu Ser Trp Val
 1               5                  10                 15
Ser Cys Leu Asp Pro Glu Gln Val Thr Cys
             20                  25

<210> SEQ ID NO 25
<211> LENGTH: 27
<212> TYPE: PRT
<213> ORGANISM: Ixodes scapularis

<400> SEQUENCE: 25

Ala Glu Arg Val Ser Glu Met Asp Ile Tyr Glu Phe Glu Ser Trp Val
 1               5                  10                 15
Ser Cys Leu Asp Pro Glu Gln Val Thr Cys Glu
             20                  25

<210> SEQ ID NO 26
<211> LENGTH: 28
<212> TYPE: PRT
<213> ORGANISM: Ixodes scapularis

<400> SEQUENCE: 26

Ala Glu Arg Val Ser Glu Met Asp Ile Tyr Glu Phe Glu Ser Trp Val
 1               5                  10                 15
Ser Cys Leu Asp Pro Glu Gln Val Thr Cys Glu Ser
             20                  25

<210> SEQ ID NO 27
<211> LENGTH: 29
<212> TYPE: PRT
<213> ORGANISM: Ixodes scapularis

<400> SEQUENCE: 27

Ala Glu Arg Val Ser Glu Met Asp Ile Tyr Glu Phe Glu Ser Trp Val
 1               5                  10                 15
Ser Cys Leu Asp Pro Glu Gln Val Thr Cys Glu Ser Gln
             20                  25

<210> SEQ ID NO 28
<211> LENGTH: 30
<212> TYPE: PRT
<213> ORGANISM: Ixodes scapularis

<400> SEQUENCE: 28

Ala Glu Arg Val Ser Glu Met Asp Ile Tyr Glu Phe Glu Ser Trp Val
 1               5                  10                 15
Ser Cys Leu Asp Pro Glu Gln Val Thr Cys Glu Ser Gln Glu
             20                  25                 30

<210> SEQ ID NO 29
<211> LENGTH: 31
<212> TYPE: PRT
```

<213> ORGANISM: Ixodes scapularis

<400> SEQUENCE: 29

Ala Glu Arg Val Ser Glu Met Asp Ile Tyr Glu Phe Glu Ser Trp Val
1               5                   10                  15
Ser Cys Leu Asp Pro Glu Gln Val Thr Cys Glu Ser Gln Glu Gly
            20                  25                  30

<210> SEQ ID NO 30
<211> LENGTH: 32
<212> TYPE: PRT
<213> ORGANISM: Ixodes scapularis

<400> SEQUENCE: 30

Ala Glu Arg Val Ser Glu Met Asp Ile Tyr Glu Phe Glu Ser Trp Val
1               5                   10                  15
Ser Cys Leu Asp Pro Glu Gln Val Thr Cys Glu Ser Gln Glu Gly Thr
            20                  25                  30

<210> SEQ ID NO 31
<211> LENGTH: 33
<212> TYPE: PRT
<213> ORGANISM: Ixodes scapularis

<400> SEQUENCE: 31

Ala Glu Arg Val Ser Glu Met Asp Ile Tyr Glu Phe Glu Ser Trp Val
1               5                   10                  15
Ser Cys Leu Asp Pro Glu Gln Val Thr Cys Glu Ser Gln Glu Gly Thr
            20                  25                  30
His

<210> SEQ ID NO 32
<211> LENGTH: 34
<212> TYPE: PRT
<213> ORGANISM: Ixodes scapularis

<400> SEQUENCE: 32

Ala Glu Arg Val Ser Glu Met Asp Ile Tyr Glu Phe Glu Ser Trp Val
1               5                   10                  15
Ser Cys Leu Asp Pro Glu Gln Val Thr Cys Glu Ser Gln Glu Gly Thr
            20                  25                  30
His Ala

<210> SEQ ID NO 33
<211> LENGTH: 35
<212> TYPE: PRT
<213> ORGANISM: Ixodes scapularis

<400> SEQUENCE: 33

Ala Glu Arg Val Ser Glu Met Asp Ile Tyr Glu Phe Glu Ser Trp Val
1               5                   10                  15
Ser Cys Leu Asp Pro Glu Gln Val Thr Cys Glu Ser Gln Glu Gly Thr
            20                  25                  30
His Ala Ser
        35

<210> SEQ ID NO 34
<211> LENGTH: 36
<212> TYPE: PRT
<213> ORGANISM: Ixodes scapularis

```
<400> SEQUENCE: 34

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr
        35

<210> SEQ ID NO 35
<211> LENGTH: 37
<212> TYPE: PRT
<213> ORGANISM: Ixodes scapularis

<400> SEQUENCE: 35

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn
        35

<210> SEQ ID NO 36
<211> LENGTH: 38
<212> TYPE: PRT
<213> ORGANISM: Ixodes scapularis

<400> SEQUENCE: 36

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg
        35

<210> SEQ ID NO 37
<211> LENGTH: 39
<212> TYPE: PRT
<213> ORGANISM: Ixodes scapularis

<400> SEQUENCE: 37

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys
        35

<210> SEQ ID NO 38
<211> LENGTH: 40
<212> TYPE: PRT
<213> ORGANISM: Ixodes scapularis

<400> SEQUENCE: 38

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr
        35                  40
```

<210> SEQ ID NO 39
<211> LENGTH: 41
<212> TYPE: PRT
<213> ORGANISM: Ixodes scapularis

<400> SEQUENCE: 39

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly
        35                  40

<210> SEQ ID NO 40
<211> LENGTH: 42
<212> TYPE: PRT
<213> ORGANISM: Ixodes scapularis

<400> SEQUENCE: 40

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln
        35                  40

<210> SEQ ID NO 41
<211> LENGTH: 43
<212> TYPE: PRT
<213> ORGANISM: Ixodes scapularis

<400> SEQUENCE: 41

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys
        35                  40

<210> SEQ ID NO 42
<211> LENGTH: 44
<212> TYPE: PRT
<213> ORGANISM: Ixodes scapularis

<400> SEQUENCE: 42

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu
        35                  40

<210> SEQ ID NO 43
<211> LENGTH: 45
<212> TYPE: PRT
<213> ORGANISM: Ixodes scapularis

<400> SEQUENCE: 43

Ala Glu Arg Val Ser Glu Met Asp Ile Tyr Glu Phe Glu Ser Trp Val
1               5                   10                  15

-continued

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu
        35                  40                  45

<210> SEQ ID NO 44
<211> LENGTH: 46
<212> TYPE: PRT
<213> ORGANISM: Ixodes scapularis

<400> SEQUENCE: 44

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln
        35                  40                  45

<210> SEQ ID NO 45
<211> LENGTH: 47
<212> TYPE: PRT
<213> ORGANISM: Ixodes scapularis

<400> SEQUENCE: 45

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys
        35                  40                  45

<210> SEQ ID NO 46
<211> LENGTH: 48
<212> TYPE: PRT
<213> ORGANISM: Ixodes scapularis

<400> SEQUENCE: 46

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

<210> SEQ ID NO 47
<211> LENGTH: 49
<212> TYPE: PRT
<213> ORGANISM: Ixodes scapularis

<400> SEQUENCE: 47

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr

<210> SEQ ID NO 48
<211> LENGTH: 50

```
<212> TYPE: PRT
<213> ORGANISM: Ixodes scapularis

<400> SEQUENCE: 48

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu
    50

<210> SEQ ID NO 49
<211> LENGTH: 51
<212> TYPE: PRT
<213> ORGANISM: Ixodes scapularis

<400> SEQUENCE: 49

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys
    50

<210> SEQ ID NO 50
<211> LENGTH: 52
<212> TYPE: PRT
<213> ORGANISM: Ixodes scapularis

<400> SEQUENCE: 50

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly
    50

<210> SEQ ID NO 51
<211> LENGTH: 53
<212> TYPE: PRT
<213> ORGANISM: Ixodes scapularis

<400> SEQUENCE: 51

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly
    50

<210> SEQ ID NO 52
```

<211> LENGTH: 54
<212> TYPE: PRT
<213> ORGANISM: Ixodes scapularis

<400> SEQUENCE: 52

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly
    50

<210> SEQ ID NO 53
<211> LENGTH: 55
<212> TYPE: PRT
<213> ORGANISM: Ixodes scapularis

<400> SEQUENCE: 53

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu
    50                  55

<210> SEQ ID NO 54
<211> LENGTH: 56
<212> TYPE: PRT
<213> ORGANISM: Ixodes scapularis

<400> SEQUENCE: 54

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn
    50                  55

<210> SEQ ID NO 55
<211> LENGTH: 57
<212> TYPE: PRT
<213> ORGANISM: Ixodes scapularis

<400> SEQUENCE: 55

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His
    50                  55

<210> SEQ ID NO 56
<211> LENGTH: 58
<212> TYPE: PRT
<213> ORGANISM: Ixodes scapularis

<400> SEQUENCE: 56

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe
    50                  55

<210> SEQ ID NO 57
<211> LENGTH: 59
<212> TYPE: PRT
<213> ORGANISM: Ixodes scapularis

<400> SEQUENCE: 57

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu
    50                  55

<210> SEQ ID NO 58
<211> LENGTH: 60
<212> TYPE: PRT
<213> ORGANISM: Ixodes scapularis

<400> SEQUENCE: 58

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr
    50                  55                  60

<210> SEQ ID NO 59
<211> LENGTH: 61
<212> TYPE: PRT
<213> ORGANISM: Ixodes scapularis

<400> SEQUENCE: 59

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu
    50                  55                  60

<210> SEQ ID NO 60
<211> LENGTH: 62
<212> TYPE: PRT
<213> ORGANISM: Ixodes scapularis

<400> SEQUENCE: 60

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu
    50                  55                  60

<210> SEQ ID NO 61
<211> LENGTH: 63
<212> TYPE: PRT
<213> ORGANISM: Ixodes scapularis

<400> SEQUENCE: 61

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys
    50                  55                  60

<210> SEQ ID NO 62
<211> LENGTH: 64
<212> TYPE: PRT
<213> ORGANISM: Ixodes scapularis

<400> SEQUENCE: 62

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

<210> SEQ ID NO 63
<211> LENGTH: 65
<212> TYPE: PRT
<213> ORGANISM: Ixodes scapularis

<400> SEQUENCE: 63

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn
65

<210> SEQ ID NO 64
<211> LENGTH: 66
<212> TYPE: PRT
<213> ORGANISM: Ixodes scapularis

<400> SEQUENCE: 64

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu
65

<210> SEQ ID NO 65
<211> LENGTH: 67
<212> TYPE: PRT
<213> ORGANISM: Ixodes scapularis

<400> SEQUENCE: 65

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser
65

<210> SEQ ID NO 66
<211> LENGTH: 68
<212> TYPE: PRT
<213> ORGANISM: Ixodes scapularis

<400> SEQUENCE: 66

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys
65

<210> SEQ ID NO 67
<211> LENGTH: 69
<212> TYPE: PRT
<213> ORGANISM: Ixodes scapularis -continued

```
<400> SEQUENCE: 67

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn
65

<210> SEQ ID NO 68
<211> LENGTH: 70
<212> TYPE: PRT
<213> ORGANISM: Ixodes scapularis

<400> SEQUENCE: 68

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp
65                  70

<210> SEQ ID NO 69
<211> LENGTH: 71
<212> TYPE: PRT
<213> ORGANISM: Ixodes scapularis

<400> SEQUENCE: 69

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala
65                  70

<210> SEQ ID NO 70
<211> LENGTH: 72
<212> TYPE: PRT
<213> ORGANISM: Ixodes scapularis

<400> SEQUENCE: 70

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45
```

```
Thr Glu Cys Gly Gly Gly Glu Asn His Phe Glu Thr Leu Leu Lys Cys
    50                  55                  60

Asn Glu Ser Cys Asn Asp Ala Pro
 65                  70
```

<210> SEQ ID NO 71
<211> LENGTH: 73
<212> TYPE: PRT
<213> ORGANISM: Ixodes scapularis

<400> SEQUENCE: 71

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
                20                  25                  30

His Ala Ser Tyr Asn Arg Lys Thr Gly Gln Cys Glu Glu Gln Lys Gly
            35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys
 65                  70
```

<210> SEQ ID NO 72
<211> LENGTH: 74
<212> TYPE: PRT
<213> ORGANISM: Ixodes scapularis

<400> SEQUENCE: 72

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
                20                  25                  30

His Ala Ser Tyr Asn Arg Lys Thr Gly Gln Cys Glu Glu Gln Lys Gly
            35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro
 65                  70
```

<210> SEQ ID NO 73
<211> LENGTH: 75
<212> TYPE: PRT
<213> ORGANISM: Ixodes scapularis

<400> SEQUENCE: 73

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
                20                  25                  30

His Ala Ser Tyr Asn Arg Lys Thr Gly Gln Cys Glu Glu Gln Lys Gly
            35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro
 65                  70                  75
```

<210> SEQ ID NO 74
<211> LENGTH: 76

```
<212> TYPE: PRT
<213> ORGANISM: Ixodes scapularis

<400> SEQUENCE: 74

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys
65                  70                  75

<210> SEQ ID NO 75
<211> LENGTH: 77
<212> TYPE: PRT
<213> ORGANISM: Ixodes scapularis

<400> SEQUENCE: 75

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser
65                  70                  75

<210> SEQ ID NO 76
<211> LENGTH: 78
<212> TYPE: PRT
<213> ORGANISM: Ixodes scapularis

<400> SEQUENCE: 76

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu
65                  70                  75

<210> SEQ ID NO 77
<211> LENGTH: 79
<212> TYPE: PRT
<213> ORGANISM: Ixodes scapularis

<400> SEQUENCE: 77

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30
```

His Ala Ser Tyr Asn Arg Lys Thr Gly Gln Cys Glu Glu Gln Lys Gly
            35                  40                  45

Thr Glu Cys Gly Gly Gly Glu Asn His Phe Glu Thr Leu Leu Lys Cys
        50                  55                  60

Asn Glu Ser Cys Asn Asp Ala Pro Lys Pro Pro Cys Ser Leu Glu
65                  70                  75

<210> SEQ ID NO 78
<211> LENGTH: 80
<212> TYPE: PRT
<213> ORGANISM: Ixodes scapularis

<400> SEQUENCE: 78

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
            35                  40                  45

Thr Glu Cys Gly Gly Gly Glu Asn His Phe Glu Thr Leu Leu Lys Cys
        50                  55                  60

Asn Glu Ser Cys Asn Asp Ala Pro Lys Pro Pro Cys Ser Leu Glu Val
65                  70                  75                  80

<210> SEQ ID NO 79
<211> LENGTH: 81
<212> TYPE: PRT
<213> ORGANISM: Ixodes scapularis

<400>

```
65                  70                  75                  80

Asp Tyr

<210> SEQ ID NO 81
<211> LENGTH: 83
<212> TYPE: PRT
<213> ORGANISM: Ixodes scapularis

<400> SEQUENCE: 81

Ala Glu Arg Val Ser Glu Met Asp Ile Tyr Glu Phe Glu Ser Trp Val
  1               5                  10                  15

Ser Cys Leu Asp Pro Glu Gln Val Thr Cys Glu Ser Gln Glu Gly Thr
             20                  25                  30

His Ala Ser Tyr Asn Arg Lys Thr Gly Gln Cys Glu Glu Gln Lys Gly
         35                  40                  45

Thr Glu Cys Gly Gly Gly Glu Asn His Phe Glu Thr Leu Leu Lys Cys
     50                  55                  60

Asn Glu Ser Cys Asn Asp Ala Pro Lys Pro Pro Cys Ser Leu Glu Val
 65                  70                  75                  80

Asp Tyr Gly

<210> SEQ ID NO 82
<211> LENGTH: 84
<212> TYPE: PRT
<213> ORGANISM: Ixodes scapularis

<400> SEQUENCE: 82

Ala Glu Arg Val Ser Glu Met Asp Ile Tyr Glu Phe Glu Ser Trp Val
  1               5                  10                  15

Ser Cys Leu Asp Pro Glu Gln Val Thr Cys Glu Ser Gln Glu Gly Thr
             20                  25                  30

His Ala Ser Tyr Asn Arg Lys Thr Gly Gln Cys Glu Glu Gln Lys Gly
         35                  40                  45

Thr Glu Cys Gly Gly Gly Glu Asn His Phe Glu Thr Leu Leu Lys Cys
     50                  55                  60

Asn Glu Ser Cys Asn Asp Ala Pro Lys Pro Pro Cys Ser Leu Glu Val
 65                  70                  75                  80

Asp Tyr Gly Val

<210> SEQ ID NO 83
<211> LENGTH: 85
<212> TYPE: PRT
<213> ORGANISM: Ixodes scapularis

<400> SEQUENCE: 83

Ala Glu Arg Val Ser Glu Met Asp Ile Tyr Glu Phe Glu Ser Trp Val
  1               5                  10                  15

Ser Cys Leu Asp Pro Glu Gln Val Thr Cys Glu Ser Gln Glu Gly Thr
             20                  25                  30

His Ala Ser Tyr Asn Arg Lys Thr Gly Gln Cys Glu Glu Gln Lys Gly
         35                  40                  45

Thr Glu Cys Gly Gly Gly Glu Asn His Phe Glu Thr Leu Leu Lys Cys
     50                  55                  60

Asn Glu Ser Cys Asn Asp Ala Pro Lys Pro Pro Cys Ser Leu Glu Val
 65                  70                  75                  80

Asp Tyr Gly Val Gly
                 85
```

<210> SEQ ID NO 84
<211> LENGTH: 86
<212> TYPE: PRT
<213> ORGANISM: Ixodes scapularis

<400> SEQUENCE: 84

Ala Glu Arg Val Ser Glu Met Asp Ile Tyr Glu Phe Glu Ser Trp Val
1               5                   10                  15

<210> SEQ ID NO 87
<211> LENGTH: 89
<212> TYPE: PRT
<213> ORGANISM: Ixodes scapularis

<400> SEQUENCE: 87

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile
                85
```

<210> SEQ ID NO 88
<211> LENGTH: 90
<212> TYPE: PRT
<213> ORGANISM: Ixodes scapularis

<400> SEQUENCE: 88

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro
                85                  90
```

<210> SEQ ID NO 89
<211> LENGTH: 91
<212> TYPE: PRT
<213> ORGANISM: Ixodes scapularis

<400> SEQUENCE: 89

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg
                85                  90
```

<210> SEQ ID NO 90
<211> LENGTH: 92
<212> TYPE: PRT
<213> ORGANISM: Ixodes scapularis

<400> SEQUENCE: 90

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp
                85                  90

<210> SEQ ID NO 91
<211> LENGTH: 93
<212> TYPE: PRT
<213> ORGANISM: Ixodes scapularis

<400> SEQUENCE: 91

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr
                85                  90

<210> SEQ ID NO 92
<211> LENGTH: 94
<212> TYPE: PRT
<213> ORGANISM: Ixodes scapularis

<400> SEQUENCE: 92

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr
                85                  90

<210> SEQ ID NO 93

<211> LENGTH: 95
<212> TYPE: PRT
<213> ORGANISM: Ixodes scapularis

<400> SEQUENCE: 93

```
Ala Glu Arg Val Ser Glu Met Asp Ile Tyr Glu Phe Glu Ser Trp Val
 1               5                  10                  15
Ser Cys Leu Asp Pro Glu Gln Val Thr Cys Glu Ser Gln Glu Gly Thr
            20                  25                  30
His Ala Ser Tyr Asn Arg Lys Thr Gly Gln Cys Glu Glu Gln Lys Gly
        35                  40                  45
Thr Glu Cys Gly Gly Gly Glu Asn His Phe Glu Thr Leu Leu Lys Cys
    50                  55                  60
Asn Glu Ser Cys Asn Asp Ala Pro Lys Pro Cys Ser Leu Glu Val
65                  70                  75                  80
Asp Tyr Gly Val Gly Arg Ala Asn Ile Pro Arg Trp Tyr Tyr Asp
                85                  90                  95
```

<210> SEQ ID NO 94
<211> LENGTH: 96
<212> TYPE: PRT
<213> ORGANISM: Ixodes scapularis

<400> SEQUENCE: 94

```
Ala Glu Arg Val Ser Glu Met Asp Ile Tyr Glu Phe Glu Ser Trp Val
 1               5                  10                  15
Ser Cys Leu Asp Pro Glu Gln Val Thr Cys Glu Ser Gln Glu Gly Thr
            20                  25                  30
His Ala Ser Tyr Asn Arg Lys Thr Gly Gln Cys Glu Glu Gln Lys Gly
        35                  40                  45
Thr Glu Cys Gly Gly Gly Glu Asn His Phe Glu Thr Leu Leu Lys Cys
    50                  55                  60
Asn Glu Ser Cys Asn Asp Ala Pro Lys Pro Cys Ser Leu Glu Val
65                  70                  75                  80
Asp Tyr Gly Val Gly Arg Ala Asn Ile Pro Arg Trp Tyr Tyr Asp Thr
                85                  90                  95
```

<210> SEQ ID NO 95
<211> LENGTH: 97
<212> TYPE: PRT
<213> ORGANISM: Ixodes scapularis

<400> SEQUENCE: 95

```
Ala Glu Arg Val Ser Glu Met Asp Ile Tyr Glu Phe Glu Ser Trp Val
 1               5                  10                  15
Ser Cys Leu Asp Pro Glu Gln Val Thr Cys Glu Ser Gln Glu Gly Thr
            20                  25                  30
His Ala Ser Tyr Asn Arg Lys Thr Gly Gln Cys Glu Glu Gln Lys Gly
        35                  40                  45
Thr Glu Cys Gly Gly Gly Glu Asn His Phe Glu Thr Leu Leu Lys Cys
    50                  55                  60
Asn Glu Ser Cys Asn Asp Ala Pro Lys Pro Cys Ser Leu Glu Val
65                  70                  75                  80
Asp Tyr Gly Val Gly Arg Ala Asn Ile Pro Arg Trp Tyr Tyr Asp Thr
                85                  90                  95
Asn
```

<210> SEQ ID NO 96
<211> LENGTH: 98
<212> TYPE: PRT
<213> ORGANISM: Ixodes scapularis

<400> SEQUENCE: 96

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn

<210> SEQ ID NO 97
<211> LENGTH: 99
<212> TYPE: PRT
<213> ORGANISM: Ixodes scapularis

<400> SEQUENCE: 97

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala

<210> SEQ ID NO 98
<211> LENGTH: 100
<212> TYPE: PRT
<213> ORGANISM: Ixodes scapularis

<400> SEQUENCE: 98

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr

```
                    85                  90                  95
Asn Asn Ala Thr
            100

<210> SEQ ID NO 99
<211> LENGTH: 101
<212> TYPE: PRT
<213> ORGANISM: Ixodes scapularis

<400> SEQUENCE: 99

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys
            100

<210> SEQ ID NO 100
<211> LENGTH: 102
<212> TYPE: PRT
<213> ORGANISM: Ixodes scapularis

<400> SEQUENCE: 100

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu
            100

<210> SEQ ID NO 101
<211> LENGTH: 103
<212> TYPE: PRT
<213> ORGANISM: Ixodes scapularis

<400> SEQUENCE: 101

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45
```

```
Thr Glu Cys Gly Gly Gly Glu Asn His Phe Glu Thr Leu Leu Lys Cys
 50                  55                  60

Asn Glu Ser Cys Asn Asp Ala Pro Lys Pro Pro Cys Ser Leu Glu Val
 65                  70                  75                  80

Asp Tyr Gly Val Gly Arg Ala Asn Ile Pro Arg Trp Tyr Tyr Asp Thr
                 85                  90                  95

Asn Asn Ala Thr Cys Glu Met
            100
```

<210> SEQ ID NO 102
<211> LENGTH: 104
<212> TYPE: PRT
<213> ORGANISM: Ixodes scapularis

<400> SEQUENCE: 102

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
                 20                  25                  30

His Ala Ser Tyr Asn Arg Lys Thr Gly Gln Cys Glu Glu Gln Lys Gly
             35                  40                  45

Thr Glu Cys Gly Gly Gly Glu Asn His Phe Glu Thr Leu Leu Lys Cys
 50                  55                  60

Asn Glu Ser Cys Asn Asp Ala Pro Lys Pro Pro Cys Ser Leu Glu Val
 65                  70                  75                  80

Asp Tyr Gly Val Gly Arg Ala Asn Ile Pro Arg Trp Tyr Tyr Asp Thr
                 85                  90                  95

Asn Asn Ala Thr Cys Glu Met Phe
            100
```

<210> SEQ ID NO 103
<211> LENGTH: 105
<212> TYPE: PRT
<213> ORGANISM: Ixodes scapularis

<400> SEQUENCE: 103

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
                 20                  25                  30

His Ala Ser Tyr Asn Arg Lys Thr Gly Gln Cys Glu Glu Gln Lys Gly
             35                  40                  45

Thr Glu Cys Gly Gly Gly Glu Asn His Phe Glu Thr Leu Leu Lys Cys
 50                  55                  60

Asn Glu Ser Cys Asn Asp Ala Pro Lys Pro Pro Cys Ser Leu Glu Val
 65                  70                  75                  80

Asp Tyr Gly Val Gly Arg Ala Asn Ile Pro Arg Trp Tyr Tyr Asp Thr
                 85                  90                  95

Asn Asn Ala Thr Cys Glu Met Phe Thr
            100                 105
```

<210> SEQ ID NO 104
<211> LENGTH: 106
<212> TYPE: PRT
<213> ORGANISM: Ixodes scapularis

<400> SEQUENCE: 104

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
 50                      55                  60

Asn Glu Ser Cys Asn Asp Ala Pro Lys Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr
            100                 105
```

<210> SEQ ID NO 105
<211> LENGTH: 107
<212> TYPE: PRT
<213> ORGANISM: Ixodes scapularis

<400> SEQUENCE: 105

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
 50                      55                  60

Asn Glu Ser Cys Asn Asp Ala Pro Lys Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly
            100                 105
```

<210> SEQ ID NO 106
<211> LENGTH: 108
<212> TYPE: PRT
<213> ORGANISM: Ixodes scapularis

<400> SEQUENCE: 106

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
 50                      55                  60

Asn Glu Ser Cys Asn Asp Ala Pro Lys Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly
            100                 105
```

<210> SEQ ID NO 107
<211> LENGTH: 109
<212> TYPE: PRT
<213> ORGANISM: Ixodes scapularis

<400> SEQUENCE: 107

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile
            100                 105

<210> SEQ ID NO 108
<211> LENGTH: 110
<212> TYPE: PRT
<213> ORGANISM: Ixodes scapularis

<400> SEQUENCE: 108

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr
            100                 105                 110

<210> SEQ ID NO 109
<211> LENGTH: 111
<212> TYPE: PRT
<213> ORGANISM: Ixodes scapularis

<400> SEQUENCE: 109

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val

```
                65                  70                  75                  80
Asp Tyr Gly Val Gly Arg Ala Asn Ile Pro Arg Trp Tyr Tyr Asp Thr
                    85                  90                  95

Asn Asn Ala Thr Cys Glu Met Phe Thr Tyr Gly Gly Ile Thr Gly
                100                 105                 110
```

<210> SEQ ID NO 110
<211> LENGTH: 112
<212> TYPE: PRT
<213> ORGANISM: Ixodes scapularis

<400> SEQUENCE: 110

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
                20                  25                  30

His Ala Ser Tyr Asn Arg Lys Thr Gly Gln Cys Glu Glu Gln Lys Gly
            35                  40                  45

Thr Glu Cys Gly Gly Gly Glu Asn His Phe Glu Thr Leu Leu Lys Cys
        50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                    85                  90                  95

Asn Asn Ala Thr Cys Glu Met Phe Thr Tyr Gly Gly Ile Thr Gly Asn
                100                 105                 110
```

<210> SEQ ID NO 111
<211> LENGTH: 113
<212> TYPE: PRT
<213> ORGANISM: Ixodes scapularis

<400> SEQUENCE: 111

```
Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
                20                  25                  30

His Ala Ser Tyr Asn Arg Lys Thr Gly Gln Cys Glu Glu Gln Lys Gly
            35                  40                  45

Thr Glu Cys Gly Gly Gly Glu Asn His Phe Glu Thr Leu Leu Lys Cys
        50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                    85                  90                  95

Asn Asn Ala Thr Cys Glu Met Phe Thr Tyr Gly Gly Ile Thr Gly Asn
                100                 105                 110

Lys
```

<210> SEQ ID NO 112
<211> LENGTH: 114
<212> TYPE: PRT
<213> ORGANISM: Ixodes scapularis

<400> SEQUENCE: 112

```
Ala Glu Arg Val Ser Glu Met Asp Ile Tyr Glu Phe Glu Ser Trp Val
 1               5                  10                  15
```

-continued

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn

<210> SEQ ID NO 113
<211> LENGTH: 115
<212> TYPE: PRT
<213> ORGANISM: Ixodes scapularis

<400> SEQUENCE: 113

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn
        115

<210> SEQ ID NO 114
<211> LENGTH: 116
<212> TYPE: PRT
<213> ORGANISM: Ixodes scapularis

<400> SEQUENCE: 114

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn

Lys Asn Asn Phe
        115

<210> SEQ ID NO 115
<211> LENGTH: 117
<212> TYPE: PRT
<213> ORGANISM: Ixodes scapularis

<400> SEQUENCE: 115

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu
        115

<210> SEQ ID NO 116
<211> LENGTH: 118
<212> TYPE: PRT
<213> ORGANISM: Ixodes scapularis

<400> SEQUENCE: 116

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu Ser
        115

<210> SEQ ID NO 117
<211> LENGTH: 119
<212> TYPE: PRT
<213> ORGANISM: Ixodes scapularis

<400> SEQUENCE: 117

Ala Glu Arg Val Ser Glu Met Asp Ile Tyr Glu Phe Glu Ser Trp Val
1               5                   10                  15

```
Ser Cys Leu Asp Pro Glu Gln Val Thr Cys Glu Ser Gln Glu Gly Thr
        20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu Ser Glu
        115

<210> SEQ ID NO 118
<211> LENGTH: 120
<212> TYPE: PRT
<213> ORGANISM: Ixodes scapularis

<400> SEQUENCE: 118

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
        20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu Ser Glu Glu
        115                 120

<210> SEQ ID NO 119
<211> LENGTH: 121
<212> TYPE: PRT
<213> ORGANISM: Ixodes scapularis

<400> SEQUENCE: 119

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
        20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95
```

Asn Asn Ala Thr Cys Glu Met Phe Thr Tyr Gly Gly Ile Thr Gly Asn
            100                 105                 110

Lys Asn Asn Phe Glu Ser Glu Glu Glu
        115                 120

<210> SEQ ID NO 120
<211> LENGTH: 122
<212> TYPE: PRT
<213> ORGANISM: Ixodes scapularis

<400> SEQUENCE: 120

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu Ser Glu Glu Glu Cys
        115                 120

<210> SEQ ID NO 121
<211> LENGTH: 123
<212> TYPE: PRT
<213> ORGANISM: Ixodes scapularis

<400> SEQUENCE: 121

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu Ser Glu Glu Glu Cys Lys
        115                 120

<210> SEQ ID NO 122
<211> LENGTH: 124
<212> TYPE: PRT
<213> ORGANISM: Ixodes scapularis

<400> SEQUENCE: 122

```
Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
                100                 105                 110

Lys Asn Asn Phe Glu Ser Glu Glu Glu Cys Lys Glu
            115                 120
```

<210> SEQ ID NO 123
<211> LENGTH: 125
<212> TYPE: PRT
<213> ORGANISM: Ixodes scapularis

<400> SEQUENCE: 123

```
Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
                100                 105                 110

Lys Asn Asn Phe Glu Ser Glu Glu Glu Cys Lys Glu Thr
            115                 120                 125
```

<210> SEQ ID NO 124
<211> LENGTH: 126
<212> TYPE: PRT
<213> ORGANISM: Ixodes scapularis

<400> SEQUENCE: 124

```
Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80
```

```
Asp Tyr Gly Val Gly Arg Ala Asn Ile Pro Arg Trp Tyr Tyr Asp Thr
            85                  90                  95

Asn Asn Ala Thr Cys Glu Met Phe Thr Tyr Gly Gly Ile Thr Gly Asn
        100                 105                 110

Lys Asn Asn Phe Glu Ser Glu Glu Cys Lys Glu Thr Cys
    115                 120                 125

<210> SEQ ID NO 125
<211> LENGTH: 127
<212> TYPE: PRT
<213> ORGANISM: Ixodes scapularis

<400> SEQUENCE: 125

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Cys Ser Leu Glu Val
65                  70                  75                  80

Asp Tyr Gly Val Gly Arg Ala Asn Ile Pro Arg Trp Tyr Tyr Asp Thr
            85                  90                  95

Asn Asn Ala Thr Cys Glu Met Phe Thr Tyr Gly Gly Ile Thr Gly Asn
        100                 105                 110

Lys Asn Asn Phe Glu Ser Glu Glu Cys Lys Glu Thr Cys Lys
    115                 120                 125

<210> SEQ ID NO 126
<211> LENGTH: 128
<212> TYPE: PRT
<213> ORGANISM: Ixodes scapularis

<400> SEQUENCE: 126

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Cys Ser Leu Glu Val
65                  70                  75                  80

Asp Tyr Gly Val Gly Arg Ala Asn Ile Pro Arg Trp Tyr Tyr Asp Thr
            85                  90                  95

Asn Asn Ala Thr Cys Glu Met Phe Thr Tyr Gly Gly Ile Thr Gly Asn
        100                 105                 110

Lys Asn Asn Phe Glu Ser Glu Glu Cys Lys Glu Thr Cys Lys Gly
    115                 120                 125

<210> SEQ ID NO 127
<211> LENGTH: 129
<212> TYPE: PRT
<213> ORGANISM: Ixodes scapularis
```

-continued

```
<400> SEQUENCE: 127

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
             20                  25                  30

His Ala Ser Tyr Asn Arg Lys Thr Gly Gln Cys Glu Glu Gln Lys Gly
         35                  40                  45

Thr Glu Cys Gly Gly Gly Glu Asn His Phe Glu Thr Leu Leu Lys Cys
     50                  55                  60

Asn Glu Ser Cys Asn Asp Ala Pro Lys Pro Cys Ser Leu Glu Val
 65                  70                  75                  80

Asp Tyr Gly Val Gly Arg Ala Asn Ile Pro Arg Trp Tyr Tyr Asp Thr
                 85                  90                  95

Asn Asn Ala Thr Cys Glu Met Phe Thr Tyr Gly Gly Ile Thr Gly Asn
                100                 105                 110

Lys Asn Asn Phe Glu Ser Glu Glu Cys Lys Glu Thr Cys Lys Gly
             115                 120                 125

Phe

<210> SEQ ID NO 128
<211> LENGTH: 130
<212> TYPE: PRT
<213> ORGANISM: Ixodes scapularis

<400> SEQUENCE: 128

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
             20                  25                  30

His Ala Ser Tyr Asn Arg Lys Thr Gly Gln Cys Glu Glu Gln Lys Gly
         35                  40                  45

Thr Glu Cys Gly Gly Gly Glu Asn His Phe Glu Thr Leu Leu Lys Cys
     50                  55                  60

Asn Glu Ser Cys Asn Asp Ala Pro Lys Pro Cys Ser Leu Glu Val
 65                  70                  75                  80

Asp Tyr Gly Val Gly Arg Ala Asn Ile Pro Arg Trp Tyr Tyr Asp Thr
                 85                  90                  95

Asn Asn Ala Thr Cys Glu Met Phe Thr Tyr Gly Gly Ile Thr Gly Asn
                100                 105                 110

Lys Asn Asn Phe Glu Ser Glu Glu Cys Lys Glu Thr Cys Lys Gly
             115                 120                 125

Phe Ser
    130

<210> SEQ ID NO 129
<211> LENGTH: 131
<212> TYPE: PRT
<213> ORGANISM: Ixodes scapularis

<400> SEQUENCE: 129

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
             20                  25                  30

His Ala Ser Tyr Asn Arg Lys Thr Gly Gln Cys Glu Glu Gln Lys Gly
         35                  40                  45
```

-continued

```
Thr Glu Cys Gly Gly Gly Glu Asn His Phe Glu Thr Leu Leu Lys Cys
 50                  55                  60

Asn Glu Ser Cys Asn Asp Ala Pro Lys Pro Pro Cys Ser Leu Glu Val
 65                  70                  75                  80

Asp Tyr Gly Val Gly Arg Ala Asn Ile Pro Arg Trp Tyr Tyr Asp Thr
                 85                  90                  95

Asn Asn Ala Thr Cys Glu Met Phe Thr Tyr Gly Gly Ile Thr Gly Asn
            100                 105                 110

Lys Asn Asn Phe Glu Ser Glu Glu Cys Lys Glu Thr Cys Lys Gly
        115                 120                 125

Phe Ser Leu
    130

<210> SEQ ID NO 130
<211> LENGTH: 132
<212> TYPE: PRT
<213> ORGANISM: Ixodes scapularis

<400> SEQUENCE: 130

Ala Glu Arg Val Ser Glu Met Asp Ile Tyr Glu Phe Glu Ser Trp Val
 1               5                  10                  15

Ser Cys Leu Asp Pro Glu Gln Val Thr Cys Glu Ser Gln Glu Gly Thr
             20                  25                  30

His Ala Ser Tyr Asn Arg Lys Thr Gly Gln Cys Glu Glu Gln Lys Gly
         35                  40                  45

Thr Glu Cys Gly Gly Gly Glu Asn His Phe Glu Thr Leu Leu Lys Cys
 50                  55                  60

Asn Glu Ser Cys Asn Asp Ala Pro Lys Pro Pro Cys Ser Leu Glu Val
 65                  70                  75                  80

Asp Tyr Gly Val Gly Arg Ala Asn Ile Pro Arg Trp Tyr Tyr Asp Thr
                 85                  90                  95

Asn Asn Ala Thr Cys Glu Met Phe Thr Tyr Gly Gly Ile Thr Gly Asn
            100                 105                 110

Lys Asn Asn Phe Glu Ser Glu Glu Cys Lys Glu Thr Cys Lys Gly
        115                 120                 125

Phe Ser Leu Leu
    130

<210> SEQ ID NO 131
<211> LENGTH: 133
<212> TYPE: PRT
<213> ORGANISM: Ixodes scapularis

<400> SEQUENCE: 131

Ala Glu Arg Val Ser Glu Met Asp Ile Tyr Glu Phe Glu Ser Trp Val
 1               5                  10                  15

Ser Cys Leu Asp Pro Gl

-continued

Asn Asn Ala Thr Cys Glu Met Phe Thr Tyr Gly Gly Ile Thr Gly Asn
            100                 105                 110

Lys Asn Asn Phe Glu Ser Glu Glu Glu Cys Lys Glu Thr Cys Lys Gly
        115                 120                 125

Phe Ser Leu Leu Lys
        130

<210> SEQ ID NO 132
<211> LENGTH: 134
<212> TYPE: PRT
<213> ORGANISM: Ixodes scapularis

<400> SEQUENCE: 132

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu Ser Glu Glu Glu Cys Lys Glu Thr Cys Lys Gly
        115                 120                 125

Phe Ser Leu Leu Lys Lys
        130

<210> SEQ ID NO 133
<211> LENGTH: 135
<212> TYPE: PRT
<213> ORGANISM: Ixodes scapularis

<400> SEQUENCE: 133

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25

<210> SEQ ID NO 134
<211> LENGTH: 136
<212> TYPE: PRT
<213> ORGANISM: Ixodes scapularis

<400> SEQUENCE: 134

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Cys Ser Leu Glu Val
65                  70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu Ser Glu Glu Cys Lys Glu Thr Cys Lys Gly
        115                 120                 125

Phe Ser Leu Leu Lys Lys Val Asn
    130                 135

<210> SEQ ID NO 135
<211> LENGTH: 137
<212> TYPE: PRT
<213> ORGANISM: Ixodes scapularis

<400> SEQUENCE: 135

Ala Glu Arg Val Ser Glu Met Asp Ile Tyr Glu

-continued

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65              70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu Ser Glu Glu Cys Lys Glu Thr Cys Lys Gly
        115                 120                 125

Phe Ser Leu Leu Lys Lys Val Asn Val Thr
    130                 135

<210> SEQ ID NO 137
<211> LENGTH: 139
<212> TYPE: PRT
<213> ORGANISM: Ixodes scapularis

<400> SEQUENCE: 137

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

Thr Glu Cys Gly Gly Gly Glu Asn His Phe Glu Thr Leu Leu Lys Cys
    50                  55                  60

Asn Glu Ser Cys Asn Asp Ala Pro Lys Pro Pro Cys Ser Leu Glu Val
65              70                  75                  80

Asp Tyr Gly Val Gly Arg Ala Asn Ile Pro Arg Trp Tyr Tyr Asp Thr
                85                  90                  95

Asn Asn Ala Thr Cys Glu Met Phe Thr Tyr Gly Gly Ile Thr Gly Asn
            100                 105                 110

Lys Asn Asn Phe Glu Ser Glu Glu Cys Lys Glu Thr Cys Lys Gly
        115                 120                 125

Phe Ser Leu Leu Lys Lys Val Asn Val Thr Ile
    130                 135

<210> SEQ ID NO 138
<211> LENGTH: 140
<212> TYPE: PRT
<213> ORGANISM: Ixodes scapularis

<400> SEQUENCE: 138

Ala Glu Arg Val Ser Glu Met Asp Ile Tyr Glu Phe Glu Ser Trp Val
1               5                   10                  15

Ser Cys Leu Asp Pro Glu Gln Val Thr Cys Glu Ser Gln Glu Gly Thr
            20                  25                  30

His Ala Ser Tyr Asn Arg Lys Thr Gly Gln Cys Glu Glu Gln Lys Gly
        35                  40                  45

-continued

```
Thr Glu Cys Gly Gly Gly Glu Asn His Phe Glu Thr Leu Leu Lys Cys
 50                  55                  60

Asn Glu Ser Cys Asn Asp Ala Pro Lys Pro Pro Cys Ser Leu Glu Val
 65                  70                  75                  80

Asp Tyr Gly Val Gly Arg Ala Asn Ile Pro Arg Trp Tyr Tyr Asp Thr
                 85                  90                  95

Asn Asn Ala Thr Cys Glu Met Phe Thr Tyr Gly Gly Ile Thr Gly Asn
            100                 105                 110

Lys Asn Phe Glu Ser Glu Glu Cys Lys Glu Thr Cys Lys Gly
        115                 120                 125

Phe Ser Leu Leu Lys Lys Val Asn Val Thr Ile Asn
    130                 135                 140
```

<210> SEQ ID NO 139
<211> LENGTH: 3
<212> TYPE: PRT
<213> ORGANISM: Ixodes scapularis

<400> SEQUENCE: 139

Thr Ile Asn
 1

<210> SEQ ID NO 140
<211> LENGTH: 4
<212> TYPE: PRT
<213> ORGANISM: Ixodes scapularis

<400> SEQUENCE: 140

Val Thr Ile Asn
 1

<210> SEQ ID NO 141
<211> LENGTH: 5
<212> TYPE: PRT
<213> ORGANISM: Ixodes scapularis

<400> SEQUENCE: 141

Asn Val Thr Ile Asn
 1               5

<210> SEQ ID NO 142
<211> LENGTH: 6
<212> TYPE: PRT
<213> ORGANISM: Ixodes scapularis

<400> SEQUENCE: 142

Val Asn Val Thr Ile Asn
 1               5

<210> SEQ ID NO 143
<211> LENGTH: 7
<212> TYPE: PRT
<213> ORGANISM: Ixodes scapularis

<400> SEQUENCE: 143

Lys Val Asn Val Thr Ile Asn
 1               5

<210> SEQ ID NO 144
<211> LENGTH: 8
<212> TYPE: PRT
<213> ORGANISM: Ixodes scapularis

```
<400> SEQUENCE: 144

Lys Lys Val Asn Val Thr Ile Asn
1               5

<210> SEQ ID NO 145
<211> LENGTH: 9
<212> TYPE: PRT
<213> ORGANISM: Ixodes scapularis

<400> SEQUENCE: 145

Leu Lys Lys Val Asn Val Thr Ile Asn
1               5

<210> SEQ ID NO 146
<211> LENGTH: 10
<212> TYPE: PRT
<213> ORGANISM: Ixodes scapularis

<400> SEQUENCE: 146

Leu Leu Lys Lys Val Asn Val Thr Ile Asn
1               5                   10

<210> SEQ ID NO 147
<211> LENGTH: 11
<212> TYPE: PRT
<213> ORGANISM: Ixodes scapularis

<400> SEQUENCE: 147

Ser Leu Leu Lys Lys Val Asn Val Thr Ile Asn
1               5                   10

<210> SEQ ID NO 148
<211> LENGTH: 12
<212> TYPE: PRT
<213> ORGANISM: Ixodes scapularis

<400> SEQUENCE: 148

Phe Ser Leu Leu Lys Lys Val Asn Val Thr Ile Asn
1               5                   10

<210> SEQ ID NO 149
<211> LENGTH: 13
<212> TYPE: PRT
<213> ORGANISM: Ixodes scapularis

<400> SEQUENCE: 149

Gly Phe Ser Leu Leu Lys Lys Val Asn Val Thr Ile Asn
1               5                   10

<210> SEQ ID NO 150
<211> LENGTH: 14
<212> TYPE: PRT
<213> ORGANISM: Ixodes scapularis

<400> SEQUENCE: 150

Lys Gly Phe Ser Leu Leu Lys Lys Val Asn Val Thr Ile Asn
1               5                   10

<210> SEQ ID NO 151
<211> LENGTH: 15
<212> TYPE: PRT
<213> ORGANISM: Ixodes scapularis

<400> SEQUENCE: 151
```

```
Cys Lys Gly Phe Ser Leu Leu Lys Lys Val Asn Val Thr Ile Asn
1               5                  10                  15
```

<210> SEQ ID NO 152
<211> LENGTH: 16
<212> TYPE: PRT
<213> ORGANISM: Ixodes scapularis

<400> SEQUENCE: 152

```
Thr Cys Lys Gly Phe Ser Leu Leu Lys Lys Val Asn Val Thr Ile Asn
1               5                  10                  15
```

<210> SEQ ID NO 153
<211> LENGTH: 17
<212> TYPE: PRT
<213> ORGANISM: Ixodes scapularis

<400> SEQUENCE: 153

```
Glu Thr Cys Lys Gly Phe Ser Leu Leu Lys Lys Val Asn Val Thr Ile
1               5                  10                  15

Asn
```

<210> SEQ ID NO 154
<211> LENGTH: 18
<212> TYPE: PRT
<213> ORGANISM: Ixodes scapularis

<400> SEQUENCE: 154

```
Lys Glu Thr Cys Lys Gly Phe Ser Leu Leu Lys Lys Val Asn Val Thr
1               5                  10                  15

Ile Asn
```

<210> SEQ ID NO 155
<211> LENGTH: 19
<212> TYPE: PRT
<213> ORGANISM: Ixodes scapularis

<400> SEQUENCE: 155

```
Cys Lys Glu Thr Cys Lys Gly Phe Ser Leu Leu Lys Lys Val Asn Val
1               5                  10                  15

Thr Ile Asn
```

<210> SEQ ID NO 156
<211> LENGTH: 20
<212> TYPE: PRT
<213> ORGANISM: Ixodes scapularis

<400> SEQUENCE: 156

```
Glu Cys Lys Glu Thr Cys Lys Gly Phe Ser Leu Leu Lys Lys Val Asn
1               5                  10                  15

Val Thr Ile Asn
            20
```

<210> SEQ ID NO 157
<211> LENGTH: 21
<212> TYPE: PRT
<213> ORGANISM: Ixodes scapularis

<400> SEQUENCE: 157

```
Glu Glu Cys Lys Glu Thr Cys Lys Gly Phe Ser Leu Leu Lys Lys Val
1               5                  10                  15

Asn Val Thr Ile Asn
```

20

<210> SEQ ID NO 158
<211> LENGTH: 22
<212> TYPE: PRT
<213> ORGANISM: Ixodes scapularis

<400> SEQUENCE: 158

Glu Glu Glu Cys Lys Glu Thr Cys Lys Gly Phe Ser Leu Leu Lys Lys
1               5                   10                  15

Val Asn Val Thr Ile Asn
            20

<210> SEQ ID NO 159
<211> LENGTH: 23
<212> TYPE: PRT
<213> ORGANISM: Ixodes scapularis

<400> SEQUENCE: 159

Ser Glu Glu Glu Cys Lys Glu Thr Cys Lys Gly Phe Ser Leu Leu Lys
1               5                   10                  15

Lys Val Asn Val Thr Ile Asn
            20

<210> SEQ ID NO 160
<211> LENGTH: 24
<212> TYPE: PRT
<213> ORGANISM: Ixodes scapularis

<400> SEQUENCE: 160

Glu Ser Glu Glu Glu Cys Lys Glu Thr Cys Lys Gly Phe Ser Leu Leu
1               5                   10                  15

Lys Lys Val Asn Val Thr Ile Asn
            20

<210> SEQ ID NO 161
<211> LENGTH: 25
<212> TYPE: PRT
<213> ORGANISM: Ixodes scapularis

<400> SEQUENCE: 161

Phe Glu Ser Glu Glu Glu Cys Lys Glu Thr Cys Lys Gly Phe Ser Leu
1               5                   10                  15

Leu Lys Lys Val Asn Val Thr Ile Asn
            20                  25

<210> SEQ ID NO 162
<211> LENGTH: 26
<212> TYPE: PRT
<213> ORGANISM: Ixodes scapularis

<400> SEQUENCE: 162

Asn Phe Glu Ser Glu Glu Glu Cys Lys Glu Thr Cys Lys Gly Phe Ser
1               5                   10                  15

Leu Leu Lys Lys Val Asn Val Thr Ile Asn
            20                  25

<210> SEQ ID NO 163
<211> LENGTH: 27
<212> TYPE: PRT
<213> ORGANISM: Ixodes scapularis

<400> SEQUENCE: 163

```
Asn Asn Phe Glu Ser Glu Glu Glu Cys Lys Glu Thr Cys Lys Gly Phe
1               5                   10                  15

Ser Leu Leu Lys Lys Val Asn Val Thr Ile Asn
            20                  25
```

<210> SEQ ID NO 164
<211> LENGTH: 28
<212> TYPE: PRT
<213> ORGANISM: Ixodes scapularis

<400> SEQUENCE: 164

```
Lys Asn Asn Phe Glu Ser Glu Glu Glu Cys Lys Glu Thr Cys Lys Gly
1               5                   10                  15

Phe Ser Leu Leu Lys Lys Val Asn Val Thr Ile Asn
            20                  25
```

<210> SEQ ID NO 165
<211> LENGTH: 29
<212> TYPE: PRT
<213> ORGANISM: Ixodes scapularis

<400> SEQUENCE: 165

```
Asn Lys Asn Asn Phe Glu Ser Glu Glu Glu Cys Lys Glu Thr Cys Lys
1               5                   10                  15

Gly Phe Ser Leu Leu Lys Lys Val Asn Val Thr Ile Asn
            20                  25
```

<210> SEQ ID NO 166
<211> LENGTH: 30
<212> TYPE: PRT
<213> ORGANISM: Ixodes scapularis

<400> SEQUENCE: 166

```
Gly Asn Lys Asn Asn Phe Glu Ser Glu Glu Glu Cys Lys Glu Thr Cys
1               5                   10                  15

Lys Gly Phe Ser Leu Leu Lys Lys Val Asn Val Thr Ile Asn
            20                  25                  30
```

<210> SEQ ID NO 167
<211> LENGTH: 31
<212> TYPE: PRT
<213> ORGANISM: Ixodes scapularis

<400> SEQUENCE: 167

```
Thr Gly Asn Lys Asn Asn Phe Glu Ser Glu Glu Glu Cys Lys Glu Thr
1               5                   10                  15

Cys Lys Gly Phe Ser Leu Leu Lys Lys Val Asn Val Thr Ile Asn
            20                  25                  30
```

<210> SEQ ID NO 168
<211> LENGTH: 32
<212> TYPE: PRT
<213> ORGANISM: Ixodes scapularis

<400> SEQUENCE: 168

```
Ile Thr Gly Asn Lys Asn Asn Phe Glu Ser Glu Glu Glu Cys Lys Glu
1               5                   10                  15

Thr Cys Lys Gly Phe Ser Leu Leu Lys Lys Val Asn Val Thr Ile Asn
            20                  25                  30
```

<210> SEQ ID NO 169

<211> LENGTH: 33
<212> TYPE: PRT
<213> ORGANISM: Ixodes scapularis

<400> SEQUENCE: 169

Gly Ile Thr Gly Asn Lys Asn Asn Phe Glu Ser Glu Glu Glu Cys Lys
1               5                   10                  15

Glu Thr Cys Lys Gly Phe Ser Leu Leu Lys Lys Val Asn Val Thr Ile
            20                  25                  30

Asn

<210> SEQ ID NO 170
<211> LENGTH: 34
<212> TYPE: PRT
<213> ORGANISM: Ixodes scapularis

<400> SEQUENCE: 170

Gly Gly Ile Thr Gly Asn Lys Asn Asn Phe Glu Ser Glu Glu Glu Cys
1               5                   10                  15

Lys Glu Thr Cys Lys Gly Phe Ser Leu Leu Lys Lys Val Asn Val Thr
            20                  25                  30

Ile Asn

<210> SEQ ID NO 171
<211> LENGTH: 35
<212> TYPE: PRT
<213> ORGANISM: Ixodes scapularis

<400> SEQUENCE: 171

Tyr Gly Gly Ile Thr Gly Asn Lys Asn Asn Phe Glu Ser Glu Glu Glu
1               5                   10                  15

Cys Lys Glu Thr Cys Lys Gly Phe Ser Leu Leu Lys Lys Val Asn Val
            20                  25                  30

Thr Ile Asn
        35

<210> SEQ ID NO 172
<211> LENGTH: 36
<212> TYPE: PRT
<213> ORGANISM: Ixodes scapularis

<400> SEQUENCE: 172

Thr Tyr Gly Gly Ile Thr Gly Asn Lys Asn Asn Phe Glu Ser Glu Glu
1               5                   10                  15

Glu Cys Lys Glu Thr Cys Lys Gly Phe Ser Leu Leu Lys Lys Val Asn
            20                  25                  30

Val Thr Ile Asn
        35

<210> SEQ ID NO 173
<211> LENGTH: 37
<212> TYPE: PRT
<213> ORGANISM: Ixodes scapularis

<400> SEQUENCE: 173

Phe Thr Tyr Gly Gly Ile Thr Gly Asn Lys Asn Asn Phe Glu Ser Glu
1               5                   10                  15

Glu Glu Cys Lys Glu Thr Cys Lys Gly Phe Ser Leu Leu Lys Lys Val
            20                  25                  30

Asn Val Thr Ile Asn

<210> SEQ ID NO 174
<211> LENGTH: 38
<212> TYPE: PRT
<213> ORGANISM: Ixodes scapularis

<400> SEQUENCE: 174

Met Phe Thr Tyr Gly Gly Ile Thr Gly Asn Lys Asn Phe Glu Ser
1               5                   10                  15

Glu Glu Glu Cys Lys Gl

```
                 1               5                  10                 15
Asn Phe Glu Ser Glu Glu Glu Cys Lys Glu Thr Cys Lys Gly Phe Ser
                20                 25                 30

Leu Leu Lys Lys Val Asn Val Thr Ile Asn
        35                  40

<210> SEQ ID NO 179
<211> LENGTH: 43
<212> TYPE: PRT
<213> ORGANISM: Ixodes scapularis

<400> SEQUENCE: 179

Asn Ala Thr Cys Glu Met Phe Thr Tyr Gly Gly Ile Thr Gly Asn Lys
  1               5                  10                 15

Asn Asn Phe Glu Ser Glu Glu Glu Cys Lys Glu Thr Cys Lys Gly Phe
                20                 25                 30

Ser Leu Leu Lys Lys Val Asn Val Thr Ile Asn
        35                  40

<210> SEQ ID NO 180
<211> LENGTH: 44
<212> TYPE: PRT
<213> ORGANISM: Ixodes scapularis

<400> SEQUENCE: 180

Asn Asn Ala Thr Cys Glu Met Phe Thr Tyr Gly Gly Ile Thr Gly Asn
  1               5                  10                 15

Lys Asn Asn Phe Glu Ser Glu Glu Glu Cys Lys Glu Thr Cys Lys Gly
                20                 25                 30

Phe Ser Leu Leu Lys Lys Val Asn Val Thr Ile Asn
        35                  40

<210> SEQ ID NO 181
<211> LENGTH: 45
<212> TYPE: PRT
<213> ORGANISM: Ixodes scapularis

<400> SEQUENCE: 181

Thr Asn Asn Ala Thr Cys Glu Met Phe Thr Tyr Gly Gly Ile Thr Gly
  1               5                  10                 15

Asn Lys Asn Asn Phe Glu Ser Glu Glu Glu Cys Lys Glu Thr Cys Lys
                20                 25                 30

Gly Phe Ser Leu Leu Lys Lys Val Asn Val Thr Ile Asn
        35                  40                 45

<210> SEQ ID NO 182
<211> LENGTH: 46
<212> TYPE: PRT
<213> ORGANISM: Ixodes scapularis

<400> SEQUENCE: 182

Asp Thr Asn Asn Ala Thr Cys Glu Met Phe Thr Tyr Gly Gly Ile Thr
  1               5                  10                 15

Gly Asn Lys Asn Asn Phe Glu Ser Glu Glu Glu Cys Lys Glu Thr Cys
                20                 25                 30

Lys Gly Phe Ser Leu Leu Lys Lys Val Asn Val Thr Ile Asn
        35                  40                 45

<210> SEQ ID NO 183
<211> LENGTH: 47
```

-continued

<212> TYPE: PRT
<213> ORGANISM: Ixodes scapularis

<400> SEQUENCE: 183

Tyr Asp Thr Asn Asn Ala Thr Cys Glu Met Phe Thr Tyr Gly Gly Ile
1               5                   10                  15

Thr Gly Asn Lys Asn Asn Phe Glu Ser Glu Glu Glu Cys Lys Glu Thr
            20                  25                  30

Cys Lys Gly Phe Ser Leu Leu Lys Val Asn Val Thr Ile Asn
        35                  40                  45

<210> SEQ ID NO 184
<211> LENGTH: 48
<212> TYPE: PRT
<213> ORGANISM: Ixodes scapularis

<400> SEQUENCE: 184

Tyr Tyr Asp Thr Asn Asn Ala Thr Cys Glu Met Phe Thr Tyr Gly Gly
1               5                   10                  15

Ile Thr Gly Asn Lys Asn Asn Phe Glu Ser Glu Glu Glu Cys Lys Glu
            20                  25                  30

Thr Cys Lys Gly Phe Ser Leu Leu Lys Lys Val Asn Val Thr Ile Asn
        35                  40                  45

<210> SEQ ID NO 185
<211> LENGTH: 49
<212> TYPE: PRT
<213> ORGANISM: Ixodes scapularis

<400> SEQUENCE: 185

Trp Tyr Tyr Asp Thr Asn Asn Ala Thr Cys Glu Met Phe Thr Tyr Gly
1               5                   10                  15

Gly Ile Thr Gly Asn Lys Asn Asn Phe Glu Ser Glu Glu Glu Cys Lys
            20                  25                  30

Glu Thr Cys Lys Gly Phe Ser Leu Leu Lys Lys Val Asn Val Thr Ile
        35                  40                  45

Asn

<210> SEQ ID NO 186
<211> LENGTH: 50
<212> TYPE: PRT
<213> ORGANISM: Ixodes scapularis

<400> SEQUENCE: 186

Arg Trp Tyr Tyr Asp Thr Asn Asn Ala Thr Cys Glu Met Phe Thr Tyr
1               5                   10                  15

Gly Gly Ile Thr Gly Asn Lys Asn Asn Phe Glu Ser Glu Glu Glu Cys
            20                  25                  30

Lys Glu Thr Cys Lys Gly Phe Ser Leu Leu Lys Lys Val Asn Val Thr
        35                  40                  45

Ile Asn
    50

<210> SEQ ID NO 187
<211> LENGTH: 51
<212> TYPE: PRT
<213> ORGANISM: Ixodes scapularis

<400> SEQUENCE: 187

Pro Arg Trp Tyr Tyr Asp Thr Asn Asn Ala Thr Cys Glu Met Phe Thr

-continued

```
                 1               5              10             15
Tyr Gly Gly Ile Thr Gly Asn Lys Asn Asn Phe Glu Ser Glu Glu
                20              25              30

Cys Lys Glu Thr Cys Lys Gly Phe Ser Leu Leu Lys Lys Val Asn Val
            35              40              45

Thr Ile Asn
    50

<210> SEQ ID NO 188
<211> LENGTH: 52
<212> TYPE: PRT
<213> ORGANISM: Ixodes scapularis

<400> SEQUENCE: 188

Ile Pro Arg Trp Tyr Tyr Asp Thr Asn Asn Ala Thr Cys Glu Met Phe
 1               5              10              15

Thr Tyr Gly Gly Ile Thr Gly Asn Lys Asn Asn Phe Glu Ser Glu Glu
                20              25              30

Glu Cys Lys Glu Thr Cys Lys Gly Phe Ser Leu Leu Lys Lys Val Asn
            35              40              45

Val Thr Ile Asn
    50

<210> SEQ ID NO 189
<211> LENGTH: 53
<212> TYPE: PRT
<213> ORGANISM: Ixodes scapularis

<400> SEQUENCE: 189

Asn Ile Pro Arg Trp Tyr Tyr Asp Thr Asn Asn Ala Thr Cys Glu Met
 1               5              10              15

Phe Thr Tyr Gly Gly Ile Thr Gly Asn Lys Asn Asn Phe Glu Ser Glu
                20              25              30

Glu Glu Cys Lys Glu Thr Cys Lys Gly Phe Ser Leu Leu Lys Lys Val
            35              40              45

Asn Val Thr Ile Asn
    50

<210> SEQ ID NO 190
<211> LENGTH: 54
<212> TYPE: PRT
<213> ORGANISM: Ixodes scapularis

<400> SEQUENCE: 190

Ala Asn Ile Pro Arg Trp Tyr Tyr Asp Thr Asn Asn Ala Thr Cys Glu
 1               5              10              15

Met Phe Thr Tyr Gly Gly Ile Thr Gly Asn Lys Asn Asn Phe Glu Ser
                20              25              30

Glu Glu Glu Cys Lys Glu Thr Cys Lys Gly Phe Ser Leu Leu Lys Lys
            35              40              45

Val Asn Val Thr Ile Asn
    50

<210> SEQ ID NO 191
<211> LENGTH: 55
<212> TYPE: PRT
<213> ORGANISM: Ixodes scapularis

<400> SEQUENCE: 191
```

Arg Ala Asn Ile Pro Arg Trp Tyr Tyr Asp Thr Asn Asn Ala Thr Cys
1               5                   10                  15

Glu Met Phe Thr Tyr Gly Gly Ile Thr Gly Asn Lys Asn Asn Phe Glu
            20                  25                  30

Ser Glu Glu Cys Lys Glu Thr Cys Lys Gly Phe Ser Leu Leu Lys
        35                  40                  45

Lys Val Asn Val Thr Ile Asn
    50                  55

<210> SEQ ID NO 192
<211> LENGTH: 56
<212> TYPE: PRT
<213> ORGANISM: Ixodes scapularis

<400> SEQUENCE: 192

Gly Arg Ala Asn Ile Pro Arg Trp Tyr Tyr Asp Thr Asn Asn Ala Thr
1               5                   10                  15

Cys Glu Met Phe Thr Tyr Gly Gly Ile Thr Gly Asn Lys Asn Asn Phe
            20                  25                  30

Glu Ser Glu Glu Cys Lys Glu Thr Cys Lys Gly Phe Ser Leu Leu
        35                  40                  45

Lys Lys Val Asn Val Thr Ile Asn
    50                  55

<210> SEQ ID NO 193
<211> LENGTH: 57
<212> TYPE: PRT
<213> ORGANISM: Ixodes scapularis

<400> SEQUENCE: 193

Val Gly Arg Ala Asn Ile Pro Arg Trp Tyr Tyr Asp Thr Asn Asn Ala
1

-continued

Tyr Gly Val Gly Arg Ala Asn Ile Pro Arg Trp Tyr Tyr Asp Thr Asn
1               5                   10                  15

Asn Ala Thr Cys Glu Met Phe Thr Tyr Gly Gly Ile Thr Gly Asn Lys
            20                  25                  30

Asn Asn Phe Glu Ser Glu Glu Cys Lys Glu Thr Cys Lys Gly Phe
        35                  40                  45

Ser Leu Leu Lys Lys Val Asn Val Thr Ile Asn
    50                  55

<210> SEQ ID NO 196
<211> LENGTH: 60
<212> TYPE: PRT
<213> ORGANISM: Ixodes scapularis

<400> SEQUENCE: 196

Asp Tyr Gly Val Gly Arg Ala Asn Ile Pro Arg Trp Tyr Tyr Asp Thr
1               5                   10                  15

Asn Asn Ala Thr Cys Glu Met Phe Thr Tyr Gly Gly Ile Thr Gly Asn
            20                  25                  30

Lys Asn Asn Phe Glu Ser Glu Glu Cys Lys Glu Thr Cys Lys Gly
        35                  40                  45

Phe Ser Leu Leu Lys Lys Val Asn Val Thr Ile Asn
    50                  55                  60

<210> SEQ ID NO 197
<211> LENGTH: 61
<212> TYPE: PRT
<213> ORGANISM: Ixodes scapularis

<400> SEQUENCE: 197

Val Asp Tyr Gly Val Gly Arg Ala Asn Ile Pro Arg Trp Tyr Tyr Asp
1               5                   10                  15

Thr Asn Asn Ala Thr Cys Glu Met Phe Thr Tyr Gly Gly Ile Thr Gly
            20                  25                  30

Asn Lys Asn Asn Phe Glu Ser Glu Glu Cys Lys Glu Thr Cys Lys
        35                  40                  45

Gly Phe Ser Leu Leu Lys Lys Val Asn Val Thr Ile Asn
    50                  55                  60

<210> SEQ ID NO 198
<211> LENGTH: 62
<212> TYPE: PRT
<213> ORGANISM: Ixodes scapularis

<400> SEQUENCE: 198

Glu Val Asp Tyr Gly Val Gly Arg Ala Asn Ile Pro Arg Trp Tyr Tyr
1               5                   10                  15

Asp Thr Asn Asn Ala Thr Cys Glu Met Phe Thr Tyr Gly Gly Ile Thr
            20                  25                  30

Gly Asn Lys Asn Asn Phe Glu Ser Glu Glu Cys Lys Glu Thr Cys
        35                  40                  45

Lys Gly Phe Ser Leu Leu Lys Lys Val Asn Val Thr Ile Asn
    50                  55                  60

<210> SEQ ID NO 199
<211> LENGTH: 63
<212> TYPE: PRT
<213> ORGANISM: Ixodes scapularis -continued

<400> SEQUENCE: 199

Leu Glu Val Asp Tyr Gly Val Gly Arg Ala Asn Ile Pro Arg Trp Tyr
1               5                   10                  15

Tyr Asp Thr Asn Asn Ala Thr Cys Glu Met Phe Thr Tyr Gly Gly Ile
            20                  25                  30

Thr Gly Asn Lys Asn Asn Phe Glu Ser Glu Glu Cys Lys Glu Thr
        35                  40                  45

Cys Lys Gly Phe Ser Leu Leu Lys Lys Val Asn Val Thr Ile Asn
50                  55                  60

<210> SEQ ID NO 200
<211> LENGTH: 64
<212> TYPE: PRT
<213> ORGANISM: Ixodes scapularis

<400> SEQUENCE: 200

Ser Leu Glu Val Asp Tyr Gly Val Gly Arg Ala Asn Ile Pro Arg Trp
1               5                   10                  15

Tyr Tyr Asp Thr Asn Asn Ala Thr Cys Glu Met Phe Thr Tyr Gly Gly
            20                  25                  30

Ile Thr Gly Asn Lys Asn Asn Phe Glu Ser Glu Glu Cys Lys Glu
        35                  40                  45

Thr Cys Lys Gly Phe Ser Leu Leu Lys Lys Val Asn Val Thr Ile Asn
50                  55                  60

<210> SEQ ID NO 201
<211> LENGTH: 65
<212> TYPE: PRT
<213> ORGANISM: Ixodes scapularis

<400> SEQUENCE: 201

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe Glu Ser Glu Glu Cys Lys
        35                  40                  45

Glu Thr Cys Lys Gly Phe Ser Leu Leu Lys Lys Val Asn Val Thr Ile
50                  55                  60

Asn
65

<210> SEQ ID NO 202
<211> LENGTH: 66
<212> TYPE: PRT
<213> ORGANISM: Ixodes scapularis

<400> SEQUENCE: 202

Pro Cys Ser Leu Glu Val Asp Tyr Gly Val Gly Arg Ala Asn Ile Pro
1               5                   10                  15

Arg Trp Tyr Tyr Asp Thr Asn Asn Ala Thr Cys Glu Met Phe Thr Tyr
            20                  25                  30

Gly Gly Ile Thr Gly Asn Lys Asn Asn Phe Glu Ser Glu Glu Cys
        35                  40                  45

Lys Glu Thr Cys Lys Gly Phe Ser Leu Leu Lys Lys Val Asn Val Thr
50                  55                  60

Ile Asn
65

<210> SEQ ID NO 203
<211> LENGTH: 67
<212> TYPE: PRT
<213> ORGANISM: Ixodes scapularis

<400> SEQUENCE: 203

Pro Pro Cys Ser Leu Glu Val Asp Tyr Gly Val Gly Arg Ala Asn Ile
1               5                   10                  15

Pro Arg Trp Tyr Tyr Asp Thr Asn Asn Ala Thr Cys Glu Met Phe Thr
            20                  25                  30

Tyr Gly Gly Ile Thr Gly Asn Lys Asn Asn Phe Glu Ser Glu Glu Glu
        35                  40                  45

Cys Lys Glu Thr Cys Lys Gly Phe Ser Leu Leu Lys Lys Val Asn Val
    50                  55                  60

Thr Ile Asn
65

<210> SEQ ID NO 204
<211> LENGTH: 68
<212> TYPE: PRT
<213> ORGANISM: Ixodes scapularis

<400> SEQUENCE: 204

Lys Pro Pro Cys Ser Leu Glu Val Asp Tyr Gly Val Gly Arg Ala Asn
1               5                   10                  15

Ile Pro Arg Trp Tyr Tyr Asp Thr Asn Asn Ala Thr Cys Glu Met Phe
            20                  25                  30

Thr Tyr Gly Gly Ile Thr Gly Asn Lys Asn Asn Phe Glu Ser Glu Glu
        35                  40                  45

Glu Cys Lys Glu Thr Cys Lys Gly Phe Ser Leu Leu Lys Lys Val Asn
    50                  55                  60

Val Thr Ile Asn
65

<210> SEQ ID NO 205
<211> LENGTH: 69
<212> TYPE: PRT
<213> ORGANISM: Ixodes scapularis

<400> SEQUENCE: 205

Pro Lys Pro Pro Cys Ser Leu Glu Val Asp Tyr Gly Val Gly Arg Ala
1               5                   10                  15

Asn Ile Pro Arg Trp Tyr Tyr Asp Thr Asn Asn Ala Thr Cys Glu Met
            20                  25                  30

Phe Thr Tyr Gly Gly Ile Thr Gly Asn Lys Asn Asn Phe Glu Ser Glu
        35                  40                  45

Glu Glu Cys Lys Glu Thr Cys Lys Gly Phe Ser Leu Leu Lys Lys Val
    50                  55                  60

Asn Val Thr Ile Asn
65

<210> SEQ ID NO 206
<211> LENGTH: 70
<212> TYPE: PRT
<213> ORGANISM: Ixodes scapularis

<400> SEQUENCE: 206

Ala Pro Lys Pro Pro Cys Ser Leu Glu Val Asp Tyr Gly Val Gly Arg

```
  1               5                  10                 15
Ala Asn Ile Pro Arg Trp Tyr Tyr Asp Thr Asn Asn Ala Thr Cys Glu
              20                 25                 30

Met Phe Thr Tyr Gly Gly Ile Thr Gly Asn Lys Asn Asn Phe Glu Ser
              35                 40                 45

Glu Glu Glu Cys Lys Glu Thr Cys Lys Gly Phe Ser Leu Leu Lys Lys
 50                  55                 60

Val Asn Val Thr Ile Asn
 65                  70

<210> SEQ ID NO 207
<211> LENGTH: 71
<212> TYPE: PRT
<213> ORGANISM: Ixodes scapularis

<400> SEQUENCE: 207

Asp Ala Pro Lys Pro Cys Ser Leu Glu Val Asp Tyr Gly Val Gly
 1               5                  10                 15

Arg Ala Asn Ile Pro Arg Trp Tyr Tyr Asp Thr Asn Asn Ala Thr Cys
              20                 25                 30

Glu Met Phe Thr Tyr Gly Gly Ile Thr Gly Asn Lys Asn Asn Phe Glu
              35                 40                 45

Ser Glu Glu Glu Cys Lys Glu Thr Cys Lys Gly Phe Ser Leu Leu Lys
 50                  55                 60

Lys Val Asn Val Thr Ile Asn
 65                  70

<210> SEQ ID NO 208
<211> LENGTH: 72
<212> TYPE: PRT
<213> ORGANISM: Ixodes scapularis

<400> SEQUENCE: 208

Asn Asp Ala Pro Lys Pro Pro Cys Ser Leu Glu Val Asp Tyr Gly Val
 1               5                  10                 15

Gly Arg Ala Asn Ile Pro Arg Trp Tyr Tyr Asp Thr Asn Asn Ala Thr
              20                 25                 30

Cys Glu Met Phe Thr Tyr Gly Gly Ile Thr Gly Asn Lys Asn Asn Phe
              35                 40                 45

Glu Ser Glu Glu Glu Cys Lys Glu Thr Cys Lys Gly Phe Ser Leu Leu
 50                  55                 60

Lys Lys Val Asn Val Thr Ile Asn
 65                  70

<210> SEQ ID NO 209
<211> LENGTH: 73
<212> TYPE: PRT
<213> ORGANISM: Ixodes scapularis

<400> SEQUENCE: 209

Cys Asn Asp Ala Pro Lys Pro Pro Cys Ser Leu Glu Val Asp Tyr Gly
 1               5                  10                 15

Val Gly Arg Ala Asn Ile Pro Arg Trp Tyr Tyr Asp Thr Asn Asn Ala
              20                 25                 30

Thr Cys Glu Met Phe Thr Tyr Gly Gly Ile Thr Gly Asn Lys Asn Asn
              35                 40                 45

Phe Glu Ser Glu Glu Glu Cys Lys Glu Thr Cys Lys Gly Phe Ser Leu
 50                  55                 60
```

Leu Lys Lys Val Asn Val Thr Ile Asn
65                  70

<210> SEQ ID NO 210
<211> LENGTH: 74
<212> TYPE: PRT
<213> ORGANISM: Ixodes scapularis

<400> SEQUENCE: 210

Ser Cys Asn Asp Ala Pro Lys Pro Cys Ser Leu Glu Val Asp Tyr
1               5                   10                  15

Gly Val Gly Arg Ala Asn Ile Pro Arg Trp Tyr Tyr Asp Thr Asn Asn
            20                  25                  30

Ala Thr Cys Glu Met Phe Thr Tyr Gly Gly Ile Thr Gly Asn Lys Asn
        35                  40                  45

Asn Phe Glu Ser Glu Glu Cys Lys Glu Thr Cys Lys Gly Phe Ser
    50                  55                  60

Leu Leu Lys Lys Val Asn Val Thr Ile Asn
65                  70

<210> SEQ ID NO 211
<211> LENGTH: 75
<212> TYPE: PRT
<213> ORGANISM: Ixodes scapularis

<400> SEQUENCE: 211

Glu Ser Cys Asn Asp Ala Pro Lys Pro Cys

```
<400> SEQUENCE: 213

Cys Asn Glu Ser Cys Asn Asp Ala Pro Lys Pro Cys Ser Leu Glu
1               5                   10                  15

Val Asp Tyr Gly Val Gly Arg Ala Asn Ile Pro Arg Trp Tyr Tyr Asp
            20                  25                  30

Thr Asn Asn Ala Thr Cys Glu Met Phe Thr Tyr Gly Gly Ile Thr Gly
            35                  40                  45

Asn Lys Asn Asn Phe Glu Ser Glu Glu Glu Cys Lys Glu Thr Cys Lys
    50                  55                  60

Gly Phe Ser Leu Leu Lys Lys Val Asn Val Thr Ile Asn
65                  70                  75

<210> SEQ ID NO 214
<211> LENGTH: 78
<212> TYPE: PRT
<213> ORGANISM: Ixodes scapularis

<400> SEQUENCE: 214

Lys Cys Asn Glu Ser Cys Asn Asp Ala Pro Lys Pro Cys Ser Leu
1               5                   10                  15

Glu Val Asp Tyr Gly Val Gly Arg Ala Asn Ile Pro Arg Trp Tyr Tyr
            20                  25                  30

Asp Thr Asn Asn Ala Thr Cys Glu Met Phe Thr Tyr Gly Gly Ile Thr
            35                  40                  45

Gly Asn Lys Asn Asn Phe Glu Ser Glu Glu Glu Cys Lys Glu Thr Cys
    50                  55                  60

Lys Gly Phe Ser Leu Leu Lys Lys Val Asn Val Thr Ile Asn
65                  70                  75

<210> SEQ ID NO 215
<211> LENGTH: 79
<212> TYPE: PRT
<213> ORGANISM: Ixodes scapularis

<400> SEQUENCE: 215

Leu Lys Cys Asn Glu Ser Cys Asn Asp Ala Pro Lys Pro Cys Ser
1               5                   10                  15

Leu Glu Val Asp Tyr Gly Val Gly Arg Ala Asn Ile Pro Arg Trp Tyr
            20                  25                  30

Tyr Asp Thr Asn Asn Ala Thr Cys Glu Met Phe Thr Tyr Gly Gly Ile
            35                  40                  45

Thr Gly Asn Lys Asn Asn Phe Glu Ser Glu Glu Glu Cys Lys Glu Thr
    50                  55                  60

Cys Lys Gly Phe Ser Leu Leu Lys Lys Val Asn Val Thr Ile Asn
65                  70                  75

<210> SEQ ID NO 216
<211> LENGTH: 80
<212> TYPE: PRT
<213> ORGANISM: Ixodes scapularis

<400> SEQUENCE: 216

Leu Leu Lys Cys Asn Glu Ser Cys Asn Asp Ala Pro Lys Pro Cys
1               5                   10                  15

Ser Leu Glu Val Asp Tyr Gly Val Gly Arg Ala Asn Ile Pro Arg Trp
            20                  25                  30

Tyr Tyr Asp Thr Asn Asn Ala Thr Cys Glu Met Phe Thr Tyr Gly Gly
            35                  40                  45
```

```
Ile Thr Gly Asn Lys Asn Asn Phe Glu Ser Glu Glu Glu Cys Lys Glu
        50                  55                  60

Thr Cys Lys Gly Phe Ser Leu Leu Lys Val Asn Val Thr Ile Asn
65                  70                  75                  80
```

<210> SEQ ID NO 217
<211> LENGTH: 81
<212> TYPE: PRT
<213> ORGANISM: Ixodes scapularis

<400> SEQUENCE: 217

```
Thr Leu Leu Lys Cys Asn Glu Ser Cys Asn Asp Ala Pro Lys Pro Pro
 1               5                  10                  15

Cys Ser Leu Glu Val Asp Tyr Gly Val Gly Arg Ala Asn Ile Pro Arg
            20                  25                  30

Trp Tyr Tyr Asp Thr Asn Asn Ala Thr Cys Glu Met Phe Thr Tyr Gly
        35                  40                  45

Gly Ile Thr Gly Asn Lys Asn Asn Phe Glu Ser Glu Glu Glu Cys Lys
    50                  55                  60

Glu Thr Cys Lys Gly Phe Ser Leu Leu Lys Val Asn Val Thr Ile
65                  70                  75                  80

Asn
```

<210> SEQ ID NO 218
<211> LENGTH: 82
<212> TYPE: PRT
<213> ORGANISM: Ixodes scapularis

<400> SEQUENCE: 218

```
Glu Thr Leu Leu Lys Cys Asn Glu Ser Cys Asn Asp Ala Pro Lys Pro
 1               5                  10                  15

Pro Cys Ser Leu Glu Val Asp Tyr Gly Val Gly Arg Ala Asn Ile Pro
            20                  25                  30

Arg Trp Tyr Tyr Asp Thr Asn Asn Ala Thr Cys Glu Met Phe Thr Tyr
        35                  40                  45

Gly Gly Ile Thr Gly Asn Lys Asn Asn Phe Glu Ser Glu Glu Glu Cys
    50                  55                  60

Lys Glu Thr Cys Lys Gly Phe Ser Leu Leu Lys Val Asn Val Thr
65                  70                  75                  80

Ile Asn
```

<210> SEQ ID NO 219
<211> LENGTH: 83
<212> TYPE: PRT
<213> ORGANISM: Ixodes scapularis

<400> SEQUENCE: 219

```
Phe Glu Thr Leu Leu Lys Cys Asn Glu Ser Cys Asn Asp Ala Pro Lys
 1               5                  10                  15

Pro Pro Cys Ser Leu Glu Val Asp Tyr Gly Val Gly Arg Ala Asn Ile
            20                  25                  30

Pro Arg Trp Tyr Tyr Asp Thr Asn Asn Ala Thr Cys Glu Met Phe Thr
        35                  40                  45

Tyr Gly Gly Ile Thr Gly Asn Lys Asn Asn Phe Glu Ser Glu Glu Glu
    50                  55                  60

Cys Lys Glu Thr Cys Lys Gly Phe Ser Leu Leu Lys Val Asn Val
65                  70                  75                  80
```

Thr Ile Asn

<210> SEQ ID NO 220
<211> LENGTH: 84
<212> TYPE: PRT
<213> ORGANISM: Ixodes scapularis

<400> SEQUENCE: 220

His Phe Glu Thr Leu Leu Lys Cys Asn Glu Ser Cys Asn Asp Ala Pro
1               5                   10                  15

Lys Pro Pro Cys Ser Leu Glu Val Asp Tyr Gly Val Gly Arg Ala Asn
            20                  25                  30

Ile Pro Arg Trp Tyr Tyr Asp Thr Asn Asn Ala Thr Cys Glu Met Phe
        35                  40                  45

Thr Tyr Gly Gly Ile Thr Gly Asn Lys Asn Asn Phe Glu Ser Glu Glu
    50                  55                  60

Glu Cys Lys Glu Thr Cys Lys Gly Phe Ser Leu Leu Lys Lys Val Asn
65                  70                  75                  80

Val Thr Ile Asn

<210> SEQ ID NO 221
<211> LENGTH: 85
<212> TYPE: PRT
<213> ORGANISM: Ixodes scapularis

<400> SEQUENCE: 221

Asn His Phe Glu Thr Leu Leu Lys Cys Asn Glu Ser Cys Asn Asp Ala
1               5                   10                  15

Pro Lys Pro Pro Cys Ser Leu Glu Val Asp Tyr Gly Val Gly Arg Ala
            20                  25                  30

Asn Ile Pro Arg Trp Tyr Tyr Asp Thr Asn Asn Ala Thr Cys Glu Met
        35                  40                  45

Phe Thr Tyr Gly Gly Ile Thr Gly Asn Lys Asn Asn Phe Glu Ser Glu
    50                  55                  60

Glu Glu Cys Lys Glu Thr Cys Lys Gly Phe Ser Leu Leu Lys Lys Val
65                  70                  75                  80

Asn Val Thr Ile Asn
            85

<210> SEQ ID NO 222
<211> LENGTH: 86
<212> TYPE: PRT
<213> ORGANISM: Ixodes scapularis

<400> SEQUENCE: 222

Glu Asn His Phe Glu Thr Leu Leu Lys Cys Asn Glu Ser Cys Asn Asp
1               5                   10                  15

Ala Pro Lys Pro Pro Cys Ser Leu Glu Val Asp Tyr Gly Val Gly Arg
            20                  25                  30

Ala Asn Ile Pro Arg Trp Tyr Tyr Asp Thr Asn Asn Ala Thr Cys Glu
        35                  40                  45

Met Phe Thr Tyr Gly Gly Ile Thr Gly Asn Lys Asn Asn Phe Glu Ser
    50                  55                  60

Glu Glu Glu Cys Lys Glu Thr Cys Lys Gly Phe Ser Leu Leu Lys Lys
65                  70                  75                  80

Val Asn Val Thr Ile Asn
            85

-continued

<210> SEQ ID NO 223
<211> LENGTH: 87
<212> TYPE: PRT
<213> ORGANISM: Ixodes scapularis

<400> SEQUENCE: 223

Gly Glu Asn His Phe Glu Thr Leu Leu Lys Cys Asn Glu Ser Cys Asn
1 5 10 15

Asp Ala Pro Lys Pro Pro Cys Ser Leu Glu Val Asp Tyr Gly Val Gly
20 25 30

Arg Ala Asn Ile Pro Arg Trp Tyr Tyr Asp Thr Asn Asn Ala Thr Cys
35 40 45

Glu Met Phe Thr Tyr Gly Gly Ile Thr Gly Asn Lys Asn Asn Phe Glu
50 55 60

Ser Glu Glu Glu Cys Lys Glu Thr Cys Lys Gly Phe Ser Leu Leu Lys
65 70 75 80

Lys Val Asn Val Thr Ile Asn
85

<210> SEQ ID NO 224
<211> LENGTH: 88
<212> TYPE: PRT
<213> ORGANISM: Ixodes scapularis

<400> SEQUENCE: 224

Gly Gly Glu Asn His Phe Glu Thr Leu Leu Lys Cys Asn Glu Ser Cys
1 5 10 15

Asn Asp Ala Pro Lys Pro Pro Cys Ser Leu Glu Val Asp Tyr Gly Val
20 25 30

Gly Arg Ala Asn Ile Pro Arg Trp Tyr Tyr Asp Thr Asn Asn Ala Thr
35 40 45

Cys Glu Met Phe Thr Tyr Gly Gly Ile Thr Gly Asn Lys Asn Asn Phe
50 55 60

Glu Ser Glu Glu Glu Cys Lys Glu Thr Cys Lys Gly Phe Ser Leu Leu
65 70 75 80

Lys Lys Val Asn Val Thr Ile Asn
85

<210> SEQ ID NO 225
<211> LENGTH: 89
<212> TYPE: PRT
<213> ORGANISM: Ixodes scapularis

<400> SEQUENCE: 225

Gly Gly Gly Glu Asn His Phe Glu Thr Leu Leu Lys Cys Asn Glu Ser
1 5 10 15

Cys Asn Asp Ala Pro Lys Pro Pro Cys Ser Leu Glu Val Asp Tyr Gly
20 25 30

Val Gly Arg Ala Asn Ile Pro Arg Trp Tyr Tyr Asp Thr Asn Asn Ala
35 40 45

Thr Cys Glu Met Phe Thr Tyr Gly Gly Ile Thr Gly Asn Lys Asn Asn
50 55 60

Phe Glu Ser Glu Glu Glu Cys Lys Glu Thr Cys Lys Gly Phe Ser Leu
65 70 75 80

Leu Lys Lys Val Asn Val Thr Ile Asn
85

<210> SEQ ID NO 226
<211> LENGTH: 90
<212> TYPE: PRT
<213> ORGANISM: Ixodes scapularis

<400> SEQUENCE: 226

Cys Gly Gly Gly Glu Asn His Phe Glu Thr Leu Leu Lys Cys Asn Glu
1               5                   10                  15

Ser Cys Asn Asp Ala Pro Lys Pro Pro Cys Ser Leu Glu Val Asp Tyr
            20                  25                  30

Gly Val Gly Arg Ala Asn Ile Pro Arg Trp Tyr Tyr Asp Thr Asn Asn
        35                  40                  45

Ala Thr Cys Glu Met Phe Thr Tyr Gly Gly Ile Thr Gly Asn Lys Asn
    50                  55                  60

Asn Phe Glu Ser Glu Glu Cys Lys Glu Thr Cys Lys Gly Phe Ser
65                  70                  75                  80

Leu Leu Lys Lys Val Asn Val Thr Ile Asn
            85                  90

<210> SEQ ID NO 227
<211> LENGTH: 91
<212> TYPE: PRT
<213> ORGANISM: Ixodes scapularis

<400> SEQUENCE: 227

Glu Cys Gly Gly Gly Glu Asn His Phe Glu Thr Leu Leu Lys Cys Asn
1               5                   10                  15

Glu Ser Cys Asn Asp Ala Pro Lys Pro Pro Cys Ser Leu Glu Val Asp
            20                  25                  30

Tyr Gly Val Gly Arg Ala Asn Ile Pro Arg Trp Tyr Tyr Asp Thr Asn
        35                  40                  45

Asn Ala Thr Cys Glu Met Phe Thr Tyr Gly Gly Ile Thr Gly Asn Lys
    50                  55                  60

Asn Asn Phe Glu Ser Glu Glu Cys Lys Glu Thr Cys Lys Gly Phe
65                  70                  75                  80

Ser Leu Leu Lys Lys Val Asn Val Thr Ile Asn
            85                  90

<210> SEQ ID NO 228
<211> LENGTH: 92
<212> TYPE: PRT
<213> ORGANISM: Ixodes scapularis

<400> SEQUENCE: 228

Thr Glu Cys Gly Gly Gly Glu Asn His Phe Glu Thr Leu Leu Lys Cys
1               5                   10                  15

Asn Glu Ser Cys Asn Asp Ala Pro Lys Pro Pro Cys Ser Leu Glu Val
            20                  25                  30

Asp Tyr Gly Val Gly Arg Ala Asn Ile Pro Arg Trp Tyr Tyr Asp Thr
        35                  40                  45

Asn Asn Ala Thr Cys Glu Met Phe Thr Tyr Gly Gly Ile Thr Gly Asn
    50                  55                  60

Lys Asn Asn Phe Glu Ser Glu Glu Cys Lys Glu Thr Cys Lys Gly
65                  70                  75                  80

Phe Ser Leu Leu Lys Lys Val Asn Val Thr Ile Asn
            85                  90

<210> SEQ ID NO 229
<211> LENGTH: 93
<212> TYPE: PRT
<213> ORGANISM: Ixodes scapularis

<400> SEQUENCE: 229

Gly Thr Glu Cys Gly Gly Gly Glu Asn His Phe Glu Thr Leu Leu Lys
1               5                   10                  15

Cys Asn Glu Ser Cys Asn Asp Ala Pro Lys Pro Pro Cys Ser Leu Glu
            20                  25                  30

Val Asp Tyr Gly Val Gly Arg Ala Asn Ile Pro Arg Trp Tyr Tyr Asp
        35                  40                  45

Thr Asn Asn Ala Thr Cys Glu Met Phe Thr Tyr Gly Gly Ile Thr Gly
    50                  55                  60

Asn Lys Asn Asn Phe Glu Ser Glu Glu Cys Lys Glu Thr Cys Lys
65                  70                  75                  80

Gly Phe Ser Leu Leu Lys Lys Val Asn Val Thr Ile Asn
                85                  90

<210> SEQ ID NO 230
<211> LENGTH: 94
<212> TYPE: PRT
<213> ORGANISM: Ixodes scapularis

<400> SEQUENCE: 230

Lys Gly Thr Glu Cys Gly Gly Gly Glu Asn His Phe Glu Thr Leu Leu
1               5                   10                  15

Lys Cys Asn Glu Ser Cys Asn Asp Ala Pro Lys Pro Pro Cys Ser Leu
            20                  25                  30

Glu Val Asp Tyr Gly Val Gly Arg Ala Asn Ile Pro Arg Trp Tyr Tyr
        35                  40                  45

Asp Thr Asn Asn Ala Thr Cys Glu Met Phe Thr Tyr Gly Gly Ile Thr
    50                  55                  60

Gly Asn Lys Asn Asn Phe Glu Ser Glu Glu Cys Lys Glu Thr Cys
65                  70                  75                  80

Lys Gly Phe Ser Leu Leu Lys Lys Val Asn Val Thr Ile Asn
                85                  90

<210> SEQ ID NO 231
<211> LENGTH: 95
<212> TYPE: PRT
<213> ORGANISM: Ixodes scapularis

<400> SEQUENCE: 231

Gln Lys Gly Thr Glu Cys Gly Gly Gly Glu Asn His Phe Glu Thr Leu
1               5                   10                  15

Leu Lys Cys Asn Glu Ser Cys Asn Asp Ala Pro Lys Pro Pro Cys Ser
            20                  25                  30

Leu Glu Val Asp Tyr Gly Val Gly Arg Ala Asn Ile Pro Arg Trp Tyr
        35                  40                  45

Tyr Asp Thr Asn Asn Ala Thr Cys Glu Met Phe Thr Tyr Gly Gly Ile
    50                  55                  60

Thr Gly Asn Lys Asn Asn Phe Glu Ser Glu Glu Cys Lys Glu Thr
65                  70                  75                  80

Cys Lys Gly Phe Ser Leu Leu Lys Lys Val Asn Val Thr Ile Asn
                85                  90                  95

<210> SEQ ID NO 232

<211> LENGTH: 96
<212> TYPE: PRT
<213> ORGANISM: Ixodes scapularis

<400> SEQUENCE: 232

Glu Gln Lys Gly Thr Glu Cys Gly Gly Glu Asn His Phe Glu Thr
1               5                   10                  15
Leu Leu Lys Cys Asn Glu Ser Cys Asn Asp Ala Pro Lys Pro Pro Cys
            20                  25                  30
Ser Leu Glu Val Asp Tyr Gly Val Gly Arg Ala Asn Ile Pro Arg Trp
        35                  40                  45
Tyr Tyr Asp Thr Asn Asn Ala Thr Cys Glu Met Phe Thr Tyr Gly Gly
    50                  55                  60
Ile Thr Gly Asn Lys Asn Asn Phe Glu Ser Glu Glu Cys Lys Glu
65                  70                  75                  80
Thr Cys Lys Gly Phe Ser Leu Leu Lys Lys Val Asn Val Thr Ile Asn
                85                  90                  95

<210> SEQ ID NO 233
<211> LENGTH: 97
<212> TYPE: PRT
<213> ORGANISM: Ixodes scapularis

<400> SEQUENCE: 233

Glu Glu Gln Lys Gly Thr Glu Cys Gly Gly Glu Asn His Phe Glu
1               5                   10                  15
Thr Leu Leu Lys Cys Asn Glu Ser Cys Asn Asp Ala Pro Lys Pro Pro
            20                  25                  30
Cys Ser Leu Glu Val Asp Tyr Gly Val Gly Arg Ala Asn Ile Pro Arg
        35                  40                  45
Trp Tyr Tyr Asp Thr Asn Asn Ala Thr Cys Glu Met Phe Thr Tyr Gly
    50                  55                  60
Gly Ile Thr Gly Asn Lys Asn Asn Phe Glu Ser Glu Glu Cys Lys
65                  70                  75                  80
Glu Thr Cys Lys Gly Phe Ser Leu Leu Lys Lys Val Asn Val Thr Ile
                85                  90                  95
Asn

<210> SEQ ID NO 234
<211> LENGTH: 98
<212> TYPE: PRT
<213> ORGANISM: Ixodes scapularis

<400> SEQUENCE: 234

Cys Glu Glu Gln Lys Gly Thr Glu Cys Gly Gly Glu Asn His Phe
1               5                   10                  15
Glu Thr Leu Leu Lys Cys Asn Glu Ser Cys Asn Asp Ala Pro Lys Pro
            20                  25                  30
Pro Cys Ser Leu Glu Val Asp Tyr Gly Val Gly Arg Ala Asn Ile Pro
        35                  40                  45
Arg Trp Tyr Tyr Asp Thr Asn Asn Ala Thr Cys Glu Met Phe Thr Tyr
    50                  55                  60
Gly Gly Ile Thr Gly Asn Lys Asn Asn Phe Glu Ser Glu Glu Cys
65                  70                  75                  80
Lys Glu Thr Cys Lys Gly Phe Ser Leu Leu Lys Lys Val Asn Val Thr
                85                  90                  95
Ile Asn

<210> SEQ ID NO 235
<211> LENGTH: 99
<212> TYPE: PRT
<213> ORGANISM: Ixodes scapularis

<400> SEQUENCE: 235

Gln Cys Glu Glu Gln Lys Gly Thr Glu Cys Gly Gly Gly Glu Asn His
1               5                   10                  15

Phe Glu Thr Leu Leu Lys Cys Asn Glu Ser Cys Asn Asp Ala Pro Lys
            20                  25                  30

Pro Pro Cys Ser Leu Glu Val Asp Tyr Gly Val Gly Arg Ala Asn Ile
        35                  40                  45

Pro Arg Trp Tyr Tyr Asp Thr Asn Asn Ala Thr Cys Glu Met Phe Thr
50                  55                  60

Tyr Gly Gly Ile Thr Gly Asn Lys Asn Asn Phe Glu Ser Glu Glu
65                  70                  75                  80

Cys Lys Glu Thr Cys Lys Gly Phe Ser Leu Leu Lys Lys Val Asn Val
                85                  90                  95

Thr Ile Asn

<210> SEQ ID NO 236
<211> LENGTH: 100
<212> TYPE: PRT
<213> ORGANISM: Ixodes scapularis

<400> SEQUENCE: 236

Gly Gln Cys Glu Glu Gln Lys Gly Thr Glu Cys Gly Gly Gly Glu Asn
1               5                   10                  15

His Phe Glu Thr Leu Leu Lys Cys Asn Glu Ser Cys Asn Asp Ala Pro
            20                  25                  30

Lys Pro Pro Cys Ser Leu Glu Val Asp Tyr Gly Val Gly Arg Ala Asn
        35                  40                  45

Ile Pro Arg Trp Tyr Tyr Asp Thr Asn Asn Ala Thr Cys Glu Met Phe
    50                  55                  60

Thr Tyr Gly Gly Ile Thr Gly Asn Lys Asn Asn Phe Glu Ser Glu Glu
65                  70                  75                  80

Glu Cys Lys Glu Thr Cys Lys Gly Phe Ser Leu Leu Lys Lys Val Asn
                85                  90                  95

Val Thr Ile Asn
            100

<210> SEQ ID NO 237
<211> LENGTH: 101
<212> TYPE: PRT
<213> ORGANISM: Ixodes scapularis

<400> SEQUENCE: 237

Thr Gly Gln Cys Glu Glu Gln Lys Gly Thr Glu Cys Gly Gly Gly Glu
1               5                   10                  15

Asn His Phe Glu Thr Leu Leu Lys Cys Asn Glu Ser Cys Asn Asp Ala
            20                  25                  30

Pro Lys Pro Pro Cys Ser Leu Glu Val Asp Tyr Gly Val Gly Arg Ala
        35                  40                  45

Asn Ile Pro Arg Trp Tyr Tyr Asp Thr Asn Asn Ala Thr Cys Glu Met
    50                  55                  60

Phe Thr Tyr Gly Gly Ile Thr Gly Asn Lys Asn Asn Phe Glu Ser Glu

```
                65                  70                  75                  80
Glu Glu Cys Lys Glu Thr Cys Lys Gly Phe Ser Leu Leu Lys Lys Val
                85                  90                  95

Asn Val Thr Ile Asn
            100

<210> SEQ ID NO 238
<211> LENGTH: 102
<212> TYPE: PRT
<213> ORGANISM: Ixodes scapularis

<400> SEQUENCE: 238

Lys Thr Gly Gln Cys Glu Glu Gln Lys Gly Thr Glu Cys Gly Gly
  1               5                  10                  15

Glu Asn His Phe Glu Thr Leu Leu Lys Cys Asn Glu Ser Cys Asn Asp
                20                  25                  30

Ala Pro Lys Pro Pro Cys Ser Leu Glu Val Asp Tyr Gly Val Gly Arg
            35                  40                  45

Ala Asn Ile Pro Arg Trp Tyr Tyr Asp Thr Asn Asn Ala Thr Cys Glu
        50                  55                  60

Met Phe Thr Tyr Gly Gly Ile Thr Gly Asn Lys Asn Phe Glu Ser
 65                  70                  75                  80

Glu Glu Glu Cys Lys Glu Thr Cys Lys Gly Phe Ser Leu Leu Lys Lys
                85                  90                  95

Val Asn Val Thr Ile Asn
            100

<210> SEQ ID NO 239
<211> LENGTH: 103
<212> TYPE: PRT
<213> ORGANISM: Ixodes scapularis

<400> SEQUENCE: 239

Arg Lys Thr Gly Gln Cys Glu Glu Gln Lys Gly Thr Glu Cys Gly Gly
  1               5                  10                  15

Gly Glu Asn His Phe Glu Thr Leu Leu Lys Cys Asn Glu Ser Cys Asn
                20                  25                  30

Asp Ala Pro Lys Pro Pro Cys Ser Leu Glu Val Asp Tyr Gly Val Gly
            35                  40                  45

Arg Ala Asn Ile Pro Arg Trp Tyr Tyr Asp Thr Asn Asn Ala Thr Cys
        50                  55                  60

Glu Met Phe Thr Tyr Gly Gly Ile Thr Gly Asn Lys Asn Phe Glu
 65                  70                  75                  80

Ser Glu Glu Glu Cys Lys Glu Thr Cys Lys Gly Phe Ser Leu Leu Lys
                85                  90                  95

Lys Val Asn Val Thr Ile Asn
            100

<210> SEQ ID NO 240
<211> LENGTH: 104
<212> TYPE: PRT
<213> ORGANISM: Ixodes scapularis

<400> SEQUENCE: 240

Asn Arg Lys Thr Gly Gln Cys Glu Glu Gln Lys Gly Thr Glu Cys Gly
  1               5                  10                  15

Gly Gly Glu Asn His Phe Glu Thr Leu Leu Lys Cys Asn Glu Ser Cys
                20                  25                  30
```

```
Asn Asp Ala Pro Lys Pro Cys Ser Leu Glu Val Asp Tyr Gly Val
        35                  40                  45

Gly Arg Ala Asn Ile Pro Arg Trp Tyr Tyr Asp Thr Asn Asn Ala Thr
    50                  55                  60

Cys Glu Met Phe Thr Tyr Gly Gly Ile Thr Gly Asn Lys Asn Asn Phe
65                  70                  75                  80

Glu Ser Glu Glu Glu Cys Lys Glu Thr Cys Lys Gly Phe Ser Leu Leu
                85                  90                  95

Lys Lys Val Asn Val Thr Ile Asn
            100

<210> SEQ ID NO 241
<211> LENGTH: 105
<212> TYPE: PRT
<213> ORGANISM: Ixodes scapularis

<400> SEQUENCE: 241

Tyr Asn Arg Lys Thr Gly Gln Cys Glu Glu Gln Lys Gly Thr Glu Cys
1               5                   10                  15

Gly Gly Gly Glu Asn His Phe Glu Thr Leu Leu Lys Cys Asn Glu Ser
            20                  25                  30

Cys Asn Asp Ala Pro Lys Pro Cys Ser Leu Glu Val Asp Tyr Gly
        35                  40                  45

Val Gly Arg Ala Asn Ile Pro Arg Trp Tyr Tyr Asp Thr Asn Asn Ala
    50                  55                  60

Thr Cys Glu Met Phe Thr Tyr Gly Gly Ile Thr Gly Asn Lys Asn
65                  70                  75                  80

Phe Glu Ser Glu Glu Glu Cys Lys Glu Thr Cys Lys Gly Phe Ser Leu
                85                  90                  95

Leu Lys Lys Val Asn Val Thr Ile Asn
            100                 105

<210> SEQ ID NO 242
<211> LENGTH: 106
<212> TYPE: PRT
<213> ORGANISM: Ixodes scapularis

<400> SEQUENCE: 242

Ser Tyr Asn Arg Lys Thr Gly Gln Cys Glu Glu Gln Lys Gly Thr Glu
1               5                   10                  15
Cys Gly Gly Gly Glu Asn His Phe Glu Thr Leu Leu Lys Cys Asn Glu
            20                  25                  30
Ser Cys Asn Asp Ala Pro Lys Pro Cys Ser Leu Glu Val Asp Tyr
        35                  40                  45
Gly Val Gly Arg Ala Asn Ile Pro Arg Trp Tyr Tyr Asp Thr Asn Asn
    50                  55                  60
Ala Thr Cys Glu Met Phe Thr Tyr Gly Gly Ile Thr Gly Asn Lys Asn
65                  70                  75                  80
Asn Phe Glu Ser Glu Glu Glu Cys Lys Glu Thr Cys Lys Gly Phe Ser
                85                  90                  95
Leu Leu Lys Lys Val Asn Val Thr Ile Asn
            100                 105

<210> SEQ ID NO 243
<211> LENGTH: 107
<212> TYPE: PRT
<213> ORGANISM: Ixodes scapularis

<400> SEQUENCE: 243

Ala Ser Tyr Asn Arg Lys Thr Gly Gln Cys Glu Glu Gln Lys Gly Thr
1               5                   10                  15
```

```
Glu Cys Gly Gly Gly Glu Asn His Phe Glu Thr Leu Leu Lys Cys Asn
             20                  25                  30

Glu Ser Cys Asn Asp Ala Pro Lys Pro Pro Cys Ser Leu Glu Val Asp
         35                  40                  45

Tyr Gly Val Gly Arg Ala Asn Ile Pro Arg Trp Tyr Tyr Asp Thr Asn
     50                  55                  60

Asn Ala Thr Cys Glu Met Phe Thr Tyr Gly Gly Ile Thr Gly Asn Lys
 65                  70                  75                  80

Asn Asn Phe Glu Ser Glu Glu Cys Lys Glu Thr Cys Lys Gly Phe
                 85                  90                  95

Ser Leu Leu Lys Lys Val Asn Val Thr Ile Asn
            100                 105
```

<210> SEQ ID NO 244
<211> LENGTH: 108
<212> TYPE: PRT
<213> ORGANISM: Ixodes scapularis

<400> SEQUENCE: 244

```
His Ala Ser Tyr Asn Arg Lys Thr Gly Gln Cys Glu Glu Gln Lys Gly
 1               5                  10                  15

Thr Glu Cys Gly Gly Gly Glu Asn His Phe Glu Thr Leu Leu Lys Cys
             20                  25                  30

Asn Glu Ser Cys Asn Asp Ala Pro Lys Pro Pro Cys Ser Leu Glu Val
         35                  40                  45

Asp Tyr Gly Val Gly Arg Ala Asn Ile Pro Arg Trp Tyr Tyr Asp Thr
     50                  55                  60

Asn Asn Ala Thr Cys Glu Met Phe Thr Tyr Gly Gly Ile Thr Gly Asn
 65                  70                  75                  80

Lys Asn Asn Phe Glu Ser Glu Glu Cys Lys Glu Thr Cys Lys Gly
                 85                  90                  95

Phe Ser Leu Leu Lys Lys Val Asn Val Thr Ile Asn
            100                 105
```

<210> SEQ ID NO 245
<211> LENGTH: 109
<212> TYPE: PRT
<213> ORGANISM: Ixodes scapularis

<400> SEQUENCE: 245

```
Thr His Ala Ser Tyr Asn Arg Lys Thr Gly Gln Cys Glu Glu Gln Lys
 1               5                  10                  15

Gly Thr Glu Cys Gly Gly Gly Glu Asn His Phe Glu Thr Leu Leu Lys
             20                  25                  30

Cys Asn Glu Ser Cys Asn Asp Ala Pro Lys Pro Pro Cys Ser Leu Glu
         35                  40                  45

Val Asp Tyr Gly Val Gly Arg Ala Asn Ile Pro Arg Trp Tyr Tyr Asp
     50                  55                  60

Thr Asn Asn Ala Thr Cys Glu Met Phe Thr Tyr Gly Gly Ile Thr Gly
 65                  70                  75                  80

Asn Lys Asn Asn Phe Glu Ser Glu Glu Cys Lys Glu Thr Cys Lys
                 85                  90                  95

Gly Phe Ser Leu Leu Lys Lys Val Asn Val Thr Ile Asn
            100                 105
```

<210> SEQ ID NO 246
<211> LENGTH: 110

-continued

```
<212> TYPE: PRT
<213> ORGANISM: Ixodes scapularis

<400> SEQUENCE: 246

Gly Thr His Ala Ser Tyr Asn Arg Lys Thr Gly Gln Cys Glu Glu Gln
1               5                   10                  15

Lys Gly Thr Glu Cys Gly Gly Gly Glu Asn His Phe Glu Thr Leu Leu
            20                  25                  30

Lys Cys Asn Glu Ser Cys Asn Asp Ala Pro Lys Pro Pro Cys Ser Leu
        35                  40                  45

Glu Val Asp Tyr Gly Val Gly Arg Ala Asn Ile Pro Arg Trp Tyr Tyr
    50                  55                  60

Asp Thr Asn Asn Ala Thr Cys Glu Met Phe Thr Tyr Gly Gly Ile Thr
65                  70                  75                  80

Gly Asn Lys Asn Asn Phe Glu Ser Glu Glu Cys Lys Glu Thr Cys
                85                  90                  95

Lys Gly Phe Ser Leu Leu Lys Lys Val Asn Val Thr Ile Asn
            100                 105                 110

<210> SEQ ID NO 247
<211> LENGTH: 111
<212> TYPE: PRT
<213> ORGANISM: Ixodes scapularis

<400> SEQUENCE: 247

Glu Gly Thr His Ala Ser Tyr Asn Arg Lys Thr Gly Gln Cys Glu Glu
1               5                   10                  15

Gln Lys Gly Thr Glu Cys Gly Gly Gly Glu Asn His Phe Glu Thr Leu
            20                  25                  30

Leu Lys Cys Asn Glu Ser Cys Asn Asp Ala Pro Lys Pro Pro Cys Ser
        35                  40                  45

Leu Glu Val Asp Tyr Gly Val Gly Arg Ala Asn Ile Pro Arg Trp Tyr
    50                  55                  60

Tyr Asp Thr Asn Asn Ala Thr Cys Glu Met Phe Thr Tyr Gly Gly Ile
65                  70                  75                  80

Thr Gly Asn Lys Asn Asn Phe Glu Ser Glu Glu Cys Lys Glu Thr
                85                  90                  95

Cys Lys Gly Phe Ser Leu Leu Lys Lys Val Asn Val Thr Ile Asn
            100                 105                 110

<210> SEQ ID NO 248
<211> LENGTH: 112
<212> TYPE: PRT
<213> ORGANISM: Ixodes scapularis

<400> SEQUENCE: 248

Gln Glu Gly Thr His Ala Ser Tyr Asn Arg Lys Thr Gly Gln Cys Glu
1               5                   10                  15

Glu Gln Lys Gly Thr Glu Cys Gly Gly Gly Glu Asn His Phe Glu Thr
            20                  25                  30

Leu Leu Lys Cys Asn Glu Ser Cys Asn Asp Ala Pro Lys Pro Pro Cys
        35                  40                  45

Ser Leu Glu Val Asp Tyr Gly Val Gly Arg Ala Asn Ile Pro Arg Trp
    50                  55                  60

Tyr Tyr Asp Thr Asn Asn Ala Thr Cys Glu Met Phe Thr Tyr Gly Gly
65                  70                  75                  80

Ile Thr Gly Asn Lys Asn Asn Phe Glu Ser Glu Glu Cys Lys Glu
```

```
                    85                  90                  95
Thr Cys Lys Gly Phe Ser Leu Leu Lys Lys Val Asn Val Thr Ile Asn
            100                 105                 110
```

<210> SEQ ID NO 249
<211> LENGTH: 113
<212> TYPE: PRT
<213> ORGANISM: Ixodes scapularis

<400> SEQUENCE: 249

```
Ser Gln Glu Gly Thr His Ala Ser Tyr Asn Arg Lys Thr Gly Gln Cys
1               5                   10                  15

Glu Glu Gln Lys Gly Thr Glu Cys Gly Gly Gly Glu Asn His Phe Glu
            20                  25                  30

Thr Leu Leu Lys Cys Asn Glu Ser Cys Asn Asp Ala Pro Lys Pro Pro
        35                  40                  45

Cys Ser Leu Glu Val Asp Tyr Gly Val Gly Arg Ala Asn Ile Pro Arg
50                  55                  60

Trp Tyr Tyr Asp Thr Asn Asn Ala Thr Cys Glu Met Phe Thr Tyr Gly
65                  70                  75                  80

Gly Ile Thr Gly Asn Lys Asn Asn Phe Glu Ser Glu Glu Cys Lys
                85                  90                  95

Glu Thr Cys Lys Gly Phe Ser Leu Leu Lys Lys Val Asn Val Thr Ile
            100                 105                 110

Asn
```

<210> SEQ ID NO 250
<211> LENGTH: 114
<212> TYPE: PRT
<213> ORGANISM: Ixodes scapularis

<400> SEQUENCE: 250

```
Glu Ser Gln Glu Gly Thr His Ala Ser Tyr Asn Arg Lys Thr Gly Gln
1               5                   10                  15

Cys Glu Glu Gln Lys Gly Thr Glu Cys Gly Gly Gly Glu Asn His Phe
            20                  25                  30

Glu Thr Leu Leu Lys Cys Asn Glu Ser Cys Asn Asp Ala Pro Lys Pro
        35                  40                  45

Pro Cys Ser Leu Glu Val Asp Tyr Gly Val Gly Arg Ala Asn Ile Pro
    50                  55                  60

Arg Trp Tyr Tyr Asp Thr Asn Asn Ala Thr Cys Glu Met Phe Thr Tyr
65                  70                  75                  80

Gly Gly Ile Thr Gly Asn Lys Asn Asn Phe Glu Ser Glu Glu Cys
                85                  90                  95

Lys Glu Thr Cys Lys Gly Phe Ser Leu Leu Lys Lys Val Asn Val Thr
            100                 105                 110

Ile Asn
```

<210> SEQ ID NO 251
<211> LENGTH: 115
<212> TYPE: PRT
<213> ORGANISM: Ixodes scapularis

<400> SEQUENCE: 251

```
Cys Glu Ser Gln Glu Gly Thr His Ala Ser Tyr Asn Arg Lys Thr Gly
1               5                   10                  15

Gln Cys Glu Glu Gln Lys Gly Thr Glu Cys Gly Gly Gly Glu Asn His
```

```
                 20                  25                  30
Phe Glu Thr Leu Leu Lys Cys Asn Glu Ser Cys Asn Asp Ala Pro Lys
             35                  40                  45

Pro Pro Cys Ser Leu Glu Val Asp Tyr Gly Val Gly Arg Ala Asn Ile
 50                  55                  60

Pro Arg Trp Tyr Tyr Asp Thr Asn Asn Ala Thr Cys Glu Met Phe Thr
 65                  70                  75                  80

Tyr Gly Gly Ile Thr Gly Asn Lys Asn Asn Phe Glu Ser Glu Glu Glu
                 85                  90                  95

Cys Lys Glu Thr Cys Lys Gly Phe Ser Leu Leu Lys Lys Val Asn Val
                100                 105                 110

Thr Ile Asn
        115

<210> SEQ ID NO 252
<211> LENGTH: 116
<212> TYPE: PRT
<213> ORGANISM: Ixodes scapularis

<400> SEQUENCE: 252

Thr Cys Glu Ser Gln Glu Gly Thr His Ala Ser Tyr Asn Arg Lys Thr
 1               5                  10                  15

Gly Gln Cys Glu Glu Gln Lys Gly Thr Glu Cys Gly Gly Gly Glu Asn
                 20                  25                  30

His Phe Glu Thr Leu Leu Lys Cys Asn Glu Ser Cys Asn Asp Ala Pro
             35                  40                  45

Lys Pro Pro Cys Ser Leu Glu Val Asp Tyr Gly Val Gly Arg Ala Asn
 50                  55                  60

Ile Pro Arg Trp Tyr Tyr Asp Thr Asn Asn Ala Thr Cys Glu Met Phe
 65                  70                  75                  80

Thr Tyr Gly Gly Ile Thr Gly Asn Lys Asn Asn Phe Glu Ser Glu Glu
                 85                  90                  95

Glu Cys Lys Glu Thr Cys Lys Gly Phe Ser Leu Leu Lys Lys Val Asn
                100                 105                 110

Val Thr Ile Asn
        115

<210> SEQ ID NO 253
<211> LENGTH: 117
<212> TYPE: PRT
<213> ORGANISM: Ixodes scapularis

<400> SEQUENCE: 253

Val Thr Cys Glu Ser Gln Glu Gly Thr His Ala Ser Tyr Asn Arg Lys
 1               5                  10                  15

Thr Gly Gln Cys Glu Glu Gln Lys Gly Thr Glu Cys Gly Gly Gly Glu
                 20                  25                  30

Asn His Phe Glu Thr Leu Leu Lys Cys Asn Glu Ser Cys Asn Asp Ala
             35                  40                  45

Pro Lys Pro Pro Cys Ser Leu Glu Val Asp Tyr Gly Val Gly Arg Ala
 50                  55                  60

Asn Ile Pro Arg Trp Tyr Tyr Asp Thr Asn Asn Ala Thr Cys Glu Met
 65                  70                  75                  80

Phe Thr Tyr Gly Gly Ile Thr Gly Asn Lys Asn Asn Phe Glu Ser Glu
                 85                  90                  95

Glu Glu Cys Lys Glu Thr Cys Lys Gly Phe Ser Leu Leu Lys Lys Val
```

-continued

```
                100               105               110
Asn Val Thr Ile Asn
        115

<210> SEQ ID NO 254
<211> LENGTH: 118
<212> TYPE: PRT
<213> ORGANISM: Ixodes scapularis

<400> SEQUENCE: 254

Gln Val Thr Cys Glu Ser Gln Glu Gly Thr His Ala Ser Tyr Asn Arg
  1               5                  10                  15

Lys Thr Gly Gln Cys Glu Glu Gln Lys Gly Thr Glu Cys Gly Gly Gly
             20                  25                  30

Glu Asn His Phe Glu Thr Leu Leu Lys Cys Asn Glu Ser Cys Asn Asp
         35                  40                  45

Ala Pro Lys Pro Pro Cys Ser Leu Glu Val Asp Tyr Gly Val Gly Arg
     50                  55                  60

Ala Asn Ile Pro Arg Trp Tyr Tyr Asp Thr Asn Asn Ala Thr Cys Glu
 65                  70                  75                  80

Met Phe Thr Tyr Gly Gly Ile Thr Gly Asn Lys Asn Phe Glu Ser
                 85                  90                  95

Glu Glu Glu Cys Lys Glu Thr Cys Lys Gly Phe Ser Leu Leu Lys Lys
                100                 105                 110

Val Asn Val Thr Ile Asn
        115

<210> SEQ ID NO 255
<211> LENGTH: 119
<212> TYPE: PRT
<213> ORGANISM: Ixodes scapularis

<400> SEQUENCE: 255

Glu Gln Val Thr Cys Glu Ser Gln Glu Gly Thr His Ala Ser Tyr Asn
  1               5                  10                  15

Arg Lys Thr Gly Gln Cys Glu Glu Gln Lys Gly Thr Glu Cys Gly Gly
             20                  25                  30

Gly Glu Asn His Phe Glu Thr Leu Leu Lys Cys Asn Glu Ser Cys Asn
         35                  40                  45

Asp Ala Pro Lys Pro Pro Cys Ser Leu Glu Val Asp Tyr Gly Val Gly
     50                  55                  60

Arg Ala Asn Ile Pro Arg Trp Tyr Tyr Asp Thr Asn Asn Ala Thr Cys
 65                  70                  75                  80

Glu Met Phe Thr Tyr Gly Gly Ile Thr Gly Asn Lys Asn Phe Glu
                 85                  90                  95

Ser Glu Glu Glu Cys Lys Glu Thr Cys Lys Gly Phe Ser Leu Leu Lys
                100                 105                 110

Lys Val Asn Val Thr Ile Asn
        115

<210> SEQ ID NO 256
<211> LENGTH: 120
<212> TYPE: PRT
<213> ORGANISM: Ixodes scapularis

<400> SEQUENCE: 256

Pro Glu Gln Val Thr Cys Glu Ser Gln Glu Gly Thr His Ala Ser Tyr
  1               5                  10                  15
```

```
Asn Arg Lys Thr Gly Gln Cys Glu Glu Gln Lys Gly Thr Glu Cys Gly
        20                  25                  30
Gly Gly Glu Asn His Phe Glu Thr Leu Leu Lys Cys Asn Glu Ser Cys
        35                  40                  45
Asn Asp Ala Pro Lys Pro Cys Ser Leu Glu Val Asp Tyr Gly Val
        50                  55                  60
Gly Arg Ala Asn Ile Pro Arg Trp Tyr Tyr Asp Thr Asn Asn Ala Thr
65                  70                  75                  80
Cys Glu Met Phe Thr Tyr Gly Gly Ile Thr Gly Asn Lys Asn Asn Phe
                85                  90                  95
Glu Ser Glu Glu Glu Cys Lys Glu Thr Cys Lys Gly Phe Ser Leu Leu
                100                 105                 110
Lys Lys Val Asn Val Thr Ile Asn
        115                 120

<210> SEQ ID NO 257
<211> LENGTH: 121
<212> TYPE: PRT
<213> ORGANISM: Ixodes scapularis

<400> SEQUENCE: 257

Asp Pro Glu Gln Val Thr Cys Glu Ser Gln Glu Gly Thr His Ala Ser
1               5                   10                  15
Tyr Asn Arg Lys Thr Gly Gln Cys Glu Glu Gln Lys Gly Thr Glu Cys
            20                  25                  30
Gly Gly Gly Glu Asn His Phe Glu Thr Leu Leu Lys Cys Asn Glu Ser
        35                  40                  45
Cys Asn Asp Ala Pro Lys Pro Cys Ser Leu Glu Val Asp Tyr Gly
    50                  55                  60
Val Gly Arg Ala Asn Ile Pro Arg Trp Tyr Tyr Asp Thr Asn Asn Ala
65                  70                  75                  80
Thr Cys Glu Met Phe Thr Tyr Gly Gly Ile Thr Gly Asn Lys Asn Asn
                85                  90                  95
Phe Glu Ser Glu Glu Glu Cys Lys Glu Thr Cys Lys Gly Phe Ser Leu
                100                 105                 110
Leu Lys Lys Val Asn Val Thr Ile Asn
            115                 120

<210> SEQ ID NO 258
<211> LENGTH: 122
<212> TYPE: PRT
<213> ORGANISM: Ixodes scapularis

<400> SEQUENCE: 258

Leu Asp Pro Glu Gln Val Thr Cys Glu Ser Gln Glu Gly Thr His Ala
1               5                   10                  15
Ser Tyr Asn Arg Lys Thr Gly Gln Cys Glu Glu Gln Lys Gly Thr Glu
        20                  25                  30
Cys Gly Gly Gly Glu Asn His Phe Glu Thr Leu Leu Lys Cys Asn Glu
        35                  40                  45
Ser Cys Asn Asp Ala Pro Lys Pro Cys Ser Leu Glu Val Asp Tyr
        50                  55                  60
Gly Val Gly Arg Ala Asn Ile Pro Arg Trp Tyr Tyr Asp Thr Asn Asn
65                  70                  75                  80
Ala Thr Cys Glu Met Phe Thr Tyr Gly Gly Ile Thr Gly Asn Lys Asn
                85                  90                  95
Asn Phe Glu Ser Glu Glu Glu Cys Lys Glu Thr Cys Lys Gly Phe Ser
                100                 105                 110
Leu Leu Lys Lys Val Asn Val Thr Ile Asn
            115                 120
```

<210> SEQ ID NO 259
<211> LENGTH: 123
<212> TYPE: PRT
<213> ORGANISM: Ixodes scapularis

<400> SEQUENCE: 259

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn His Phe Glu Thr Leu Leu Lys Cys Asn
        35                  40                  45

Glu Ser Cys Asn Asp Ala Pro Lys Pro Pro Cys Ser Leu Glu Val Asp
    50                  55                  60

Tyr Gly Val Gly Arg Ala Asn Ile Pro Arg Trp Tyr Tyr Asp Thr Asn
65                  70                  75                  80

Asn Ala Thr Cys Glu Met Phe Thr Tyr Gly Gly Ile Thr Gly Asn Lys
                85                  90                  95

Asn Asn Phe Glu Ser Glu Glu Cys Lys Glu Thr Cys Lys Gly Phe
            100                 105                 110

Ser Leu Leu Lys Lys Val Asn Val Thr Ile Asn
        115                 120

<210> SEQ ID NO 260
<211> LENGTH: 124
<212> TYPE: PRT
<213> ORGANISM: Ixodes scapularis

<400> SEQUENCE: 260

Ser Cys Leu Asp Pro Glu Gln Val Thr Cys Glu Ser Gln Glu Gly Thr
1               5                   10                  15

His Ala Ser Tyr Asn Arg Lys Thr Gly Gln Cys Glu Glu Gln Lys Gly
            20                  25                  30

Thr Glu Cys Gly Gly Gly Glu Asn His Phe Glu Thr Leu Leu Lys Cys
        35                  40                  45

Asn Glu Ser Cys Asn Asp Ala Pro Lys Pro Pro Cys Ser Leu Glu Val
    50                  55                  60

Asp Tyr Gly Val Gly Arg Ala Asn Ile Pro Arg Trp Tyr Tyr Asp Thr
65                  70                  75                  80

Asn Asn Ala Thr Cys Glu Met Phe Thr Tyr Gly Gly Ile Thr Gly Asn
                85                  90                  95

Lys Asn Asn Phe Glu Ser Glu Glu Cys Lys Glu Thr Cys Lys Gly
            100                 105                 110

Phe Ser Leu Leu Lys Lys Val Asn Val Thr Ile Asn
        115                 120

<210> SEQ ID NO 261
<211> LENGTH: 125
<212> TYPE: PRT
<213> ORGANISM: Ixodes scapularis

<400> SEQUENCE: 261

Val Ser Cys Leu Asp Pro Glu Gln Val Thr Cys Glu Ser Gln Glu Gly
1               5                   10                  15

Thr His Ala Ser Tyr Asn Arg Lys Thr Gly Gln Cys Glu Glu Gln Lys
            20                  25                  30

Gly Thr Glu Cys Gly Gly Glu Asn His Phe Glu Thr Leu Leu Lys
        35                  40                  45

Cys Asn Glu Ser Cys Asn Asp Ala Pro Lys Pro Cys Ser Leu Glu
    50                  55                  60

Val Asp Tyr Gly Val Gly Arg Ala Asn Ile Pro Arg Trp Tyr Tyr Asp
65               70                  75                  80

Thr Asn Asn Ala Thr Cys Glu Met Phe Thr Tyr Gly Gly Ile Thr Gly
                85                  90                  95

Asn Lys Asn Asn Phe Glu Ser Glu Glu Cys Lys Glu Thr Cys Lys
            100                 105                 110

Gly Phe Ser Leu Leu Lys Lys Val Asn Val Thr Ile Asn
            115                 120                 125

<210> SEQ ID NO 262
<211> LENGTH: 126
<212> TYPE: PRT
<213> ORGANISM: Ixodes scapularis

<400> SEQUENCE: 262

Trp Val Ser Cys Leu Asp Pro Glu Gln Val Thr Cys Glu Ser Gln Glu
1               5                   10                  15

Gly Thr His Ala Ser Tyr Asn Arg Lys Thr Gly Gln Cys Glu Glu Gln
            20                  25                  30

Lys Gly Thr Glu Cys Gly Gly Gly Glu Asn His Phe Glu Thr Leu Leu
        35                  40                  45

Lys Cys Asn Glu Ser Cys Asn Asp Ala Pro Lys Pro Cys Ser Leu
    50                  55                  60

Glu Val Asp Tyr Gly Val Gly Arg Ala Asn Ile Pro Arg Trp Tyr Tyr
65               70                  75                  80

Asp Thr Asn Asn Ala Thr Cys Glu Met Phe Thr Tyr Gly Gly Ile Thr
                85                  90                  95

Gly Asn Lys Asn Asn Phe Glu Ser Glu Glu Cys Lys Glu Thr Cys
            100                 105                 110

Lys Gly Phe Ser Leu Leu Lys Lys Val Asn Val Thr Ile Asn
            115                 120                 125

<210> SEQ ID NO 263
<211> LENGTH: 127
<212> TYPE: PRT
<213> ORGANISM: Ixodes scapularis

<400> SEQUENCE: 263

Ser Trp Val Ser Cys Leu Asp Pro Glu Gln Val Thr Cys Glu Ser Gln
1               5                   10                  15

Glu Gly Thr His Ala Ser Tyr Asn Arg Lys Thr Gly Gln Cys Glu Glu
            20                  25                  30

Gln Lys Gly Thr Glu Cys Gly Gly Gly Glu Asn His Phe Glu Thr Leu
        35                  40                  45

Leu Lys Cys Asn Glu Ser Cys Asn Asp Ala Pro Lys Pro Cys Ser
    50                  55                  60

Leu Glu Val Asp Tyr Gly Val Gly Arg Ala Asn Ile Pro Arg Trp Tyr
65               70                  75                  80

Tyr Asp Thr Asn Asn Ala Thr Cys Glu Met Phe Thr Tyr Gly Gly Ile
                85                  90                  95

Thr Gly Asn Lys Asn Asn Phe Glu Ser Glu Glu Cys Lys Glu Thr
            100                 105                 110

```
Cys Lys Gly Phe Ser Leu Leu Lys Lys Val Asn Val Thr Ile Asn
        115                 120                 125
```

<210> SEQ ID NO 264
<211> LENGTH: 128
<212> TYPE: PRT
<213> ORGANISM: Ixodes scapularis

<400> SEQUENCE: 264

```
Glu Ser Trp Val Ser Cys Leu Asp Pro Glu Gln Val Thr Cys Glu Ser
1               5                   10                  15
Gln Glu Gly Thr His Ala Ser Tyr Asn Arg Lys Thr Gly Gln Cys Glu
            20                  25                  30
Glu Gln Lys Gly Thr Glu Cys Gly Gly Gly Glu Asn His Phe Glu Thr
        35                  40                  45
Leu Leu Lys Cys Asn Glu Ser Cys Asn Asp Ala Pro Lys Pro Pro Cys
    50                  55                  60
Ser Leu Glu Val Asp Tyr Gly Val Gly Arg Ala Asn Ile Pro Arg Trp
65                  70                  75                  80
Tyr Tyr Asp Thr Asn Asn Ala Thr Cys Glu Met Phe Thr Tyr Gly Gly
                85                  90                  95
Ile Thr Gly Asn Lys Asn Asn Phe Glu Ser Glu Glu Cys Lys Glu
            100                 105                 110
Thr Cys Lys Gly Phe Ser Leu Leu Lys Lys Val Asn Val Thr Ile Asn
        115                 120                 125
```

<210> SEQ ID NO 265
<211> LENGTH: 129
<212> TYPE: PRT
<213> ORGANISM: Ixodes scapularis

<400> SEQUENCE: 265

```
Phe Glu Ser Trp Val Ser Cys Leu Asp Pro Glu Gln Val Thr Cys Glu
1               5                   10                  15
Ser Gln Glu Gly Thr His Ala Ser Tyr Asn Arg Lys Thr Gly Gln Cys
            20                  25                  30
Glu Glu Gln Lys Gly Thr Glu Cys Gly Gly Gly Glu Asn His Phe Glu
        35                  40                  45
Thr Leu Leu Lys Cys Asn Glu Ser Cys Asn Asp Ala Pro Lys Pro Pro
    50                  55                  60
Cys Ser Leu Glu Val Asp Tyr Gly Val Gly Arg Ala Asn Ile Pro Arg
65                  70                  75                  80
Trp Tyr Tyr Asp Thr Asn Asn Ala Thr Cys Glu Met Phe Thr Tyr Gly
                85                  90                  95
Gly Ile Thr Gly Asn Lys Asn Asn Phe Glu Ser Glu Glu Cys Lys
            100                 105                 110
Glu Thr Cys Lys Gly Phe Ser Leu Leu Lys Lys Val Asn Val Thr Ile
        115                 120                 125
Asn
```

<210> SEQ ID NO 266
<211> LENGTH: 130
<212> TYPE: PRT
<213> ORGANISM: Ixodes scapularis

<400> SEQUENCE: 266

```
Glu Phe Glu Ser Trp Val Ser Cys Leu Asp Pro Glu Gln Val Thr Cys
1               5                   10                  15
```

```
Glu Ser Gln Glu Gly Thr His Ala Ser Tyr Asn Arg Lys Thr Gly Gln
            20                  25                  30

Cys Glu Glu Gln Lys Gly Thr Glu Cys Gly Gly Gly Glu Asn His Phe
        35                  40                  45

Glu Thr Leu Leu Lys Cys Asn Glu Ser Cys Asn Asp Ala Pro Lys Pro
    50                  55                  60

Pro Cys Ser Leu Glu Val Asp Tyr Gly Val Gly Arg Ala Asn Ile Pro
65                  70                  75                  80

Arg Trp Tyr Tyr Asp Thr Asn Asn Ala Thr Cys Glu Met Phe Thr Tyr
                85                  90                  95

Gly Gly Ile Thr Gly Asn Lys Asn Asn Phe Glu Ser Glu Glu Glu Cys
            100                 105                 110

Lys Glu Thr Cys Lys Gly Phe Ser Leu Leu Lys Lys Val Asn Val Thr
        115                 120                 125

Ile Asn
    130

<210> SEQ ID NO 267
<211> LENGTH: 131
<212> TYPE: PRT
<213> ORGANISM: Ixodes scapularis

<400> SEQUENCE: 267

Tyr Glu Phe Glu Ser Trp Val Ser Cys Leu Asp Pro Glu Gln Val Thr
1               5                   10                  15

Cys Glu Ser Gln Glu Gly Thr His Ala Ser Tyr Asn Arg Lys Thr Gly
            20                  25                  30

Gln Cys Glu Glu Gln Lys Gly Thr Glu Cys Gly Gly Gly Glu Asn His
        35                  40                  45

Phe Glu Thr Leu Leu Lys Cys Asn Glu Ser Cys Asn Asp Ala Pro Lys
    50                  55                  60

Pro Pro Cys Ser Leu Glu Val Asp Tyr Gly Val Gly Arg Ala Asn Ile
65                  70                  75                  80

Pro Arg Trp Tyr Tyr Asp Thr Asn Asn Ala Thr Cys Glu Met Phe Thr
                85                  90                  95

Tyr Gly Gly Ile Thr Gly Asn Lys Asn Asn Phe Glu Ser Glu Glu Glu
            100                 105                 110

Cys Lys Glu Thr Cys Lys Gly Phe Ser Leu Leu Lys Lys Val Asn Val
        115                 120                 125

Thr Ile Asn
    130

<210> SEQ ID NO 268
<211> LENGTH: 132
<212> TYPE: PRT
<213> ORGANISM: Ixodes scapularis

<400> SEQUENCE: 268

Ile Tyr Glu Phe Glu Ser Trp Val Ser Cys Leu Asp Pro Glu Gln Val
1               5                   10                  15

Thr Cys Glu Ser Gln Glu Gly Thr His Ala Ser Tyr Asn Arg Lys Thr
            20                  25                  30

Gly Gln Cys Glu Glu Gln Lys Gly Thr Glu Cys Gly Gly Gly Glu Asn
        35                  40                  45

His Phe Glu Thr Leu Leu Lys Cys Asn Glu Ser Cys Asn Asp Ala Pro
    50                  55                  60
```

-continued

```
Lys Pro Pro Cys Ser Leu Glu Val Asp Tyr Gly Val Gly Arg Ala Asn
65                  70                  75                  80

Ile Pro Arg Trp Tyr Tyr Asp Thr Asn Asn Ala Thr Cys Glu Met Phe
                85                  90                  95

Thr Tyr Gly Gly Ile Thr Gly Asn Lys Asn Asn Phe Glu Ser Glu Glu
            100                 105                 110

Glu Cys Lys Glu Thr Cys Lys Gly Phe Ser Leu Leu Lys Lys Val Asn
        115                 120                 125

Val Thr Ile Asn
    130

<210> SEQ ID NO 269
<211> LENGTH: 133
<212> TYPE: PRT
<213> ORGANISM: Ixodes scapularis
<400> SEQUENCE: 269

Asp Ile Tyr Glu Phe Glu Ser Trp Val Ser Cys Leu Asp Pro Glu Gln
 1               5                  10                  15

Val Thr Cys Glu Ser Gln Glu Gly Thr His Ala Ser Tyr Asn Arg Lys
            20                  25                  30

Thr Gly Gln Cys Glu Glu Gln Lys Gly Thr Glu Cys Gly Gly Gly Glu
        35                  40                  45

Asn His Phe Glu Thr Leu Leu Lys Cys Asn Glu Ser Cys Asn Asp Ala
    50                  55                  60

Pro Lys Pro Pro Cys Ser Leu Glu Val Asp Tyr Gly Val Gly Arg Ala
65                  70                  75                  80

Asn Ile Pro Arg Trp Tyr Tyr Asp Thr Asn Asn Ala Thr Cys Glu Met
                85                  90                  95

Phe Thr Tyr Gly Gly Ile Thr Gly Asn Lys Asn Asn Phe Glu Ser Glu
            100                 105                 110

Glu Glu Cys Lys Glu Thr Cys Lys Gly Phe Ser Leu Leu Lys Lys Val
        115                 120                 125

Asn Val Thr Ile Asn
    130

<210> SEQ ID NO 270
<211> LENGTH: 134
<212> TYPE: PRT
<213> ORGANISM: Ixodes scapularis
<400> SEQUENCE: 270

Met Asp Ile Tyr Glu Phe Glu Ser Trp Val Ser Cys Leu Asp Pro Glu
 1               5                  10                  15

Gln Val Thr Cys Glu Ser Gln Glu Gly Thr His Ala Ser Tyr Asn Arg
            20                  25                  30

Lys Thr Gly Gln Cys Glu Glu Gln Lys Gly Thr Glu Cys Gly Gly Gly
        35                  40                  45

Glu Asn His Phe Glu Thr Leu Leu Lys Cys Asn Glu Ser Cys Asn Asp
    50                  55                  60

Ala Pro Lys Pro Pro Cys Ser Leu Glu Val Asp Tyr Gly Val Gly Arg
65                  70                  75                  80

Ala Asn Ile Pro Arg Trp Tyr Tyr Asp Thr Asn Asn Ala Thr Cys Glu
                85                  90                  95

Met Phe Thr Tyr Gly Gly Ile Thr Gly Asn Lys Asn Asn Phe Glu Ser
            100                 105                 110

Glu Glu Glu Cys Lys Glu Thr Cys Lys Gly Phe Ser Leu Leu Lys Lys
            115                 120                 125

Val Asn Val Thr Ile Asn
    130

<210> SEQ ID NO 271
<211> LENGTH: 135
<212> TYPE: PRT
<213> ORGANISM: Ixodes scapularis

<400> SEQUENCE: 271

Glu Met Asp Ile Tyr Glu Phe Glu Ser Trp Val Ser Cys Leu Asp Pro
1               5                   10                  15

Glu Gln Val Thr Cys Glu Ser Gln Glu Gly Thr His Ala Ser Tyr Asn
            20                  25                  30

Arg Lys Thr Gly Gln Cys Glu Glu Gln Lys Gly Thr Glu Cys Gly Gly
        35                  40                  45

Gly Glu Asn His Phe Glu Thr Leu Leu Lys Cys Asn Glu Ser Cys Asn
    50                  55                  60

Asp Ala Pro Lys Pro Pro Cys Ser Leu Glu Val Asp Tyr Gly Val Gly
65                  70                  75                  80

Arg Ala Asn Ile Pro Arg Trp Tyr Tyr Asp Thr Asn Asn Ala Thr Cys
                85                  90                  95

Glu Met Phe Thr Tyr Gly Gly Ile Thr Gly Asn Lys Asn Asn Phe Glu
            100                 105                 110

Ser Glu Glu Glu Cys Lys Glu Thr Cys Lys Gly Phe Ser Leu Leu Lys
        115                 120                 125

Lys Val Asn Val Thr Ile Asn
    130                 135

<210> SEQ ID NO 272
<211> LENGTH: 136
<212> TYPE: PRT
<213> ORGANISM: Ixodes scapularis

<400> SEQUENCE: 272

Ser Glu Met Asp Ile Tyr Glu Phe Glu Ser Trp Val Ser Cys Leu Asp
1               5                   10                  15

Pro Glu Gln Val Thr Cys Glu Ser Gln Glu Gly Thr His Ala Ser Tyr
            20                  25                  30

Asn Arg Lys Thr Gly Gln Cys Glu Glu Gln Lys Gly Thr Glu Cys Gly
        35                  40                  45

Gly Gly Glu Asn His Phe Glu Thr Leu Leu Lys Cys Asn Glu Ser Cys
    50                  55                  60

Asn Asp Ala Pro Lys Pro Pro Cys Ser Leu Glu Val Asp Tyr Gly Val
65                  70                  75                  80

Gly Arg Ala Asn Ile Pro Arg Trp Tyr Tyr Asp Thr Asn Asn Ala Thr
                85                  90                  95

Cys Glu Met Phe Thr Tyr Gly Gly Ile Thr Gly Asn Lys Asn Asn Phe
            100                 105                 110

Glu Ser Glu Glu Glu Cys Lys Glu Thr Cys Lys Gly Phe Ser Leu Leu
        115                 120                 125

Lys Lys Val Asn Val Thr Ile Asn
    130                 135

<210> SEQ ID NO 273

```
<211> LENGTH: 137
<212> TYPE: PRT
<213> ORGANISM: Ixodes scapularis

<400> SEQUENCE: 273

Val Ser Glu Met Asp Ile Tyr Glu Phe Glu Ser Trp Val Ser Cys Leu
 1               5                  10                  15

Asp Pro Glu Gln Val Thr Cys Glu Ser Gln Glu Gly Thr His Ala Ser
            20                  25                  30

Tyr Asn Arg Lys Thr Gly Gln Cys Glu Glu Gln Lys Gly Thr Glu Cys
        35                  40                  45

Gly Gly Gly Glu Asn His Phe Glu Thr Leu Leu Lys Cys Asn Glu Ser
    50                  55                  60

Cys Asn Asp Ala Pro Lys Pro Cys Ser Leu Glu Val Asp Tyr Gly
65                  70                  75                  80

Val Gly Arg Ala Asn Ile Pro Arg Trp Tyr Tyr Asp Thr Asn Asn Ala
                85                  90                  95

Thr Cys Glu Met Phe Thr Tyr Gly Gly Ile Thr Gly Asn Lys Asn Asn
            100                 105                 110

Phe Glu Ser Glu Glu Cys Lys Glu Thr Cys Lys Gly Phe Ser Leu
        115                 120                 125

Leu Lys Lys Val Asn Val Thr Ile Asn
    130                 135

<210> SEQ ID NO 274
<211> LENGTH: 138
<212> TYPE: PRT
<213> ORGANISM: Ixodes scapularis

<400> SEQUENCE: 274

Arg Val Ser Glu Met Asp Ile Tyr Glu Phe Glu Ser Trp Val Ser Cys
 1               5                  10                  15

Leu Asp Pro Glu Gln Val Thr Cys Glu Ser Gln Glu Gly Thr His Ala
            20                  25                  30

Ser Tyr Asn Arg Lys Thr Gly Gln Cys Glu Glu Gln Lys Gly Thr Glu
        35                  40                  45

Cys Gly Gly Gly Glu Asn His Phe Glu Thr Leu Leu Lys Cys Asn Glu
    50                  55                  60

Ser Cys Asn Asp Ala Pro Lys Pro Cys Ser Leu Glu Val Asp Tyr
65                  70                  75                  80

Gly Val Gly Arg Ala Asn Ile Pro Arg Trp Tyr Tyr Asp Thr Asn Asn
                85                  90                  95

Ala Thr Cys Glu Met Phe Thr Tyr Gly Gly Ile Thr Gly Asn Lys Asn
            100                 105                 110

Asn Phe Glu Ser Glu Glu Cys Lys Glu Thr Cys Lys Gly Phe Ser
        115                 120                 125

Leu Leu Lys Lys Val Asn Val Thr Ile Asn
    130                 135

<210> SEQ ID NO 275
<211> LENGTH: 139
<212> TYPE: PRT
<213> ORGANISM: Ixodes scapularis

<400> SEQUENCE: 275

Glu Arg Val Ser Glu Met Asp Ile Tyr Glu Phe Glu Ser Trp Val Ser
 1               5                  10                  15
```

```
Cys Leu Asp Pro Glu Gln Val Thr Cys Glu Ser Gln Glu Gly Thr His
         20                  25                  30
Ala Ser Tyr Asn Arg Lys Thr Gly Gln Cys Glu Glu Gln Lys Gly Thr
         35                  40                  45
Glu Cys Gly Gly Gly Glu Asn His Phe Glu Thr Leu Leu Lys Cys Asn
 50                  55                  60
Glu Ser Cys Asn Asp Ala Pro Lys Pro Cys Ser Leu Glu Val Asp
 65                  70                  75                  80
Tyr Gly Val Gly Arg Ala Asn Ile Pro Arg Trp Tyr Tyr Asp Thr Asn
             85                  90                  95
Asn Ala Thr Cys Glu Met Phe Thr Tyr Gly Ile Thr Gly Asn Lys
             100                 105                 110
Asn Asn Phe Glu Ser Glu Glu Cys Lys Glu Thr Cys Lys Gly Phe
         115                 120                 125
Ser Leu Leu Lys Lys Val Asn Val Thr Ile Asn
    130                 135
```

<210> SEQ ID NO 276
<211> LENGTH: 51
<212> TYPE: PRT
<213> ORGANISM: Ixodes scapularis

<400> SEQUENCE: 276

```
Cys Leu Asp Pro Glu Gln Val Thr Cys Glu Ser Gln Glu Gly Thr His
 1               5                   10                  15
Ala Ser Tyr Asn Arg Lys Thr Gly Gln Cys Glu Glu Gln Lys Gly Thr
             20                  25                  30
Glu Cys Gly Gly Gly Glu Asn His Phe Glu Thr Leu Leu Lys Cys Asn
         35                  40                  45
Glu Ser Cys
     50
```

<210> SEQ ID NO 277
<211> LENGTH: 50
<212> TYPE: PRT
<213> ORGANISM: Ixodes scapularis

<400> SEQUENCE: 277

```
Leu Asp Pro Glu Gln Val Thr Cys Glu Ser Gln Glu Gly Thr His Ala
 1               5                   10                  15
Ser Tyr Asn Arg Lys Thr Gly Gln Cys Glu Glu Gln Lys Gly Thr Glu
             20                  25                  30
Cys Gly Gly Gly Glu Asn His Phe Glu Thr Leu Leu Lys Cys Asn Glu
         35                  40                  45
Ser Cys
 50
```

<210> SEQ ID NO 278
<211> LENGTH: 49
<212> TYPE: PRT
<213> ORGANISM: Ixodes scapularis

<400> SEQUENCE: 278

```
Asp Pro Glu Gln Val Thr Cys Glu Ser Gln Glu Gly Thr His Ala Ser
 1               5                   10                  15
Tyr Asn Arg Lys Thr Gly Gln Cys Glu Glu Gln Lys Gly Thr Glu Cys
             20                  25                  30
Gly Gly Gly Glu Asn His Phe Glu Thr Leu Leu Lys Cys Asn Glu Ser
```

```
                35                  40                  45

Cys

<210> SEQ ID NO 279
<211> LENGTH: 48
<212> TYPE: PRT
<213> ORGANISM: Ixodes scapularis

<400> SEQUENCE: 279

Pro Glu Gln Val Thr Cys Glu Ser Gln Glu Gly Thr His Ala Ser Tyr
1               5                   10                  15

Asn Arg Lys Thr Gly Gln Cys Glu Glu Gln Lys Gly Thr Glu Cys Gly
            20                  25                  30

Gly Gly Glu Asn His Phe Glu Thr Leu Leu Lys Cys Asn Glu Ser Cys
        35                  40                  45

<210> SEQ ID NO 280
<211> LENGTH: 47
<212> TYPE: PRT
<213> ORGANISM: Ixodes scapularis

<400> SEQUENCE: 280

Glu Gln Val Thr Cys Glu Ser Gln Glu Gly Thr His Ala Ser Tyr Asn
1               5                   10                  15

Arg Lys Thr Gly Gln Cys Glu Glu Gln Lys Gly Thr Glu Cys Gly Gly
            20                  25                  30

Gly Glu Asn His Phe Glu Thr Leu Leu Lys Cys Asn Glu Ser Cys
        35                  40                  45

<210> SEQ ID NO 281
<211> LENGTH: 46
<212> TYPE: PRT
<213> ORGANISM: Ixodes scapularis

<400> SEQUENCE: 281

Gln Val Thr Cys Glu Ser Gln Glu Gly Thr His Ala Ser Tyr Asn Arg
1               5                   10                  15

Lys Thr Gly Gln Cys Glu Glu Gln Lys Gly Thr Glu Cys Gly Gly Gly
            20                  25                  30

Glu Asn His Phe Glu Thr Leu Leu Lys Cys Asn Glu Ser Cys
        35                  40                  45

<210> SEQ ID NO 282
<211> LENGTH: 45
<212> TYPE: PRT
<213> ORGANISM: Ixodes scapularis

<400> SEQUENCE: 282

Val Thr Cys Glu Ser Gln Glu Gly Thr His Ala Ser Tyr Asn Arg Lys
1               5                   10                  15

Thr Gly Gln Cys Glu Glu Gln Lys Gly Thr Glu Cys Gly Gly Gly Glu
            20                  25                  30

Asn His Phe Glu Thr Leu Leu Lys Cys Asn Glu Ser Cys
        35                  40                  45

<210> SEQ ID NO 283
<211> LENGTH: 44
<212> TYPE: PRT
<213> ORGANISM: Ixodes scapularis

<400> SEQUENCE: 283
```

Thr Cys Glu Ser Gln Glu Gly Thr His Ala Ser Tyr Asn Arg Lys Thr
1               5                   10                  15

Gly Gln Cys Glu Glu Gln Lys Gly Thr Glu Cys Gly Gly Gly Glu Asn
                20                  25                  30

His Phe Glu Thr Leu Leu Lys Cys Asn Glu Ser Cys
                35                  40

<210> SEQ ID NO 284
<211> LENGTH: 43
<212> TYPE: PRT
<213> ORGANISM: Ixodes scapularis

<400> SEQUENCE: 284

Cys Glu Ser Gln Glu Gly Thr His Ala Ser Tyr Asn Arg Lys Thr Gly
1               5                   10                  15

Gln Cys Glu Glu Gln Lys Gly Thr Glu Cys Gly Gly Gly Glu Asn His
                20                  25                  30

Phe Glu Thr Leu Leu Lys Cys Asn Glu Ser Cys
                35                  40

<210> SEQ ID NO 285
<211> LENGTH: 42
<212> TYPE: PRT
<213> ORGANISM: Ixodes scapularis

<400> SEQUENCE: 285

Glu Ser Gln Glu Gly Thr His Ala Ser Tyr Asn Arg Lys Thr Gly Gln
1               5                   10                  15

Cys Glu Glu Gln Lys Gly Thr Glu Cys Gly Gly Gly Glu Asn His Phe
                20                  25                  30

Glu Thr Leu Leu Lys Cys Asn Glu Ser Cys
                35                  40

<210> SEQ ID NO 286
<211> LENGTH: 41
<212> TYPE: PRT
<213> ORGANISM: Ixodes scapularis

<400> SEQUENCE: 286

Ser Gln Glu Gly Thr His Ala Ser Tyr Asn Arg Lys Thr Gly Gln Cys
1               5                   10                  15

Glu Glu Gln Lys Gly Thr Glu Cys Gly Gly Gly Glu Asn His Phe Glu
                20                  25                  30

Thr Leu Leu Lys Cys Asn Glu Ser Cys
                35                  40

<210> SEQ ID NO 287
<211> LENGTH: 40
<212> TYPE: PRT
<213> ORGANISM: Ixodes scapularis

<400> SEQUENCE: 287

Gln Glu Gly Thr His Ala Ser Tyr Asn Arg Lys Thr Gly Gln Cys Glu
1               5                   10                  15

Glu Gln Lys Gly Thr Glu Cys Gly Gly Gly Glu Asn His Phe Glu Thr
                20                  25                  30

Leu Leu Lys Cys Asn Glu Ser Cys
                35                  40

<210> SEQ ID NO 288
<211> LENGTH: 39
<212> TYPE: PRT
<213> ORGANISM: Ixodes scapularis

<400> SEQUENCE: 288

Glu Gly Thr His Ala Ser Tyr Asn Arg Lys Thr Gly Gln Cys Glu Glu
1               5                   10                  15

Gln Lys Gly Thr Glu Cys Gly Gly Gly Glu Asn His Phe Glu Thr Leu
            20                  25                  30

Leu Lys Cys Asn Glu Ser Cys
        35

<210> SEQ ID NO 289
<211> LENGTH: 38
<212> TYPE: PRT
<213> ORGANISM: Ixodes scapularis

<400> SEQUENCE: 289

Gly Thr His Ala Ser Tyr Asn Arg Lys Thr Gly Gln Cys Glu Glu Gln
1               5                   10                  15

Lys Gly Thr Glu Cys Gly Gly Gly Glu Asn His Phe Glu Thr Leu Leu
            20                  25                  30

Lys Cys Asn Glu Ser Cys
        35

<210> SEQ ID NO 290
<211> LENGTH: 37
<212> TYPE: PRT
<213> ORGANISM: Ixodes scapularis

<400> SEQUENCE: 290

Thr His Ala Ser Tyr Asn Arg Lys Thr Gly Gln Cys Glu Glu Gln Lys
1               5                   10                  15

Gly Thr Glu Cys Gly Gly Gly Glu Asn His Phe Glu Thr Leu Leu Lys
            20                  25                  30

Cys Asn Glu Ser Cys
        35

<210> SEQ ID NO 291
<211> LENGTH: 36
<212> TYPE: PRT
<213> ORGANISM: Ixodes scapularis

<400> SEQUENCE: 291

His Ala Ser Tyr Asn Arg Lys Thr Gly Gln Cys Glu Glu Gln Lys Gly
1               5                   10                  15

Thr Glu Cys Gly Gly Gly Glu Asn His Phe Glu Thr Leu Leu Lys Cys
            20                  25                  30

Asn Glu Ser Cys
        35

<210> SEQ ID NO 292
<211> LENGTH: 35
<212> TYPE: PRT
<213> ORGANISM: Ixodes scapularis

<400> SEQUENCE: 292

Ala Ser Tyr Asn Arg Lys Thr Gly Gln Cys Glu Glu Gln Lys Gly Thr
1               5                   10                  15

Glu Cys Gly Gly Gly Glu Asn His Phe Glu Thr Leu Leu Lys Cys Asn

```
                    20                  25                  30

Glu Ser Cys
        35

<210> SEQ ID NO 293
<211> LENGTH: 34
<212> TYPE: PRT
<213> ORGANISM: Ixodes scapularis

<400> SEQUENCE: 293

Ser Tyr Asn Arg Lys Thr Gly Gln Cys Glu Glu Gln Lys Gly Thr Glu
 1               5                  10                  15

Cys Gly Gly Gly Glu Asn His Phe Glu Thr Leu Leu Lys Cys Asn Glu
                20                  25                  30

Ser Cys

<210> SEQ ID NO 294
<211> LENGTH: 33
<212> TYPE: PRT
<213> ORGANISM: Ixodes scapularis

<400> SEQUENCE: 294

Tyr Asn Arg Lys Thr Gly Gln Cys Glu Glu Gln Lys Gly Thr Glu Cys
 1               5                  10                  15

Gly Gly Gly Glu Asn His Phe Glu Thr Leu Leu Lys Cys Asn Glu Ser
                20                  25                  30

Cys

<210> SEQ ID NO 295
<211> LENGTH: 32
<212> TYPE: PRT
<213> ORGANISM: Ixodes scapularis

<400> SEQUENCE: 295

Asn Arg Lys Thr Gly Gln Cys Glu Glu Gln Lys Gly Thr Glu Cys Gly
 1               5                  10                  15

Gly Gly Glu Asn His Phe Glu Thr Leu Leu Lys Cys Asn Glu Ser Cys
                20                  25                  30

<210> SEQ ID NO 296
<211> LENGTH: 31
<212> TYPE: PRT
<213> ORGANISM: Ixodes scapularis

<400> SEQUENCE: 296

Arg Lys Thr Gly Gln Cys Glu Glu Gln Lys Gly Thr Glu Cys Gly Gly
 1               5                  10                  15

Gly Glu Asn His Phe Glu Thr Leu Leu Lys Cys Asn Glu Ser Cys
                20                  25                  30

<210> SEQ ID NO 297
<211> LENGTH: 30
<212> TYPE: PRT
<213> ORGANISM: Ixodes scapularis

<400> SEQUENCE: 297

Lys Thr Gly Gln Cys Glu Glu Gln Lys Gly Thr Glu Cys Gly Gly Gly
 1               5                  10                  15

Glu Asn His Phe Glu Thr Leu Leu Lys Cys Asn Glu Ser Cys
                20                  25                  30
```

<210> SEQ ID NO 298
<211> LENGTH: 29
<212> TYPE: PRT
<213> ORGANISM: Ixodes scapularis

<400> SEQUENCE: 298

Thr Gly Gln Cys Glu Glu Gln Lys Gly Thr Glu Cys Gly Gly Gly Glu
1               5                   10                  15

Asn His Phe Glu Thr Leu Leu Lys Cys Asn Glu Ser Cys
            20                  25

<210> SEQ ID NO 299
<211> LENGTH: 28
<212> TYPE: PRT
<213> ORGANISM: Ixodes scapularis

<400> SEQUENCE: 299

Gly Gln Cys Glu Glu Gln Lys Gly Thr Glu Cys Gly Gly Gly Glu Asn
1               5                   10                  15

His Phe Glu Thr Leu Leu Lys Cys Asn Glu Ser Cys
            20                  25

<210> SEQ ID NO 300
<211> LENGTH: 27
<212> TYPE: PRT
<213> ORGANISM: Ixodes scapularis

<400> SEQUENCE: 300

Gln Cys Glu Glu Gln Lys Gly Thr Glu Cys Gly Gly Gly Glu Asn His
1               5                   10                  15

Phe Glu Thr Leu Leu Lys Cys Asn Glu Ser Cys
            20                  25

<210> SEQ ID NO 301
<211> LENGTH: 26
<212> TYPE: PRT
<213> ORGANISM: Ixodes scapularis

<400> SEQUENCE: 301

Cys Glu Glu Gln Lys Gly Thr Glu Cys Gly Gly Gly Glu Asn His Phe
1               5                   10                  15

Glu Thr Leu Leu Lys Cys Asn Glu Ser Cys
            20                  25

<210> SEQ ID NO 302
<211> LENGTH: 25
<212> TYPE: PRT
<213> ORGANISM: Ixodes scapularis

<400> SEQUENCE: 302

Glu Glu Gln Lys Gly Thr Glu Cys Gly Gly Gly Glu Asn His Phe Glu
1               5                   10                  15

Thr Leu Leu Lys Cys Asn Glu Ser Cys
            20                  25

<210> SEQ ID NO 303
<211> LENGTH: 24
<212> TYPE: PRT
<213> ORGANISM: Ixodes scapularis

<400> SEQUENCE: 303

Glu Gln Lys Gly Thr Glu Cys Gly Gly Gly Glu Asn His Phe Glu Thr

```
                1               5                  10                 15

Leu Leu Lys Cys Asn Glu Ser Cys
            20

<210> SEQ ID NO 304
<211> LENGTH: 23
<212> TYPE: PRT
<213> ORGANISM: Ixodes scapularis

<400> SEQUENCE: 304

Gln Lys Gly Thr Glu Cys Gly Gly Gly Glu Asn His Phe Glu Thr Leu
 1               5                  10                 15

Leu Lys Cys Asn Glu Ser Cys
            20

<210> SEQ ID NO 305
<211> LENGTH: 22
<212> TYPE: PRT
<213> ORGANISM: Ixodes scapularis

<400> SEQUENCE: 305

Lys Gly Thr Glu Cys Gly Gly Gly Glu Asn His Phe Glu Thr Leu Leu
 1               5                  10                 15

Lys Cys Asn Glu Ser Cys
            20

<210> SEQ ID NO 306
<211> LENGTH: 21
<212> TYPE: PRT
<213> ORGANISM: Ixodes scapularis

<400> SEQUENCE: 306

Gly Thr Glu Cys Gly Gly Gly Glu Asn His Phe Glu Thr Leu Leu Lys
 1               5                  10                 15

Cys Asn Glu Ser Cys
            20

<210> SEQ ID NO 307
<211> LENGTH: 20
<212> TYPE: PRT
<213> ORGANISM: Ixodes scapularis

<400> SEQUENCE: 307

Thr Glu Cys Gly Gly Gly Glu Asn His Phe Glu Thr Leu Leu Lys Cys
 1               5                  10                 15

Asn Glu Ser Cys
            20

<210> SEQ ID NO 308
<211> LENGTH: 19
<212> TYPE: PRT
<213> ORGANISM: Ixodes scapularis

<400> SEQUENCE: 308

Glu Cys Gly Gly Gly Glu Asn His Phe Glu Thr Leu Leu Lys Cys Asn
 1               5                  10                 15

Glu Ser Cys

<210> SEQ ID NO 309
<211> LENGTH: 18
<212> TYPE: PRT
<213> ORGANISM: Ixodes scapularis
```

```
<400> SEQUENCE: 309

Cys Gly Gly Gly Glu Asn His Phe Glu Thr Leu Leu Lys Cys Asn Glu
 1               5                  10                  15

Ser Cys

<210> SEQ ID NO 310
<211> LENGTH: 17
<212> TYPE: PRT
<213> ORGANISM: Ixodes scapularis

<400> SEQUENCE: 310

Gly Gly Gly Glu Asn His Phe Glu Thr Leu Leu Lys Cys Asn Glu Ser
 1               5                  10                  15

Cys

<210> SEQ ID NO 311
<211> LENGTH: 16
<212> TYPE: PRT
<213> ORGANISM: Ixodes scapularis

SEQUENCE: 311

Gly Gly Glu Asn His Phe Glu Thr Leu Leu Lys Cys Asn Glu Ser Cys
 1               5                  10                  15

<210> SEQ ID NO 312
<211> LENGTH: 15
<212> TYPE: PRT
<213> ORGANISM: Ixodes scapularis

<400> SEQUENCE: 312

Gly Glu Asn His Phe Glu Thr Leu Leu Lys Cys Asn Glu Ser Cys
 1               5                  10                  15

<210> SEQ ID NO 313
<211> LENGTH: 14
<212> TYPE: PRT
<213> ORGANISM: Ixodes scapularis

<400> SEQUENCE: 313

Glu Asn His Phe Glu Thr Leu Leu Lys Cys Asn Glu Ser Cys
 1               5                  10

<210> SEQ ID NO 314
<211> LENGTH: 13
<212> TYPE: PRT
<213> ORGANISM: Ixodes scapularis

<400> SEQUENCE: 314

Asn His Phe Glu Thr Leu Leu Lys Cys Asn Glu Ser Cys
 1               5                  10

<210> SEQ ID NO 315
<211> LENGTH: 12
<212> TYPE: PRT
<213> ORGANISM: Ixodes scapularis

<400> SEQUENCE: 315

His Phe Glu Thr Leu Leu Lys Cys Asn Glu Ser Cys
 1               5                  10

<210> SEQ ID NO 316
```

```
<211> LENGTH: 11
<212> TYPE: PRT
<213> ORGANISM: Ixodes scapularis

<400> SEQUENCE: 316

Phe Glu Thr Leu Leu Lys Cys Asn Glu Ser Cys
 1               5                  10

<210> SEQ ID NO 317
<211> LENGTH: 10
<212> TYPE: PRT
<213> ORGANISM: Ixodes scapularis

<400> SEQUENCE: 317

Glu Thr Leu Leu Lys Cys Asn Glu Ser Cys
 1               5                  10

<210> SEQ ID NO 318
<211> LENGTH: 9
<212> TYPE: PRT
<213> ORGANISM: Ixodes scapularis

<400> SEQUENCE: 318

Thr Leu Leu Lys Cys Asn Glu Ser Cys
 1               5

<210> SEQ ID NO 319
<211> LENGTH: 8
<212> TYPE: PRT
<213> ORGANISM: Ixodes scapularis

<400> SEQUENCE: 319

Leu Leu Lys Cys Asn Glu Ser Cys
 1               5

<210> SEQ ID NO 320
<211> LENGTH: 7
<212> TYPE: PRT
<213> ORGANISM: Ixodes scapularis

<400> SEQUENCE: 320

Leu Lys Cys Asn Glu Ser Cys
 1               5

<210> SEQ ID NO 321
<211> LENGTH: 6
<212> TYPE: PRT
<213> ORGANISM: Ixodes scapularis

<400> SEQUENCE: 321

Lys Cys Asn Glu Ser Cys
 1               5

<210> SEQ ID NO 322
<211> LENGTH: 5
<212> TYPE: PRT
<213> ORGANISM: Ixodes scapularis

<400> SEQUENCE: 322

Cys Asn Glu Ser Cys
 1               5

<210> SEQ ID NO 323
<211> LENGTH: 4
<212> TYPE: PRT
```

<213> ORGANISM: Ixodes scapularis

<400> SEQUENCE: 323

Asn Glu Ser Cys
 1

<210> SEQ ID NO 324
<211> LENGTH: 3

```
<400> SEQUENCE: 328

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn His Phe Glu Thr Leu Leu Lys Cys
        35                  40                  45

<210> SEQ ID NO 329
<211> LENGTH: 46
<212> TYPE: PRT
<213> ORGANISM: Ixodes scapularis

<400> SEQUENCE: 329

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn His Phe Glu Thr Leu Leu Lys
        35                  40                  45

<210> SEQ ID NO 330
<211> LENGTH: 45
<212> TYPE: PRT
<213> ORGANISM: Ixodes scapularis

<400> SEQUENCE: 330

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn His Phe Glu Thr Leu Leu
        35                  40                  45

<210> SEQ ID NO 331
<211> LENGTH: 44
<212> TYPE: PRT
<213> ORGANISM: Ixodes scapularis

<400> SEQUENCE: 331

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn His Phe Glu Thr Leu
        35                  40

<210> SEQ ID NO 332
<211> LENGTH: 43
<212> TYPE: PRT
<213> ORGANISM: Ixodes scapularis

<400> SEQUENCE: 332

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn His Phe Glu Thr
        35                  40
```

```
<210> SEQ ID NO 333
<211> LENGTH: 42
<212> TYPE: PRT
<213> ORGANISM: Ixodes scapularis

<400> SEQUENCE: 333

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn His Phe Glu
        35                  40

<210> SEQ ID NO 334
<211> LENGTH: 41
<212> TYPE: PRT
<213> ORGANISM: Ixodes scapularis

<400> SEQUENCE: 334

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn His Phe
        35                  40

<210> SEQ ID NO 335
<211> LENGTH: 40
<212> TYPE: PRT
<213> ORGANISM: Ixodes scapularis

<400> SEQUENCE: 335

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn His
        35                  40

<210> SEQ ID NO 336
<211> LENGTH: 39
<212> TYPE: PRT
<213> ORGANISM: Ixodes scapularis

<400> SEQUENCE: 336

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu Cys Gly Gly Gly Glu Asn
        35

<210> SEQ ID NO 337
<211> LENGTH: 38
<212> TYPE: PRT
<213> ORGANISM: Ixodes scapularis

<400> SEQUENCE: 337

Cys Leu Asp Pro Glu Gln Val Thr Cys Glu Ser Gln Glu Gly Thr His
1               5                   10                  15
```

```
Ala Ser Tyr Asn Arg Lys Thr Gly Gln Cys Glu Glu Gln Lys Gly Thr
            20                  25                  30

Glu Cys Gly Gly Gly Glu
        35

<210> SEQ ID NO 338
<211> LENGTH: 37
<212> TYPE: PRT
<213> ORGANISM: Ixodes scapularis

<400> SEQUENCE: 338

Cys Leu Asp Pro Glu Gln Val Thr Cys Glu Ser Gln Glu Gly Thr His
  1               5                  10                  15

Ala Ser Tyr Asn Arg Lys Thr Gly Gln Cys Glu Glu Gln Lys Gly Thr
            20                  25                  30

Glu Cys Gly Gly Gly
        35

<210> SEQ ID NO 339
<211> LENGTH: 36
<212> TYPE: PRT
<213> ORGANISM: Ixodes scapularis

<400> SEQUENCE: 339

Cys Leu Asp Pro Glu Gln Val Thr Cys Glu Ser Gln Glu Gly Thr His
  1               5                  10                  15

Ala Ser Tyr Asn Arg Lys Thr Gly Gln Cys Glu Glu Gln Lys Gly Thr
            20                  25                  30

Glu Cys Gly Gly
        35

<210> SEQ ID NO 340
<211> LENGTH: 35
<212> TYPE: PRT
<213> ORGANISM: Ixodes scapularis

<400> SEQUENCE: 340

Cys Leu Asp Pro Glu Gln Val Thr Cys Glu Ser Gln Glu Gly Thr His
  1               5                  10                  15

Ala Ser Tyr Asn Arg Lys Thr Gly Gln Cys Glu Glu Gln Lys Gly Thr
            20                  25                  30

Glu Cys Gly
        35

<210> SEQ ID NO 341
<211> LENGTH: 34
<212> TYPE: PRT
<213> ORGANISM: Ixodes scapularis

<400> SEQUENCE: 341

Cys Leu Asp Pro Glu Gln Val Thr Cys Glu Ser Gln Glu Gly Thr His
  1               5                  10                  15

Ala Ser Tyr Asn Arg Lys Thr Gly Gln Cys Glu Glu Gln Lys Gly Thr
            20                  25                  30

Glu Cys

<210> SEQ ID NO 342
<211> LENGTH: 33
<212> TYPE: PRT
<213> ORGANISM: Ixodes scapularis
```

<400> SEQUENCE: 342

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

Glu

<210> SEQ ID NO 343
<211> LENGTH: 32
<212> TYPE: PRT
<213> ORGANISM: Ixodes scapularis

<400> SEQUENCE: 343

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly Thr
            20                  25                  30

<210> SEQ ID NO 344
<211> LENGTH: 31
<212> TYPE: PRT
<213> ORGANISM: Ixodes scapularis

<400> SEQUENCE: 344

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys Gly
            20                  25                  30

<210> SEQ ID NO 345
<211> LENGTH: 30
<212> TYPE: PRT
<213> ORGANISM: Ixodes scapularis

<400> SEQUENCE: 345

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln Lys
            20                  25                  30

<210> SEQ ID NO 346
<211> LENGTH: 29
<212> TYPE: PRT
<213> ORGANISM: Ixodes scapularis

<400> SEQUENCE: 346

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu Gln
            20                  25

<210> SEQ ID NO 347
<211> LENGTH: 28
<212> TYPE: PRT
<213> ORGANISM: Ixodes scapularis

<400> SEQUENCE: 347

Cys Leu Asp Pro Glu Gln Val Thr Cys Glu Ser Gln Glu Gly Thr His
1               5                   10                  15

Ala Ser Tyr Asn Arg Lys Thr Gly Gln Cys Glu Glu
            20                  25

```
                20              25

<210> SEQ ID NO 348
<211> LENGTH: 27
<212> TYPE: PRT
<213> ORGANISM: Ixodes scapularis

<400> SEQUENCE: 348

Cys Leu Asp Pro Glu Gln Val Thr Cys Glu Ser Gln Glu Gly Thr His
 1               5                  10                  15

Ala Ser Tyr Asn Arg Lys Thr Gly Gln Cys Glu
            20                  25

<210> SEQ ID NO 349
<211> LENGTH: 26
<212> TYPE: PRT
<213> ORGANISM: Ixodes scapularis

<400> SEQUENCE: 349

Cys Leu Asp Pro Glu Gln Val Thr Cys Glu Ser Gln Glu Gly Thr His
 1               5                  10                  15

Ala Ser Tyr Asn Arg Lys Thr Gly Gln Cys
            20                  25

<210> SEQ ID NO 350
<211> LENGTH: 25
<212> TYPE: PRT
<213> ORGANISM: Ixodes scapularis

<400> SEQUENCE: 350

Cys Leu Asp Pro Glu Gln Val Thr Cys Glu Ser Gln Glu Gly Thr His
 1               5                  10                  15

Ala Ser Tyr Asn Arg Lys Thr Gly Gln
            20                  25

<210> SEQ ID NO 351
<211> LENGTH: 24
<212> TYPE: PRT
<213> ORGANISM: Ixodes scapularis

<400> SEQUENCE: 351

Cys Leu Asp Pro Glu Gln Val Thr Cys Glu Ser Gln Glu Gly Thr His
 1               5                  10                  15

Ala Ser Tyr Asn Arg Lys Thr Gly
            20

<210> SEQ ID NO 352
<211> LENGTH: 23
<212> TYPE: PRT
<213> ORGANISM: Ixodes scapularis

<400> SEQUENCE: 352

Cys Leu Asp Pro Glu Gln Val Thr Cys Glu Ser Gln Glu Gly Thr His
 1               5                  10                  15

Ala Ser Tyr Asn Arg Lys Thr
            20

<210> SEQ ID NO 353
<211> LENGTH: 22
<212> TYPE: PRT
<213> ORGANISM: Ixodes scapularis

<400> SEQUENCE: 353
```

```
Cys Leu Asp Pro Glu Gln Val Thr Cys Glu Ser Gln Glu Gly Thr His
1               5                   10                  15

Ala Ser Tyr Asn Arg Lys
            20

<210> SEQ ID NO 354
<211> LENGTH: 21
<212> TYPE: PRT
<213> ORGANISM: Ixodes scapularis

<400> SEQUENCE: 354

Cys Leu Asp Pro Glu Gln Val Thr Cys Glu Ser Gln Glu Gly Thr His
1               5                   10                  15

Ala Ser Tyr Asn Arg
            20

<210> SEQ ID NO 355
<211> LENGTH: 20
<212> TYPE: PRT
<213> ORGANISM: Ixodes scapularis

<400> SEQUENCE: 355

Cys Leu Asp Pro Glu Gln Val Thr Cys Glu Ser Gln Glu Gly Thr His
1               5                   10                  15

Ala Ser Tyr Asn
            20

<210> SEQ ID NO 356
<211> LENGTH: 19
<212> TYPE: PRT
<213> ORGANISM: Ixodes scapularis

<400> SEQUENCE: 356

Cys Leu Asp Pro Glu Gln Val Thr Cys Glu Ser Gln Glu Gly Thr His
1               5                   10                  15

Ala Ser Tyr

<210> SEQ ID NO 357
<211> LENGTH: 18
<212> TYPE: PRT
<213> ORGANISM: Ixodes scapularis

<400> SEQUENCE: 357

Cys Leu Asp Pro Glu Gln Val Thr Cys Glu Ser Gln Glu Gly Thr His
1               5                   10                  15

Ala Ser

<210> SEQ ID NO 358
<211> LENGTH: 17
<212> TYPE: PRT
<213> ORGANISM: Ixodes scapularis

<400> SEQUENCE: 358

Cys Leu Asp Pro Glu Gln Val Thr Cys Glu Ser Gln Glu Gly Thr His
1               5                   10                  15

Ala

<210> SEQ ID NO 359
<211> LENGTH: 16
<212> TYPE: PRT
<213> ORGANISM: Ixodes scapularis
```

<400> SEQUENCE: 359

Cys Leu Asp Pro Glu Gln Val Thr Cys Glu Ser Gln Glu Gly Thr His
1               5                   10                  15

<210> SEQ ID NO 360
<211> LENGTH: 15
<212> TYPE: PRT
<213> ORGANISM: Ixodes scapularis

<400> SEQUENCE: 360

Cys Leu Asp Pro Glu Gln Val Thr Cys Glu Ser Gln Glu Gly Thr
1               5                   10                  15

<210> SEQ ID NO 361
<211> LENGTH: 14
<212> TYPE: PRT
<213> ORGANISM: Ixodes scapularis

<400> SEQUENCE: 361

Cys Leu Asp Pro Glu Gln Val Thr Cys Glu Ser Gln Glu Gly
1               5                   10

<210> SEQ ID NO 362
<211> LENGTH: 13
<212> TYPE: PRT
<213> ORGANISM: Ixodes scapularis

<400> SEQUENCE: 362

Cys Leu Asp Pro Glu Gln Val Thr Cys Glu Ser Gln Glu
1               5                   10

<210> SEQ ID NO 363
<211> LENGTH: 12
<212> TYPE: PRT
<213> ORGANISM: Ixodes scapularis

<400> SEQUENCE: 363

Cys Leu Asp Pro Glu Gln Val Thr Cys Glu Ser Gln
1               5                   10

<210> SEQ ID NO 364
<211> LENGTH: 11
<212> TYPE: PRT
<213> ORGANISM: Ixodes scapularis

<400> SEQUENCE: 364

Cys Leu Asp Pro Glu Gln Val Thr Cys Glu Ser
1               5                   10

<210> SEQ ID NO 365
<211> LENGTH: 10
<212> TYPE: PRT
<213> ORGANISM: Ixodes scapularis

<400> SEQUENCE: 365

Cys Leu Asp Pro Glu Gln Val Thr Cys Glu
1               5                   10

<210> SEQ ID NO 366
<211> LENGTH: 9
<212> TYPE: PRT
<213> ORGANISM: Ixodes scapularis

<400> SEQUENCE: 366

```
Cys Leu Asp Pro Glu Gln Val Thr Cys
 1               5

<210> SEQ ID NO 367
<211> LENGTH: 8
<212> TYPE: PRT
<213> ORGANISM: Ixodes scapularis

<400> SEQUENCE: 367

Cys Leu Asp Pro Glu Gln Val Thr
 1               5

<210> SEQ ID NO 368
<211> LENGTH: 7
<212> TYPE: PRT
<213> ORGANISM: Ixodes scapularis

<400> SEQUENCE: 368

Cys Leu Asp Pro Glu Gln Val
 1               5

<210> SEQ ID NO 369
<211> LENGTH: 6
<212> TYPE: PRT
<213> ORGANISM: Ixodes scapularis

<400> SEQUENCE: 369

Cys Leu Asp Pro Glu Gln
 1               5

<210> SEQ ID NO 370
<211> LENGTH: 5
<212> TYPE: PRT
<213> ORGANISM: Ixodes scapularis

<400> SEQUENCE: 370

Cys Leu Asp Pro Glu
 1               5

<210> SEQ ID NO 371
<211> LENGTH: 4
<212> TYPE: PRT
<213> ORGANISM: Ixodes scapularis

<400> SEQUENCE: 371

Cys Leu Asp Pro
 1

<210> SEQ ID NO 372
<211> LENGTH: 3
<212> TYPE: PRT
<213> ORGANISM: Ixodes scapularis

<400> SEQUENCE: 372

Cys Leu Asp
 1

<210> SEQ ID NO 373
<211> LENGTH: 51
<212> TYPE: PRT
<213> ORGANISM: Ixodes scapularis

<400> SEQUENCE: 373

Cys Ser Leu Glu Val Asp Tyr Gly Val Gly Arg Ala Asn Ile Pro Arg
```

```
                1               5                   10                  15
Trp Tyr Tyr Asp Thr Asn Asn Ala Thr Cys Glu Met Phe Thr Tyr Gly
                    20                  25                  30

Gly Ile Thr Gly Asn Lys Asn Asn Phe Glu Ser Glu Glu Glu Cys Lys
            35                  40                  45

Glu Thr Cys
        50

<210> SEQ ID NO 374
<211> LENGTH: 50
<212> TYPE: PRT
<213> ORGANISM: Ixodes scapularis

<400> SEQUENCE: 374

Ser Leu Glu Val Asp Tyr Gly Val Gly Arg Ala Asn Ile Pro Arg Trp
1               5                   10                  15

Tyr Tyr Asp Thr Asn Asn Ala Thr Cys Glu Met Phe Thr Tyr Gly Gly
                20                  25                  30

Ile Thr Gly Asn Lys Asn Asn Phe Glu Ser Glu Glu Glu Cys Lys Glu
            35                  40                  45

Thr Cys
    50

<210> SEQ ID NO 375
<211> LENGTH: 49
<212> TYPE: PRT
<213> ORGANISM: Ixodes scapularis

<400> SEQUENCE: 375

Leu Glu Val Asp Tyr Gly Val Gly Arg Ala Asn Ile Pro Arg Trp Tyr
1               5                   10                  15

Tyr Asp Thr Asn Asn Ala Thr Cys Glu Met Phe Thr Tyr Gly Gly Ile
                20                  25                  30

Thr Gly Asn Lys Asn Asn Phe Glu Ser Glu Glu Glu Cys Lys Glu Thr
            35                  40                  45

Cys

<210> SEQ ID NO 376
<211> LENGTH: 48
<212> TYPE: PRT
<213> ORGANISM: Ixodes scapularis

<400> SEQUENCE: 376

Glu Val Asp Tyr Gly Val Gly Arg Ala Asn Ile Pro Arg Trp Tyr Tyr
1               5                   10                  15

Asp Thr Asn Asn Ala Thr Cys Glu Met Phe Thr Tyr Gly Gly Ile Thr
                20                  25                  30

Gly Asn Lys Asn Asn Phe Glu Ser Glu Glu Glu Cys Lys Glu Thr Cys
            35                  40                  45

<210> SEQ ID NO 377
<211> LENGTH: 47
<212> TYPE: PRT
<213> ORGANISM: Ixodes scapularis

<400> SEQUENCE: 377

Val Asp Tyr Gly Val Gly Arg Ala Asn Ile Pro Arg Trp Tyr Tyr Asp
1               5                   10                  15

Thr Asn Asn Ala Thr Cys Glu Met Phe Thr Tyr Gly Gly Ile Thr Gly
```

```
                20              25              30
Asn Lys Asn Asn Phe Glu Ser Glu Glu Cys Lys Glu Thr Cys
         35              40              45

<210> SEQ ID NO 378
<211> LENGTH: 46
<212> TYPE: PRT
<213> ORGANISM: Ixodes scapularis

<400> SEQUENCE: 378

Asp Tyr Gly Val Gly Arg Ala Asn Ile Pro Arg Trp Tyr Tyr Asp Thr
 1               5                  10                  15
Asn Asn Ala Thr Cys Glu Met Phe Thr Tyr Gly Gly Ile Thr Gly Asn
             20                  25                  30
Lys Asn Asn Phe Glu Ser Glu Glu Cys Lys Glu Thr Cys
         35                  40                  45

<210> SEQ ID NO 379
<211> LENGTH: 45
<212> TYPE: PRT
<213> ORGANISM: Ixodes scapularis

<400> SEQUENCE: 379

Tyr Gly Val Gly Arg Ala Asn Ile Pro Arg Trp Tyr Tyr Asp Thr Asn
 1               5                  10                  15
Asn Ala Thr Cys Glu Met Phe Thr Tyr Gly Gly Ile Thr Gly Asn Lys
             20                  25                  30
Asn Asn Phe Glu Ser Glu Glu Cys Lys Glu Thr Cys
         35                  40                  45

<210> SEQ ID NO 380
<211> LENGTH: 44
<212> TYPE: PRT
<213> ORGANISM: Ixodes scapularis

<400> SEQUENCE: 380

Gly Val Gly Arg Ala Asn Ile Pro Arg Trp Tyr Tyr Asp Thr Asn Asn
 1               5                  10                  15
Ala Thr Cys Glu Met Phe Thr Tyr Gly Gly Ile Thr Gly Asn Lys Asn
             20                  25                  30
Asn Phe Glu Ser Glu Glu Cys Lys Glu Thr Cys
         35                  40

<210> SEQ ID NO 381
<211> LENGTH: 43
<212> TYPE: PRT
<213> ORGANISM: Ixodes scapularis

<400> SEQUENCE: 381

Val Gly Arg Ala Asn Ile Pro Arg Trp Tyr Tyr Asp Thr Asn Asn Ala
 1               5                  10                  15
Thr Cys Glu Met Phe Thr Tyr Gly Gly Ile Thr Gly Asn Lys Asn Asn
             20                  25                  30
Phe Glu Ser Glu Glu Cys Lys Glu Thr Cys
         35                  40

<210> SEQ ID NO 382
<211> LENGTH: 42
<212> TYPE: PRT
<213> ORGANISM: Ixodes scapularis
```

-continued

```
<400> SEQUENCE: 382

Gly Arg Ala Asn Ile Pro Arg Trp Tyr Tyr Asp Thr Asn Asn Ala Thr
1               5                  10                  15
Cys Glu Met Phe Thr Tyr Gly Gly Ile Thr Gly Asn Lys Asn Asn Phe
            20                  25                  30
Glu Ser Glu Glu Glu Cys Lys Glu Thr Cys
        35                  40

<210> SEQ ID NO 383
<211> LENGTH: 41
<212> TYPE: PRT
<213> ORGANISM: Ixodes scapularis

<400> SEQUENCE: 383

Arg Ala Asn Ile Pro Arg Trp Tyr Tyr Asp Thr Asn Asn Ala Thr Cys
1               5                  10                  15
Glu Met Phe Thr Tyr Gly Gly Ile Thr Gly Asn Lys Asn Asn Phe Glu
            20                  25                  30
Ser Glu Glu Glu Cys Lys Glu Thr Cys
        35                  40

<210> SEQ ID NO 384
<211> LENGTH: 40
<212> TYPE: PRT
<213> ORGANISM: Ixodes scapularis

<400> SEQUENCE: 384

Ala Asn Ile Pro Arg Trp Tyr Tyr Asp Thr Asn Asn Ala Thr Cys Glu
1               5                  10                  15
Met Phe Thr Tyr Gly Gly Ile Thr Gly Asn Lys Asn Asn Phe Glu Ser
            20                  25                  30
Glu Glu Glu Cys Lys Glu Thr Cys
        35                  40

<210> SEQ ID NO 385
<211> LENGTH: 39
<212> TYPE: PRT
<213> ORGANISM: Ixodes scapularis

<400> SEQUENCE: 385

Asn Ile Pro Arg Trp Tyr Tyr Asp Thr Asn Asn Ala Thr Cys Glu Met
1               5                  10                  15
Phe Thr Tyr Gly Gly Ile Thr Gly Asn Lys Asn Asn Phe Glu Ser Glu
            20                  25                  30
Glu Glu Cys Lys Glu Thr Cys
        35

<210> SEQ ID NO 386
<211> LENGTH: 38
<212> TYPE: PRT
<213> ORGANISM: Ixodes scapularis

<400> SEQUENCE: 386

Ile Pro Arg Trp Tyr Tyr Asp Thr Asn Asn Ala Thr Cys Glu Met Phe
1               5                  10                  15
Thr Tyr Gly Gly Ile Thr Gly Asn Lys Asn Asn Phe Glu Ser Glu Glu
            20                  25                  30
Glu Cys Lys Glu Thr Cys
        35
```

```
<210> SEQ ID NO 387
<211> LENGTH: 37
<212> TYPE: PRT
<213> ORGANISM: Ixodes scapularis

<400> SEQUENCE: 387

Pro Arg Trp Tyr Tyr Asp Thr Asn Asn Ala Thr Cys Glu Met Phe Thr
 1               5                  10                  15

Tyr Gly Gly Ile Thr Gly Asn Lys Asn Asn Phe Glu Ser Glu Glu Glu
            20                  25                  30

Cys Lys Glu Thr Cys
         35

<210> SEQ ID NO 388
<211> LENGTH: 36
<212> TYPE: PRT
<213> ORGANISM: Ixodes scapularis

<400> SEQUENCE: 388

Arg Trp Tyr Tyr Asp Thr Asn Asn Ala Thr Cys Glu Met Phe Thr Tyr
 1               5                  10                  15

Gly Gly Ile Thr Gly Asn Lys Asn Asn Phe Glu Ser Glu Glu Glu Cys
            20                  25                  30

Lys Glu Thr Cys
         35

<210> SEQ ID NO 389
<211> LENGTH: 35
<212> TYPE: PRT
<213> ORGANISM: Ixodes scapularis

<400> SEQUENCE: 389

Trp Tyr Tyr Asp Thr Asn Asn Ala Thr Cys Glu Met Phe Thr Tyr Gly
 1               5                  10                  15

Gly Ile Thr Gly Asn Lys Asn Asn Phe Glu Ser Glu Glu Glu Cys Lys
            20                  25                  30

Glu Thr Cys
         35

<210> SEQ ID NO 390
<211> LENGTH: 34
<212> TYPE: PRT
<213> ORGANISM: Ixodes scapularis

<400> SEQUENCE: 390

Tyr Tyr Asp Thr Asn Asn Ala Thr Cys Glu Met Phe Thr Tyr Gly Gly
 1               5                  10                  15

Ile Thr Gly Asn Lys Asn Asn Phe Glu Ser Glu Glu Glu Cys Lys Glu
            20                  25                  30

Thr Cys

<210> SEQ ID NO 391
<211> LENGTH: 33
<212> TYPE: PRT
<213> ORGANISM: Ixodes scapularis

<400> SEQUENCE: 391

Tyr Asp Thr Asn Asn Ala Thr Cys Glu Met Phe Thr Tyr Gly Gly Ile
 1               5                  10                  15

Thr Gly Asn Lys Asn Asn Phe Glu Ser Glu Glu Glu Cys Lys Glu Thr
```

```
                    20                  25                  30

Cys

<210> SEQ ID NO 392
<211> LENGTH: 32
<212> TYPE: PRT
<213> ORGANISM: Ixodes scapularis

<400> SEQUENCE: 392

Asp Thr Asn Asn Ala Thr Cys Glu Met Phe Thr Tyr Gly Gly Ile Thr
 1               5                  10                  15

Gly Asn Lys Asn Asn Phe Glu Ser Glu Glu Cys Lys Glu Thr Cys
            20                  25                  30

<210> SEQ ID NO 393
<211> LENGTH: 31
<212> TYPE: PRT
<213> ORGANISM: Ixodes scapularis

<400> SEQUENCE: 393

Thr Asn Asn Ala Thr Cys Glu Met Phe Thr Tyr Gly Gly Ile Thr Gly
 1               5                  10                  15

Asn Lys Asn Asn Phe Glu Ser Glu Glu Cys Lys Glu Thr Cys
            20                  25                  30

<210> SEQ ID NO 394
<211> LENGTH: 30
<212> TYPE: PRT
<213> ORGANISM: Ixodes scapularis

<400> SEQUENCE: 394

Asn Asn Ala Thr Cys Glu Met Phe Thr Tyr Gly Gly Ile Thr Gly Asn
 1               5                  10                  15

Lys Asn Asn Phe Glu Ser Glu Glu Cys Lys Glu Thr Cys
            20                  25                  30

<210> SEQ ID NO 395
<211> LENGTH: 29
<212> TYPE: PRT
<213> ORGANISM: Ixodes scapularis

<400> SEQUENCE: 395

Asn Ala Thr Cys Glu Met Phe Thr Tyr Gly Gly Ile Thr Gly Asn Lys
 1               5                  10                  15

Asn Asn Phe Glu Ser Glu Glu Cys Lys Glu Thr Cys
            20                  25

<210> SEQ ID NO 396
<211> LENGTH: 28
<212> TYPE: PRT
<213> ORGANISM: Ixodes scapularis

<400> SEQUENCE: 396

Ala Thr Cys Glu Met Phe Thr Tyr Gly Gly Ile Thr Gly Asn Lys Asn
 1               5                  10                  15

Asn Phe Glu Ser Glu Glu Cys Lys Glu Thr Cys
            20                  25

<210> SEQ ID NO 397
<211> LENGTH: 27
<212> TYPE: PRT
<213> ORGANISM: Ixodes scapularis
```

-continued

```
<400> SEQUENCE: 397

Thr Cys Glu Met Phe Thr Tyr Gly Gly Ile Thr Gly Asn Lys Asn Asn
1               5                   10                  15

Phe Glu Ser Glu Glu Glu Cys Lys Glu Thr Cys
            20                  25

<210> SEQ ID NO 398
<211> LENGTH: 26
<212> TYPE: PRT
<213> ORGANISM: Ixodes scapularis

<400> SEQUENCE: 398

Cys Glu Met Phe Thr Tyr Gly Gly Ile Thr Gly Asn Lys Asn Asn Phe
1               5                   10                  15

Glu Ser Glu Glu Glu Cys Lys Glu Thr Cys
            20                  25

<210> SEQ ID NO 399
<211> LENGTH: 25
<212> TYPE: PRT
<213> ORGANISM: Ixodes scapularis

<400> SEQUENCE: 399

Glu Met Phe Thr Tyr Gly Gly Ile Thr Gly Asn Lys Asn Asn Phe Glu
1               5                   10                  15

Ser Glu Glu Glu Cys Lys Glu Thr Cys
            20                  25

<210> SEQ ID NO 400
<211> LENGTH: 24
<212> TYPE: PRT
<213> ORGANISM: Ixodes scapularis

<400> SEQUENCE: 400

Met Phe Thr Tyr Gly Gly Ile Thr Gly Asn Lys Asn Asn Phe Glu Ser
1               5                   10                  15

Glu Glu Glu Cys Lys Glu Thr Cys
            20

<210> SEQ ID NO 401
<211> LENGTH: 23
<212> TYPE: PRT
<213> ORGANISM: Ixodes scapularis

<400> SEQUENCE: 401

Phe Thr Tyr Gly Gly Ile Thr Gly Asn Lys Asn Asn Phe Glu Ser Glu
1               5                   10                  15

Glu Glu Cys Lys Glu Thr Cys
            20

<210> SEQ ID NO 402
<211> LENGTH: 22
<212> TYPE: PRT
<213> ORGANISM: Ixodes scapularis

<400> SEQUENCE: 402

Thr Tyr Gly Gly Ile Thr Gly Asn Lys Asn Asn Phe Glu Ser Glu Glu
1               5                   10                  15

Glu Cys Lys Glu Thr Cys
            20
```

```
<210> SEQ ID NO 403
<211> LENGTH: 21
<212> TYPE: PRT
<213> ORGANISM: Ixodes scapularis

<400> SEQUENCE: 403

Tyr Gly Gly Ile Thr Gly Asn Lys Asn Asn Phe Glu Ser Glu Glu Glu
 1               5                  10                  15

Cys Lys Glu Thr Cys
            20

<210> SEQ ID NO 404
<211> LENGTH: 20
<212> TYPE: PRT
<213> ORGANISM: Ixodes scapularis

<400> SEQUENCE: 404

Gly Gly Ile Thr Gly Asn Lys Asn Asn Phe Glu Ser Glu Glu Glu Cys
 1               5                  10                  15

Lys Glu Thr Cys
            20

<210> SEQ ID NO 405
<211> LENGTH: 19
<212> TYPE: PRT
<213> ORGANISM: Ixodes scapularis

<400> SEQUENCE: 405

Gly Ile Thr Gly Asn Lys Asn Asn Phe Glu Ser Glu Glu Glu Cys Lys
 1               5                  10                  15

Glu Thr Cys

<210> SEQ ID NO 406
<211> LENGTH: 18
<212> TYPE: PRT
<213> ORGANISM: Ixodes scapularis

<400> SEQUENCE: 406

Ile Thr Gly Asn Lys Asn Asn Phe Glu Ser Glu Glu Glu Cys Lys Glu
 1               5                  10                  15

Thr Cys

<210> SEQ ID NO 407
<211> LENGTH: 17
<212> TYPE: PRT
<213> ORGANISM: Ixodes scapularis

<400> SEQUENCE: 407

Thr Gly Asn Lys Asn Asn Phe Glu Ser Glu Glu Glu Cys Lys Glu Thr
 1               5                  10                  15

Cys

<210> SEQ ID NO 408
<211> LENGTH: 16
<212> TYPE: PRT
<213> ORGANISM: Ixodes scapularis

<400> SEQUENCE: 408

Gly Asn Lys Asn Asn Phe Glu Ser Glu Glu Glu Cys Lys Glu Thr Cys
 1               5                  10                  15
```

```
<210> SEQ ID NO 409
<211> LENGTH: 15
<212> TYPE: PRT
<213> ORGANISM: Ixodes scapularis

<400> SEQUENCE: 409

Asn Lys Asn Asn Phe Glu Ser Glu Glu Glu Cys Lys Glu Thr Cys
1               5                   10                  15

<210> SEQ ID NO 410
<211> LENGTH: 14
<212> TYPE: PRT
<213> ORGANISM: Ixodes scapularis

<400> SEQUENCE: 410

Lys Asn Asn Phe Glu Ser Glu Glu Glu Cys Lys Glu Thr Cys
1               5                   10

<210> SEQ ID NO 411
<211> LENGTH: 13
<212> TYPE: PRT
<213> ORGANISM: Ixodes scapularis

<400> SEQUENCE: 411

Asn Asn Phe Glu Ser Glu Glu Glu Cys Lys Glu Thr Cys
1               5                   10

<210> SEQ ID NO 412
<211> LENGTH: 12
<212> TYPE: PRT
<213> ORGANISM: Ixodes scapularis

<400> SEQUENCE: 412

Asn Phe Glu Ser Glu Glu Glu Cys Lys Glu Thr Cys
1               5                   10

<210> SEQ ID NO 413
<211> LENGTH: 11
<212> TYPE: PRT
<213> ORGANISM: Ixodes scapularis

<400> SEQUENCE: 413

Phe Glu Ser Glu Glu Glu Cys Lys Glu Thr Cys
1               5                   10

<210> SEQ ID NO 414
<211> LENGTH: 10
<212> TYPE: PRT
<213> ORGANISM: Ixodes scapularis

<400> SEQUENCE: 414

Glu Ser Glu Glu Glu Cys Lys Glu Thr Cys
1               5                   10

<210> SEQ ID NO 415
<211> LENGTH: 9
<212> TYPE: PRT
<213> ORGANISM: Ixodes scapularis

<400> SEQUENCE: 415

Ser Glu Glu Glu Cys Lys Glu Thr Cys
1               5

<210> SEQ ID NO 416
<211> LENGTH: 8
```

-continued

```
<212> TYPE: PRT
<213> ORGANISM: Ixodes scapularis

<400> SEQUENCE: 416

Glu Glu Glu Cys Lys Glu Thr Cys
 1               5

<210> SEQ ID NO 417
<211> LENGTH: 7
<212> TYPE: PRT
<213> ORGANISM: Ixodes scapularis

<400> SEQUENCE: 417

Glu Glu Cys Lys Glu Thr Cys
 1               5

<210> SEQ ID NO 418
<211> LENGTH: 6
<212> TYPE: PRT
<213> ORGANISM: Ixodes scapularis

<400> SEQUENCE: 418

Glu Cys Lys Glu Thr Cys
 1               5

<210> SEQ ID NO 419
<211> LENGTH: 5
<212> TYPE: PRT
<213> ORGANISM: Ixodes scapularis

<400> SEQUENCE: 419

Cys Lys Glu Thr Cys
 1               5

<210> SEQ ID NO 420
<211> LENGTH: 4
<212> TYPE: PRT
<213> ORGANISM: Ixodes scapularis

<400> SEQUENCE: 420

Lys Glu Thr Cys
 1

<210> SEQ ID NO 421
<211> LENGTH: 3
<212> TYPE: PRT
<213> ORGANISM: Ixodes scapularis

<400> SEQUENCE: 421

Glu Thr Cys
 1

<210> SEQ ID NO 422
<211> LENGTH: 50
<212> TYPE: PRT
<213> ORGANISM: Ixodes scapularis

<400> SEQUENCE: 422

Cys Ser Leu Glu Val Asp Tyr Gly Val Gly Arg Ala Asn Ile Pro Arg
 1               5                  10                  15

Trp Tyr Tyr Asp Thr Asn Asn Ala Thr Cys Glu Met Phe Thr Tyr Gly
                20                  25                  30

Gly Ile Thr Gly Asn Lys Asn Asn Phe Glu Ser Glu Glu Glu Cys Lys
            35                  40                  45
```

```
Glu Thr
    50

<210> SEQ ID NO 423
<211> LENGTH: 49
<212> TYPE: PRT
<213> ORGANISM: Ixodes scapularis

<400> SEQUENCE: 423

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe Glu Ser Glu Glu Glu Cys Lys
        35                  40                  45

Glu

<210> SEQ ID NO 424
<211> LENGTH: 48
<212> TYPE: PRT
<213> ORGANISM: Ixodes scapularis

<400> SEQUENCE: 424

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe Glu Ser Glu Glu Glu Cys Lys
        35                  40                  45

<210> SEQ ID NO 425
<211> LENGTH: 47
<212> TYPE: PRT
<213> ORGANISM: Ixodes scapularis

<400> SEQUENCE: 425

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe Glu Ser Glu Glu Glu Cys
        35                  40                  45

<210> SEQ ID NO 426
<211> LENGTH: 46
<212> TYPE: PRT
<213> ORGANISM: Ixodes scapularis

<400> SEQUENCE: 426

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe Glu Ser Glu Glu Glu
        35                  40                  45

<210> SEQ ID NO 427
<211> LENGTH: 45
<212> TYPE: PRT
<213> ORGANISM: Ixodes scapularis
```

```
<400> SEQUENCE: 427

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe Glu Ser Glu Glu
        35                  40                  45

<210> SEQ ID NO 428
<211> LENGTH: 44
<212> TYPE: PRT
<213> ORGANISM: Ixodes scapularis

<400> SEQUENCE: 428

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe Glu Ser Glu
        35                  40

<210> SEQ ID NO 429
<211> LENGTH: 43
<212> TYPE: PRT
<213> ORGANISM: Ixodes scapularis

<400> SEQUENCE: 429

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe Glu Ser
        35                  40

<210> SEQ ID NO 430
<211> LENGTH: 42
<212> TYPE: PRT
<213> ORGANISM: Ixodes scapularis

<400> SEQUENCE: 430

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe Glu
        35                  40

<210> SEQ ID NO 431
<211> LENGTH: 41
<212> TYPE: PRT
<213> ORGANISM: Ixodes scapularis

<400> SEQUENCE: 431

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn Phe
        35                  40
```

<210> SEQ ID NO 432
<211> LENGTH: 40
<212> TYPE: PRT
<213> ORGANISM: Ixodes scapularis

<400> SEQUENCE: 432

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn Asn
        35                  40

<210> SEQ ID NO 433
<211> LENGTH: 39
<212> TYPE: PRT
<213> ORGANISM: Ixodes scapularis

<400> SEQUENCE: 433

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys Asn
        35

<210> SEQ ID NO 434
<211> LENGTH: 38
<212> TYPE: PRT
<213> ORGANISM: Ixodes scapularis

<400> SEQUENCE: 434

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn Lys
        35

<210> SEQ ID NO 435
<211> LENGTH: 37
<212> TYPE: PRT
<213> ORGANISM: Ixodes scapularis

<400> SEQUENCE: 435

Cys Ser Leu Glu Val Asp Tyr Gly Val Gly Arg Ala Asn Ile Pro Arg
1               5                   10                  15

Trp Tyr Tyr Asp Thr Asn Asn Ala Thr Cys Glu Met Phe Thr Tyr Gly
            20                  25                  30

Gly Ile Thr Gly Asn
        35

<210> SEQ ID NO 436
<211> LENGTH: 36
<212> TYPE: PRT
<213> ORGANISM: Ixodes scapularis

<400> SEQUENCE: 436

Cys Ser Leu Glu Val Asp Tyr Gly Val Gly Arg Ala Asn Ile Pro Arg
1               5                   10                  15

```
Trp Tyr Tyr Asp Thr Asn Asn Ala Thr Cys Glu Met Phe Thr Tyr Gly
            20                  25                  30

Gly Ile Thr Gly
        35

<210> SEQ ID NO 437
<211> LENGTH: 35
<212> TYPE: PRT
<213> ORGANISM: Ixodes scapularis

<400> SEQUENCE: 437

Cys Ser Leu Glu Val Asp Tyr Gly Val Gly Arg Ala Asn Ile Pro Arg
 1               5                  10                  15

Trp Tyr Tyr Asp Thr Asn Asn Ala Thr Cys Glu Met Phe Thr Tyr Gly
            20                  25                  30

Gly Ile Thr
        35

<210> SEQ ID NO 438
<211> LENGTH: 34
<212> TYPE: PRT
<213> ORGANISM: Ixodes scapularis

<400> SEQUENCE: 438

Cys Ser Leu Glu Val Asp Tyr Gly Val Gly Arg Ala Asn Ile Pro Arg
 1               5                  10                  15

Trp Tyr Tyr Asp Thr Asn Asn Ala Thr Cys Glu Met Phe Thr Tyr Gly
            20                  25                  30

Gly Ile

<210> SEQ ID NO 439
<211> LENGTH: 33
<212> TYPE: PRT
<213> ORGANISM: Ixodes scapularis

<400> SEQUENCE: 439

Cys Ser Leu Glu Val Asp Tyr Gly Val Gly Arg Ala Asn Ile Pro Arg
 1               5                  10                  15

Trp Tyr Tyr Asp Thr Asn Asn Ala Thr Cys Glu Met Phe Thr Tyr Gly
            20                  25                  30

Gly

<210> SEQ ID NO 440
<211> LENGTH: 32
<212> TYPE: PRT
<213> ORGANISM: Ixodes scapularis

<400> SEQUENCE: 440

Cys Ser Leu Glu Val Asp Tyr Gly Val Gly Arg Ala Asn Ile Pro Arg
 1               5                  10                  15

Trp Tyr Tyr Asp Thr Asn Asn Ala Thr Cys Glu Met Phe Thr Tyr Gly
            20                  25                  30

<210> SEQ ID NO 441
<211> LENGTH: 31
<212> TYPE: PRT
<213> ORGANISM: Ixodes scapularis

<400> SEQUENCE: 441

Cys Ser Leu Glu Val Asp Tyr Gly Val Gly Arg Ala Asn Ile Pro Arg
```

```
1               5                  10                 15
Trp Tyr Tyr Asp Thr Asn Asn Ala Thr Cys Glu Met Phe Thr Tyr
            20                  25                 30

<210> SEQ ID NO 442
<211> LENGTH: 30
<212> TYPE: PRT
<213> ORGANISM: Ixodes scapularis

<400> SEQUENCE: 442

Cys Ser Leu Glu Val Asp Tyr Gly Val Gly Arg Ala Asn Ile Pro Arg
1               5                  10                 15

Trp Tyr Tyr Asp Thr Asn Asn Ala Thr Cys Glu Met Phe Thr
            20                  25                 30

<210> SEQ ID NO 443
<211> LENGTH: 29
<212> TYPE: PRT
<213> ORGANISM: Ixodes scapularis

<400> SEQUENCE: 443

Cys Ser Leu Glu Val Asp Tyr Gly Val Gly Arg Ala Asn Ile Pro Arg
1               5                  10                 15

Trp Tyr Tyr Asp Thr Asn Asn Ala Thr Cys Glu Met Phe
            20                  25

<210> SEQ ID NO 444
<211> LENGTH: 28
<212> TYPE: PRT
<213> ORGANISM: Ixodes scapularis

<400> SEQUENCE: 444

Cys Ser Leu Glu Val Asp Tyr Gly Val Gly Arg Ala Asn Ile Pro Arg
1               5                  10                 15

Trp Tyr Tyr Asp Thr Asn Asn Ala Thr Cys Glu Met
            20                  25

<210> SEQ ID NO 445
<211> LENGTH: 27
<212> TYPE: PRT
<213> ORGANISM: Ixodes scapularis

<400> SEQUENCE: 445

Cys Ser Leu Glu Val Asp Tyr Gly Val Gly Arg Ala Asn Ile Pro Arg
1               5                  10                 15

Trp Tyr Tyr Asp Thr Asn Asn Ala Thr Cys Glu
            20                  25

<210> SEQ ID NO 446
<211> LENGTH: 26
<212> TYPE: PRT
<213> ORGANISM: Ixodes scapularis

<400> SEQUENCE: 446

Cys Ser Leu Glu Val Asp Tyr Gly Val Gly Arg Ala Asn Ile Pro Arg
1               5                  10                 15

Trp Tyr Tyr Asp Thr Asn Asn Ala Thr Cys
            20                  25

<210> SEQ ID NO 447
<211> LENGTH: 25
<212> TYPE: PRT
```

<213> ORGANISM: Ixodes scapularis

<400> SEQUENCE: 447

Cys Ser Leu Glu Val Asp Tyr Gly Val Gly Arg Ala Asn Ile Pro Arg
1 5 10 15

Trp Tyr Tyr Asp Thr Asn Asn Ala Thr
20 25

<210> SEQ ID NO 448
<211> LENGTH: 24
<212> TYPE: PRT
<213> ORGANISM: Ixodes scapularis

<400> SEQUENCE: 448

Cys Ser Leu Glu Val Asp Tyr Gly Val Gly Arg Ala Asn Ile Pro Arg
1 5 10 15

Trp Tyr Tyr Asp Thr Asn Asn Ala
20

<210> SEQ ID NO 449
<211> LENGTH: 23
<212> TYPE: PRT
<213> ORGANISM: Ixodes scapularis

<400> SEQUENCE: 449

Cys Ser Leu Glu Val Asp Tyr Gly Val Gly Arg Ala Asn Ile Pro Arg
1 5 10 15

Trp Tyr Tyr Asp Thr Asn Asn
20

<210> SEQ ID NO 450
<211> LENGTH: 22
<212> TYPE: PRT
<213> ORGANISM: Ixodes scapularis

<400> SEQUENCE: 450

Cys Ser Leu Glu Val Asp Tyr Gly Val Gly Arg Ala Asn Ile Pro Arg
1 5 10 15

Trp Tyr Tyr Asp Thr Asn
20

<210> SEQ ID NO 451
<211> LENGTH: 21
<212> TYPE: PRT
<213> ORGANISM: Ixodes scapularis

<400> SEQUENCE: 451

Cys Ser Leu Glu Val Asp Tyr Gly Val Gly Arg Ala Asn Ile Pro Arg
1 5 10 15

Trp Tyr Tyr Asp Thr
20

<210> SEQ ID NO 452
<211> LENGTH: 20
<212> TYPE: PRT
<213> ORGANISM: Ixodes scapularis

<400> SEQUENCE: 452

Cys Ser Leu Glu Val Asp Tyr Gly Val Gly Arg Ala Asn Ile Pro Arg
1 5 10 15

Trp Tyr Tyr Asp
20

<210> SEQ ID NO 453
<211> LENGTH: 19
<212> TYPE: PRT
<213> ORGANISM: Ixodes scapularis

<400> SEQUENCE: 453

Cys Ser Leu Glu Val Asp Tyr Gly Val Gly Arg Ala Asn Ile Pro Arg
1               5                   10                  15

Trp Tyr Tyr

<210> SEQ ID NO 454
<211> LENGTH: 18
<212> TYPE: PRT
<213> ORGANISM: Ixodes scapularis

<400> SEQUENCE: 454

Cys Ser Leu Glu Val Asp Tyr Gly Val Gly Arg Ala Asn Ile Pro Arg
1               5                   10                  15

Trp Tyr

<210> SEQ ID NO 455
<211> LENGTH: 17
<212> TYPE: PRT
<213> ORGANISM: Ixodes scapularis

<400> SEQUENCE: 455

Cys Ser Leu Glu Val Asp Tyr Gly Val Gly Arg Ala Asn Ile Pro Arg
1               5                   10                  15

Trp

<210> SEQ ID NO 456
<211> LENGTH: 16
<212> TYPE: PRT
<213> ORGANISM: Ixodes scapularis

<400> SEQUENCE: 456

Cys Ser Leu Glu Val Asp Tyr Gly Val Gly Arg Ala Asn Ile Pro Arg
1               5                   10                  15

<210> SEQ ID NO 457
<211> LENGTH: 15
<212> TYPE: PRT
<213> ORGANISM: Ixodes scapularis

<400> SEQUENCE: 457

Cys Ser Leu Glu Val Asp Tyr Gly Val Gly Arg Ala Asn Ile Pro
1               5                   10                  15

<210> SEQ ID NO 458
<211> LENGTH: 14
<212> TYPE: PRT
<213> ORGANISM: Ixodes scapularis

<400> SEQUENCE: 458

Cys Ser Leu Glu Val Asp Tyr Gly Val Gly Arg Ala Asn Ile
1               5                   10

<210> SEQ ID NO 459
<211> LENGTH: 13
<212> TYPE: PRT
<213> ORGANISM: Ixodes scapularis -continued

```
<400> SEQUENCE: 459

Cys Ser Leu Glu Val Asp Tyr Gly Val Gly Arg Ala Asn
  1               5                  10

<210> SEQ ID NO 460
<211> LENGTH: 12
<212> TYPE: PRT
<213> ORGANISM: Ixodes scapularis

<400> SEQUENCE: 460

Cys Ser Leu Glu Val Asp Tyr Gly Val Gly Arg Ala
  1               5                  10

<210> SEQ ID NO 461
<211> LENGTH: 11
<212> TYPE: PRT
<213> ORGANISM: Ixodes scapularis

<400> SEQUENCE: 461

Cys Ser Leu Glu Val Asp Tyr Gly Val Gly Arg
  1               5                  10

<210> SEQ ID NO 462
<211> LENGTH: 10
<212> TYPE: PRT
<213> ORGANISM: Ixodes scapularis

<400> SEQUENCE: 462

Cys Ser Leu Glu Val Asp Tyr Gly Val Gly
  1               5                  10

<210> SEQ ID NO 463
<211> LENGTH: 9
<212> TYPE: PRT
<213> ORGANISM: Ixodes scapularis

<400> SEQUENCE: 463

Cys Ser Leu Glu Val Asp Tyr Gly Val
  1               5

<210> SEQ ID NO 464
<211> LENGTH: 8
<212> TYPE: PRT
<213> ORGANISM: Ixodes scapularis

<400> SEQUENCE: 464

Cys Ser Leu Glu Val Asp Tyr Gly
  1               5

<210> SEQ ID NO 465
<211> LENGTH: 7
<212> TYPE: PRT
<213> ORGANISM: Ixodes scapularis

<400> SEQUENCE: 465

Cys Ser Leu Glu Val Asp Tyr
  1               5

<210> SEQ ID NO 466
<211> LENGTH: 6
<212> TYPE: PRT
<213> ORGANISM: Ixodes scapularis

<400> SEQUENCE: 466
```

-continued

Cys Ser Leu Glu Val Asp
1               5

<210> SEQ ID NO 467
<211> LENGTH: 5
<212> TYPE: PRT
<213> ORGANISM: Ixodes scapularis

<400> SEQUENCE: 467

Cys Ser Leu Glu Val
1               5

<210> SEQ ID NO 468
<211> LENGTH: 4
<212> TYPE: PRT
<213> ORGANISM: Ixodes scapularis

<400> SEQUENCE: 468

Cys Ser Leu Glu
1

<210> SEQ ID NO 469
<211> LENGTH: 3
<212> TYPE: PRT
<213> ORGANISM: Ixodes scapularis

<400> SEQUENCE: 469

Cys Ser Leu
1

<210> SEQ ID NO 470
<211> LENGTH: 498
<212> TYPE: DNA
<213> ORGANISM: Ixodes scapularis

<400> SEQUENCE: 470

```
atgcgcgctg tttcctgctt cctatattat ggagttgctt ggattgcact tggaagttgg      60
ggtgcgtcaa gttcagcaga acgtgttagc gaaatggaca tctatgagtt cgaatcctgg     120
gtatcttgtc ttgatcccga acaagtaacg tgtgaaagcc aagagggaac gcacgcttca     180
tacaaccgaa aaacgggaca gtgtgaagag caaaagggaa cagagtgtgg aggaggcgag     240
aatcactttg aaactttgtt gaagtgcaac gaatcttgca cgatgctccc gaagccacct     300
tgctcgctgg aagtagatta tggtgttgga agagctaaca taccacgatg gtattatgac     360
accaacaatg caacttgcga aatgttcacc tatgggggaa taactggcaa taaaaacaat     420
tttgaatccg aggaagagtg taaggaaact tgcaagggtt tttctctgtt aaagaaagta     480
aatgtcacta ttaactga                                                   498
```

<210> SEQ ID NO 471
<211> LENGTH: 165
<212> TYPE: PRT
<213> ORGANISM: Ixodes scapularis

<400> SEQUENCE: 471

Met Arg Ala Val Ser Cys Phe Leu Tyr Tyr Gly Val Ala Trp Ile Ala
1               5                   10                  15

Leu Gly Ser Trp Gly Ala Ser Ser Ala Glu Arg Val Ser Glu Met
            20                  25                  30

Asp Ile Tyr Glu Phe Glu Ser Trp Val Ser Cys Leu Asp Pro Glu Gln
        35                  40                  45

```
Val Thr Cys Glu Ser Gln Gly Thr His Ala Ser Tyr Asn Arg Lys
    50                  55                  60

Thr Gly Gln Cys Glu Glu Gln Lys Gly Thr Glu Cys Gly Gly Gly Glu
65                  70                  75                  80

Asn His Phe Glu Thr Leu Leu Lys Cys Asn Glu Ser Cys Asn Asp Ala
                85                  90                  95

Pro Lys Pro Pro Cys Ser Leu Glu Val Asp Tyr Gly Val Gly Arg Ala
            100                 105                 110

Asn Ile Pro Arg Trp Tyr Tyr Asp Thr Asn Asn Ala Thr Cys Glu Met
            115                 120                 125

Phe Thr Tyr Gly Gly Ile Thr Gly Asn Lys Asn Asn Phe Glu Ser Glu
    130                 135                 140

Glu Glu Cys Lys Glu Thr Cys Lys Gly Phe Ser Leu Leu Lys Lys Val
145                 150                 155                 160

Asn Val Thr Ile Asn
                165

<210> SEQ ID NO 472
<211> LENGTH: 160
<212> TYPE: PRT
<213> ORGANISM: H. sapiens

<400> SEQUENCE: 472

Asp Ser Glu Glu Asp Glu His Thr Ile Ile Thr Asp Thr Glu Leu
1               5                   10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Asn Ile Phe Thr
            35                  40                  45

Arg Gln Cys Glu Glu Phe Ile Tyr Gly Gly Cys Glu Gly Asn Gln Asn
    50                  55                  60

Arg Phe Glu Ser Leu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

<210> SEQ ID NO 473
<211> LENGTH: 7
<212> TYPE: DNA
<213> ORGANISM: Artificial Sequence
<220> FEATURE:
<223> OTHER INFORMATION: Kozak consensus sequence
<220> FEATURE:
<221> NAME/KEY: misc_feature
<222> LOCATION: (1)...(7)
<223> OTHER INFORMATION: n = A,T,C or G

<400> SEQUENCE: 473 annatgg                                                         7
```

```
<210> SEQ ID NO 474
<211> LENGTH: 24
<212> TYPE: DNA
<213> ORGANISM: Artificial Sequence
<220> FEATURE:
<223> OTHER INFORMATION: forward primer

<400> SEQUENCE: 474
aaaatgggcg ctgtttcctg cttc                                              24

<210> SEQ ID NO 475
<211> LENGTH: 27
<212> TYPE: DNA
<213> ORGANISM: Artificial Sequence
<220> FEATURE:
<223> OTHER INFORMATION: reverse primer

<400> SEQUENCE: 475
ggatgatcag ttaatagtga catttac                                           27
```

IXODES SCAPULARIS TISSUE FACTOR PATHWAY INHIBITOR

RELATED APPLICATIONS

This application is a continuation and claims the benefit of priority of International Application No. PCT/US01/42472 filed Oct. 5, 2001, designating the United States of America and published in English, which claims the benefit of priority of U.S. Provisional Application No. 60/240,575 filed Oct. 5, 2000, both of which are hereby expressly incorporated by reference in their entireties.

FIELD OF THE INVENTION

The present invention relates to the field of molecular biology. The present invention discloses the discovery of the novel protein Ixolaris. Ixolaris has anticoagulant activity and can be isolated and purified from the salivary glands of ticks or made by recombinant methods using various DNA expression techniques.

BACKGROUND OF THE INVENTION

Following tissue injury, exposition of membrane-bound Tissue Factor (TF), is a crucial step in the initiation of blood coagulation. TF binds to blood coagulation Factor VIIa, and the binary Factor VIIa/TF complex then activates Factor X to Factor Xa, leading to thrombin generation and fibrin formation (Broze, G. J. Jr. et al. 1988 *Blood* 71:335–343; Pedersen, A. H. et al. 1990 *J Biol Chem* 254:16786–16793; Rao, L. V. M., and Rapaport, S. I. 1987 *Blood* 69:645–651). Initiation of blood coagulation by Factor VIIa/TF is under control of tissue factor pathway inhibitor (TFPI) (Pedersen, A. H. et al. 1990 *J Biol Chem* 254:16786–16793; Rao, L. V. M., and Rapaport, S. I. 1987 *Blood* 69:645–651; Broze, G. J. Jr, and Miletich, J. P. 1987 *PNAS* USA 84:1886–1890; Rapaport, S. I. 1989 *Blood* 73:359–365), a 34- to 43-kDa multidomain protein with an acidic aminoterminus, three typical Kunitz-type inhibitor domains, and a basic carboxy terminus (Girard, T. J. et al. 1990 *Science* 248:1421–1424: Wun, T-C. et al. 1988 *J Biol Chem* 263:6001–6004). The second Kunitz domain binds and inhibits Factor Xa, and the first Kunitz domain binds to Factor VIIa/TF through formation of a final quarternary inhibitory complex consisting of Factor Xa-TFPI-Factor VIIa/TF (Lindhout, T., Fransen, J., and Willems, G. 1995 *Thromb Haemost* 74:910–915; Hamamoto, T. et al 1993 *J Biol Chem* 268:8704–8710; Broze, G. J. et al. 1990 *Biochemistry* 29:7539–7546; Rao, L. V. M., and Ruf, W. 1995 *Biochemistry* 34:10867–10871;. Baugh, R. J. et al. 1998 *J Biol Chem* 273:4378–4386; Wesselschmidt, R. et al. 1992 *Blood* 79:2004–2010). In addition to TFPI and other physiologic inhibitors of blood coagulation (e.g., antithrombin), a number of coagulation inhibitors from the salivary gland of blood-sucking invertebrates have been characterized (Law, L. H., Ribeiro, J. M., and Wells, M. A. 1992 *Annu Rev Biochem* 61:87–111; Markwardt, F. 1994 *Pharmazie* 49:313–316).

Ticks, such as *Ixodes scapularis*, are ectoparasites that feed for several days with their mouthparts embedded in their vertebrate hosts. *Ixodes scapularis* is a vector of Lyme disease. Lyme disease is a spirochetal illness caused by *Borrelia burgdorferi*, which is injected into the vertebrate host together with tick saliva. A number of pharmacologic properties have been described in *I. scapularis* saliva including inhibitors of neutrophil function (Ribeiro, J. M. C., Weis, J. J., and Telford, S. R. III 1990 *Exp Parasitol* 70:382–388), anticomplement (Ribeiro, J. M. C., 1987 *Exp Parasitol* 64:347–353; Valenzuela, J. G. et al. 2000 *J Biol Chem* 275:18717–18723), and anaphilatoxin-inactivating activities (Ribeiro, J. M. C., and Spielman A. 1986 *Exp Parasitol* 62:292–297) in addition to antiinflammatory and immunosuppresive components (Ribeiro, J. M. C. et al. 1985 *J Exp Med* 161:332–344). Antihemostatic compounds have also been molecularly characterized in the soft tick *O. moubatta*, including a platelet integrin $\alpha_{IIb}\beta_3$ integrin antagonist (Karczewski, J. et al. 1994 *J Biol Chem* 269:6702–6708) and inhibitors of blood coagulation such as ornithodorin, a thrombin inhibitor (Locht, A. et al. 1996 *EMBO J* 15:6011–6017), and tick anticoagulant peptide, a Factor Xa inhibitor (Waxman, L. et al. 1990 *Science* 248:593–596). The presence of thrombin and Factor Xa inhibitors seems to be a successful strategy evolutionarily developed by ticks to successfully feed on blood, because both molecules play an essential role in two key steps necessary for maintenance of the blood coagulation cascade (Jenny, N. S., and Mann K. G. in: Thrombosis and Hemorrhage, 2d ed. 1998, Loscalzo J, Schafer AI eds. Baltimore, Md.: Williams and Wilkins 1998 p 3; Davie, E. W. et al. 1991 *Biochemistry* 30:10363–10370) however, an inhibitor of Factor VIIa/TF has not yet been molecularly characterized.

SEGUE TO THE DESCRIPTION

To understand the complexity of *I. scapularis* saliva, with a primary focus on antihemostatic molecules, massive sequencing of a cDNA library of the salivary gland of *I. scapularis* has been performed. Together with a complementary functional approach, a clone with sequence homology to TFPI has been expressed as an active molecule and its anticoagulant mechanism studied. The recombinant protein has the same properties found in saliva. This molecule, called Ixolaris, is characterized as a specific inhibitor of FactorVIIa/TF, with unique binding properties to Factor X.

SUMMARY OF THE INVENTION

Saliva of the hard tick, *Ixodes scapularis*, has a repertoire of compounds that counteracts host defenses. Following sequencing of an *I. scapularis* salivary gland cDNA library, a clone with sequence homology to tissue factor pathway inhibitor (TFPI) was identified. This cDNA codes for a mature protein, herein called Ixolaris, with 140 amino acids containing 10 cysteines and two Kunitz-like domains. Recombinant Ixolaris inhibits Factor VIIa(FVIIa)-induced Factor X(FX) activation with an $IC_{50}$ in the pM range. Ixolaris behaves as a fast-and-tight ligand of FXa and des-Gla-FXa (γ-carboxyglutamic acid domainless FXa), increasing their esterolytic activity ~2 fold. Ixolaris blocks the amidolytic activity of FVIIa/TF only in the presence of DEGR-FX or DEGR-FXa, but not des-Gla-DEGR-FXa. This result indicates that both FXa and FX are scaffolds for Ixolaris and implies that Gla-domain is necessary for Ixolaris/FX(a)/FVIIa/TF complex formation. Additionally, we show that Ixolaris inhibits FIX activation by FVIIa/TF (Factor VIIa exosite inhibitor), and remarkable inhibition was achieved in the presence of FX/FXa. Ixolaris/FXa forms a 1:1 complex with FVIIa/TF. Western blotting using antibodies to Factor X and Factor VIIa shows that Ixolaris shifts the migration pattern of both Factor X and Factor Xa, but not Factor VIIa. Ixolaris also inhibits Factor Xa generated by human umbilical vein endothelial cells (HUVEC) expressing TF. Ixolaris is envisioned as being useful as an alternative anticoagulant in cardiovascular diseases as well as a vaccine target to prevent Lyme disease.

SUMMARY OF SEQUENCES

Appendix A depicts Ixolaris and its carboxy truncations. Appendix B depicts Ixolaris and its amino truncations.

BRIEF DESCRIPTION OF THE DRAWINGS

FIG. 3. (A) Nucleotide sequence (SEQ ID NO: 470) and deduced amino acid sequence of Ixolaris (SEQ ID NO: 471). The nucleotides and amino acids are numbered from the translation starting site ATG. The signal peptide sequence is underlined. (B) Alignment of mature Ixolaris (SEQ ID NO: 138) with human TFPI (SEQ ID NO: 472). Identical amino acids are in bold and underlined.

DETAILED DESCRIPTION OF THE INVENTION

Hemostasis is the physiological mechanism by which an organism prevents blood loss at a site of injury. The process is comprised of activation of the blood coagulation cascade, vasoconstriction and platelet aggregation. Specifically, exposure of blood to the cell surface tissue factor (TF) and formation of the TF/VII (VIIa) complex initiate the blood coagulation. The TF/VIIa complex then activates both factors IX and X leading to thrombin generation and fibrin formation. Abnormal coagulation underlies pathogenesis of many serious illnesses. In particular, induced expression of TF and TF-mediated coagulation occurs in atherosclerotic plaques, sepsis, malignancy, ARDS and glomerulonephritis. A plasma physiological inhibitor that counteracts the activity of TF/VIIa has been identified—Tissue Factor Pathway Inhibitor (TFPI). TFPI has also been studied for therapeutic purposes. Accordingly, alternative strategies to prevent initiation of blood coagulation, such as the identification of new inhibitors of TF/VIIa, can lead ultimately to the identification of new potential therapeutic agents. In this context, we cloned and expressed tick's tissue factor pathway inhibitor, named Ixolaris. Recombinant Ixolaris is a highly specific inhibitor of the extrinsic pathway that blocks generation of Xa by TF/VIIa with an apparent Ki in the pM range. The mechanism of action of Ixolaris has been studied in detail. Because inactivation of Ixolaris by antibodies will make transmission of *Borrelia burgdorferi* (the bacteria responsible for Lyme disease) to humans more difficult, Ixolaris is envisioned as a vaccine to protect humans (and their pets) against Lyme disease. It can also be useful as an anticoagulant and antimetastatic molecule in a number of pathological conditions.

Ixolaris is envisioned as being effective as an anti-coagulant molecule to prevent or ameliorate the morbidity of cardiovascular syndromes, including, but not limited to, coronary heart disease, deep vein thrombosis, pos-infarctus angioplasty, hypercoagulable states, restenosis, arterial thrombosis, microvascular anastomosis, stroke and ischemia-reperfusion injury. Ixolaris is also envisioned as being effective as an anti-metastatic molecule for the treatment of malignant tumors that stain positively to TF (e.g. breast, lung, pancreas, colon, and stomach cancers). It is also envisioned as being used as an anti-coagulant molecule to prevent sepsis-related hypercoagulation states, particularly, endotoxin-induced tissue factor-mediated disseminated intravascular coagulation (DIC). Additionally, it is also envisioned as being effective as an anticoagulant to prevent or ameliorate Acute Respiratory Distress Syndrome (ARDS). Furthermore, it is envisioned as acting as a prototype molecule to study the structure and function of blood coagulation factors involved in the initiation of blood coagulation by the extrinsic pathway, particularly factor Xa, X, and Factor VIIa/TF.

Figure 1:
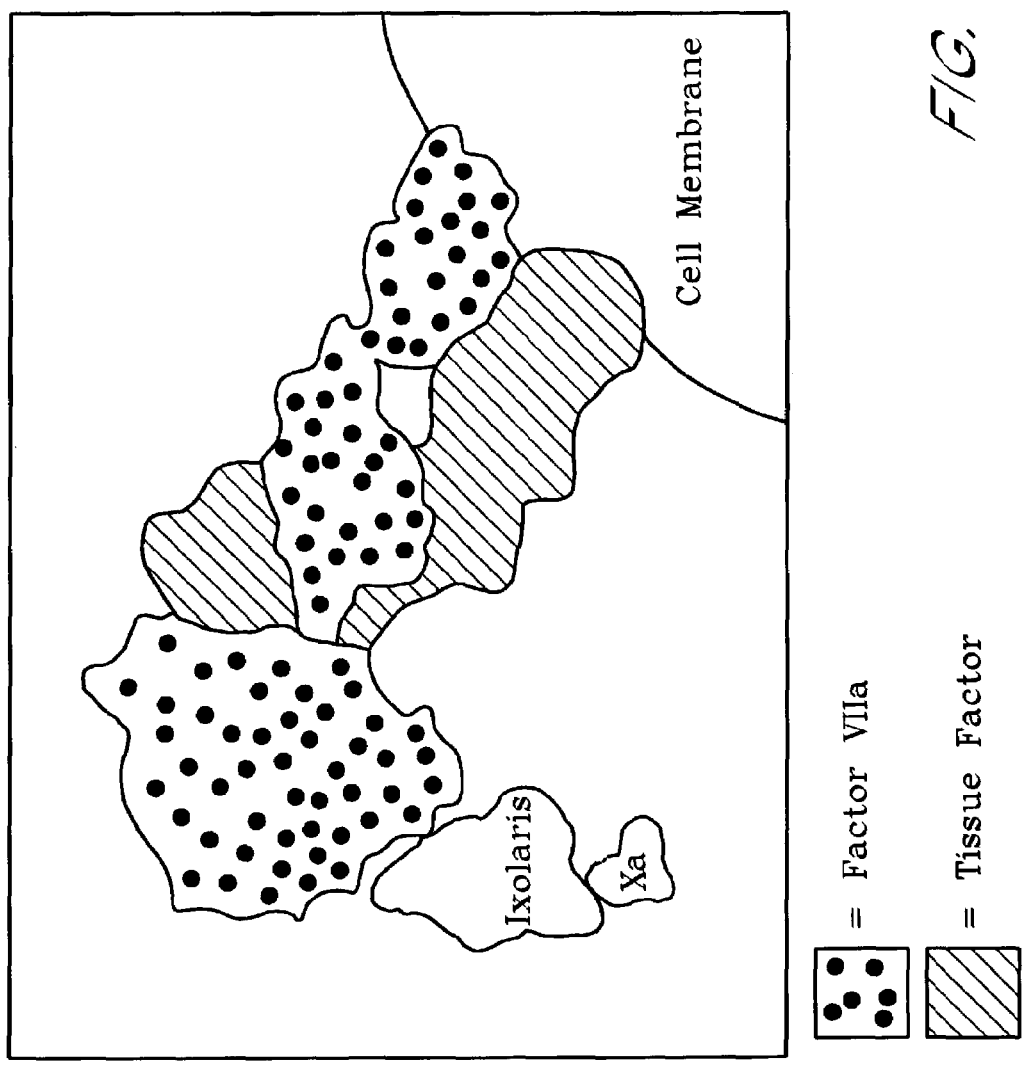
FIG. 1. Hypothetical Model for Ixolaris Binding. The second Kunitz domain of Ixolaris binds to Factor Xa or Factor X. Subsequently, the first Kunitz domain of Ixolaris in this complex binds to the Factor VIIa/TF complex.
Figure 2:
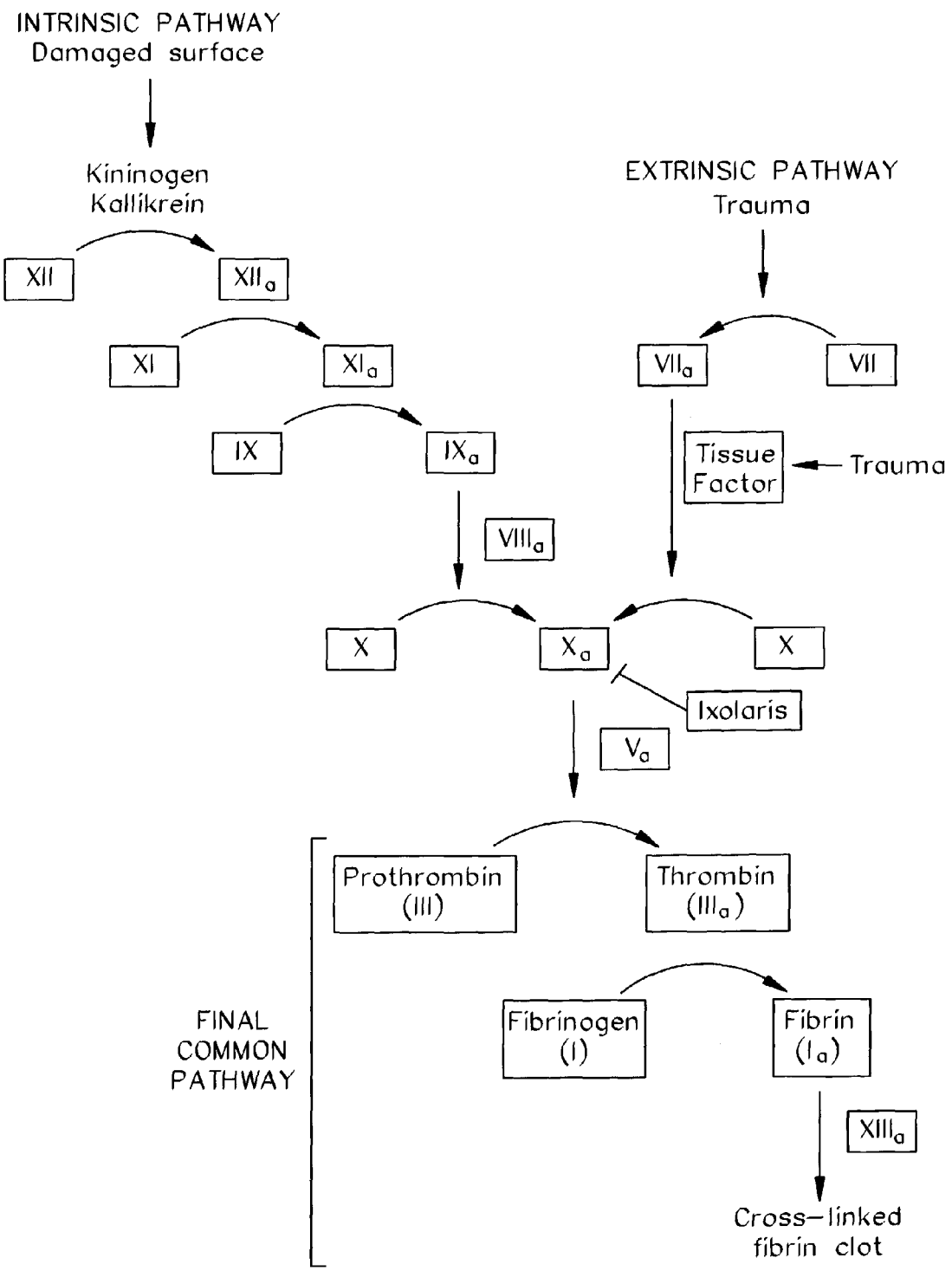
FIG. 2. Blood Coagulation Cascade. Ixolaris disrupts the extrinsic pathway in the blood coagulation cascade by inhibiting factor VIIa dependent Factor X activation. By inhibiting Factor Xa and Factor VIIa/TF, Ixolaris prevents thrombin generation and fibrin formation. Through this mechanism blood coagulation is inhibited.
Figure 3A:
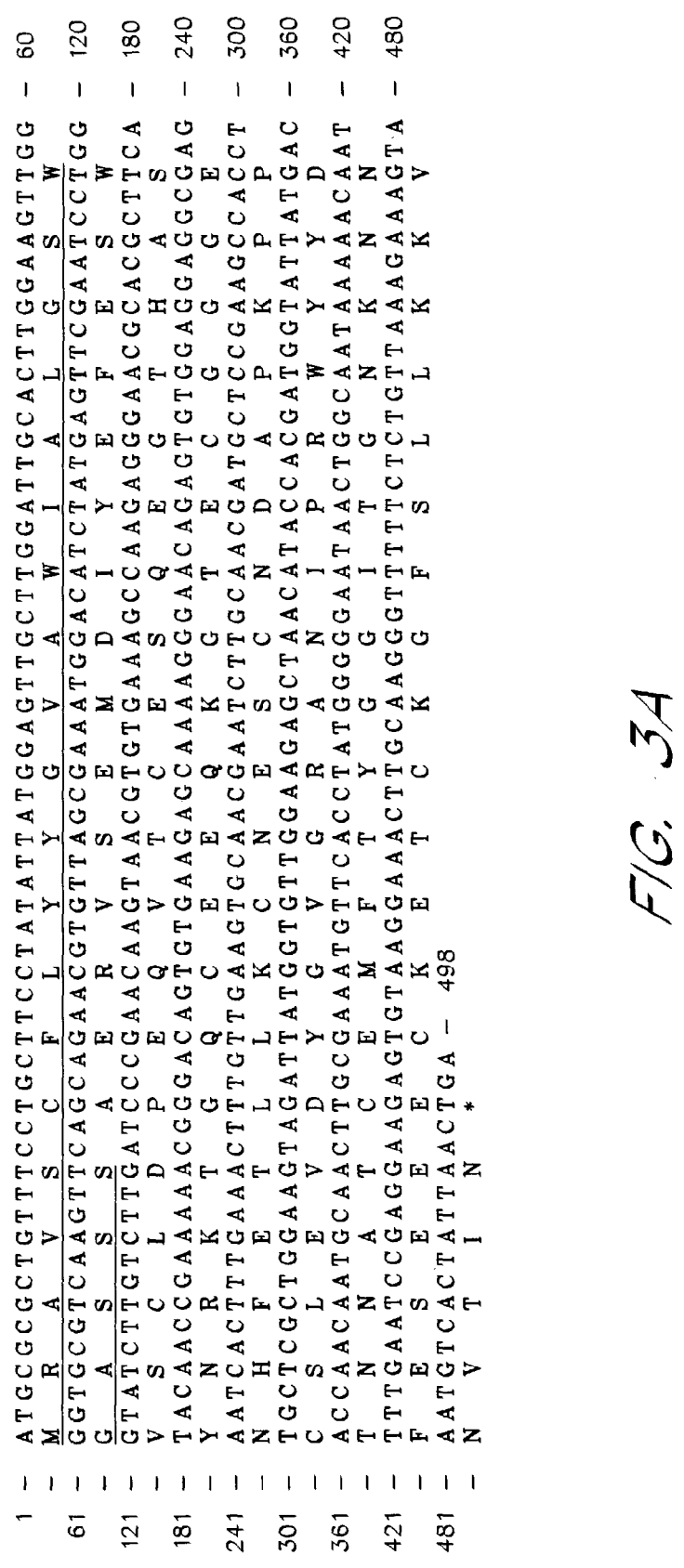
Figure 4:
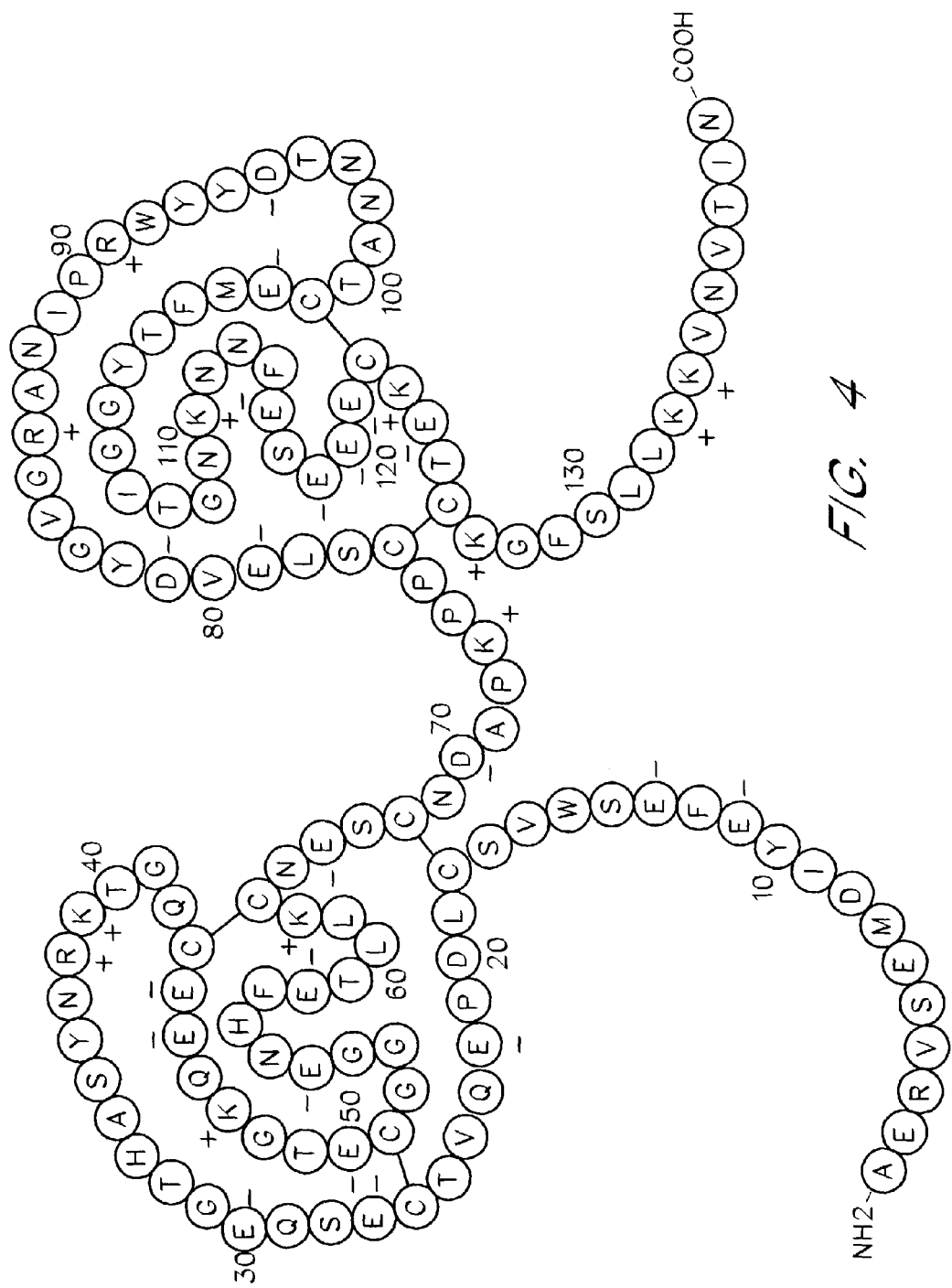
FIG. 4. Predicted secondary folding structure for Ixolaris. Disulfide bonds are assumed on the basis of the crystal structure of bovine pancreatic trypsin inhibitor (Huber, R. et al. 1974 *J Mol Biol* 89:73–101). The charges of the amino acid side chains are shown. Predicted N-linked glycosylation sites are $Asn^{65}$, $Asn^{98}$, and $Asn^{136}$.

A salivary gland cDNA library of the tick *Ixodes scapularis* was randomly cloned and sequenced, identifying a cDNA with high similarity to rabbit tissue factor pathway inhibitor. The full-length nucleotide (SEQ ID NO: 470) and deduced amino acid sequences (SEQ ID NO: 471) of Ixodes TFPI-like protein are shown in FIG. 3A. The translated protein has a short hydrophobic sequence of 25 amino acids typical of signal peptide and an alanine at the N-terminus, according to Signal P software for prediction of N-terminal of proteins (Nielsen, H. et al. 1997 *Protein Eng* 10:1–6). The mature protein, herein called Ixolaris, contains 140 amino acids (15.7 kDa) (SEQ ID NO: 138), including 10 cysteines and a pI of 4.56. Ixolaris is similar to other members of the Kunitz family of proteins including human TFPI precursor (e value=$4e^{-14}$, P10646); lacunin from *Manduca sexta* ($1e^{-12}$, AAF04457.1); hepatocyte growth factor pathway inhibitor ($8e^{-12}$, AAF02490.1); inter-α-trypsin inhibitor (bikunin) ($7e^{-11}$, P04365); amyloid-precursor-like protein ($1e^{-11}$, CAA54906.1); and basic pancreatic trypsin inhibitor (aprotinin, $1e^{-05}$, 1510193A). For comparison, the alignment of Ixolaris and human TFPI sequence (SEQ ID NO: 472) is shown (FIG. 3B). FIG. 4 shows the predicted structure of Ixolaris assumed on the basis of the crystal structure of bovine pancreatic trypsin inhibitor (Huber, R. et al. 1974 *J Mol Biol* 89:73–101).

Figure 5A:
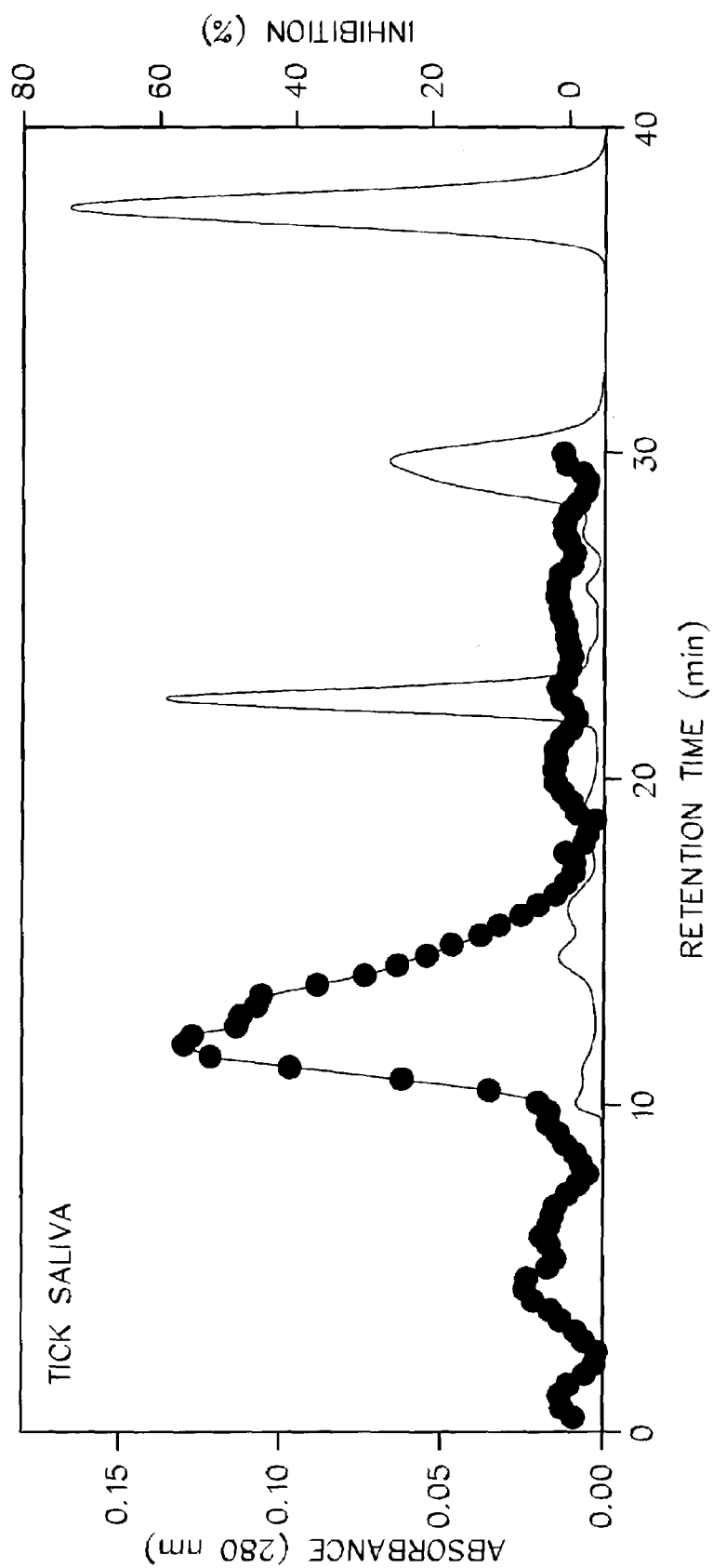
FIG. 5. Identification of TFPI-like activity in the saliva of *I. Scapularis* (30 µL) (A) or the 20×concentrated supernatant of High Five cells transfected with the full-length clone coding for Ixolaris (B). Molecular sieving chromatography was done with a 3.2×300 mm Superdex 75 column eluted at 0.05 mL/min with 10 mM Hepes buffer pH 7.2, 0.15 M NaCl. Fractions were collected every two drops, with time recording for change in fractions done by a program linking the fraction collector to a computer. An aliquot was taken from each fraction and tested for inhibition of Factor X activation by factor VIIa/Tissue Factor, as described in Example. Absorbance at 280 nm (—); inhibitory activity (-●-).

Ixolaris sequence indicates the existence of a salivary anticoagulant directed toward the extrinsic pathway. Thus, we tested chromatographically separated saliva of *I. scapularis* in an assay measuring activation of Factor X by Factor VIIa/TF. Inhibition of Factor X activation was detected in fractions eluted between 11 and 17 minutes of retention time (FIG. 5A). Because control experiments showed that the activity was not related to a specific inhibitor of Factor Xa, we concluded that saliva of *I. scapularis* contains TFPI-like molecule(s). Inhibition of α-thrombin and trypsin amidolytic activity was also found in other fractions, indicating that other protease inhibitor(s) are present in the salivary gland of *I. scapularis*.

Figure 5B:
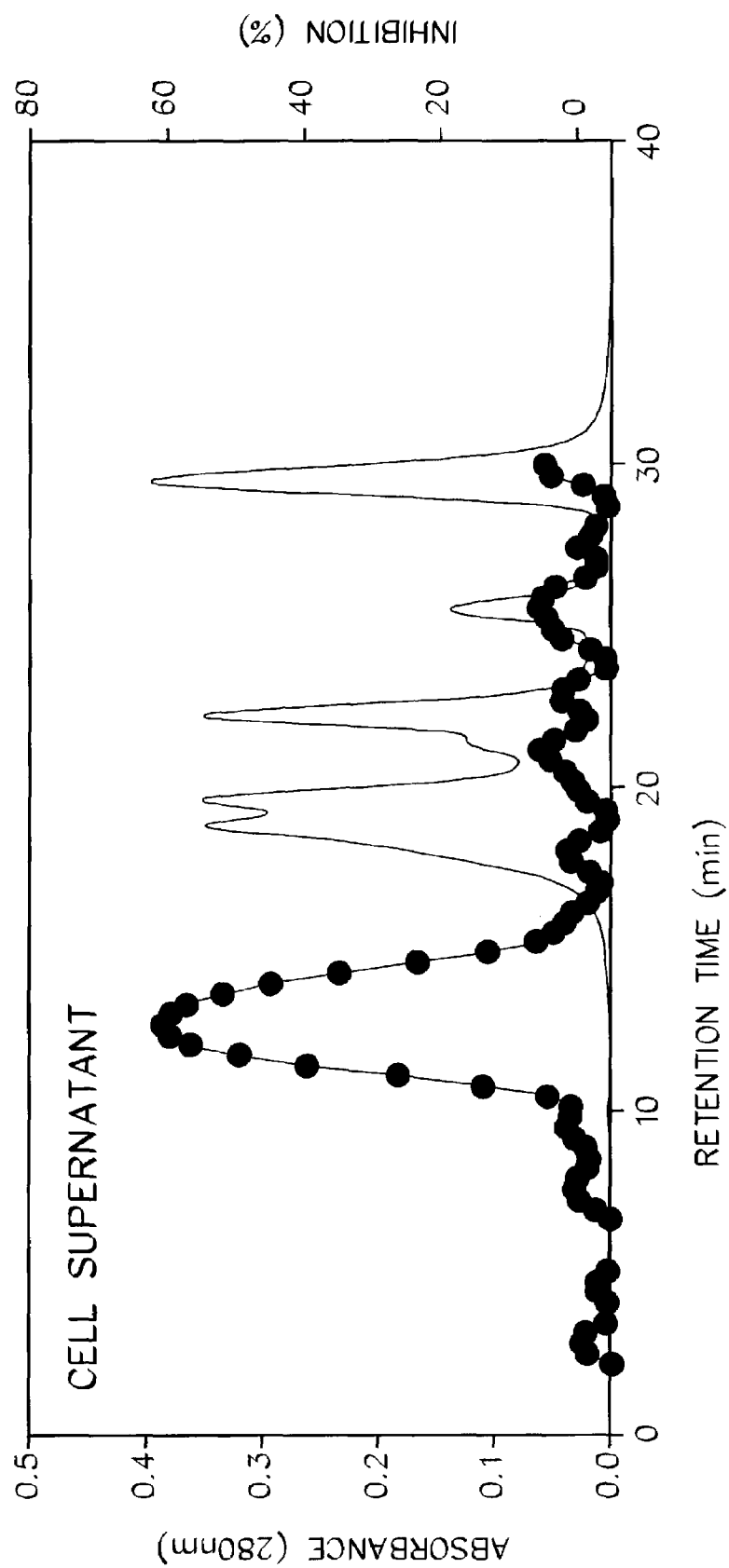

To determine whether Ixolaris accounts for the inhibitory activity identified in the saliva, the full-length cDNA of Ixolaris was expressed in insect cells as described in Example. The concentrated supernatant was applied to a gel-filtration column under conditions identical to those described in FIG. 5A. Inhibitory activity was found with the same retention time as described for the salivary fractions (FIG. 5B). No activity was found with the supernatants of cells transfected with the control plasmid. These data indicate that Ixolaris and the salivary TFPI-like molecule have similar chromatographic properties on gel-filtration.

Figures 6A, 6B:
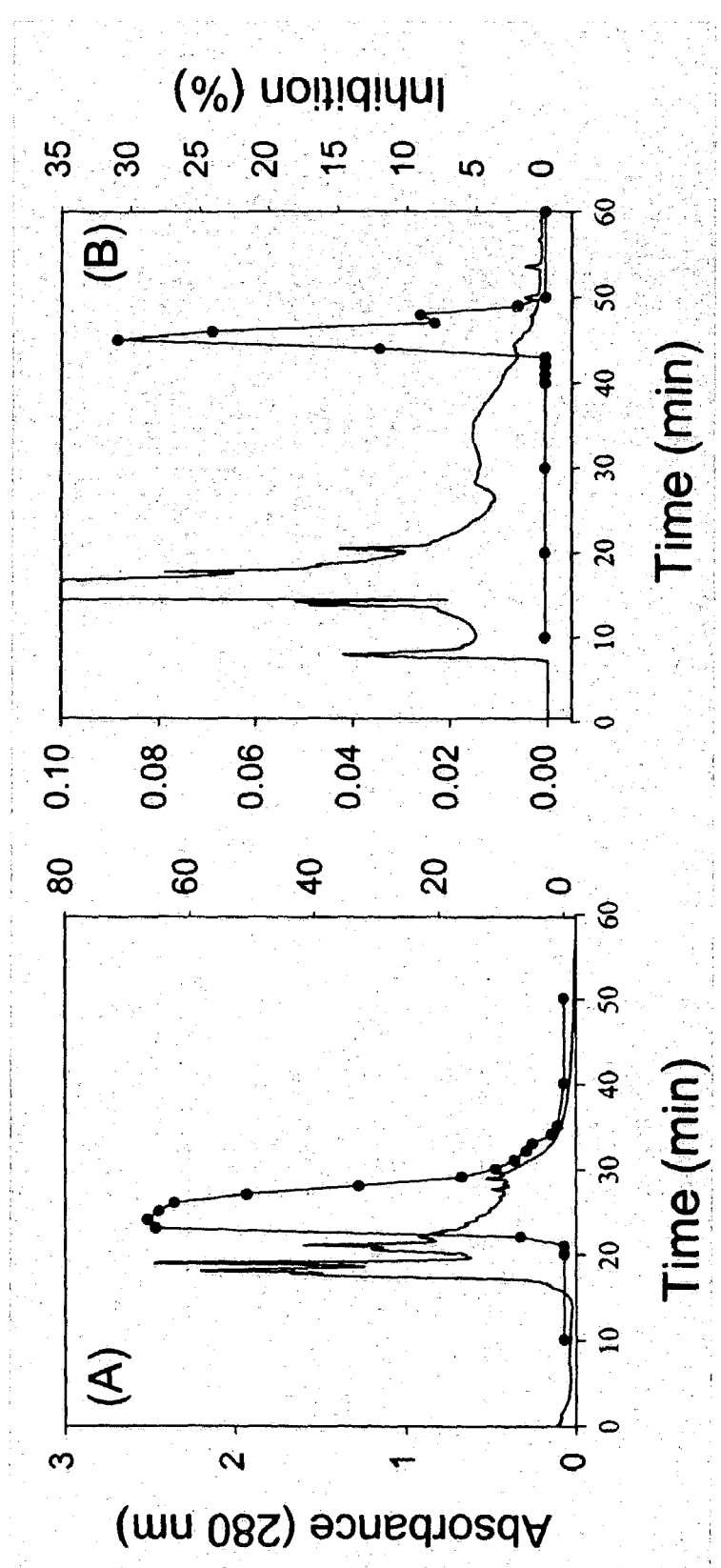
FIG. 6. Purification of Ixolaris. Recombinant Ixolaris was purified in (A) a MonoQ anion-exchange column, (B) Vydac 218TP510 octadecyl-silica reverse-phase column and (C) Macrosphere octadecylsilica reverse-phase column (—). Column fractions were diluted 1:4,000 (A), 1:125,000 (B), and 1:800,000 (C) and measured for inhibition of Factor VIIa/TF-mediated Factor X activation (-●-). (D) An aliquot (0.2 µg) of the fraction eluted at 83 minutes of retention time was treated under non-reducing (Lane 1, NR) and reducing (lane 2, R) conditions and applied to 12% NU-PAGE (MOPS buffer) in the presence of an antioxidant. Lane 3, N: PAGE of Ixolaris under native conditions. Arrows and arrowheads show Ixolaris. Gels were silver stained.
Figures 6C, 6D:
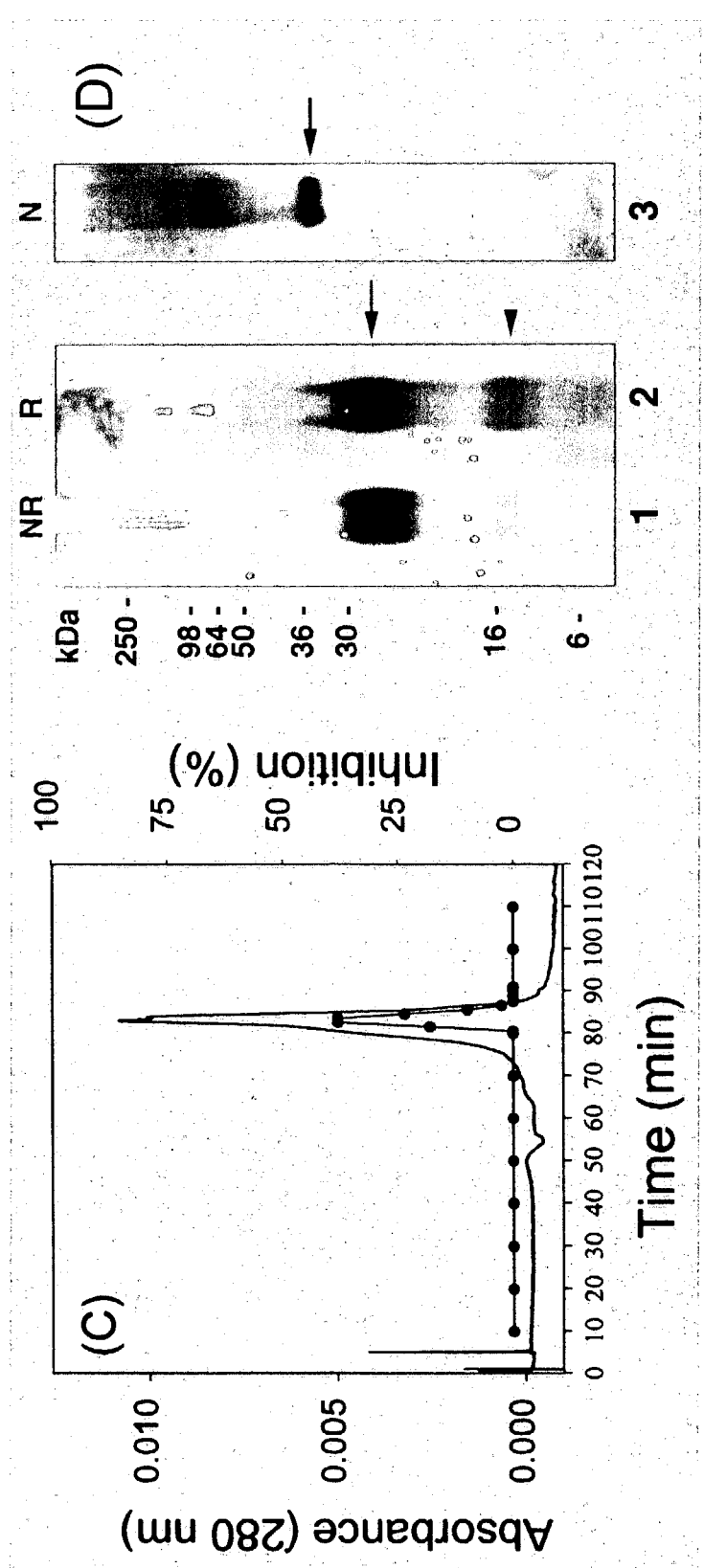

To obtain larger amounts of purified Ixolaris, supernatants of transfected cells were chromatographically purified (FIG. 6). The resulting final fraction was analyzed by PAGE under denaturing and non-reducing conditions (FIG. 6D, lane 1, NR), where a major band of approximately 24 kDa in addition to a minor component of approximately 15.5 kDa were silver stained. Under reducing conditions, a band of approximately 27 kDa and a minor component of approximately 15.5 kDa band were detected (FIG. 6D, lane 2, R). PAGE of the sample under native conditions shows that only one major band has been stained (FIG. 6D, lane 3, N).

Figure 7A:
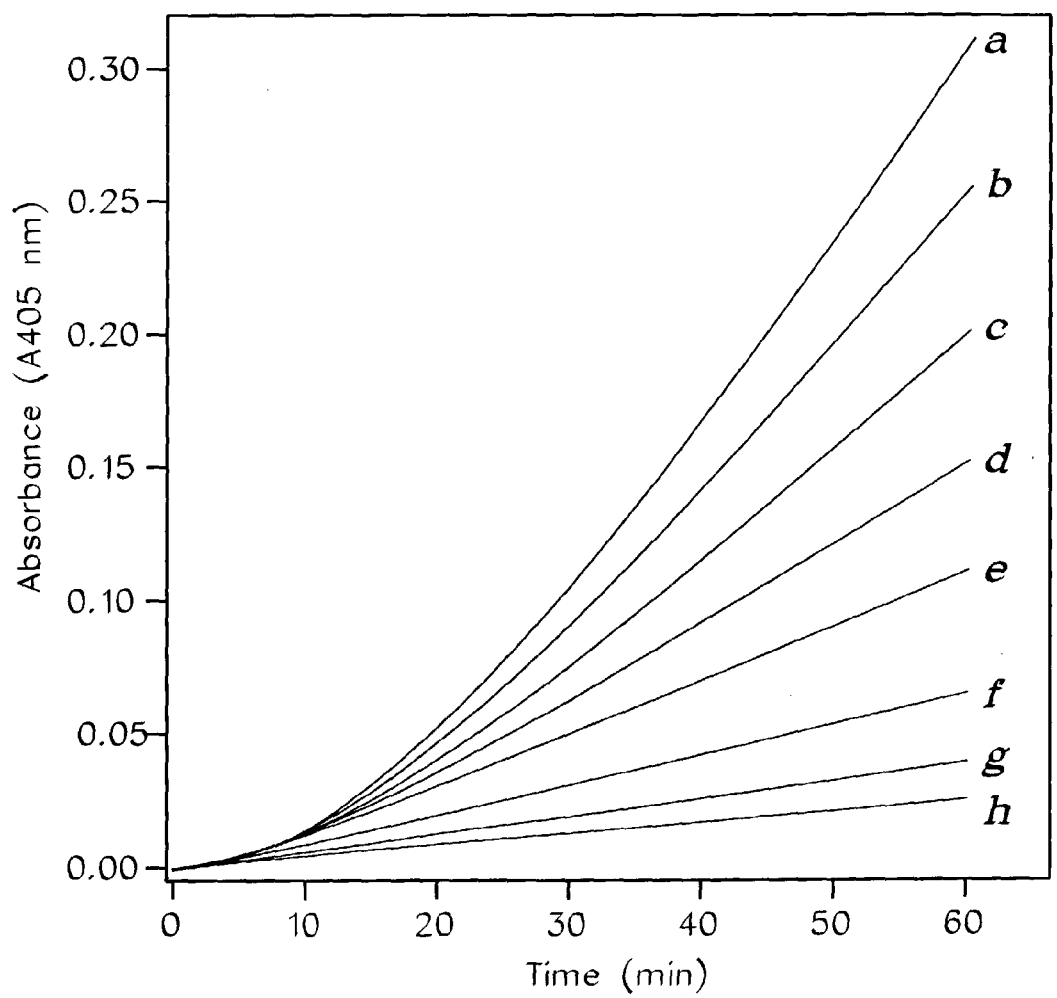
FIG. 7. Inhibition of Factor VIIa/TF-induced Factor X activation by Ixolaris. (A) Progress curves: Factor VIIa (1 nM)/TF (0.2 pM) was added to a mixture containing Factor X (200 nM), previously incubated with increasing concentrations of Ixolaris (a, 0 nM; b, 0.1 nM; c, 0.25 nM; d, 0.5 nM; e, 1 nM; f, 2.5 nM; g, 5 nM; h, 10 nM), and S2222 (250 µM). (B) The data generated in (A) were transformed as described in Example to estimate steady-state Factor Xa production, between 0–4 minutes. (C) For determination of the $IC_{50}$, Vs and Vo obtained between 0–4 minutes were plotted against Ixolaris concentration, at different Factor X concentration: (●) 3 nM; (■) 15 nM; (▲) 40 nM; (▼) 75 nM; (○) 100 nM; (□) 140 nM; (Δ) 175 nM; (∇) 200 nM (n=3). (D) Increase of the $K_{0.5}$ at different concentrations of Factor X. Vs, inhibited velocity; Vo, control (uninhibited velocity). Progress curves are representative experiments.
Figure 7B:
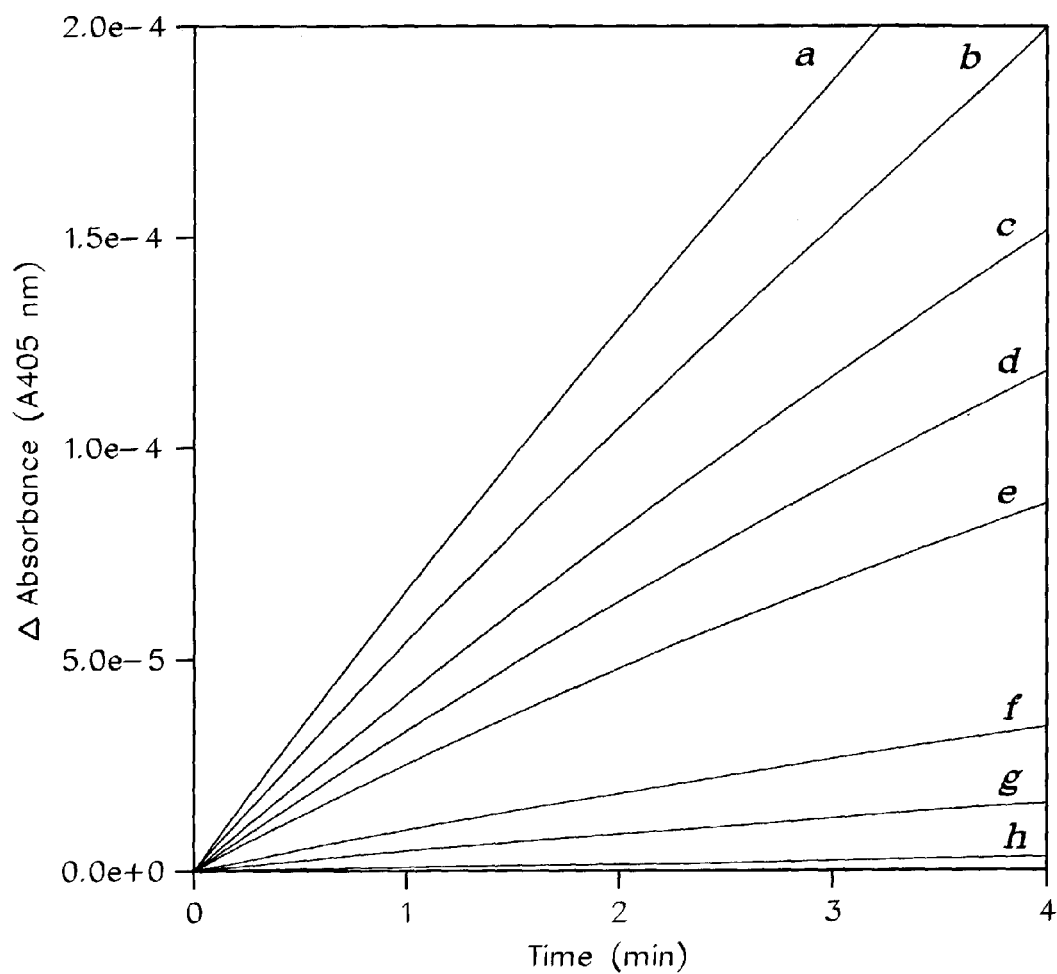
Figure 7C:
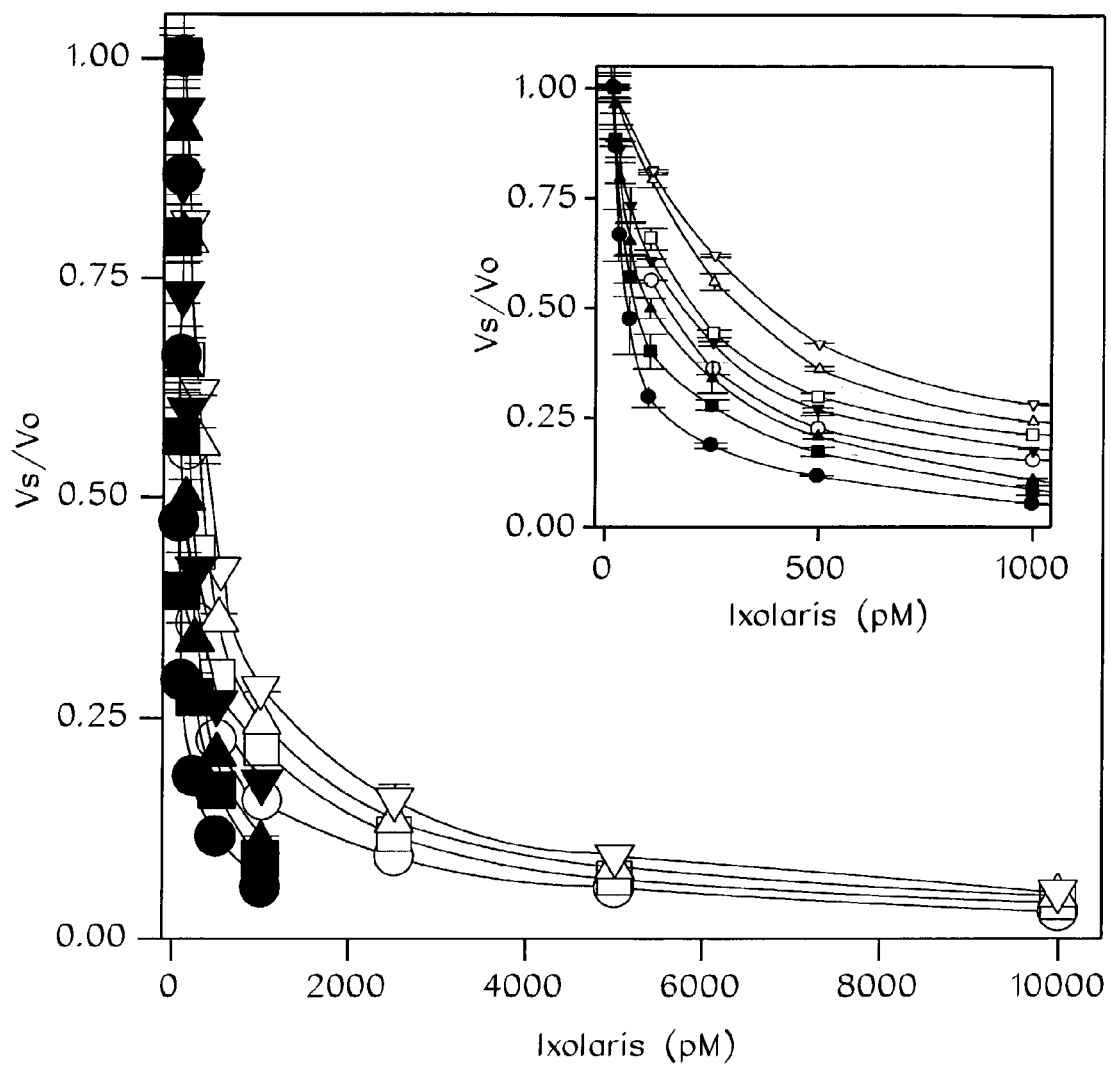
Figure 7D:
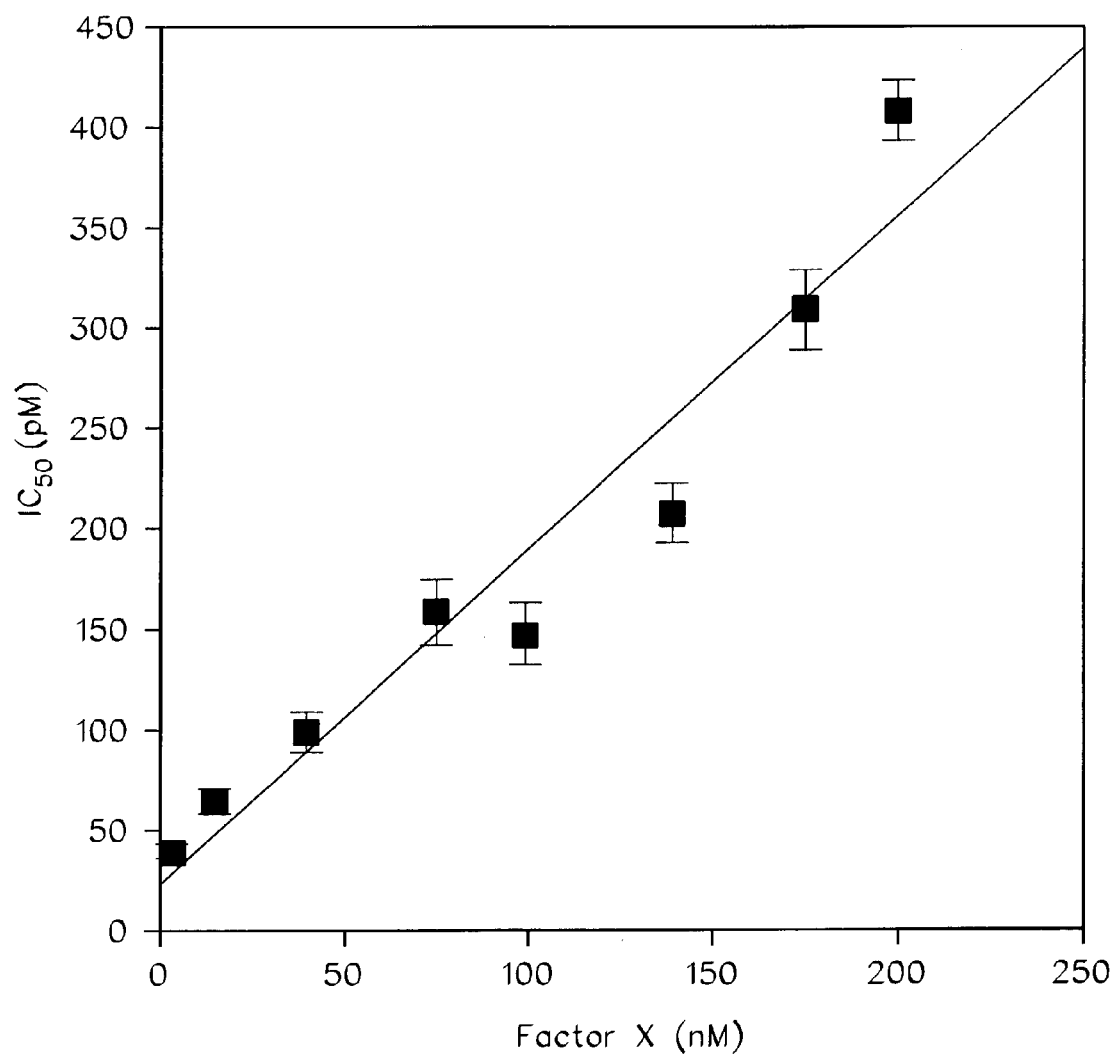

The mechanism of inhibition of blood coagulation by Ixolaris was then studied. In these experiments, Ixolaris (0–10 nM) and Factor X (200 nM) were incubated at 37° C. for 15 minutes, followed by addition of Factor VIIa (1 nM)/TF (0.2 pM) and chromogenic substrate for Factor Xa (S2222). The progress curves were characterized by a lag-phase, followed by significant hydrolytic increase between 5 and 20 minutes, and a linear augmentation thereafter showing accumulative production of Factor Xa (FIG. 7A). To estimate the production of Factor Xa at each minute, Δ absorbance (A 405/min) was used (Lindhout, T. et al. 1995 *Thromb Haemost* 74:910–915) and a linear increase of Factor Xa production was thus observed (FIG. 7B). Experiments were then performed at different concentrations of Factor X, ranging from 3 to 200 nM. Data were transformed according to Vs/Vo, where Vs and Vo are the velocities of Factor Xa production in the presence and absence of inhibitor, respectively. Experimental results indicate that Ixolaris blocks Factor Xa production at all Factor X concentrations tested (FIG. 7C), However, significant increases of Ixolaris $IC_{50}$ was attained at higher Factor X concentrations; from 30 pM at 3 nM FX to 420 pM at 200 nM FX (FIG. 7C). At 1 nM Factor X, $IC_{50}$ as low as 3 pM was obtained. Ixolaris $IC_{50}$ varied linearly as a function of Factor X concentration (FIG. 7D). Under identical experimental conditions, recombinant full-length clone human TFPI (0–10 nM) blocks Factor Xa production with $IC_{50}$ of approximately 610 pM at 15 nM Factor X, approximately 620 pM at 75 nM Factor X and approximately 625 pM at 200 nM Factor X. The remarkable effect of Factor X concentration in the $IC_{50}$ of Ixolaris for this assay, but not for human TFPI, was strong evidence that both molecules operate by distinct mechanisms.

Figure 8A:
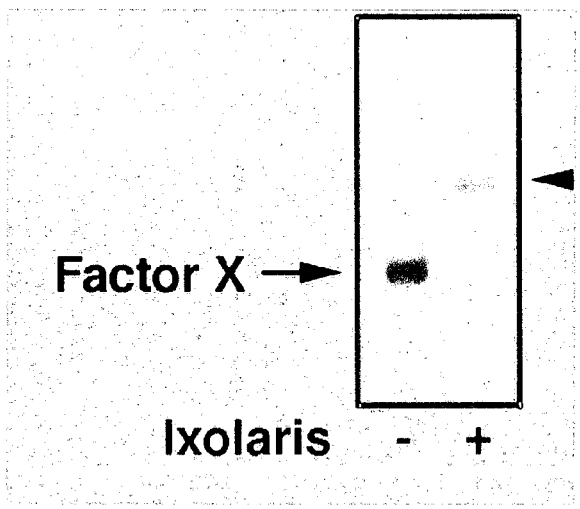
FIG. 8. Ixolaris binds to Factor X, and Factor Xa, but not to Factor VIIa. Ixolaris (20 nM) was preincubated with Factor X (20 nM), Factor Xa (20 nM), or Factor VIIa (20 nM). PAGE of the sample under non-denaturating conditions was followed by transfer of proteins to PVDF membrane. Factor Xa and Factor VIIa detection was performed using polyclonal anti-Factor Xa or monoclonal antibody anti-Factor VIIa, described in Example. (A) Lane 1, Factor X; lane 2, Factor X plus Ixolaris. (B) Lane 1, Factor Xa; lane 2, Factor Xa plus Ixolaris. (C) Lane 1, Factor VIIa; lane 2, Factor VIIa plus Ixolaris. Each blotting is a representative experiment. Arrows, enzyme; arrowheads, enzyme-inhibitor complex.
Figure 8B:
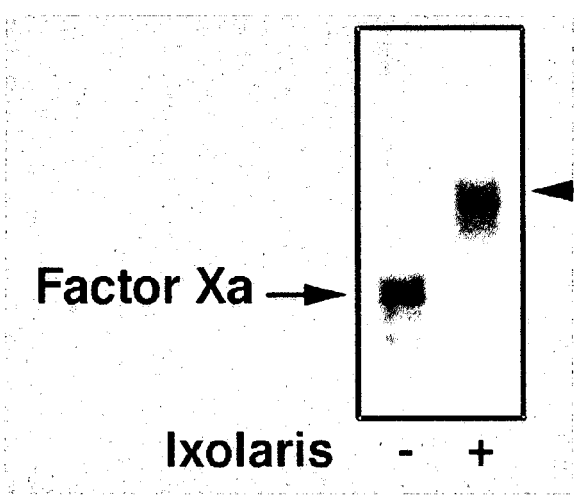
Figure 8C:
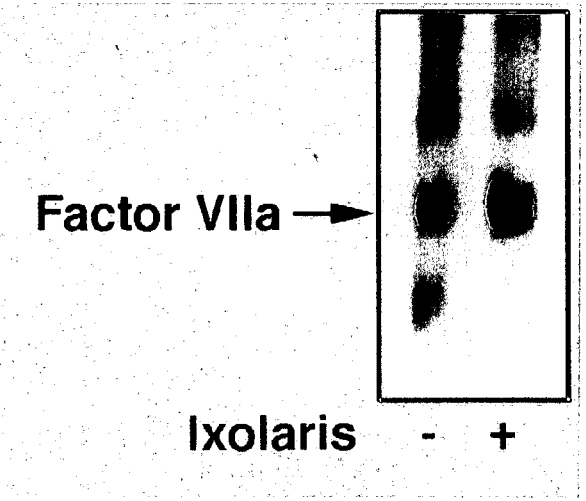

To detect Ixolaris binding to Factor X and Factor Xa, reactants were incubated in equimolar concentrations (20 nM) for 15 minutes at 37° C. followed by PAGE under non-denaturing conditions. Proteins were transferred to PVDF membrane. Experiments were performed using anti-human Factor X polyclonal antibodies. Results indicate complex formation between Ixolaris and Factor X (FIG. 8A) and Factor Xa (FIG. 8B). On the other hand, complex formation between Ixolaris and Factor VIIa was not detected using anti-human Factor VIIa MoAb (FIG. 8C), even when 10 times molar excess Ixolaris was used, indicating that Ixolaris is not a tight-inhibitor of VIIa, in contrast to Factor X and Factor Xa.

Figure 9A:
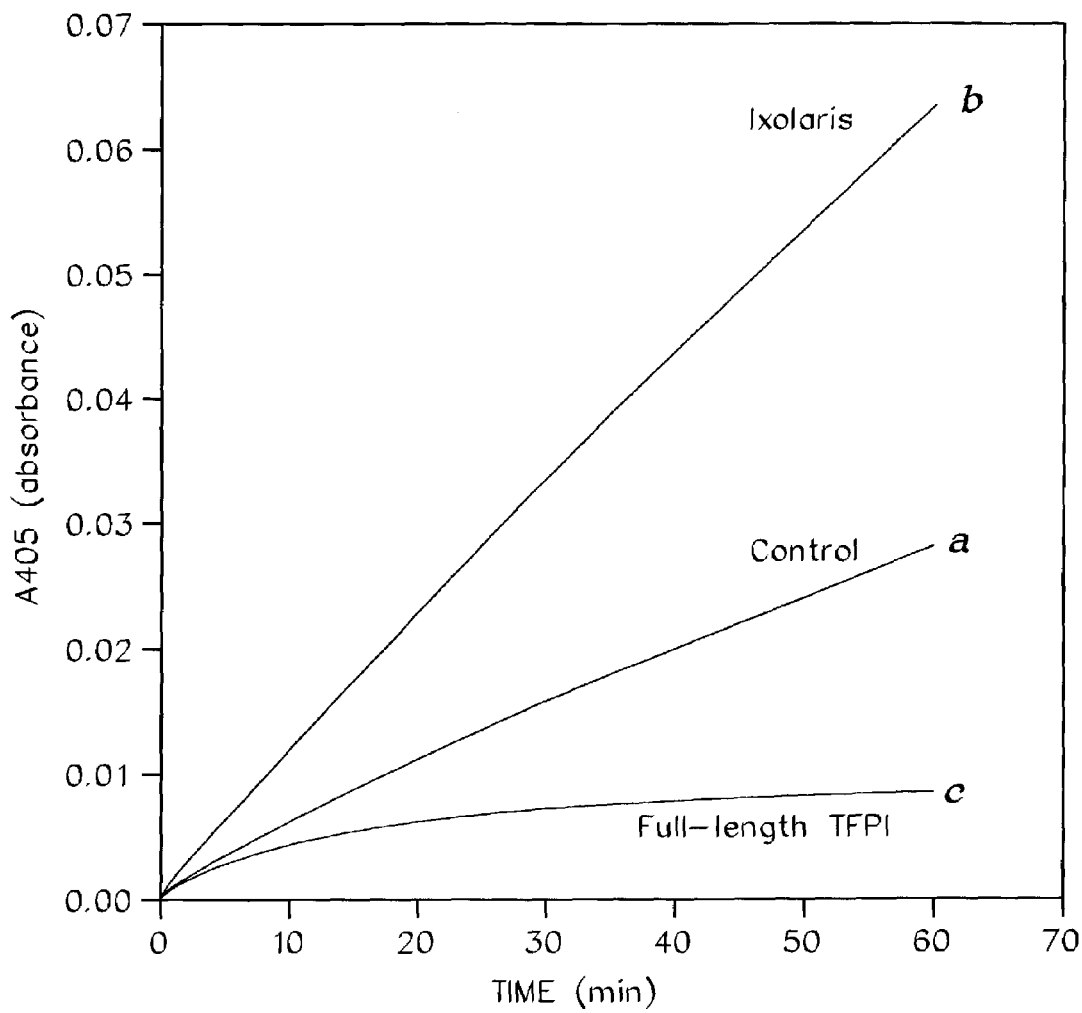
FIG. 9. Ixolaris binds to Factor Xa and Factor X. (A) Buffer (control; curve a), Ixolaris (0.8 nM, curve b), or human TFPI (20 nM, curve c) and chromogenic substrate (S2222, 250 µM) were incubated at 37° C. for 15 min before addition of Factor Xa (125 pM). (B) Factor Xa (125 pM) and Ixolaris (0–1600 pM) were incubated at 37° C. for 15 min followed by addition of S2222 (250 µM). Reaction was followed for 1 hour at 37° C. $ED_{50}$ 159±3.8 pM. Inset: progress curves of the effects of Ixolaris on Factor Xa esterolytic activity: Ixolaris (a) 0 nM; (b) 40 pM; (c) 80 pM; (d) 160 pM; (e) 300 pM; (f) 600 pM; and (g) 1600 pM. (C) Ixolaris (1.6 nM) was incubated with Factor Xa (125 pM), des-Gla-Factor Xa (600 pM), or thrombin (150 pM), followed by addition of S2222, or S2238 for thrombin. (D) Ixolaris (400 pM) was added to a mixture containing Factor Xa (640 pM) and (■) DEGR-FXa (0–3.2 nM), or (●) des-Gla-DEGR-FXa (0–4.8 nM), or (▲) DEGR-FX (0–3.2 nM). After 15 min incubation, reactions were inititated with S2222 (250 µM). Inset: Ixolaris was incubated with DEGR-FXa (0–3.2 nM), or des-Gla-DEGR-FXa (0–3.2 nM), or DEGR-FX (0–3.2 nM), and S2222 (250 µM) followed by addition of Factor Xa (640 pM). Reactants were diluted in Buffer A and substrate hydrolysis was detected at 405 nm. Experiments were performed 3–4 times, in duplicates or triplicates.
Figure 9B:
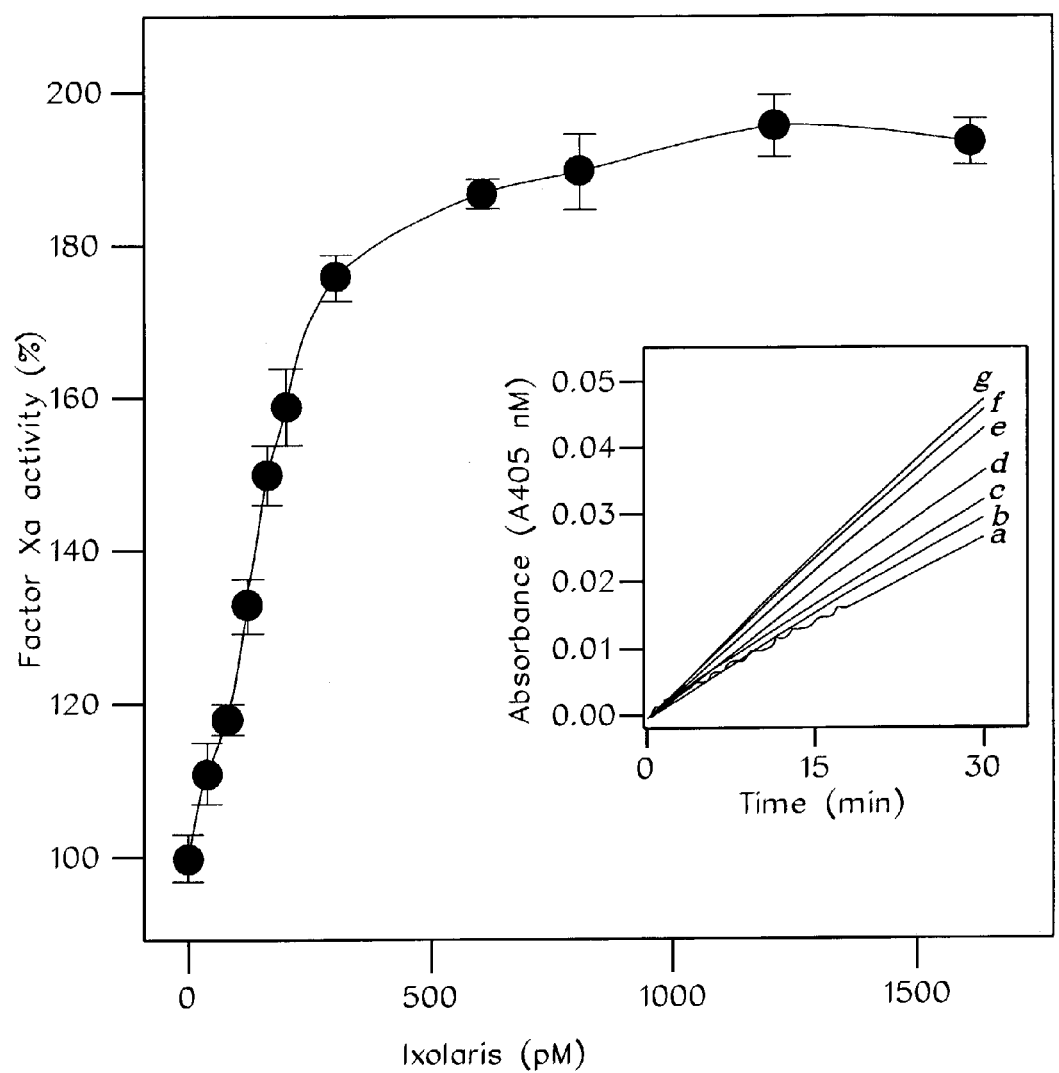
Figure 9C:
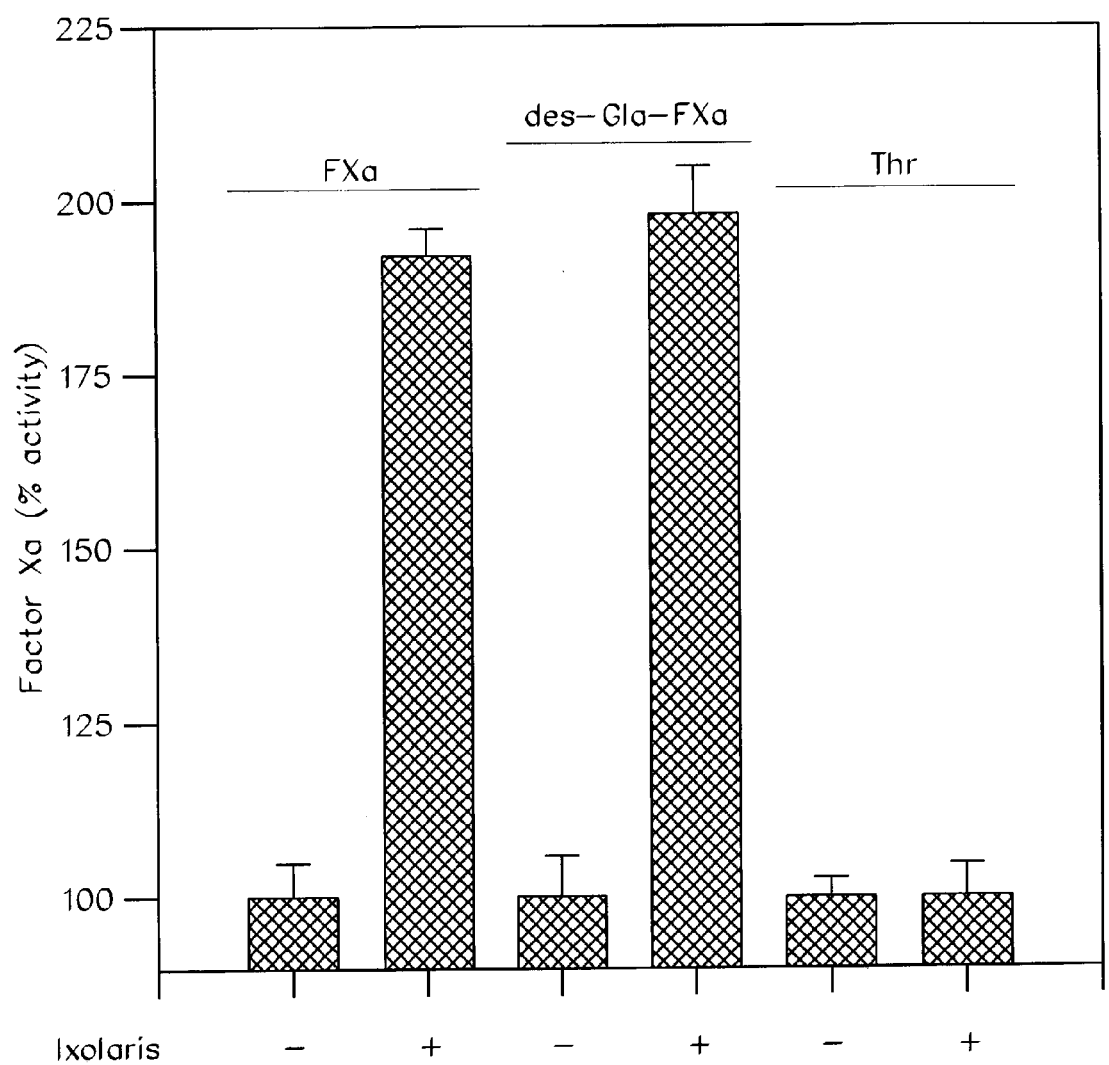

To determine whether the binding of Ixolaris to Factor Xa was accompanied by a change in the esterolytic activity of Factor Xa, inhibitor and chromogenic substrate (S2222) were incubated for 15 minutes at 37° C., followed by addition of Factor Xa (125 pM). Ixolaris, at a concentration similar to the enzyme, instantaneously increased Factor Xa activity (FIG. 9A) indicating that it is a tight-and-fast ligand of Factor Xa, with an $ED_{50}$ of 159±3.8 pM (FIG. 9B). In contrast, full-length human TFPI behaves as a typical slow-binding inhibitor of Factor Xa (Wesselschmidt, R. et al. 1992 *Blood* 79:2004–2010) (FIG. 9A). Similar results were obtained with γ-carboxyglutamic acid domainless Factor Xa (des-Gla-Factor Xa), (FIG. 9C) whose proteolytic activity increased 1.98 fold in the presence of Ixolaris (control, 0.4 nM des-Gla-Factor Xa: 1.4±0.12 units of $V_{max}$; 0.4 nM des-Gla-Factor Xa plus 1.6 nM Ixolaris: 2.78±0.1 units of $V_{max}$; triplicate determination). Similar results were obtained for Factor Xa, but not for thrombin (FIG. 9C).

Figure 9D:
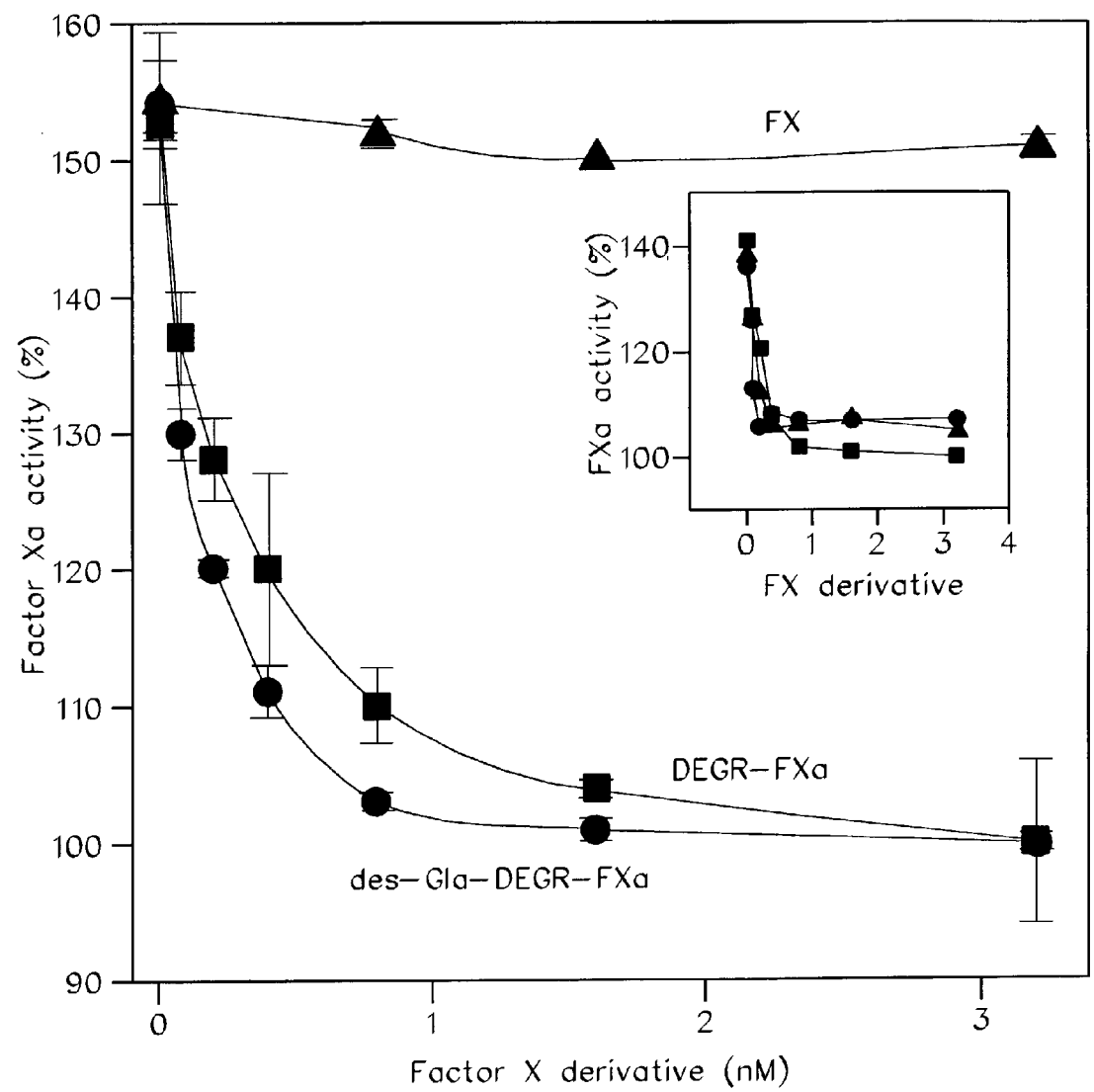

Because both Factor Xa and Factor X interact with Ixolaris as determined by native PAGE, we aimed to determine the relative affinities of Ixolaris for Factor X and Factor Xa. FIG. 9D shows that Ixolaris (400 pM) increases by ~40% the amidolytic activity of Factor Xa (640 pM). When Ixolaris (400 pM) was incubated for 15 min with a preformed mixture of Factor Xa (640 pM) and increasing concentrations (0–3.2 nM) of DEGR-Factor Xa, or des-Gla-DEGR-Factor Xa, followed by addition of S2222, the Ixolaris-dependent increase of Factor Xa activity was inhibited. Interestingly, this effect was not observed when increasing concentrations of Factor X were used (up to 16 nM). However, when Ixolaris was preincubated with Factor X or DEGR-Factor Xa and S2222, followed by addition of Factor Xa, inhibition of Ixolaris-enhanced increase of Factor Xa amidolytic activity was attained in all cases (inset, triplicate determination). Thus, Ixolaris binds with fast-and-tight kinetics to Factor Xa, whereas it binds to Factor X with lower apparent affinity and/or with slow kinetics, as indicated by the competition experiments with Factor Xa (FIG. 9D).

Figure 10A:
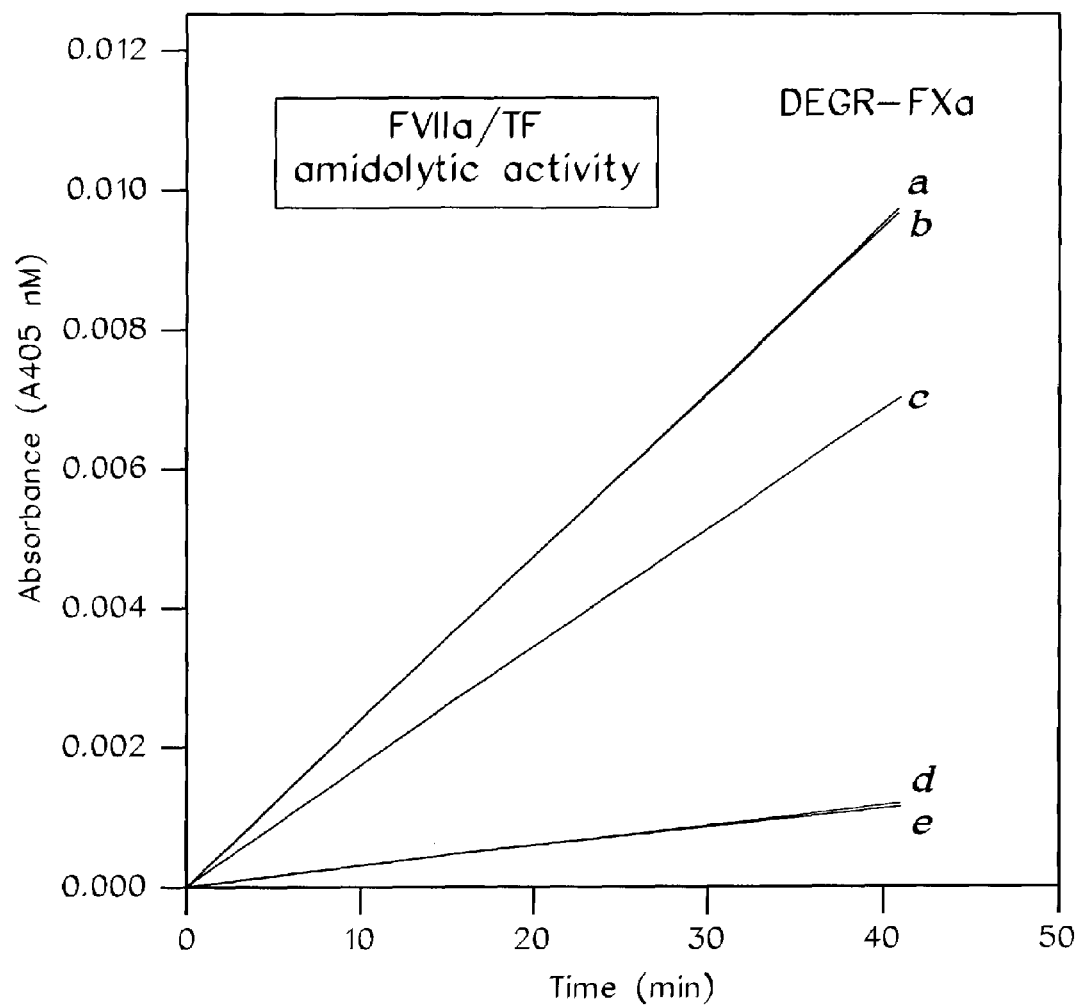
FIG. 10. Factor Xa and Factor X are scaffolds for Ixolaris in assays for FVIIa/TF amidolytic activity. (A) Ixolaris (15 nM) and DEGR-Factor Xa (0–8 nM) were incubated for 15 min in the presence of S2288 (250 µM) followed by the addition of Factor VIIa/TF (1 nM). a, control; b, Ixolaris; c, Ixolaris plus 0.08 nM DEGR-Factor Xa; d, Ixolaris plus 0.8 nM DEGR-Factor Xa; e, Ixolaris plus 8 nM DEGR-Factor Xa. (B) Ixolaris (15 nM) and DEGR-Factor X (0–8 nM) were incubated for 15 min in the presence of S2222 (250 µM) followed by the addition of Factor VIIa/TF (1 nM). a, control; b, Ixolaris; c, Ixolaris plus 0.08 nM DEGR-Factor X; d, Ixolaris plus 0.8 nM DEGR-Factor X; e, Ixolaris plus 8 nM DEGR-Factor X. (C) Vs/Vo transformation of the data in (A) for DEGR-Factor Xa (●), (B) for DEGR-Factor X (▲). Ixolaris in the presence of des-Gla-DEGR-Factor Xa did not affect Factor VIIa/TF amidolytic activity (■). (D) Factor VIIa (1 nM)/TF (0.2 pM) was incubated for 10 min with buffer; 100 pM Ixolaris; 100 pM DEGR-Factor X/Ixolaris; 100 pM DEGR-Factor Xa/Ixolaris; 100 pM DEGR-des-Gla-Factor Xa and added to Factor X (200 nM) and S2222 (250 µM). Chromogenic substrate hydrolysis was followed at absorbance reading at 405 nm, for 1 hour. Three independent experiments were performed.
Figure 10B:
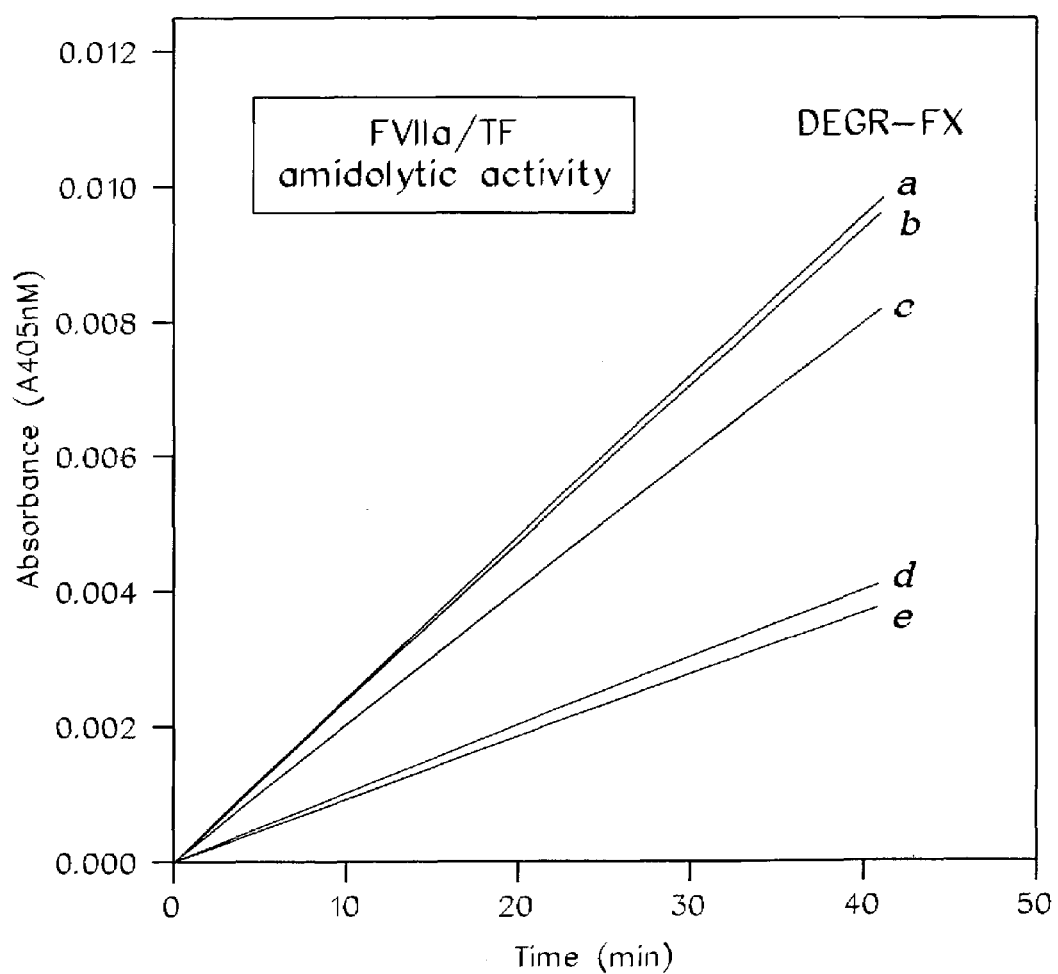
Figure 10C:
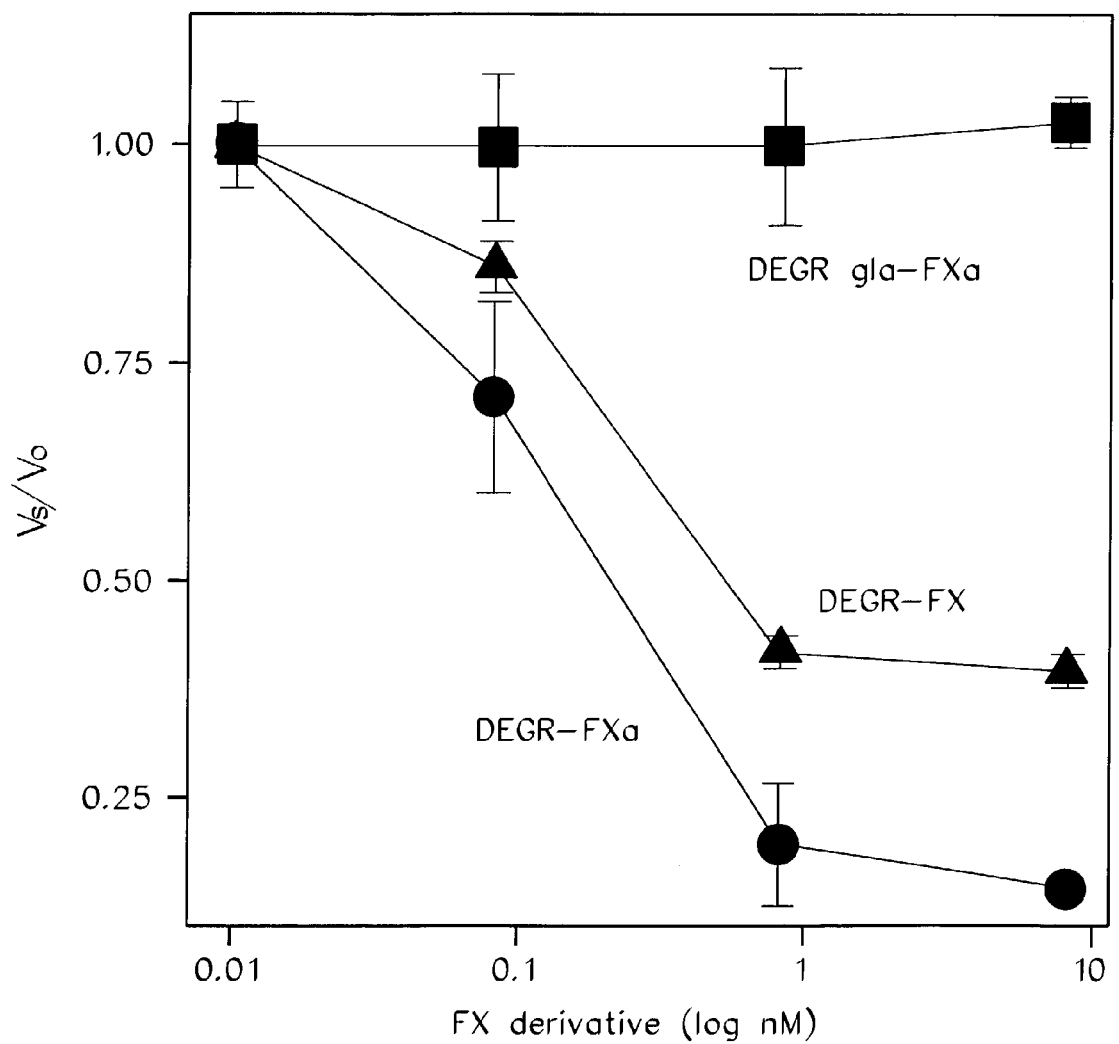

TFPI blocks the catalytic activity of Factor VIIa, in a Factor Xa dependent manner (Broze, G. J. Jr. et al. 1988 *Blood* 71:335–343; Pedersen, A. H. et al. 1990 *J Biol Chem* 254:16786–16793; Rao, L. V. M., and Rapaport, S. I. 1987 *Blood* 69:645–651; Broze, G. J. Jr. and Miletich, J. P. 1987 *PNAS* USA 84:1886–1890; Rapaport, S. I. 1989 *Blood* 73359–365). In an attempt to determine whether Ixolaris (or Ixolaris Factor X/Xa complex) inhibits Factor VIIa/TF catalytic activity, inhibitor and increasing concentrations of DEGR-Factor Xa (0–4 nM) or DEGR-Factor X (0–4 nM) were incubated with S2288 (1 mM) for 15 minutes, followed by addition of Factor VIIa (1 nM)/TF (1 nM) to start reactions. The rationale for using DEGR-Factor X is based upon experiments showing that serine catalytic site mutated Factor X ($FX^{S195A}$) has been used as an effective scaffold for NAPc2, a TFPI-like molecule from *Ancylostoma caninum* (Bergum, P. W. et al. 2001 *J Biol Chem* 276:10063–10071). FIGS. 10B and 10C shows that no inhibition of the Factor VIIa/TF amidolytic activity was obtained in the presence of Ixolaris alone (up to 266 nM). However, instantaneous inhibition was attained in a dose-dependent manner in the presence of DEGR-Factor Xa (FIG. 10A). When DEGR-Factor X was used as a scaffold, immediate inhibition was observed as well (FIG. 10B). In contrast to DEGR-Factor Xa, however, inhibition of Factor VIIa/TF amidolytic activity by Ixolaris/Factor X was reproducibly and consistently partial, and never total at the highest DEGR-Factor X concentration tested (8 nM). FIG. 10C summarizes the effects of both scaffolds in the amidolytic activity of Factor VIIa/TF, and it also shows that des-Gla-DEGR-Factor Xa did not affect the amidolytic activity of Factor VIIa/TF. It seems plausible to indicate that γ-carboxyglutamic acid is involved with Ixolaris/FX-FVIIa/TF complex formation.

Figure 10D:
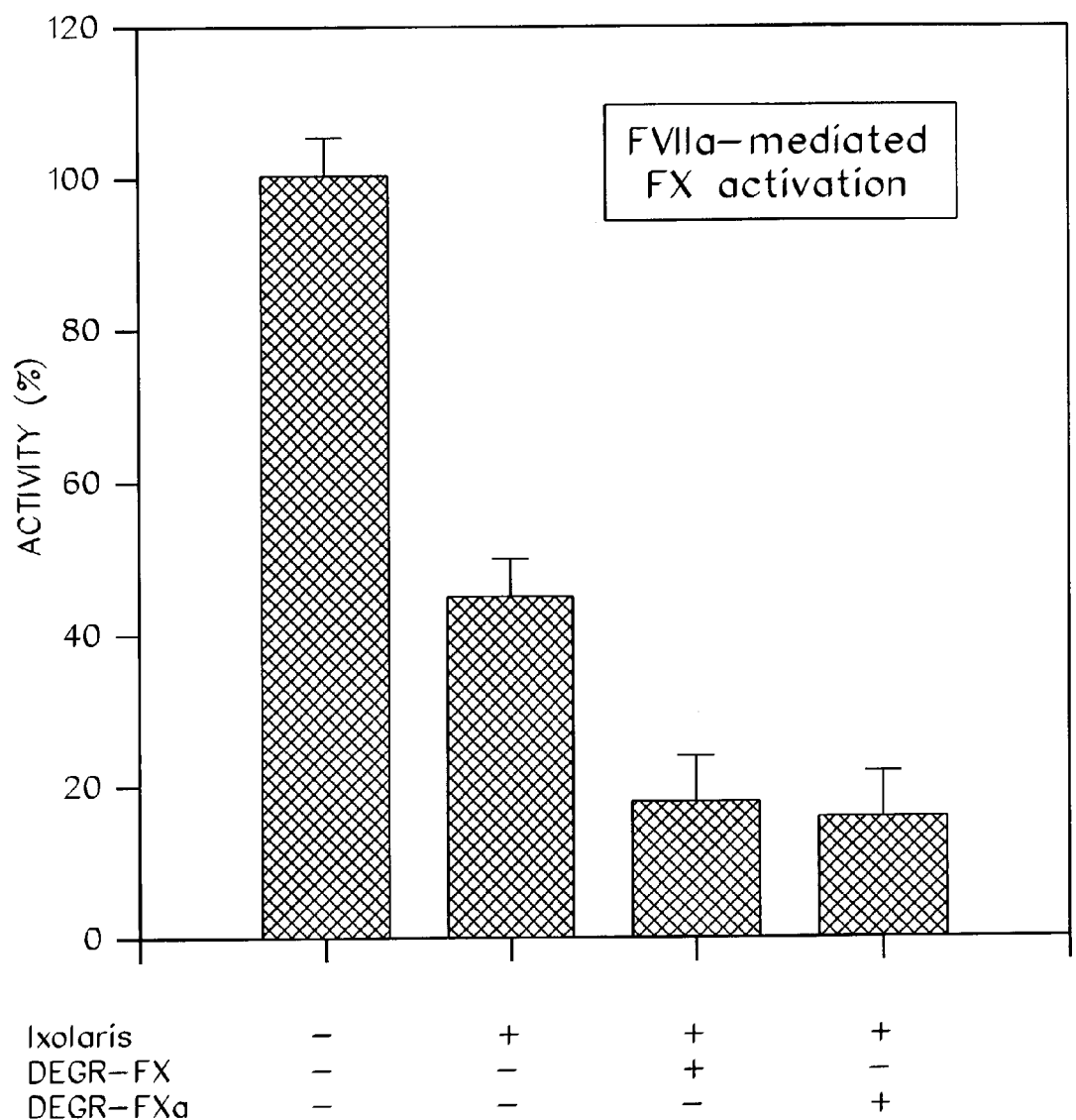

Interestingly, the partial inhibition of Factor VIIa/TF amidolytic activity after incubation with Ixolaris/Factor X is similar to the pattern described for a Factor VIIa peptide exosite inhibitor selected from naïve peptide libraries displayed on M13 phage (Dennis, M. S. et al. 2000 *Nature* 404:465–470). This information led us to hypothesize that Ixolaris/Factor X could be interacting with Factor VIIa exosite. To test this hypothesis, Factor VIIa/TF (1 nM/0.2 pM) was incubated for 15 min with buffer, Ixolaris alone (100 pM), Ixolaris/DEGR-Factor X (100 pM), Ixolaris/DEGR-Factor Xa (100 pM) or Ixolaris/DEGR-des-Gla-Factor Xa (100 pM). Subsequently this mixture was added to Factor X (200 nM). FIG. 10D shows that in the presence of buffer, Factor Xa was produced after addition of Factor VIIa/TF to Factor X (control). However, incubation of Ixolaris alone with Factor VIIa/TF resulted in ~65% inhibition, that was enhanced (>85%) with Ixolaris-DEGR-Factor X or Ixolaris/DEGR-Factor Xa. Ixolaris/DEGR-des-Gla-Factor Xa had little effect in this assay. The data from in FIG. 10D immediately indicated that Ixolaris in the absence of scaffolds inhibits the interactions of Factor VIIa/TF with macromolecular substrates at a site distinct (exosite) from the catalytic site, this interaction being positively modulated by Factor X and Factor Xa, and dependent on γ-carboxyglutamic acid residues.

Figure 11A:
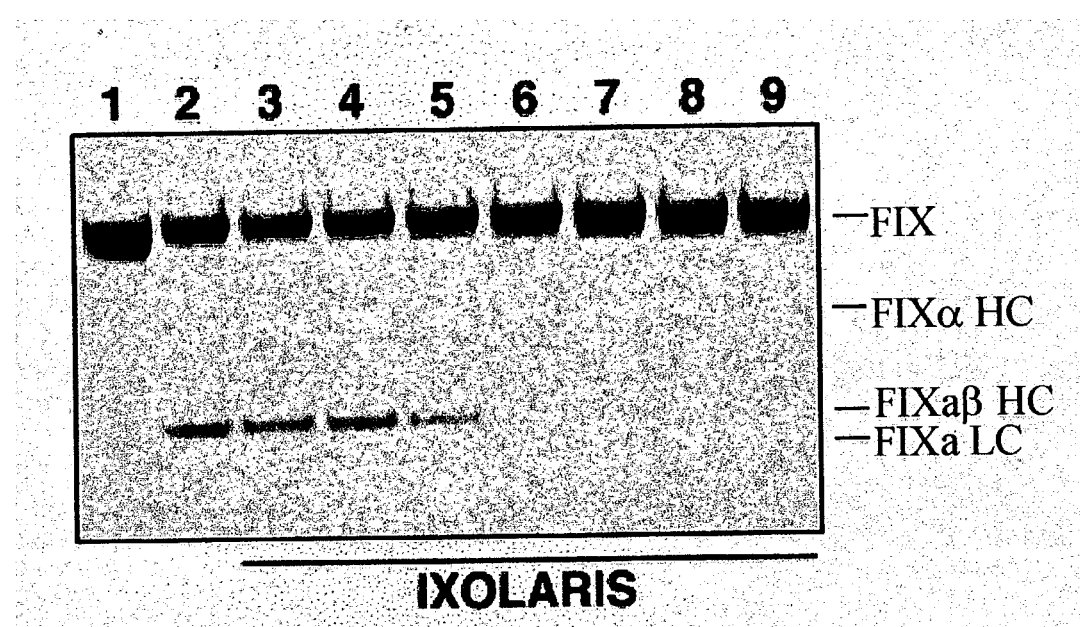
FIG. 11. Ixolaris is a direct inhibitor of Factor VIIa/TF-mediated FIX activation. (A) Factor VIIa/TF (1 nM) was incubated with Ixolaris (0–266 nM) followed by addition of Factor IX (1.4 μM). Factor IXa activation was identified by 4–12% NU-PAGE. The bands correspond to (from the top): uncleaved Factor IX, the heavy chain of Factor IXα, the heavy chain of Factor IXαβ, and the light chain of Factor αβ. Lane 1, 0 min incubation between Factor VIIa/TF and Factor IX. Other lanes, 40 min incubation. Ixolaris concentration are: lane 2, 0 nM; lane 3, 0.26 nM; lane 4, 1.04 nM; lane 5, 2.66 nM; lane 6, 10.4 nM; lane 7, 26.6 nM; lane 8, 104 nM; lane 9, 266 nM (n=4). (B) Densitometry of the bands corresponding to the heavy chain of Factor IXαβ, the light chain of Factor IXαβ is shown. (C) Quantification of the densitometry (for Factor IXαβ) shows dose-dependent inhibition of Factor VIIa/TF-mediated Factor IX activation by Ixolaris (●). No inhibition of Factor VIIa/TF (1 nM/1 nM) amidolytic activity upon S2288 by Ixolaris was detected (○) (n=3).
Figure 11B:
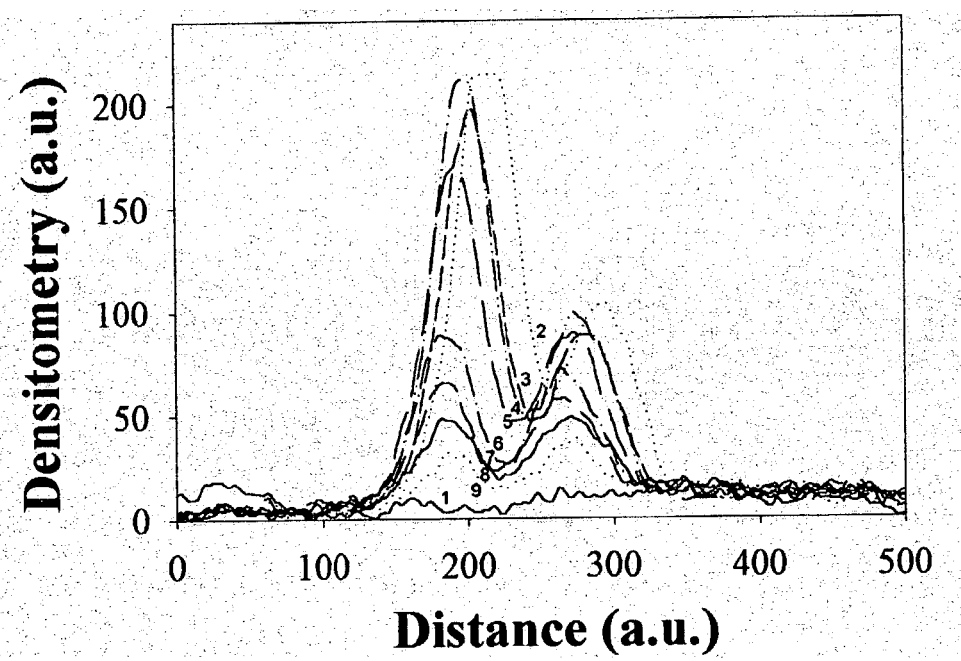
Figure 11C:
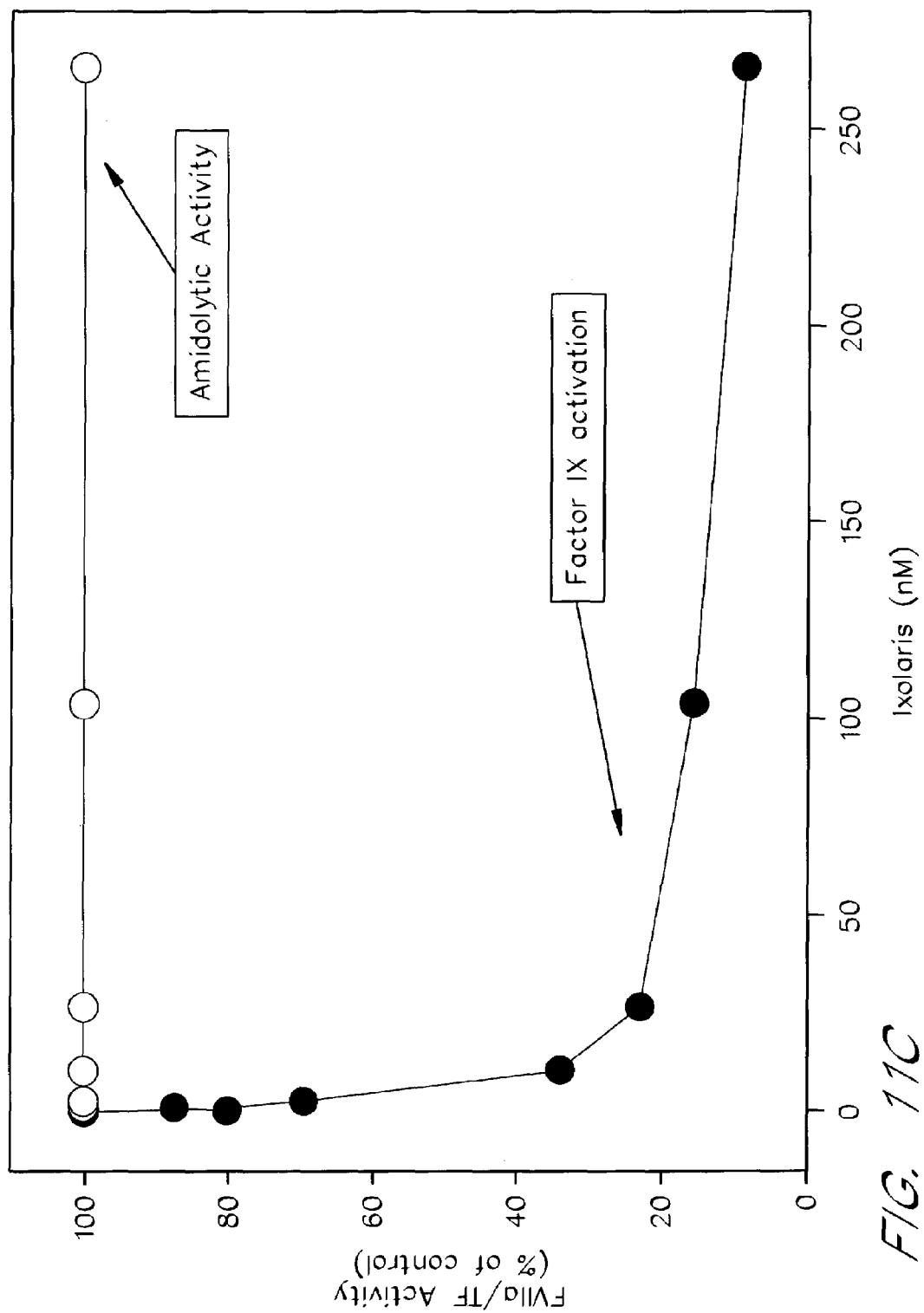

Experiments were then performed in an attempt to characterize Ixolaris as a Factor VIIa exosite inhibitor. Factor VIIa/TF catalyzes the activation of Factor IX to Factor IXa. Factor IX activation proceeds throught two consecutive steps. Cleavage of the $Arg^{145}$–$Ala^{146}$ peptide bond yields the intermediate heavy-chain fragment, indicative of Factor IXα. Subsequent cleavage of $Arg^{180}$–$Val^{181}$ bond releases the 35-aminoacid activation peptide and generates the heavy chain fragment of active Factor IXaβ. FIG. 11A shows that Factor IX was not activated when incubation with Factor VIIa/TF was not allowed to proceed (0 min incubation time, lane 1). However, after 40 min of Factor IX incubation with Factor VIIa/TF, bands corresponding to the heavy chain of Factor IXα, the heavy chain of Factor IXaβ, and the light chain of Factor aβ can be visualized in the NU-PAGE gel (Lane 2). When Ixolaris (0–266 nM) was preincubated with Factor VIIa/TF, a dose-dependent inhibition of Factor IX activation was attained (lanes 3–9). Densitometry of the bands corresponding to heavy chain of Factor IXaβ was performed to quantify the effects of Ixolaris (FIG. 11B). The results are plotted as a function of Ixolaris concentration (0–266 nM) showing a dose-dependent inhibition of Factor IX activation by Factor VIIa/TF (1 nM) (FIG. 11C). By comparison, Ixolaris in the same concentration range (up to 266 nM) did not affect the amidolytic activity of Factor VIIa/TF (1 nM) (FIG. 11C). Accordingly, Ixolaris inhibits Factor VIIa/TF interactions with macromolecules (exosite mediated) but is not an inhibitor of small chromogenic substrates cleavage by Factor VIIa/TF (catalytic site mediated).

Figure 12A:
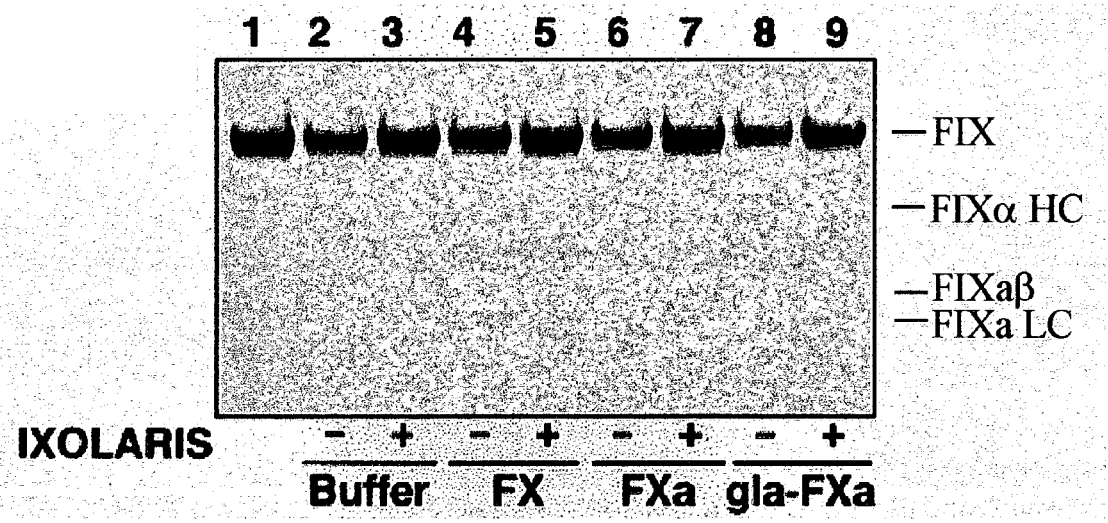
FIG. 12. Factor X and Factor Xa are scaffolds for Ixolaris in FVIIa/TF-mediated Factor IX activation assays. (A) Ixolaris (10 nM) was incubated with Factor X derivatives followed by addition of Factor VIIa/TF (0.5 nM). Lane 1, no incubation; lane 2, 0 nM Ixolaris; lane 3, Ixolaris (10 nM); lane 4, DEGR-FX (7.5 nM); lane 5, DEGR-FX (7.5 nM) plus Ixolaris (10 nM); lane 6, DEGR-FXa (7.5 nM); lane 7, DEGR-FXa (7.5 nM) plus Ixolaris (10 nM); lane 8, des-Gla-DEGR-FXa (7.5 nM); lane 9, des-Gla-DEGR-FXa (7.5 nM) plus Ixolaris (10 nM). (B) Ixolaris (20 nM) was incubated with Factor X derivatives followed by addition of Factor VIIa/TF (0.5 nM). Lane 1, no incubation; lane 2, 0 nM Ixolaris; lane 3, Ixolaris (20 nM); lane 4, DEGR-FX (15 nM); lane 5, DEGR-FX (15 nM) plus Ixolaris (20 nM); lane 6, DEGR-FXa (15 nM); lane 7, DEGR-FXa (15 nM) plus Ixolaris (20 nM); lane 8, des-Gla-DEGR-FXa (15 nM); lane 9, des-Gla-DEGR-FXa (15 nM) plus Ixolaris (20 nM). (C) Quantification of the bands corresponding to the heavy chain of Factor IXα,β was performed as in FIG. 11.
Figure 12B:
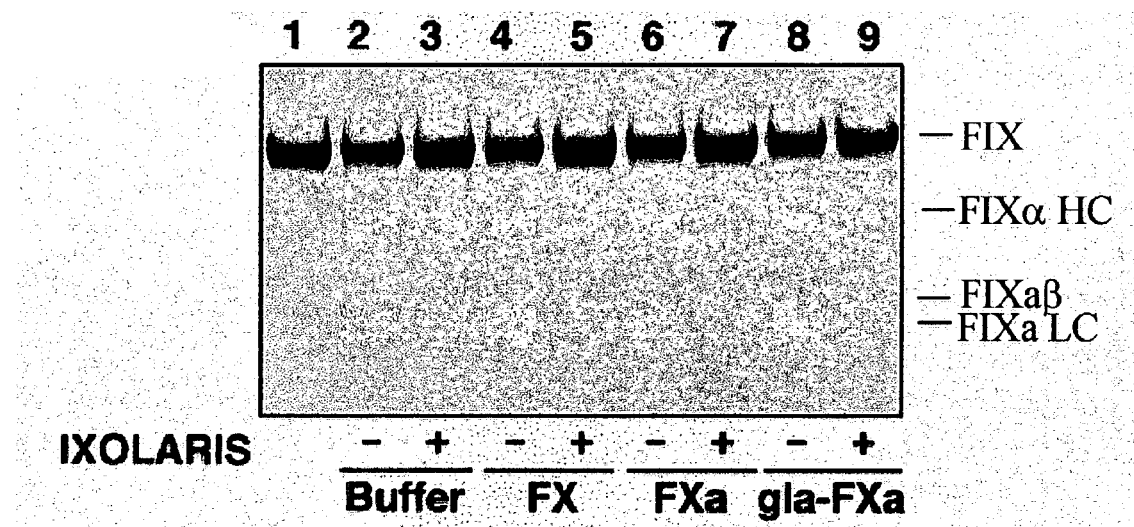

Next we tested the effects of scaffolds for Ixolaris in this assay. FIG. 12A shows that Ixolaris partially inhibits Factor IX activation (lane 3); however, this inhibition was remarkable when Factor VIIa/TF was incubated with Ixolaris/DEGR-FX (lane 5), and Ixolaris/DEGR-Factor Xa (lane 7). At higher concentrations of Ixolaris and Factor X/Xa inhibition was even more pronounced (FIG. 12B). This set of data confirmed that both Factor Xa and Factor X are scaffolds for Ixolaris, increasing its affinity for Factor VIIa/TF. As expected, we could not detect inhibition with Ixolaris/des-Gla-FXa (lane 9) indicating that γ-carboxyglutamic acid has a definite role in Ixolaris/FX(a) interaction with FVIIa/TF. Actually, in the presence of Ixolaris/DEGR-des-Gla-FXa, Ixolaris produced less inhibition in this assay. Band densitometry was performed for quantification of the results presented in FIG. 12A and FIG. 12B, as summarized in FIG. 12C.

Figure 13A:
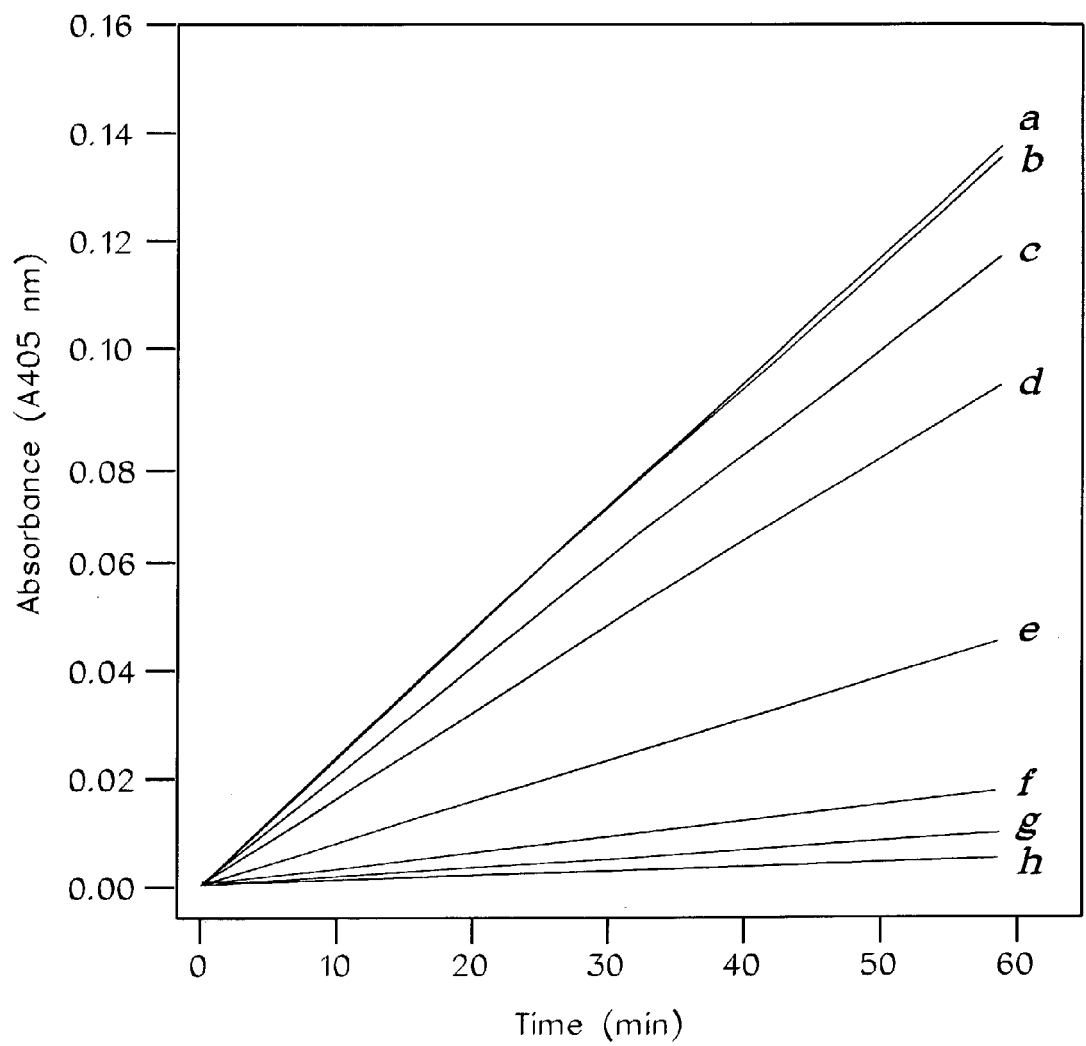
FIG. 13. Ixolaris inhibits Factor VIIa-TF amidolytic activity in a DEGR-Factor Xa-dependent manner. Ixolaris was incubated with DEGR-Factor Xa (0–4 nM) for 15 minutes at 37° C. followed by addition of Factor VIIa/TF (1 nM/0.8 nM) for 15 minutes at 37° C. S2288 (1 mM) was added, and reactions were followed for 1 hour. (A) Linear regression of the progress curves of the inhibition of Factor VIIa-TF esterolytic activity by Ixolaris (3 nM) in the presence of increasing concentrations of DEGR-Factor Xa: (a) 0 nM; (c) 0.1 nM; (d) 0.25 nM; (e) 0.5 nM; (f) 1 nM; (g) 2.5 nM; (h) 5 nM. In (b), Ixolaris was added in the absence of DEGR-Factor Xa. (B) Progress curves are expressed as Vs/Vo, yielding an $IC_{50}$ of 0.41±0.04 nM in the presence of DEGR-Factor Xa and Ixolaris (●). No inhibition was detected in the absence of Ixolaris (■).
Figure 13B:
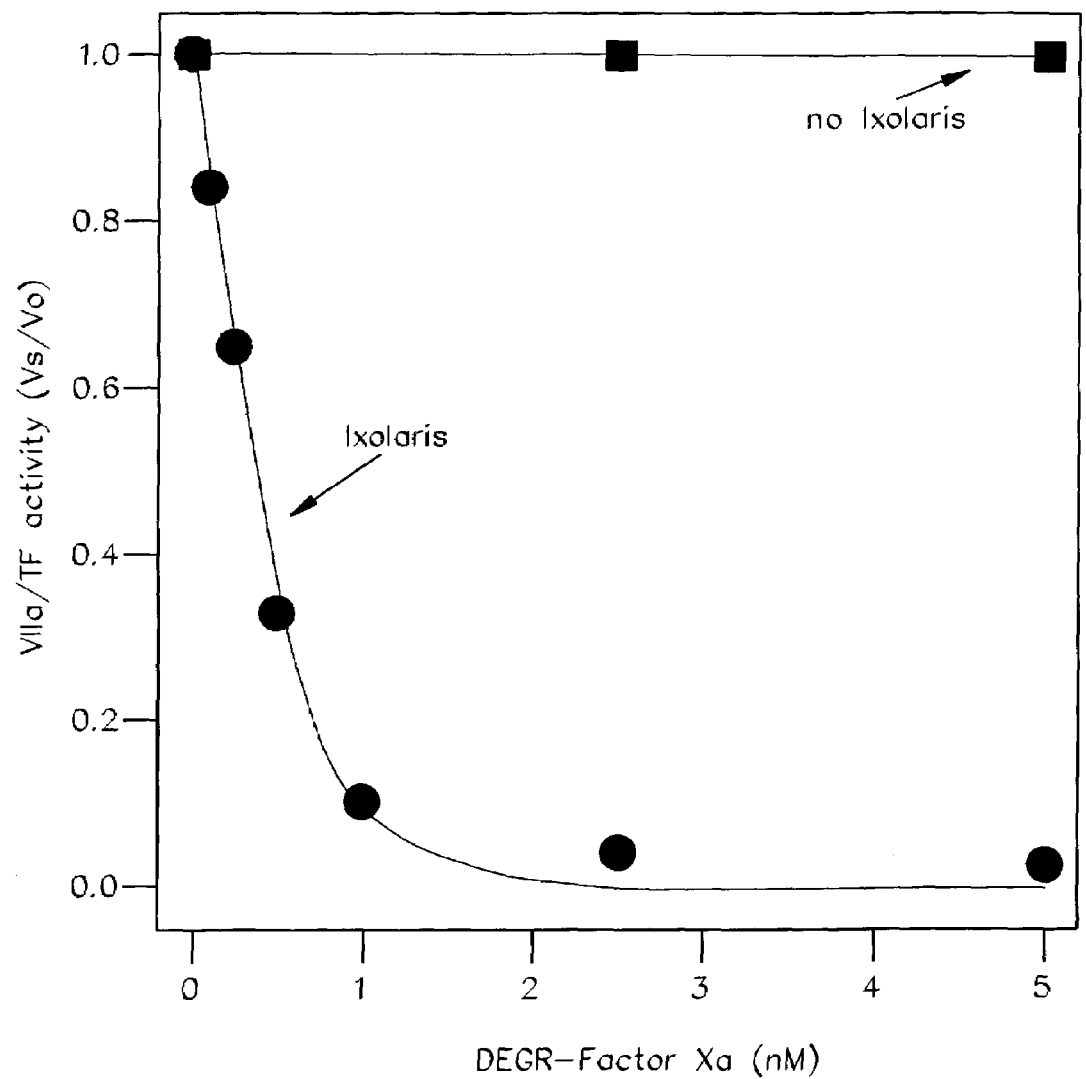

We then attempted to determine the stoichiometry of the interaction between Ixolaris/Factor Xa and Factor VIIa/TF. FIG. 13A shows the progress curves for inhibition of Factor VIIa (1 nM)/TF (0.8 nM) amidolytic activity on S2288 by Ixolaris (3 nM) in the presence of increasing concentrations of DEGR-Factor Xa (0–5 nM). A transformation of the data as Vs/Vo yields an $IC_{50}$ of 0.41±0.04 nM. Almost complete (>95%) inhibition was observed at Ixolaris/DEGR-FXa concentration of 1 nM (FIG. 13B). This result indicates that Ixolaris, Factor Xa, Factor VIIa and TF react stoichiometrically. The finding that Ixolaris inhibits Factor VIIa-TF activity in a Factor Xa-dependent manner was confirmed by increasing the concentration of Ixolaris (0–5 nM) at one concentration of DEGR-Factor Xa (3 nM).

Figure 14:
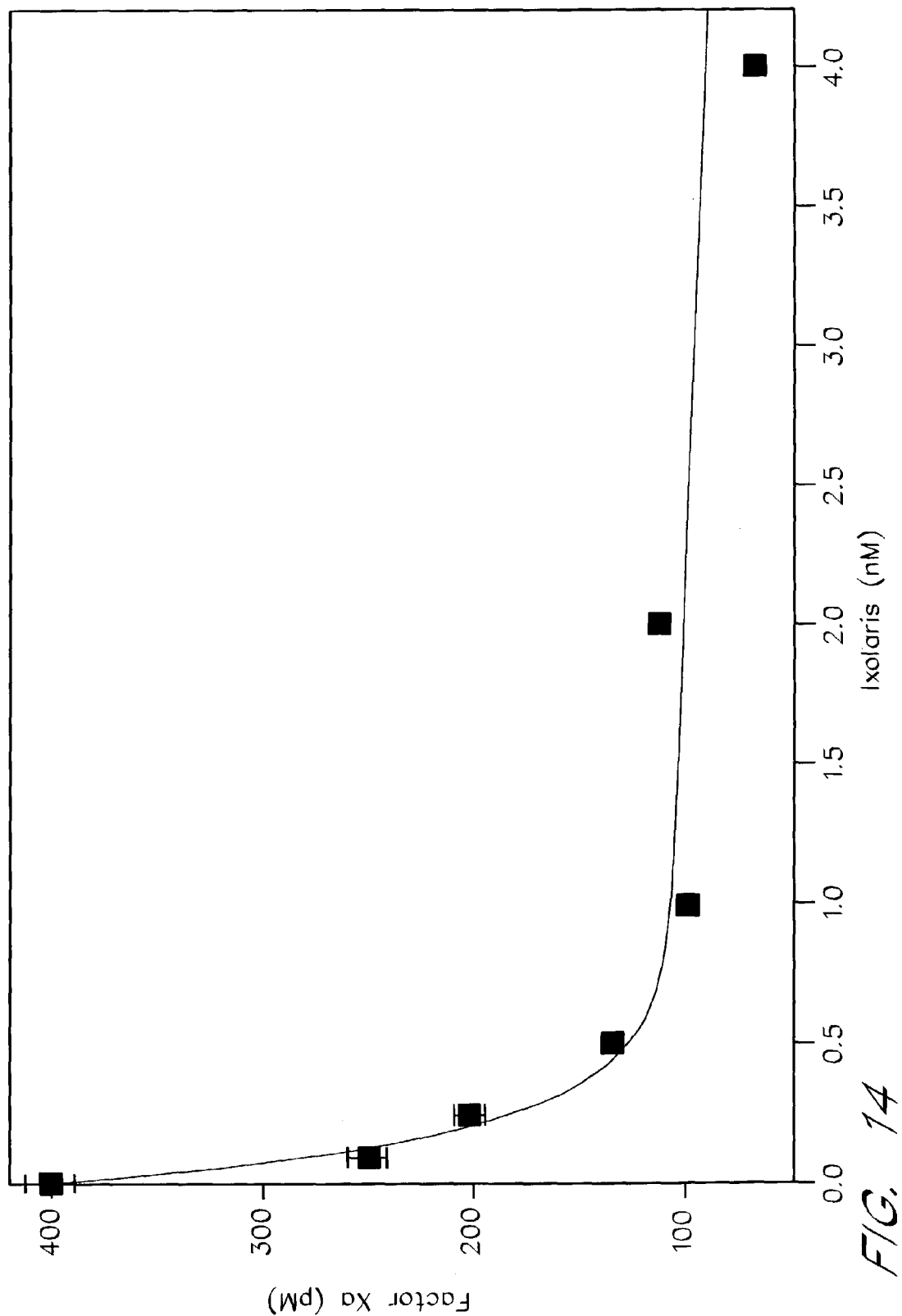
FIG. 14. Ixolaris inhibits HUVEC-triggered formation of Factor Xa. A mixture of Factor X (200 nM) and Ixolaris (0–8 nM) previously incubated together at 37° C. for 15 min was added to confluent HUVECs. This step was followed immediately by addition of Factor VIIa (1 nM) to start reactions. After 30 min, 100 μl was removed and added to a 96 well plate containing 100 μl of S2222 (500 μM) diluted in 50 mM Hepes, 100 mM NaCl, 50 mM EDTA, 0.5% BSA, pH 7.4. Absorbance reading at 405 nm (substrate hydrolysis) was followed for 1 h and Factor Xa concentration was estimated by a standard curve, using known concentrations of Factor Xa. Appropriate controls were run in parallel: HUVEC that have not been exposed to LPS (68.4±8.7 pM Factor Xa). LPS-exposed HUVEC in the absence of Factor VIIa (78.08±6.59 pM Factor Xa). Data is the mean ±SE of triplicate experiment. Experiments were performed with HUVEC in the $2^{nd}$ or $3^{rd}$ passages.

In an attempt to study the effects of Ixolaris under relevant physiological conditions, human umbilical vein endothelial cells (HUVEC) were stimulated to express TF after 4-hours incubation with lipopolysaccharide (LPS). Then a mixture containing Factor X (200 nM) and Ixolaris (0–4 nM) previously incubated together for 15 min was added to the cells, followed by immediate addition of Factor VIIa (1 nM). After 30 min, Factor Xa production was detected using chromogenic substrate for Factor Xa. FIG. 14 shows that Ixolaris dose-dependently inhibits Factor Xa production, with an $IC_{50}$~500 pM.

Table 1 shows that Ixolaris is a specific inhibitor for Factor VIIa/TF-induced Factor X activation.

TABLE 1

Specificity of Ixolaris to Factor VIIa/TF-induced Factor X activation. Ixolaris (32 nM, final concentration) was preincubated for 15 minutes at 37° C. with the enzymes listed below, followed by addition of the appropriate chromogenic substrate. Reactions were followed for 30 minutes at 37° C., and the effect of Ixolaris was estimated by setting the initial velocity obtained in the presence of enzyme alone (without inhibitor) as 100%.

| Enzymes/Substrates | Residual activity (%) |
|---|---|
| VIIa/TF (6.4 pM)/S2288 (1 mM) | 0 |
| Thrombin (125 pM)/S2238 (250 μM) | 103 ± 1.56 |
| Chymotrypsin (22.4 nM)/S2222 (250 μM) | 101.5 ± 0.09 |
| Factor XIa (58.7 pM)/S2256 (250 μM) | 89.2 ± 3.1 |
| Reptilase (0.3125 BU/mL)/S2238 (250 μM) | 98.5 ± 0.52 |
| Plasmin (5 mU/mL)/S2251 (250 μM) | 107.5 ± 0.75 |
| Elastase (250 pM)/Substrate (500 μM) | 106 ± 8.02 |
| Tryptase (0.4 μg/mL)/S2222 (250 μM) | 101 ± 0.07 |

Ixolaris

The recombinant tick salivary protein of this invention, called Ixolaris, potently inhibits factor VIIa/TF-induced Factor X activation with an $IC_{50}$ in the pM range. Ixolaris is functionally and structurally distinct from its endogenous counterpart, TFPI (Broze, G. J. et al. 1990 Biochemistry 29:7539–7546; Sprecher, C. A. et al. 1994 PNAS USA 91:3353–3357; Laskowski, M. Jr. and Kato I. 1980 Annu Rev Biochem 49:593–626): although the six cysteines that characterize the first Kunitz domain (Laskowski, M. Jr, and Kato I. 1980 Annu Rev Biochem 49:593–626) of TFPI are conserved in Ixolaris, only four of six cysteines present in the second Kunitz domain of human TFPI are present. Also, whereas the sixth and the first cysteines that, respectively, terminate and initiate the first and second Kunitz domains in human TFPI are separated by 20 amino acids, only 7 amino acids separate the corresponding cysteines in Ixolaris. Additionally, the Kunitz-type domain 2 in Ixolaris is unusual by containing 4 additional amino acids between the fourth and fifth cysteine residues, making this loop longer than most Kunitz-type family members. Also, the presumed $P_1$ reactive-site residue of the first domain in Ixolaris is Glu, whereas Lys occupies this position in TFPI (Broze, G. J. et a. 1990 Biochemistry 29:7539–7546). Finally, Ixolaris has a short and basic carboxy terminus but, unlike TFPI, it has only 14 amino acids where the positively charged amino acids are not organized as a cluster. In human TFPI, this basic carboxy terminus has been consistently shown to increase its anticoagulant activity (Wesselschmidt, R. et al. 1992 Blood 79:2004–2010; Nordfang, O. et al. 1991 Biochemistry 30:10371–10376) and to shorten its half-life (Warshawasky, I. et al. 1995 J Clin Invest 95:1173–1181; Ho, G. et al. 2000 Blood 95:1973–1978). The Ixolaris cDNA also encodes three putative N-linked glycosylation sites, at $Asn^{65}$, $Asn^{98}$, and $Asn^{136}$. Consistent with a calculated mass of 15.7 kDa for the carbohydrate-free protein, we could detect a band of ~15.5 kDa in the gels loaded with recombinant Ixolaris; however, an intense smear was observed in PAGE of Ixolaris at a molecular weight range of ~24 kDa. Accordingly, it is likely that these Asn residues are indeed glycosylated, and this is the most abundant form (>95%) of the secreted recombinant molecule.

TFPI and Ixolaris are unrelated in many functional aspects. Ixolaris is a highly specific inhibitor that, unlike human TFPI, does not inhibit trypsin or chymotrypsin (Petersen, L. C. et al. 1996 Eur J Biochem 235:310–316). Ixolaris increases the amidolytic activity of Factor Xa toward chromogenic substrates and behaves as a fast ligand of Factor Xa, in contrast to TFPI, a typical Factor Xa slow-binding inhibitor (Wesselschmidt, R. et al. 1992 Blood 79:2004–2010). Additionally, Ixolaris binds to des-Gla-Factor Xa and to a tripeptidyl chloromethylketone covalently occupied catalytic site of Factor Xa (DEGR-Factor Xa), two properties not shared by TFPI (Broze, G. J. Jr. et al. 1988 Blood 71:335–343; Hamamoto, T. et al. 1993 J Biol Chem 268:8704–8710). This result indicates that Ixolaris binds at the exosite of Factor Xa and implies that γ-carboxyglutamic acid is not involved in the interaction between enzyme and inhibitor. Remarkably, Ixolaris also binds to Factor X, in addition to Factor Xa, although relative affinities or the kinetics of the interaction (slow vs. fast) may be different as depicted in the competition experiments shown in FIG. 9D (inset). This result may be due to how the exosite is exposed in Factor Xa in comparison to a putative Factor X proexosite (Krishnaswamy, S. and Betz, A. 1997 Biochemistry 36:12080–12086). Interestingly, it has been recently shown that NAPc2, a TFPI-like molecule from Ancylostoma caninum, also binds to Factor X (in addition to Factor Xa). NAPc2 also displays slow association kinetics for interaction with Factor X that is at 5~10 lower rates than those measured with Factor Xa (Bergum, P. W. et al. 2001 J Biol Chem 276:10063–10071). It has been proposed that the structural features of Factor X requires an induced fit during the association phase of NAPc2 with Factor X (Bergum, P. W. et al. 2001 J Biol Chem 276:10063–10071). We suggest that a similar mechanism may operate for Ixolaris.

According to the data gathered in FIGS. 10 and 12, it is also clear that both zymogen (DEGR-Factor X) and enzyme (DEGR-Factor Xa) operate as scaffolds for Ixolaris. Because Ixolaris/Factor X only partially attenuates Factor VIIa/TF amidolytic activity it was hypothesized that inhibitor/zymogen complex does not have complete access to the catalytic site of Factor VIIa, or alternatively, it binds to a site distinct (exosite) from the catalytic site. This pattern of inhibition is consistent with Factor VIIa exosite inhibitors recently described in a naïve peptide library displayed on M13 phage (Dennis, M. S. et al. 2000 Nature 404:465–470). These inhibitors block the interactions of Factor VIIa/TF with macromolecular substrates, but only partially attenuate the amidolytic activity of FVIIa/TF. In the experiments described here, Ixolaris alone also prevents Factor IX activation by Factor VIIa/TF (exosite mediator), without affecting Factor VIIa/TF amidolytic (catalytic) activity (S2288) (FIGS. 10C, 11C). This result indicates that Ixolaris interacts with Factor VIIa exosite. Because inhibition is this assays occurs at [I]>>[E], we conclude that Ixolaris is not a tight inhibitor of Factor VIIa/TF; this point is consistent with no detection of complex formation between enzyme and inhibitor as assessed in native PAGE. Importantly, control experiments revealed that this inhibition was not due to trace levels of Factor X or Factor Xa contaminating the Factor IX preparation. Interestingly, TFPI also partly blocks the amidolytic activity of Factor VIIa/TF (Pedersen, A. H. et al. 1990 J Biol Chem 254:16786–16793; Hamamoto, T. et al. 1993 J Biol Chem 268:8704–8710; Iakhiaev, A. et al. 2001 Thromb Haemost 85:458–463), whereas it completely inhibits the activation of Factor IX by Factor VIIa in complex with cell surface TF, in the absence of scaffolds (Hamamoto, T. et al. 1993 J Biol Chem 268:8704–8710). More recently it has been shown that TFPI-Xa complex interacts with both the catalytic site and the macromolecular substrate exosite of Factor VIIa/TF (Iakhiaev, A. et al. 2001 *Thromb Haemost* 85:458–463). Accordingly, there is a contrast between TFPI, which interacts also with the catalytic site, and Ixolaris, which interacts solely with the exosite. In a recept paper, Baugh et al. (Baugh, R. J. et al. 2000 *J Biol Chem* 275: 28826–28833) concluded that exosite-dependent interactions play a predominant role in determining the affinity for protein substrates and kinetics of interaction involving at least two enzymes of the blood coagulation cascade. Clearly, this point has important implications for the targeting of enzyme exosites by a natural inhibitor like Ixolaris that will effectively disrupt coagulation enzyme complexes.

Figure 12C:
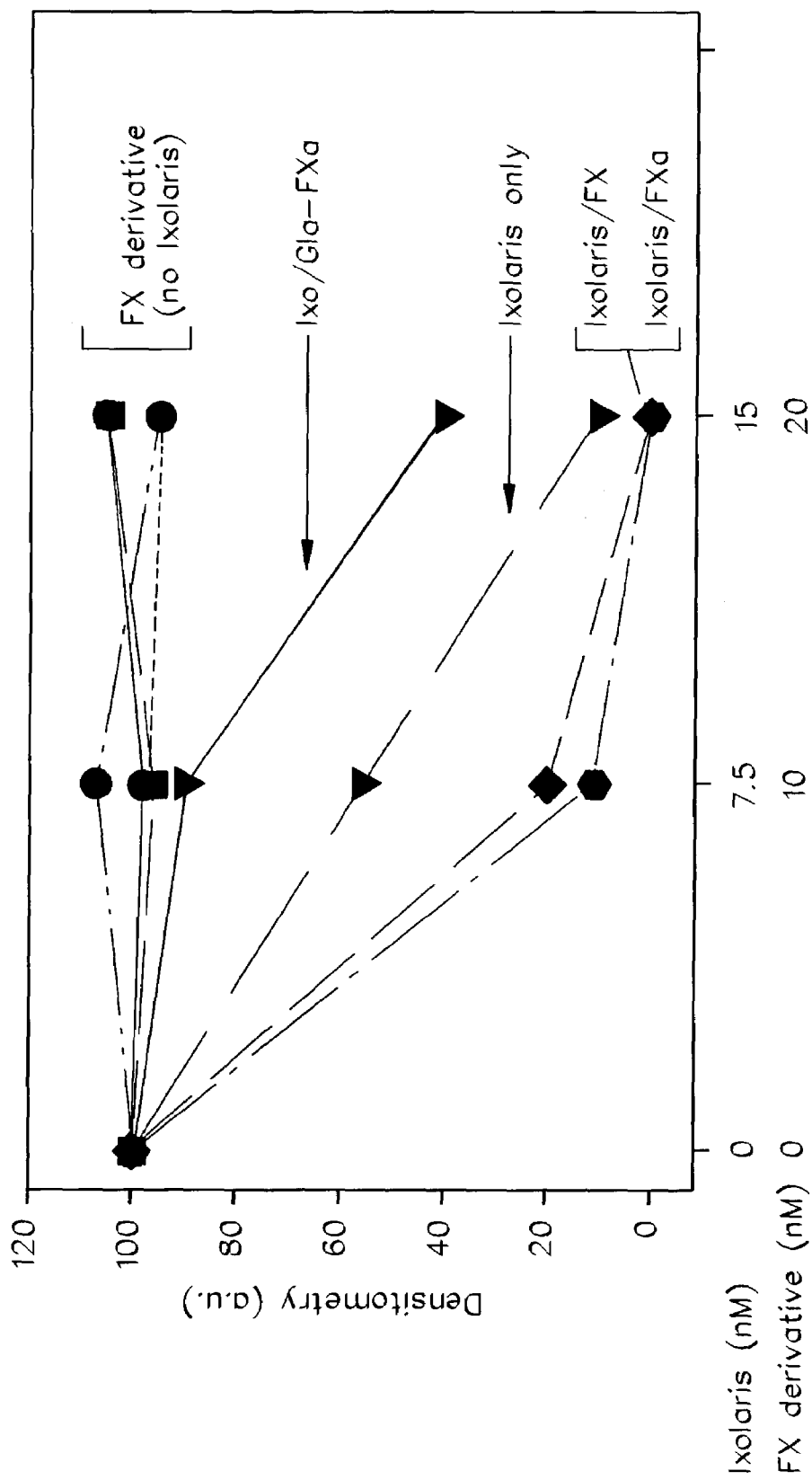

The anionic Gla-domain of Factor X is known to play a crucial role in the interaction of Factor Xa with pro-coagulant membrane surface, and directly with Factor VIIa/TF complex (Ruf, W. et al. 1999 *Biochemistry* 38:1957–1966). To demonstrate the importance of this domain for the activity of scaffolds we used DEGR-des-Gla-Factor Xa, a Factor X derivative lacking the Gla-domain. The binding of des-Gla-FXa to Ixolaris was similar to Factor Xa (FIGS. 9C, 9D), demonstrating that this domain is not crucial for inhibitor binding to zymogen/enzyme. However, DEGR-des-Gla-Factor Xa was a completely ineffective scaffold for Ixolaris in the inhibition of Factor VIIa/TF-mediated FIX activation and amidolytic activity. Actually, des-Gla-Factor Xa attenuated the inhibition of Factor VIIa/TF activity detected in the presence of Ixolaris alone (FIG. 10D and FIG. 12C). Accordingly, it seems that des-Gla-Factor Xa tight-binding to Ixolaris prevents its interaction with Factor VIIa/TF, an interaction that is characteristically not tight. In other words, in the absence of Gla-Domain, des-Gla-Factor Xa and Factor VIIa/TF compete for Ixolaris.

Regarding the interaction of Ixolaris with Factor Xa and Ixolaris/Factor X(a) with VIIa/TF, they are kinetically fast. In fact, instantaneous increase of chromogenic substrate hydrolysis was attained when Factor Xa was added to a mixture containing Ixolaris and S2222 (FIG. 9A). Likewise, Factor VIIa/TF amidolytic activity was immediately blocked when the enzyme was added to a mixture containing Ixolaris/Factor Xa and S2288 (FIG. 10A), or Ixolaris/Factor X and S2288 (FIG. 10B). This finding is also consistent with the data presented in FIG. 7B, where the production of Factor Xa was blocked without delay when Factor VIIa/TF was added to a mixture containing Ixolaris/Factor X and S2222.

Our results also show that Ixolaris blocks the catalytic activity of Factor VIIa/TF in the presence of increasing concentrations of DEGR-Factor Xa, and maximal inhibition was attained with a 1:1 stoichiometry, indicating that Ixolaris/Factor Xa behaves as a tight inhibitor of Factor VIIa/TF. Due to the tight interaction between Ixolaris and Factor X detected by native PAGE, we suggest that Ixolaris forms a stable complex with physiologic concentration of Factor X. This finding seems relevant since Ixolaris/Factor X may inhibit Factor VIIa/TF before Factor Xa production. Similar conclusions have been obtained for NAPc2 that also shares with Ixolaris dependency on Factor X and Factor Xa as scaffolds (Bergum, P. W. et al. 2001 *J Biol Chem* 276:10063–10071; Stanssens, P. et al. 1996 *PNAS* USA 93:2149–2154). However, both molecules differ from each other in structural and kinetic aspects. NAPc2 is a protein of 84 amino acids with a distinct pattern of cysteines when compared to Ixolaris. Also, we could not identify an arginine between two cysteines that have been characterized in NAPc2 as the cleavage site for Factor Xa. NAPc2 partially blocks Factor Xa proteolytic activity toward chromogenic substrates, whereas Ixolaris enhances it. Moreover, NAPc2 at high concentrations, but not Ixolaris, blocks the amidolytic activity of Factor VIIa/TF. In addition, Ixolaris/DEGR-FXa behaves as a fast inhibitor of Factor VIIa/TF, whereas NAPc2/DEGR-FXa is a slow inhibitor of Factor VIIa/TF (Bergum, P. W. et al. 2001 *J Biol Chem* 276:10063–10071; Stanssens, P. et al. 1996 *PNAS* USA 93:2149–2154).

Despite clear structural and functional differences among Ixolaris, NAPc2, and human TFPI, these inhibitors may affect Factor Xa production in an equivalent manner through binding to Factor Xa (or Factor X) preceding formation of a quaternary complex consisting of inhibitor/Factor X(a)/Factor VIIa/TF (Sprecher, C. A. et al. 1994 *PNAS* USA 91:3353–3357). However, we cannot predict at present whether the first and second Kunitz domains of Ixolaris bind respectively to Factor Xa and Factor VIIa, as described for human TFPI (Sprecher, C. A. et al. 1994 *PNAS* USA 91:3353–3357). It also remains to be determined how the presence of scaffolds induces Ixolaris to block the catalytic activity of Factor VIIa/TF. Finally, the finding that Ixolaris blocks Factor Xa generation by endothelial cells expressing TF indicates that Ixolaris exerts anticoagulant effect under relevant physiological conditions.

The proposed inhibitory mechanism of Ixolaris is schematically shown below. Ixolaris binds to Factor X (step 1) or Factor Xa (step 2). Subsequently, this interaction is followed by stable complex formation with Factor VIIa/TF (step 3 or 3'). In vitro, Ixolaris also binds to Factor VIIa/TF, in the absence of scaffolds (step 4), the physiological relevance of this interaction being currently unknown since Ixolaris should circulate bound to Factor X in the blood.

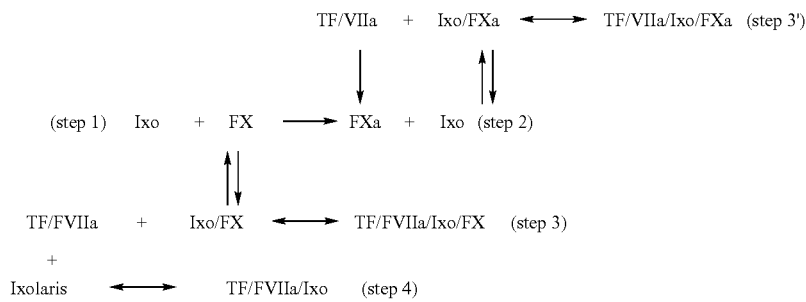

Novel molecules that block initiation of blood coagulation, such as Ixolaris, are envisioned as being useful as inhibitors to prevent or ameliorate a number of pathologic conditions leading to cardiovascular diseases provoked or amplified by abnormal expression of TFPI (Weitz, J. I. in: Hematology 2000 City, ST, The American Society of Hematology Education (Program Book) p 266–268; Bajaj, M. S. and Bajaj S. P. 1997 *Thromb Haemost* 78:471–477; Brown, D. M. et al. 1996 *Arch Surg* 131:1086–1090; Warr T. A. et al. 1990 *Blood* 75:1481–1489; Han, X. et al. 1999 *Arterioscler Thromb Vasc Biol* 19:2563–2567; Blomberg, M. E. and Cappello, M. 1999 *Cancer J* 5:132–138; Jonge, E. et al. 1999 *Blood* 95:1124–1129). More recently, NAPc2 was shown to be effective in preventing deep-venous thrombosis in patients undergoing total knee replacement surgery (Lee, A. et al. 2000 *Blood* 96:491a). Given the finding that Ixolaris is a fast ligand of Factor Xa (indicating rapid inhibition) and that it has a short carboxy terminus (suggesting less cell surface binding and slow clearance in vivo) (Warshawasky, I. et al. 1995 *J Clin Invest* 95:1173–1181; Ho, G. et al. 2000 *Blood* 95:1973–1978; Petersen, L. C. et al. 1996 *Eur J Biochem* 235:310–316) and the recent studies suggesting that agents targeting Factor VIIa/TF (eg, VIIai, anti-TF antibodies, TFPI) may induce less bleeding than agents that target coagulation at later stages (Jeske, W. et al. 1996 *Sem Thromb Hemost* 22:213–219; Himber, J. et al. 1997 *Thromb Haemost* 78:1142–1149; Harker, L. A. et al. 1996 *Haemostasis* 26:76–82), Ixolaris is envisioned as being an alternative to conventional anticoagulants such as heparin in a number of clinical conditions. Finally, because Ixolaris presumably participates in the feeding process of the tick, it is envisioned as being useful, together with other molecules such as Ixodes anticomplement (Isac) (Valenzuela et al. 2000 *J. Biol. Chem.* 275:18717–23), as a target for a vaccine (Thanassi and Schoen 2000 *Ann. Intern. Med.* 132:661–668) to prevent Lyme disease.

Definitions

The term "isolated" requires that a material be removed from its original environment (e.g., the natural environment if it is naturally occurring). For example, a naturally occurring polynucleotide or polypeptide present in a living cell is not isolated, but the same polynucleotide or polypeptide, separated from some or all of the coexisting materials in the natural system, is isolated.

The term "purified" does not require absolute purity; rather it is intended as a relative definition, with reference to the purity of the material in its natural state. Purification of natural material to at least one order of magnitude, preferably two or three magnitudes, and more preferably four or five orders of magnitude is expressly contemplated.

The term "enriched" means that the concentration of the material is at least about 2, 5, 10, 100, or 1000 times its natural concentration (for example), advantageously 0.01% by weight. Enriched preparations of about 0.5%, 1%, 5%, 10%, and 20% by weight are also contemplated.

The Ixolaris Gene

The cDNA sequence (SEQ. ID. NO. 470) and deduced amino acid sequence (SEQ. ID. No. 471) of Ixolaris are shown in FIG. 3. The signal sequence extends from amino acid residue 1 to 25. The mature protein contains 140 amino acids, including 10 cysteines (SEQ ID NO: 138).

The Ixolaris nucleotide sequences of the invention include: (a) the cDNA sequence shown in FIG. 3; (b) nucleotide sequence that encodes the amino acid sequence shown in FIG. 3, its functional domains, truncations thereof, as well as substitutions, insertions, and deletions (including fusion proteins) thereof; (c) any nucleotide sequence that hybridizes to the complement of the cDNA sequence shown in FIG. 3 under highly stringent conditions, e.g., hybridization to filter-bound DNA in 0.5 M $NaHPO_4$, 7% sodium dodecyl sulfate (SDS), 1 mM EDTA at 65° C., and washing in 0.1 times SSC/0.1% SDS at 68° C. (Ausubel F. M. et al. eds. 1989 Current Protocols in Molecular Biology, Vol. I, Green Publishing Associates, Inc., and John Wiley & sons, Inc., New York, at p. 2.10.3) and encodes a functionally equivalent gene product; and (d) any nucleotide sequence that hybridizes to the complement of the cDNA sequence shown in FIG. 3 under less stringent conditions, such as moderately stringent conditions, e.g., washing in 0.2 times SSC/0.1% SDS at 42° C. (Ausubel et al. 1989, supra), yet which still encodes a functionally equivalent gene product. Functional equivalents of Ixolaris include those naturally occurring and engineered, as judged by any of a number of criteria, including, but not limited to, the binding affinity for Factor Xa, X, or VIIa, the resulting biological effect of factor Xa, X, or VIIa binding, anticoagulant activity, generation of antibodies that specifically bind Ixolaris, and identification of compounds that can be used to modulate coagulation function.

The invention also includes nucleic acid molecules, preferably DNA molecules, that hybridize to, and are therefore the complements of, the nucleotide sequences (a) through (d), in the preceding paragraph.

In addition to the Ixolaris nucleotide sequences described above, full or partial length Ixolaris cDNA present in the same species and/or homologs of the Ixolaris gene present in other species can be identified and readily isolated, without undue experimentation, by molecular biological techniques well known in the art. For example, expression libraries of cDNAs synthesized from salivary gland mRNA derived from the organism of interest can be screened using labeled Factor Xa, X, or VIIa derived from that species, e.g., a Factor Xa, X, or VIIa fusion protein. Alternatively, such cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more domains of the Ixolaris gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15–30 base pairs of the Ixolaris nucleotide sequence, as shown in FIG. 3. The hybridization washing conditions used should be of a lower stringency when the cDNA library is derived from an organism different from the type of organism from which the labeled sequence was derived. With respect to the cloning of a human Ixolaris homolog, using tick Ixolaris probes, for example, hybridization can, for example, be performed at 65° C. overnight in Church's buffer (7% SDS, 250 mM $NaHPO_4$, 2 µM EDTA, 1% BSA). Washes can be done with 2 times SSC, 0.1% SDS at 65° C. and then at 0.1 times SSC, 0.1% SDS at 65° C.

Low stringency conditions are well known to those of skill in the art, and will vary predictably depending on the specific organisms from which the library and the labeled sequences are derived. For guidance regarding these and other hybridization conditions see, for example, Sambrook et al. 1989 Molecular Cloning, A Laboratory Manual, Cold Springs Harbor Press, N.Y.; Ausubel et al. 1989 Current Protocols in Molecular Biology, Green Publishing Associates and Wiley Interscience, N.Y.

Alternatively, the labeled Ixolaris nucleotide probe may be used to screen a genomic library derived from the organism of interest, again, using appropriately stringent conditions.

Further, a full or partial length Ixolaris cDNA present in the same species and/or homologs of the Ixolaris gene present in other species may be isolated from nucleic acid of the organism of interest by performing PCR using two degenerate oligonucleotide primer pools designed on the basis of amino acid sequences within the Ixolaris gene product disclosed herein. The template for the reaction may be cDNA obtained by reverse transcription of mRNA prepared from, for example, cell lines or tissue, such as salivary gland, known or suspected to express an Ixolaris gene allele.

The PCR product may be subcloned and sequenced to ensure that the amplified sequences represent the sequences of an Ixolaris gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the Ixolaris gene, such as, for example, salivary gland). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al. 1989, supra.

In addition to nucleotide sequences encoding the full-length Ixolaris protein 140-mer, other embodiments of the invention may include nucleotide sequences encoding truncations of the Ixolaris protein which exhibit binding affinity for Factor Xa, X, or VIIa, the resulting biological effect of Factor Xa, X, or VIIa binding, anticoagulant activity, generation of antibodies that specifically bind Ixolaris, or identification of compounds that can be used to modulate coagulation function. Truncations of Ixolaris peptides may comprise peptides of between 3 and 140 amino acid residues (i.e., peptides ranging in size from a tripeptide to a 140-mer polypeptide), as shown in Appendix A (Table I) and Appendix B (Table II). Peptide sequences in these tables are listed from amino (left) to carboxy (right) terminus. "X" may represent an amino group (—NH$_2$) and "Z" may represent a carboxyl (—COOH) group. Alternatively, "X" may represent a hydrophobic group, including but not limited to carbobenzyl, dansyl, or T-butoxycarbonyl; an acetyl group; a 9-fluorenylmethoxy-carbonyl (FMOC) group; or a covalently attached macromolecular group, including but not limited to a lipid-fatty acid conjugate, polyethylene glycol, carbohydrate or peptide group. Further, "Z" may represent an amino group; a T-butoxycarbonyl group; or a covalently attached macromolecular group, including but not limited to a lipid-fatty acid conjugate, polyethylene glycol, carbohydrate or peptide group. A preferred "X" or "Z" macromolecular group is a peptide group.

The invention encompasses nucleotide sequences that encode not only Ixolaris but also its functional domains, besides truncations thereof, as well as substitutions, insertions, and deletions (including fusion proteins) thereof. These include, but are not limited to nucleotide sequences encoding a Kunitz domain of the Ixolaris protein. It is believed that a Kunitz domain is responsible for the observed anticoagulant activity. Certain representative Kunitz domains include the amino acid sequences depicted in FIG. 3, particularly the sequences between the cysteines designated as cysteine 1 and cysteine 10; also between amino acids 18 and 68 (first Kunitz domain) and its amino and carboxy truncations:

| Sequence | |
|---|---|
| CLDPEQVTCESQEGTHASYNRKTGQCEEQKGTECGGGENHFETLLKCNESC | (SEQ ID NO:276) |
| LDPEQVTCESQEGTHASYNRKTGQCEEQKQTECGGGENHFETLLKCNESC | (SEQ ID NO:277) |
| DPEQVTCESQEGTHASYNRKTGQCEEQKGTECGGGENHFETLLKCNESC | (SEQ ID NO:278) |
| PEQVTCESQEGTHASYNRKTGQCEEQKGTECGGGENHFETLLKCNESC | (SEQ ID NO:279) |
| EQVTCESQEGTHASYNRKTGQCEEQKGTECGGGENHFETLLKCNESC | (SEQ ID NO:280) |
| QVTCESQEGTHASYNRKTGQCEEQKGTECGGGENHFETLLKCNESC | (SEQ ID NO:281) |
| VTCESQEGTHASYNRKTGQCEEQKGTECGGGENHFETLLKCNESC | (SEQ ID NO:282) |
| TCESQEGTHASYNRKTGQCEEQKGTECGGGENHFETLLKCNESC | (SEQ ID NO:283) |
| CESQEGTHASYNRKTGQCEEQKGTECGGGENHFETLLKCNESC | (SEQ ID NO:284) |
| ESQEGTHASYNRKTGQCEEQKGTECGGGENHFETLLKCNESC | (SEQ ID NO:285) |
| SQEGTHASYNRKTGQCEEQKGTECGGGENHFETLLKCNESC | (SEQ ID NO:286) |
| QEGTHASYNRKTGQCEEQKGTECGGGENHFETLLKCNESC | (SEQ ID NO:287) |
| EGTHASYNRKTGQCEEQKGTECGGGENHFETLLKCNESC | (SEQ ID NO:288) |
| GTHASYNRKTGQCEEQKGTECGGGENHFETLLKCNESC | (SEQ ID NO:289) |

```
THASYNRKTGQCEEQKGTECGGGENHFETLLKCNESC        (SEQ ID NO:290)
 HASYNRKTGQCEEQKGTECGGGENHFETLLKCNESC        (SEQ ID NO:291)
  ASYNRKTGQCEEQKGTECGGGENHFETLLKCNESC        (SEQ ID NO:292)
   SYNRKTGQCEEQKGTECGGGENHFETLLKCNESC        (SEQ ID NO:293)
    YNRKTGQCEEQKGTECGGGENHFETLLKCNESC        (SEQ ID NO:294)
     NRKTGQCEEQKGTECGGGENHFETLLKCNESC        (SEQ ID NO:295)
      RKTGQCEEQKGTECGGGENHFETLLKCNESC        (SEQ ID NO:296)
       KTGQCEEQKGTECGGGENHFETLLKCNESC        (SEQ ID NO:297)
        TGQCEEQKGTECGGGENHFETLLKCNESC        (SEQ ID NO:298)
         GQCEEQKGTECGGGENHFETLLKCNESC        (SEQ ID NO:299)
          QCEEQKGTECGGGENHFETLLKCNESC        (SEQ ID NO:300)
           CEEQKGTECGGGENHFETLLKCNESC        (SEQ ID NO:301)
            EEQKGTECGGGENHFETLLKCNESC        (SEQ ID NO:302)
             EQKGTECGGGENHFETLLKCNESC        (SEQ ID NO:303)
              QKGTECGGGENHFETLLKCNESC        (SEQ ID NO:304)
               KGTECGGGENHFETLLKCNESC        (SEQ ID NO:305)
                GTECGGGENHFETLLKCNESC        (SEQ ID NO:306)
                 TECGGGENHFETLLKCNESC        (SEQ ID NO:307)
                  ECGGGENHFETLLKCNESC        (SEQ ID NO:308)
                   CGGGENHFETLLKCNESC        (SEQ ID NO:309)
                    GGGENHFETLLKCNESC        (SEQ ID NO:310)
                     GGENHFETLLKCNESC        (SEQ ID NO:311)
                      GENHFETLLKCNESC        (SEQ ID NO:312)
                       ENHFETLLKCNESC        (SEQ ID NO:313)
                        NHFETLLKCNESC        (SEQ ID NO:314)
                         HFETLLKCNESC        (SEQ ID NO:315)
                          FETLLKCNESC        (SEQ ID NO:316)
                           ETLLKCNESC        (SEQ ID NO:317)
                            TLLKCNESC        (SEQ ID NO:318)
                             LLKCNESC        (SEQ ID NO:319)
                              LKCNESC        (SEQ ID NO:320)
                               KCNESC        (SEQ ID NO:321)
                                CNESC        (SEQ ID NO:322)
                                 NESC        (SEQ ID NO:323)
                                  ESC        (SEQ ID NO:324)
CLDPEQVTCESQEGTHASYNRKTGQCEEQKGTECGGGENHFETLLKCNESC  (SEQ ID NO:276)
CLDPEQVTCESQEGTHASYNRKTGQCEEQKGTECGGGENHFETLLKCNES   (SEQ ID NO:325)
CLDPEQVTCESQEGTHASYNRKTGQCEEQKGTEGGGGENHFETLLKCNE    (SEQ ID NO:326)
CLDPEQVTCESQEGTHASYNRKTGQCEEQKGTECGGGENHFETLLKCN     (SEQ ID NO:327)
CLDPEQVTCESQEGTHASYNRKTGQCEEQKGTECGGGENHFETLLKC      (SEQ ID NO:328)
```

-continued

| | |
|---|---|
| CLDPEQVTCESQEGTHASYNRKTGQCEEQKGTECGGGENHFETLLK | (SEQ ID NO:329) |
| CLDPEQVTCESQEGTHASYNRKTGQCEEQKGTECGGGENHFETLL | (SEQ ID NO:330) |
| CLDPEQVTCESQEGTHASYNRKTGQCEEQKGTECGGGENHFETL | (SEQ ID NO:331) |
| CLDPEQVTCESQEGTHASYNRKTGQCEEQKGTECGGGENHFET | (SEQ ID NO:332) |
| CLDPEQVTCESQEGTHASYNRKTGQCEEQKGTECGGGENHFE | (SEQ ID NO:333) |
| CLDPEQVTCESQEGTHASYNRKTGQCEEQKGTECGGGENHF | (SEQ ID NO:334) |
| CLDPEQVTCESQEGTHASYNRKTGQCEEQKGTECGGGENH | (SEQ ID NO:335) |
| CLDPEQVTCESQEGTHASYNRKTGQCEEQKGTECGGGEN | (SEQ ID NO:336) |
| CLDPEQVTCESQEGTHASYNRKTGQCEEQKGTECGGGE | (SEQ ID NO:337) |
| CLDPEQVTCESQEGTHASYNRKTGQCEEQKGTECGGG | (SEQ ID NO:338) |
| CLDPEQVTCESQEGTHASYNRKTGQCEEQKGTECGG | (SEQ ID NO:339) |
| CLDPEQVTCESQEGTHASYNRKTGQCEEQKGTECG | (SEQ ID NO:340) |
| CLDPEQVTCESQEGTHASYNRKTGQCEEQKGTEC | (SEQ ID NO:341) |
| CLDPEQVTCESQEGTHASYNRKTGQCEEQKGTE | (SEQ ID NO:342) |
| CLDPEQVTCESQEGTHASYNRKTGQCEEQKGT | (SEQ ID NO:343) |
| CLDPEQVTCESQEGTHASYNRKTGQCEEQKG | (SEQ ID NO:344) |
| CLDPEQVTCESQEGTHASYNRKTGQCEEQK | (SEQ ID NO:345) |
| CLDPEQVTCESQEGTHASYNRKTGQCEEQ | (SEQ ID NO:346) |
| CLDPEQVTCESQEGTHASYNRKTGQCEE | (SEQ ID NO:347) |
| CLDPEQVTCESQEGTHASYNRKTGQCE | (SEQ ID NO:348) |
| CLDPEQVTCESQEGTHASYNRKTGQC | (SEQ ID NO:349) |
| CLDPEQVTCESQEGTHASYNRKTGQ | (SEQ ID NO:350) |
| CLDPEQVTCESQEGTHASYNRKTG | (SEQ ID NO:351) |
| CLDPEQVTCESQEGTHASYNRKT | (SEQ ID NO:352) |
| CLDPEQVTCESQEGTHASYNRK | (SEQ ID NO:353) |
| CLDPEQVTCESQEGTHASYNR | (SEQ ID NO:354) |
| CLDPEQVTCESQEGTHASYN | (SEQ ID NO:355) |
| CLDPEQVTCESQEGTHASY | (SEQ ID NO:356) |
| CLDPEQVTCESQEGTHAS | (SEQ ID NO:357) |
| CLDPEQVTCESQEGTHA | (SEQ ID NO:358) |
| CLDPEQVTCESQEGTH | (SEQ ID NO:359) |
| CLDPEQVTCESQEGT | (SEQ ID NO:360) |
| CLDPEQVTCESQEG | (SEQ ID NO:361) |
| CLDPEQVTCESQE | (SEQ ID NO:362) |
| CLDPEQVTCESQ | (SEQ ID NO:363) |
| CLDPEQVTCES | (SEQ ID NO:364) |
| CLDPEQVTCE | (SEQ ID NO:365) |
| CLDPEQVTC | (SEQ ID NO:366) |
| CLDPEQVT | (SEQ ID NO:367) |
| CLDPEQV | (SEQ ID NO:368) |

| | |
|---|---|
| CLDPEQ | (SEQ ID NO:369) |
| CLDPE | (SEQ ID NO:370) |
| CLDP | (SEQ ID NO:371) |
| CLD | (SEQ ID NO:372) | as well as between amino acids 76 and 126 (second Kunitz domain) and its amino and carboxy truncations:

| | |
|---|---|
| CSLEVDYGVGRANIPRWYYDTNNATCEMFTYGGITGNKNNFESEEECKETC | (SEQ ID NO:373) |
| SLEVDYGVGRANIPRWYYDTNNATCEMFTYGGITGNKNNFESEEECKETC | (SEQ ID NO:374) |
| LEVDYGVGRANIPRWYYDTNNATCEMFTYGGITGNKNNFESEEECKETC | (SEQ ID NO:375) |
| EVDYGVGRANIPRWYYDTNNATCEMFTYGGITGNKNNFESEEECKETC | (SEQ ID NO:376) |
| VDYGVGRANIPRWYYDTNNATCEMFTYGGITGNKNNFESEEECKETC | (SEQ ID NO:377) |
| DYGVGRANIPRWYYDTNNATCEMFTYGGITGNKNNEESEEECKETC | (SEQ ID NO:378) |
| YGVGRANIPRWYYDTNNATCEMFTYGGITGNKNNFESEEECKETC | (SEQ ID NO:379) |
| GVGRANIPRWYYDTNNATCEMFTYGGITGNKNNFESEEECKETC | (SEQ ID NO:380) |
| VGRANIPRWYYDTNNATCEMFTYGGITGNKNNFESEEECKETC | (SEQ ID NO:381) |
| GRANIPRWYYDTNNATCEMFTYGGITGNKNNFESEEECKETC | (SEQ ID NO:382) |
| RANIPRWYYDTNNATCEMFTYGGITGNKNNFESEEECKETC | (SEQ ID NO:383) |
| ANIPRWYYDTNNATCEMFTYGGITGNKNNFESEEECKETC | (SEQ ID NO:384) |
| NIPRWYYDTNNATCEMFTYGGITGNKNNFESEEECKETC | (SEQ ID NO:385) |
| IPRWYYDTNNATCEMFTYGGITGNKNNFESEEECKETC | (SEQ ID NO:386) |
| PRWYYDTNNATCEMFTYGGITGNKNNEESEEECKETC | (SEQ ID NO:387) |
| RWYYDTNNATCEMETYGGITGNKNNFESEEECKETC | (SEQ ID NO:388) |
| WYYDTNNATCEMFTYGGITGNKNNFESEEECKETC | (SEQ ID NO:389) |
| YYDTNNATCEMFTYGGITGNKNNFESEEECKETC | (SEQ ID NO:390) |
| YDTNNATCEMFTYGGITGNKNNFESEEECKETC | (SEQ ID NO:391) |
| DTNNATCEMFTYGGITGNKNNFESEEECKETC | (SEQ ID NO:392) |
| TNNATCEMFTYGGITGNKNNFESEEECKETC | (SEQ ID NO:393) |
| NNATCEMFTYGGITGNKNNFESEEECKETC | (SEQ ID NO:394) |
| NATCEMFTYGGITGNKNNFESEEECKETC | (SEQ ID NO:395) |
| ATCEMFTYGGITGNKNNFESEEECKETC | (SEQ ID NO:396) |
| TCEMFTYGGITGNKNNFESEEECKETC | (SEQ ID NO:397) |
| CEMFTYGGITGNKNNFESEEECKETC | (SEQ ID NO:398) |
| EMFTYGGITGNKNNFESEEECKETC | (SEQ ID NO:399) |
| MFTYGGITGNKNNFESEEECKETC | (SEQ ID NO:400) |
| FTYGGITGNKNNFESEEECKETC | (SEQ ID NO:401) |
| TYGGITGNKNNFESEEECKETC | (SEQ ID NO:402) |
| YGGITGNKNNFESEEECKETC | (SEQ ID NO:403) |
| GGITGNKNNFESEEECKETC | (SEQ ID NO:404) |
| GITGNKNNFESEEECKETC | (SEQ ID NO:405) |

| | |
|---|---|
| ITGNKNNFESEEECKETC | (SEQ ID NO:406) |
| TGNKNNFESEEECKETC | (SEQ ID NO:407) |
| GNKNNFESEEECKETC | (SEQ ID NO:408) |
| NKNNFESEEECKETC | (SEQ ID NO:409) |
| KNNFESEEECKETC | (SEQ ID NO:410) |
| NNFESEEECKETC | (SEQ ID NO:411) |
| NFESEEECKETC | (SEQ ID NO:412) |
| FESEEECKETC | (SEQ ID NO:413) |
| ESEEECKETC | (SEQ ID NO:414) |
| SEEECKETC | (SEQ ID NO:415) |
| EEECKETC | (SEQ ID NO:416) |
| EECKETC | (SEQ ID NO:417) |
| ECKETC | (SEQ ID NO:418) |
| CKETC | (SEQ ID NO:419) |
| KETC | (SEQ ID NO:420) |
| ETC | (SEQ ID NO:421) |
| CSLEVDYGVGRANIPRWYYDTNNATCEMFTYGGITGNKNNFESEEECKETC | (SEQ ID NO:373) |
| CSLEVDYGVGRANIPRWYYDTNNATCEMFTYGGITGNKNNFESEEECKET | (SEQ ID NO:422) |
| CSLEVDYGVGRANIPRWYYDTNNATCEMFTYGGITGNKNNFESEEECKE | (SEQ ID NO:423) |
| CSLEVDYGVGRANIPRWYYDTNNATCEMFTYGGITGNKNNFESEEECK | (SEQ ID NO:424) |
| CSLEVDYGVGRANIPRWYYDTNNATCEMFTYGGITGNKNNFESEEEC | (SEQ ID NO:425) |
| CSLEVDYGVGRANIPRWYYDTNNATCEMFTYGGITGNKNNFESEEE | (SEQ ID NO:426) |
| CSLEVDYGVGRANIPRWYYDTNNATCEMFTYGGITGNKNNFESEE | (SEQ ID NO:427) |
| CSLEVDYGVGRANIPRWYYDTNNATCEMFTYGGITGNKNNFESE | (SEQ ID NO:428) |
| CSLEVDYGVGRANIPRWYYDTNNATCEMFTYGGITGMKNNFES | (SEQ ID NO:429) |
| CSLEVDYGVGRANIPRWYYDTNNATCEMFTYGGITGNKNNFE | (SEQ ID NO:430) |
| CSLEVDYGVGRANIPRWYYDTNNATCEMFTYGGITGNKNNF | (SEQ ID NO:431) |
| CSLEVDYGVGRANIPRWYYDTNNATCEMFTYGGITGNKNN | (SEQ ID NO:432) |
| CSLEVDYGVGRANIPRWYYDTNNATCEMFTYGGITGNKN | (SEQ ID NO:433) |
| CSLEVDYGVGRANIPRWYYDTNNATCEMFTYGGITGNK | (SEQ ID NO:434) |
| CSLEVDYGVGRANIPRWYYDTNNATCEMFTYGGITGN | (SEQ ID NO:435) |
| CSLEVDYGVGRANIPRWYYDTNNATCEMFTYGGITG | (SEQ ID NO:436) |
| CSLEVDYGVGRANIPRWYYDTNNATCEMFTYGGIT | (SEQ ID NO:437) |
| CSLEVDYGVGRANIPRWYYDTNNATCEMFTYGGI | (SEQ ID NO:438) |
| CSLEVDYGVGRANIPRWYYDTNNATCEMFTYGG | (SEQ ID NO:439) |
| CSLEVDYGVGRANIPRWYYDTNNATCEMFTYG | (SEQ ID NO:440) |
| CSLEVDYGVGRANIPRWYYDTNNATCEMFTY | (SEQ ID NO:441) |
| CSLEVDYGVGRANIPRWYYDTNNATCEMFT | (SEQ ID NO:442) |
| CSLEVDYGVGRANIPRWYYDTNNATCEMF | (SEQ ID NO:443) |
| CSLEVDYGVGRANIPRWYYDTNNATCEM | (SEQ ID NO:444) |

-continued

| | |
|---|---|
| CSLEVDYGVGRANIPRWYYDTNNATCE | (SEQ ID NO:445) |
| CSLEVDYGVGRANIPRWYYDTNNATC | (SEQ ID NO:446) |
| CSLEVDYGVGRANIPRWYYDTNNAT | (SEQ ID NO:447) |
| CSLEVDYGVGRANIPRWYYDTNNA | (SEQ ID NO:448) |
| CSLEVDYGVGRANIPRWYYDTNN | (SEQ ID NO:449) |
| CSLEVDYGVGRANIPRWYYDTN | (SEQ ID NO:450) |
| CSLEVDYGVGRANIPRWYYDT | (SEQ ID NO:451) |
| CSLEVDYGVGRANIPRWYYD | (SEQ ID NO:452) |
| CSLEVDYGVGRANIPRWYY | (SEQ ID NO:453) |
| CSLEVDYGVGRANIPRWY | (SEQ ID NO:454) |
| CSLEVDYGVGRANIPRW | (SEQ ID NO:455) |
| CSLEVDYGVGRANIPR | (SEQ ID NO:456) |
| CSLEVDYGVGRANIP | (SEQ ID NO:457) |
| CSLEVDYGVGRANI | (SEQ ID NO:458) |
| CSLEVDYGVGRAN | (SEQ ID NO:459) |
| CSLEVDYGVGRA | (SEQ ID NO:460) |
| CSLEVDYGVGR | (SEQ ID NO:461) |
| CSLEVDYGVG | (SEQ ID NO:462) |
| CSLEVDYGV | (SEQ ID NO:463) |
| CSLEVDYG | (SEQ ID NO:464) |
| CSLEVDY | (SEQ ID NO:465) |
| CSLEVD | (SEQ ID NO:466) |
| CSLEV | (SEQ ID NO:467) |
| CSLE | (SEQ ID NO:468) |
| CSL | (SEQ ID NO:469) |

Amino acid substitutions may be of a conserved or non-conserved nature. Conserved amino acid substitutions consist of replacing one or more amino acids of the Ixolaris or Ixolaris-related sequence with amino acids of similar charge, size, and/or hydrophobicity characteristics, such as, for example, a glutamic acid (E) to aspartic acid (D) amino acid substitution. Non-conserved substitutions consist of replacing one or more amino acids of the Ixolaris or Ixolaris-related sequence with amino acids possessing dissimilar charge, size, and/or hydrophobicity characteristics, such as, for example, a glutamic acid (E) to valine (V) substitution. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. One or more such substitutions may be introduced into the Ixolaris or Ixolaris-related sequence, as long as such substitutions result in variants which exhibit binding affinity for Factor Xa, X, or VIIa, the resulting biological effect of Factor Xa, X, or VIIa binding, anticoagulant activity, generation of antibodies that specifically bind Ixolaris, or identification of compounds that can be used to modulate coagulation function.

Amino acid insertions may consist of single amino acid residues or stretches of residues. The insertions may be made at the carboxy or amino terminal end of the Ixolaris or Ixolaris-related sequence, as well as at a position internal to the sequence. Such insertions made at either the carboxy or amino terminus of the sequence of interest may be of a broader size range. One or more such insertions may be introduced into the Ixolaris or Ixolaris-related sequence, as long as such insertions result in variants which exhibit binding affinity for Factor Xa, X, or VIIa, the resulting biological effect of Factor Xa, X, or VIIa binding, anticoagulant activity, generation of antibodies that specifically bind Ixolaris, or identification of compounds that can be used to modulate coagulation function.

Deletions of Ixolaris or Ixolaris-related sequences are also within the scope of the invention. Such deletions consist of the removal of one or more amino acids from the Ixolaris or Ixolaris-related sequence. Such deletions may involve a single contiguous or greater than one discrete portion of the original sequences. One or more such deletions may be introduced into the Ixolaris or Ixolaris-related sequence, as long as such deletions result in variants which exhibit binding affinity for Factor Xa, X, or VIIa, the resulting biological effect of Factor Xa, X, or VIIa binding, anticoagulant activity, generation of antibodies that specifically bind Ixolaris, or identification of compounds that can be used to modulate coagulation function.

The invention also encompasses (a) DNA vectors that contain any of the foregoing Ixolaris or Ixolaris-related coding sequences and/or their complements; (b) DNA expression vectors that contain any of the foregoing Ixolaris or Ixolaris-related coding sequences operatively associated with a regulatory element that directs the expression of the coding sequences; and (c) genetically engineered host cells that contain any of the foregoing Ixolaris or Ixolaris-related coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast alpha-mating factors.

Ixolaris Proteins, Polypeptides and Peptides

The Ixolaris protein, its functional domains, truncations thereof, as well as substitutions, insertions, and deletions (including fusion proteins) thereof can be prepared for a number of uses, including, but not limited to, binding Factor Xa, X, or VIIa, the resulting biological effect of Factor Xa, X, or VIIa binding, anticoagulant activity, generation of antibodies that specifically bind Ixolaris, and identification of compounds that can be used to modulate coagulation function.

The amino acid sequences of the invention include the amino acid sequence shown in FIG. 3 (SEQ. ID. No: 471). Further, Ixolaris and Ixolaris-related amino acid sequences are encompassed by the invention, including mature Ixolaris protein, its functional domains, truncations thereof, as well as substitutions, insertions, and deletions thereof. In fact, any Ixolaris or Ixolaris-related protein, polypeptide or peptide encoded by the Ixolaris or Ixolaris-related nucleotide sequences described in the section above are within the scope of the invention.

The preferred isolated Ixolaris and Ixolaris-related amino acid sequences of the present invention may be isolated and purified from natural sources. Preferred as natural sources are ticks; suitable ticks include *Ixodes scapularis, Ixodes ricinus*, and *Ornithodorus moubatta*. Especially preferred as a natural source is *Ixodes scapularis*.

The preferred amino acid sequences of the present invention are isolated from their natural source by methods known in the biochemical arts. These methods include preparing a soluble extract and enriching the extract using chromatographic methods on different solid support matrices. An example of a preferred method of purification of an isolated protein of the present invention would include that as disclosed in the Example.

The preferred isolated Ixolaris and Ixolaris-related amino acid sequences of the present invention may be synthesized by standard methods known in the chemical arts.

The isolated amino acid sequences of the present invention may be prepared using solid-phase synthesis, such as that described by Merrifield, 1964 *J Amer Chem Soc* 85:2149 or other equivalent methods known in the chemical arts, such as the method described by Houghten 1985 *PNAS USA* 82:5132 (1985).

Alternatively, the preferred isolated Ixolaris and Ixolaris-related amino acid sequences of the present invention may be made by recombinant DNA methods taught herein and well known in the biological arts (Sambrook et al. 1989 Molecular Cloning, A Laboratory Manual, Cold Springs Harbor Press, N.Y.; Ausubel et al. 1989 Current Protocols in Molecular Biology, Green Publishing Associates and Wiley Interscience, N.Y.). Such methods can be used to construct expression vectors containing the cDNA and other nucleotide sequences described in the section above and appropriate transcriptional and translational control signals. These methods include, for example, in vitro recombinant DNA techniques, synthetic techniques, and in vivo genetic recombination.

A variety of host-expression vector systems may be utilized to express the cDNA and other nucleotide sequences of the invention. The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing Ixolaris and Ixolaris-related nucleotide sequences; yeast (e.g., Saccharomyces, Pichia) transformed with recombinant yeast expression vectors containing Ixolaris and Ixolaris-related nucleotide sequences; insect cell systems infected with recombinant virus expression vectors (e.g., baculovirus) containing Ixolaris and Ixolaris-related nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Ixolaris and Ixolaris-related nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5 K promoter).

In bacterial systems, a number of expression vectors may be advantageously selected depending upon the use intended for the Ixolaris and Ixolaris-related gene product being expressed. For example, when a large quantity of such a protein is to be produced, for the generation of pharmaceutical compositions of Ixolaris and Ixolaris-related amino acid sequences or for raising antibodies that specifically bind to the Ixolaris and Ixolaris-related amino acid sequences, for example, vectors which direct the expression of high levels of fusion protein products that are readily purified may be desirable. Such vectors include, but are not limited to, the *E. coli* expression vector pUR278 (Ruther et al. 1983 *EMBO J* 2:1791), in which the Ixolaris and Ixolaris-related coding sequence may be ligated individually into the vector in frame with the lacZ coding region so that a fusion protein is produced; pIN vectors (Inouye & Inouye 1985 *Nucleic Acids Res* 13:3101–3109; Van Heeke & Schuster 1989 *J Biol Chem* 264:5503–5509) and the like. pGEX vectors may also be used to express foreign sequences as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. The Ixolaris and Ixolaris-related gene coding sequence may be cloned individually into non-essential regions (for example the polyhedrin gene) of the virus and placed under control of an AcNPV promoter (for example the polyhedrin promoter). Successful insertion of Ixolaris and Ixolaris-related gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al. 1983 *J Virol* 46:584; Smith, U.S. Pat. No. 4,215,051).

In mammalian host cells, a number of viral-based expression systems may be utilized. In cases where an adenovirus is used as an expression vector, the Ixolaris and Ixolaris-related nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1or E3) will result in a recombinant virus that is viable and capable of expressing the Ixolaris and Ixolaris-related gene product in infected hosts (e.g., see Logan & Shenk 1984 *PNAS* USA 81:3655–3659). Specific initiation signals may also be required for efficient translation of inserted Ixolaris and Ixolaris-related nucleotide sequences. These signals include the ATG initiation codon and adjacent sequences. In cases where an entire Ixolaris gene or cDNA, including its own initiation codon and adjacent sequences, is inserted into the appropriate expression vector, no additional translational control signals may be needed. However, in cases where only a portion of the Ixolaris coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al. 1987 *Methods in Enzymol* 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, and in particular, salivary gland cell lines.

For long-term, high-yield production of recombinant proteins, stable expression is preferred. For example, cell lines which stably express the Ixolaris and Ixolaris-related nucleotide sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Ixolaris and Ixolaris-related gene product.

A number of selection systems may be used, including but not limited to the herpes simplex virus thymidine kinase (Wigler, et al. 1977 *Cell* 11:223), hypoxanthine-guanine phosphoribosyltransferase (Szybalska & Szybalski 1962 *PNAS* USA 48:2026), and adenine phosphoribosyltransferase (Lowy, et al. 1980 *Cell* 22:817) genes can be employed in tk-, hgprt- or aprt-cells, respectively. Also, antimetabolite resistance can be used as the basis of selection for the following genes: dhfr, which confers resistance to methotrexate (Wigler, et al. 1980 *PNAS* USA 77:3567; O'Hare, et al. 1981 *PNAS* USA 78:1527); gpt, which confers resistance to mycophenolic acid (Mulligan & Berg 1981 *PNAS* USA 78:2072); neo, which confers resistance to the aminoglycoside G-418 (Colberre-Garapin, et al. 1981 *J Mol Biol* 150:1); and hygro, which confers resistance to hygromycin (Santerre et al. 1984 *Gene* 30:147)

Alternatively, any fusion protein may be readily purified by utilizing an antibody specific for the fusion protein being expressed. For example, a system described by Janknecht et al allows for the ready purification of non-denatured fusion proteins expressed in human cell lines (Janknecht et al. 1991 *PNAS* USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni2+nitriloacetic acid-agarose columns and histidine-tagged proteins are selectively eluted with imidazole-containing buffers.

Antibodies to Ixolaris Proteins

Antibodies that specifically recognize one or more epitopes of Ixolaris, or epitopes of conserved variants of Ixolaris, or peptide fragments of Ixolaris are also encompassed by the invention. Such antibodies include but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above.

The antibodies of the invention may be used, for example, for diagnostic purposes and for the identification of concentration levels of Ixolaris in various biological fluids. Immunoassays utilizing these antibodies may be used as a diagnostic test, such as to detect infection of a mammalian host by a tick or to detect Ixolaris from a tick in a tissue of the mammalian host. Also, such immunoassays may be used in the detection and isolation of Ixolaris from tissue homogenates, cloned cells, and the like. Alternatively, antibodies against Ixolaris can be used as a vaccine against tick infections in mammals. Or, antibodies can be used in conjunction with drug screening schemes.

For the production of antibodies, various host animals may be immunized by injection with Ixolaris, an Ixolaris peptide (e.g., one corresponding to a functional domain), truncated Ixolaris proteins, polypeptides, or peptides, functional equivalents of Ixolaris or variants of Ixolaris. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975 *Nature* 256:495–497; and U.S. Pat. No. 4,376,110), the human B-cell hybridoma technique (Kosbor et al. 1983 *Immunology Today* 4:72; Cole et al. 1983 *PNAS* USA 80:2026–2030), and the EBV-hybridoma technique (Cole et al. 1985 Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al. 1984 *PNAS* USA 81:6851–6855; Neuberger et al. 1984 *Nature* 312:604–608; Takeda et al. 1985 *Nature* 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird 1988 *Science* 242:423–426; Huston et al. 1988 *PNAS* USA 85:5879–5883; and Ward et al. 1989 *Nature* 334:544–546) can be adapted to produce single chain antibodies against Ixolaris gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the F(ab') 2 fragments. Alternatively, Fab expression libraries may be constructed (Huse et al. 1989 *Science* 246:1275–1281) to allow rapid and easy identification of monoclonal Fab fragments with the desired specificity.

Antibodies to Ixolaris can, in turn, be utilized to generate anti-idiotype antibodies that "mimic" Ixolaris, using techniques well known to those skilled in the art. (See, e.g., Greenspan & Bona 1993 *FASEB J* 7(5):437–444; and Nissinoff 1991 *J Immunol* 147(8):2429–2438). For example antibodies which bind to a Kunitz domain and competitively inhibit the binding of Factor Xa, X, or VIIa to Ixolaris can be used to generate anti-idiotypes that "mimic" the Kunitz domain and, therefore, bind and neutralize Ixolaris. Such neutralizing anti-idiotypes or Fab fragments of such anti-idiotypes can be used in regimens to neutralize Ixolaris.

Diagnostic and Prognostic Assays of Ixolaris

A variety of methods can be employed for the diagnostic and prognostic evaluation of Ixolaris and Ixolaris gene specific nucleic acid molecules for the identification and concentration levels of Ixolaris and Ixolaris gene specific nucleic acid molecules in various biological tissues and fluids. These assays may be used to detect infection of a mammalian host by a tick or to detect Ixolaris from a tick in a tissue of a mammalian host. Also, such assays may be used in the detection of Ixolaris expression patterns to aid in diagnosis and prognosis of pathological states associated with Ixolaris.

Such methods may, for example, utilize reagents such as the Ixolaris nucleotide sequences described above, Ixolaris amino acid sequences described above, and Ixolaris antibodies described above. Specifically, such reagents may be used, for example, for: (1) the detection of the presence of Ixolaris expression or the detection of either an over- or under-expression of Ixolaris mRNA; (2) the detection of the presence of Ixolaris gene product or the detection of either an over- or under-abundance of Ixolaris gene product; and (3) the detection of the presence of Ixolaris antibodies.

The methods described herein may be performed, for example, by utilizing pre-packaged diagnostic kits comprising at least one specific Ixolaris nucleotide sequence, Ixolaris amino acid sequence or Ixolaris antibody reagent described herein, which may be conveniently used, e.g., in clinical settings, to diagnose patients exhibiting a pathological state associated with Ixolaris.

Information about Ixolaris gene specific nucleic acid molecules can be detected by utilizing a number of techniques. Nucleic acid from any nucleated cell can be used as the starting point for such assay techniques, and may be isolated according to standard nucleic acid preparation procedures which are well known to those of skill in the art. The use of microarrays to deternine gene expression requires DNA from the Ixolaris gene that can serve as a probe for detecting which genes in the microarray are active in different types of cells.

DNA may be used in hybridization or amplification assays. Such assays may include, but are not limited to, Southern analyses, dot blots, single stranded conformational polymorphism analyses (SSCP), restriction fragment length polymorphims (RFLPs) and PCR analyses.

Such diagnostic methods for the detection of Ixolaris gene specific nucleic acid molecules can involve for example, contacting and incubating nucleic acids, including recombinant DNA molecules, cloned genes or degenerate variants thereof, obtained from a sample, e.g., derived from a patient sample or other appropriate cellular source, with one or more labeled nucleic acid reagents, including recombinant DNA molecules, cloned genes or degenerate variants thereof under conditions favorable for the specific annealing of these reagents to their complementary sequences within the Ixolaris gene. Preferably, the lengths of these nucleic acid reagents are at least 15 to 30 nucleotides. After incubation, all non-annealed nucleic acids are removed from the nucleic acid:Ixolaris molecule hybrid. The presence of nucleic acids which have hybridized, if any such molecules exist, is then detected. Using such a detection scheme, the nucleic acid from the cell type or tissue of interest can be immobilized, for example, to a solid support, such as a membrane, or a plastic surface such as that on a microtiter plate or polystyrene beads. In this case, after incubation, non-annealed, labeled nucleic acid reagents are easily removed. Detection of the remaining, annealed, labeled Ixolaris nucleic acid reagents is accomplished using standard techniques well-known to those in the art. The Ixolaris gene sequences to which the nucleic acid reagents have annealed can be compared to the annealing pattern expected from a control gene sequence in order to detect Ixolaris gene specific nucleic acid molecules.

Alternative diagnostic methods for the detection of Ixolaris gene specific nucleic acid molecules, in patient samples or other appropriate cell sources, may involve their amplification, e.g., by PCR (the experimental embodiment set forth in Mullis, K. B. 1987 U.S. Pat. No. 4,683,202), followed by the detection of the amplified molecules using techniques well known to those of skill in the art. The resulting amplified sequences can be compared to those which would be expected if the nucleic acid being amplified contained control gene copies in order to detect Ixolaris gene specific nucleic acid molecules.

The level of Ixolaris gene expression can also be assayed by detecting and measuring Ixolaris transcription. For example, RNA from a cell type or tissue known, or suspected to express the Ixolaris gene, such as salivary gland, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based therapy or, alternatively, to test the effect of compounds on the expression of the Ixolaris gene. Such analyses may reveal both quantitative and qualitative aspects of the expression pattern of the Ixolaris gene, including activation or inactivation of Ixolaris gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the Ixolaris nucleic acid reagents described above. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such Ixolaris gene expression assays "in situ", ie., directly upon tissue sections (fixed and/or frozen) of patient tissue obtained from biopsies or resections, such that no nucleic acid purification is necessary. Nucleic acid reagents such as those described above may be used as probes and/or primers for such in situ procedures (See, for example, Nuovo, G. J. 1992 "PCR In Situ Hybridization: Protocols And Applications", Raven Press, NY).

Alternatively, if a sufficient quantity of the appropriate cells can be obtained, standard Northern analysis can be performed to determine the level of mRNA expression of the Ixolaris gene.

Immunoassays and non-immunoassays for Ixolaris gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying Ixolaris gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled Ixolaris antibody or Ixolaris gene product. The solid phase support may then be washed with the buffer a second time to remove unbound antibody or gene product. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of Ixolaris antibody or Ixolaris gene product may be determined according to well known methods. Those skilled in the art will be able to determine operative and optimal assay conditions for each determination by employing routine experimentation.

With respect to antibodies, one of the ways in which the Ixolaris antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.; Voller, A. et al. 1978 *J Clin Pathol* 31:507–520; Butler, J. E. 1981 *Meth Enzymol* 73:482–523; Maggio, E. (ed.) 1980, Enzyme Immunoassay, CRC Press, Boca Raton, Fla.; Ishikawa, E. et al., (eds.) 1981 Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alphaglycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect Ixolaris through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Screening Assays for Compounds that Bind Ixolaris

The following assays are designed to identify compounds that interact with (e.g., bind to) Ixolaris.

Such compounds may include, but are not limited to, peptides such as, for example, soluble peptides, including but not limited to members of random peptide libraries; (see, e.g., Lam, K. S. et al. 1991 *Nature* 354:82–84; Houghten, R. et al. 1991 *Nature* 354:84–86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al. 1993 *Cell* 72:767–778), antibodies (including, but not limited to, polyclonal, monoclonal, humanized, anti-idiotypic, chimeric or single chain antibodies, and FAb, F(ab')2 and FAb expression library fragments, and epitope-binding fragments thereof), and small organic or inorganic molecules.

Computer modelling and searching technologies permit identification of compounds, or the improvement of already identified compounds, that can modulate Ixolaris activity. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a seach can be manual, but is preferably computer assisted. These compounds found from this search are potential Ixolaris modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of Ixolaris will be apparent to those of skill in the art.

Examples of molecular modelling systems are the CHARMM and QUANTA programs (Polygen Corporation, Waltham, Mass.). CHARMM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific-proteins, such as Rotivinen, et al. 1988 *Acta Pharmaceutical Fennica* 97:159–166; Ripka, 1988 *New Scientist* 54–57; McKinaly and Rossmann 1989 *Annu Rev Pharmacol Toxiciol* 29:111–122; Perry and Davies, OSAR: Quantitative Structure-Activity Relationships in Drug Design pp. 189–193 (Alan R. Liss, Inc. 1989); Lewis and Dean, 1989 *Proc R. Soc Lond* 236:125–140 and 141–162; and, with respect to a model receptor for nucleic acid components, Askew, et al. 1989 *J Am Chem Soc* 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in modulating the blood coagulation cascade.

In Vitro Screening Assays

In vitro systems may be designed to identify compounds capable of interacting with (e.g., binding to) Ixolaris. The principle of the assays used to identify compounds that bind to Ixolaris involves preparing a reaction mixture of Ixolaris and the test compound under conditions and for a time sufficient to allow the two components to interact and bind, thus forming a complex which can be removed and/or detected in the reaction mixture. The Ixolaris species used can vary depending upon the goal of the screening assay.

The screening assays can be conducted in a variety of ways. For example, one method to conduct such an assay would involve anchoring the Ixolaris protein, polypeptide, peptide or fusion protein or the test substance onto a solid phase and detecting Ixolaris/test compound complexes anchored on the solid phase at the end of the reaction. In one embodiment of such a method, the Ixolaris reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for Ixolaris protein, polypeptide, peptide or fusion protein or the test compound to anchor any complexes formed in solution, and a labeled antibody specific for the other component of the possible complex to detect anchored complexes.

In Vivo Screening Assays

In vivo systems may be designed to identify compounds capable of interacting with (e.g., binding to) Ixolaris. One method which detects protein interactions in vivo, the two-hybrid system, is described in detail for illustration only and not by way of limitation. One version of this system has been described (Chien et al. 1991 *PNAS* USA, 88:9578–9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to an Ixolaris nucleotide sequence encoding Ixolaris, an Ixolaris polypeptide, peptide or fusion protein, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, Ixolaris may be used as the bait gene product. Total genomic or cDNA sequences are fused to the DNA encoding an activation domain. This library and a plasmid encoding a hybrid of a bait Ixolaris gene product fused to the DNA-binding domain are cotransformed into a yeast reporter strain, and the resulting transformants are screened for those that express the reporter gene. For example, and not by way of limitation, a bait Ixolaris gene sequence, such as the open reading frame of Ixolaris (or a Kunitz domain), can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait Ixolaris gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait Ixolaris gene-GAL4 fusion plasmid into a yeast strain which contains a lacZ gene driven by a promoter which contains GAL4 activation sequence. A cDNA encoded protein, fused to GAL4 transcriptional activation domain, that interacts with bait Ixolaris gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait Ixolaris gene-interacting protein using techniques routinely practiced in the art.

Assays for Compounds that Modulate the Interaction of Binding Partners with Ixolaris The macromolecules that interact with Ixolaris are referred to, for purposes of this discussion, as "binding partners". These binding partners are likely to be involved in the Ixolaris mediated blood coagulation cascade. Therefore, it is desirable to identify compounds that modulate the interaction of such binding partners with Ixolaris.

The basic principle of the assay systems used to identify compounds that modulate the interaction between Ixolaris and its binding partner (e.g., Factor Xa, X, or VIIa, or Factor VIIa/TF complex) involves preparing a reaction mixture containing Ixolaris protein, polypeptide, peptide or fusion protein as described above, and the binding partner under conditions and for a time sufficient to allow the two to interact and bind, thus forming a complex. In order to test a compound for modulating activity, the reaction mixture is prepared in the presence and absence of the test compound. The test compound may be initially included in the reaction mixture, or may be added at a time subsequent to the addition of the Ixolaris moiety and its binding partner. Control reaction mixtures are incubated without the test compound or with a placebo. The formation of any complexes between the Ixolaris moiety and the binding partner is then detected. The formation of a complex in the control reaction, but not in the reaction mixture containing the test compound, indicates that the compound modulates the interaction of Ixolaris and the interactive binding partner.

The assay for compounds that modulate the interaction of Ixolaris and binding partners can be conducted in a heterogeneous or homogeneous format. Heterogeneous assays involve anchoring either the Ixolaris moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that inhibit the interaction by competition can be identified by conducting the reaction in the presence of the test substance; i.e., by adding the test substance to the reaction mixture prior to or simultaneously with the Ixolaris moiety and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the Ixolaris moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the Ixolaris gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment, a homogeneous assay can be used. In this approach, a preformed complex of the Ixolaris moiety and the interactive binding partner is prepared in which either the Ixolaris or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt Ixolaris/binding partner interaction can be identified.

In a particular embodiment, an Ixolaris fusion can be prepared for immobilization. For example, Ixolaris or a peptide fragment, e.g., corresponding to a Kunitz domain, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above. This antibody can be labeled with the radioactive isotope $^{125}$I, for example, by methods routinely practiced in the art. In a heterogeneous assay, e.g., the GST-Ixolaris fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the Ixolaris gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-Ixolaris fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the Ixolaris/binding partner interaction can be detected by adding the labeled antibody and measuring the radioactivity associated with the beads.

In another embodiment, these same techniques can be employed using peptide fragments that correspond to a Kunitz domain of Ixolaris and/or the interactive binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the binding partner is obtained, short gene segments can be engineered to express peptide fragments of the protein, which can then be tested for binding activity and purified or synthesized.

Assays for Identification of Compounds that Modulate Coagulation

Compounds, including but not limited to binding compounds identified via assay techniques such as those described in the sections can be tested for the ability to modulate the blood coagulation cascade. The assays described above can identify compounds which affect Ixolaris activity (e.g., compounds that bind to Ixolaris, inhibit binding of the natural ligand, and either activate signal transduction (agonists) or block activation (antagonists), and compounds that bind to the natural ligand of Ixolaris and neutralize ligand activity). Such compounds can be used as part of a therapeutic regimen.

The invention encompasses cell-based and animal model-based assays for the identification of compounds exhibiting such an ability to modulate the blood coagulation cascade.

Cell-based systems can be used to identify compounds which may act to modulate the blood coagulation cascade. Such cell systems can include, for example, recombinant or non-recombinant cells, such as cell lines, which express a tissue factor. In addition, expression host cells (e.g., COS cells, CHO cells, fibroblasts) genetically engineered to express a tissue factor and to respond to activation by Ixolaris, e.g., as measured by a chemical or phenotypic change, induction of another host cell gene, change in ion flux, tyrosine phosphorylation of host cell proteins, etc., can be used as an end point in the assay.

In addition, animal-based systems may be used to identify compounds capable of modulating the blood coagulation cascade. Such animal models may be used as test substrates for the identification of pharmaceuticals, therapies and interventions which may be effective in such modulation. For example, animal models may be exposed to a compound, suspected of exhibiting an ability to modulate the blood coagulation cascade, at a sufficient concentration and for a time sufficient to elicit such a modulation in the exposed animals. The response of the animals to the exposure may be monitored by assessing the responses associated with activation or deactivation of the blood coagulation cascade.

Vaccine and Pharmaceutical Preparations and Methods of Administration and Other Uses The compounds of the present invention when made and selected as disclosed are useful as potent inhibitors of blood coagulation in vitro and in vivo. As such, these compounds are useful as in vitro diagnostic reagents to prevent the clotting of blood and are also useful as in vivo pharmaceutical agents to inhibit the blood coagulation cascade in mammals.

The compounds of the present invention are useful as in vitro diagnostic reagents for inhibiting clotting in blood drawing tubes. The use of stoppered test tubes having a vacuum therein as a means to draw blood obtained by venipuncture into the tube is well known in the medical arts (Kasten, B. L., "Specimen Collection", Laboratory Test Handbook, 2nd Edition, Lexi-Comp Inc., Cleveland pp. 16–17 eds. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of blood clotting and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes, for example, with heparin salts, EDTA salts, citrate salts or oxalate salts.

The amount to be added to such tubes, or effective amount, is that amount sufficient to inhibit the formation of a blood clot when mammalian blood is drawn into the tube. The compounds of the present invention are added to blood collection tubes in such amounts that, when combined with 2 to 10 ml of mammalian blood, the concentration of such compounds will be sufficient to inhibit the formation of blood clots. Typically, this effective amount is that required to give a final concentration in the blood of about 1 to 10,000 nM, with 10 to 1000 nM being preferred.

The compounds of the present invention may also be used to prepare diagnostic compositions. In one embodiment, diagnostic compositions are prepared by dissolving the compounds of the present invention into diagnostically acceptable carriers, which carriers include phosphate buffered saline (0.01 M sodium phosphate, 0.15 M sodium chloride, pH 7.2), or Tris buffered saline (0.05 M Tris-HCl 0.15 M sodium chloride, pH 8.0). In another embodiment, the compounds of the present invention may be blended with other solid diagnostically acceptable carriers by methods well known in the art to provide solid diagnostic compositions. These carriers include buffer salts.

The addition of the compounds of the present invention to blood collection tubes may be accomplished by methods well known in the art, which methods include introduction of a liquid diagnostic composition thereof, a solid diagnostic composition thereof, or a liquid diagnostic composition which is lyophilized in such tubes to a solid plug of a solid diagnostic composition.

The use of blood collection tubes containing the diagnostic compositions of the present invention comprises contacting a effective amount of such diagnostic composition with mammalian blood drawn into the tube. Typically, when a sample of 2 to 10 ml of mammalian blood is drawn into a blood collection tube and contacted with such diagnostic composition therein; the effective amount to be used will include those concentrations of the comopunds formulated as a diagnostic composition which in the blood sample are sufficient to inhibit the formation of blood clots. Preferred effective concentrations would be about 1 to 10,000 nM, with 10 to 1000 nM being especially preferred.

According to an alternate aspect of our invention, the nucleic acid and amino acid compounds of the present invention are also useful as pharmaceutical agents for modulating the blood coagulation cascade in a mammal. This modulation of the blood coagulation cascade includes facilitating or inhibiting coagulation. Preferred is inhibiting.

The nucleic acid and amino acid compounds can alternatively be used, with suitable adjuvants, as a gene or component vaccine against tick and tick-borne infections in mammals. Immunization with tick vaccine may be used in both the prophylaxis and therapy of parasitic infections. Disease conditions caused and transmitted by ticks may be treated by administering to an animal infected with these parasites anti-Ixolaris antibody.

The vaccine or pharmaceutical compositions of the present invention are administered in vivo, ordinarily in a mammal, preferably in a human. In employing them in vivo, the vaccine or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In addition to the active ingredients, these vaccine and pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

After pharmaceutical compositions have been prepared, they can be placed in an appropriate container and labeled for treatment of an indicated condition.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of cell lines, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example Ixolaris or fragments thereof, antibodies of Ixolaris, agonists, antagonists or etc of Ixolaris, which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. For the present invention, alone or as part of a pharmaceutical composition, such doses are between about 0.01 mg/kg and 100 mg/kg body weight, preferably between about 0.01 and 10 mg/kg, body weight.

EXAMPLE 1

Materials. Factor VIIa, Tissue Factor (lipidated), TFPI-depleted plasma, truncated $TFPI_{(1-161)}$ (4900T), and full-length TFPI (4900PC) were purchased from American Diagnostica (Greenwich, Conn.). Factor X, Factor Xa, Factor XIa, Factor IX, Factor V, prothrombin, thrombin, [5-(dimethylamino)-1-naphthalenesulfonyl]glutamylgly cylarginyl chloromethyl ketone (dansyl-Glu-Gly-Arg-CK or DEGR-CK), elastase, and activated protein C chromogenic substrate were purchased from CalBiochem (San Diego, Calif.). γ-Carboxyglutamic acid domainless Factor Xa (Gla-Factor Xa) and Human DEGR-Factor Xa (Factor VII/VIIa free; 0 units/mg of Factor Xa), and monoclonal anti-human Factor VIIa were obtained from Hematologic Technologies (Essex Junction, Vt.). Goat anti-human Factor X affinity-purified IgG was from Enzyme Research Laboratoires (South Bend, Ind.). Chromogenic substrates for Factor Xa (N-Benzoyl-L-isoleucyl-L-glutamyl-glycyl-L-arginine-p-nitroaniline hydrochloride, S2222), thrombin (H-D-Phenylalanyl-L-pipecolyl-L-arginine-p-nitroaniline dihydrochloride, S2238), Factor VIIa (H-D-Isoleucyl-L-prolyl-L-arginine-p-nitroaniline dihydrochloride, S2288), Factor XIa (L-Pyroglutamyl-L-proplyl-L-arginine-p-nitroaniline dihydrochloride, S2366), and plasmin (H-D-Valyl-L-leucyl-L-lysine-p-nitroaniline dihydrochloride, S2251) were purchased from Chromogenix (Milano, Italy). Thrombomax with calcium reagent, trypsin, chymotrypsin, clastase, tryptase, and rabbit anti-goat alkaline phosphatase (AP)-coupled secondary antibody was obtained from Sigma Chemical (St. Louis, Mo.). Anti-mouse AP-coupled secondary antibody and Western Blue stabilized substrate for AP were obtained from Promega (Madison, Wis.). Reptilase (Bothrops atrox thrombin-like enzyme) and coat-test kit for Factor VIII were obtained from Diagnostica Stago (Les Ulis, France). Precast 12% Tris glycine gel, precast 12% Nu-PAGE, MES buffer, NuPAGE LDS sample buffer, and NuPAGE antioxidant were purchased from Novex Experimental Technology (Santa Cruz, Calif.). Silver-staining kit was obtained from Bio-Rad (Hercules, Calif.). Macrosphere octadecylsilica column was from Alltech (Deerfield, Ill.), Centripep filters from Millipore (Bedford, Mass.), and MonoQ column from Amersham Pharmacia Biotech (Piscataway, N.J.). Vydac C18 column was purchased from The Separation Group, Inc. (Hesperia, Calif.). Other equipment used were CM-4100 pumps and SM-4100 UV detector from ThermoSeparation Products (Riviera Beach, Fla.) and a FC203-B fraction collector from Gilson (Middleton, Wis.).

Ticks and tick saliva. Tick saliva was obtained by inducing partially engorged adult female *I. scapularis* to salivate into capillary tubes using the modified (Valenzuela, J. G. et al. 2000 *J Biol Chem* 275:18717–18723) pilocarpine induction method (Tatchell, R. J. 1967 *J Parasitol* 53:1106–1107). Tick salivary gland extracts were prepared by collecting glands from partially engorged female *I. scapularis* as described (Valenzuela, J. G. et al. 2000 *J Biol Chem* 275:18717–18723). Glands were stored frozen at −75° C. until needed.

Salivaty gland cDNA construction. This procedure was performed as detailed before (Valenzuela, J. G. et al. 2000 *J Biol Chem* 275:18717–18723). Briefly, the Micro-FastTrack mRNA isolation kit (Invitrogen, San Diego, Calif.) was used to isolate the mRNA. The *I. scapularis* salivary gland mRNA (200 ng) was reverse-transcribed to cDNA, followed by double-strand synthesis and ligated into a Lambda Triplex2 vector, and the resulting ligation reaction was packed using Gigapack gold III from Stratagene/Biocrest (Cedar Creek, Tenn.). The library obtained was plated by infecting log-phase XL1-blue cells. Randomly picked clones from this library were sequenced exactly as described before (Valenzuela, J. G. et al. 2000 *J Biol Chem* 275:18717–18723). After identifying a cDNA with high similarity to TFPI following blastx program of the cDNA against the National Center for Biotechnological Information (NCBI) non-redundant database (Altschul, S. F. et al. 1997 *Nucl Acid Res* 25:3389–3402), an aliquot (~100 ng) of Ixolaris PCR sample was re-amplified, and the entire cDNA was fully sequenced using custom primers.

Ixolaris Expression vector. For expression of Ixolaris, full-length cDNA was used as a template to amplify only the cDNA that begins at the initial methionine and ends at the first stop codon. A Kozak consensus sequence (ANN<u>ATG</u>G) (SEQ ID NO:473) was added, the DNA amplified forward primer: 5'-AAA ATG GGC GCT GTT TCC TGC TTC-3' (SEQ ID NO:474); reverse primer: 5'-GGA TGA TCA GTT AAT AGT GAC ATT TAC-3' (SEQ ID NO:475) and cloned into the vector pIB/V5-His TOPO (Invitrogen, San Diego, Calif.) following manufacturer's specifications. Amplification conditions were: 1 hold at 95° C. for 1 min, and 25 cycles at 94° C. for 1 min, 55° C. for 30 s, and 68° C. for 1 min. Amplified products were visualized on a 1.1% agarose gel with ethidium bromide. The single amplified product obtained was immediately cloned into the vector pIB/V5-His TOPO (Invitrogen, San Diego, Calif.) following manufacturer's specifications. The ligation mixture was used to transform TOP10 cells (Invitrogen), and the cells were incubated overnight at 37° C. Eight colonies were selected and mixed with 10 μL of sterile water. Five μL of each sample were transfered to Luria broth with ampicillin (100 μg/mL) and grown at 37° C. The remaining 5 μL were used as a template for a PCR reaction using two vector-specific primers from the pIB/V5-His TOPO vector to confirm the presence of the insert and for sequencing analysis. After visualization of the PCR product on a 1.1% agarose gel, we completely sequenced the eight PCR products described above with a CEQ2000 DNA sequencing instrument (Beckman Coulter, Fullerton, Calif.). We chose two samples, one of which contained the complete sequence (from methionine to stop codon) in the correct orientation of Ixolaris for expression on this vector. The second sample (control), was the complete Ixolaris sequence in reverse orientation for expression in this cell vector. Cells containing the sample and control were grown overnight at 37° C. on Luria broth with ampicillin (100 µg/mL), and plasmid isolation was performed using the Wizard miniprep kit (Promega). After plasmid isolation, the sample and control plasmids were washed three times with ultrapure water using an Amicon-100 (Millipore), the concentration of sample was measured, and the samples were stored at −30° C. before High Five cell transformation.

Expression of Ixolaris in insect cell line BTI-TN-5B1-4 (High Five). High Five cells (Invitrogen) were cultivated in High Five serum-free medium (Invitrogen) supplemented with 10 µg/mL gentamycin. Cell density of $2.0 \times 10^6$ cells/mL and 60% to 70% confluency were used for transfection of *I. scapularis* TFPI cDNA and *I. scapularis* TFPI anti-sense construct (control). Transfections were performed using 70 µL of Insectin-Plus Liposomes (Invitrogen) added to 5 mL of Ultimate Insect Serum-Free medium (Invitrogen) containing 1 µg plasmid DNA/mL of medium in a 15-mL sterile tube. After vortexing for 10 seconds, the mixture was incubated at room temperature for 15 minutes. The mixture was then added very slowly to a monolayer of High Five cells (in a 25-cm² flask) from which the culture medium had just been removed. The flasks were then transferred to a rocking platform at a speed of 2 side-to-side per minute for 4 hours at room temperature. Finally, the cells were incubated at 27° C. for up to 4 days. After 2 days of incubation, the supernatant (5 mL) was collected and stored for further analysis. High Five cells (Invitrogen), cultivated in High Five serum-free medium (Invitrogen) supplemented with 10 µg/mL gentamycin were used for transfection with Ixolaris and anti-sense (control) constructs plasmid as indicated by the manufacturer. After 2 days of incubation, the supernatant (5 mL) was collected and stored for further analysis.

Sequence analysis. Sequence similarity searches were performed using the Blast (Altschul, S. F. et al. 1997 *Nucl Acids Res* 25:3389–3402) program. Cleavage site predictions of the mature proteins used the SignalP (Nielsen, H. et al. 1997 *Protein Eng* 10:1–6) program. Alignments of protein sequences were done with the ClustalW program version 1.7 (Thompson, J. D. et al. 1994 *Nucl Acids Res* 22:4673–4686). Protein parameters were obtained at http://www.mbshortcuts.com: $M_r$, 15738.35; pI, 4.56; Σ A280, 20260; A280/cm (1 mg/mL), 1.287. Detection of N-linked glycosylation sites was obtained at http://molbio.info.nih.gov/molbio/gcglite.

Chromatographic procedures and purification of recombinant Ixolaris. Supernatants of transformed cells were filtrated with Centriprep filter (50 kDa cutoff). The filtrate was concentrated 20 fold using a Centriprep (3 kDa cutoff). One mL of concentrated supernatant (~8 mg) was diluted to 5 mL with water and applied to a 5×100 mm Pharmacia MonoQ eluted with a gradient from 25 mM Hepes pH 7.2 to 1 M NaCl in the same buffer, for 1 hour, at 0.5 mL/minute. Active fractions were pooled and applied to a Vydac 218TP510 octadecyl-silica column (10×250 mm) eluted at 1.5 mL/minute with a 60-minute gradient from 10% to 80% acetonitrile in water containing 0.1% trifluoroacetic acid (TFA). Active fractions were pooled, diluted with water to 8 mL, and re-chromatographed in a 2.1×250 mm Macrosphere octadecylsilica column eluted at 0.2 mL/minute for 55 minutes, and at 0.1 mL/minute afterward.

Estimation of Ixolaris concentration. Concentration of Ixolaris (corrected for $\Sigma_{280}$) was estimated by the area of absorbance at A280 nm (calibration with BSA) of the peak containing Ixolaris activity obtained in the last purification step (FIG. 6C). Human TFPI nominal concentration was estimated according to the concentration provided by the manufacturer.

PAGE of recombinant Ixolaris. Three µL of SDS (20%)+ 30 µL of Fraction 83 (~0.5 µg Ixolaris in acetonitrile) obtained from the last purification step of Ixolaris (FIG. 6C) were vacuum dried overnight at room temperature. The sample was resuspended in 30 µL of distilled water and divided in two aliquots. NU-PAGE loading buffer was added to sample #1 (15 µL, 0.25 µg) (denaturing conditions), and DTT was included in the loading buffer for sample #2 (reducing conditions). The samples were boiled for 5 minutes at 100° C., and additional reducing agent (β-mercaptoethanol, 1% final concentration) was added to sample #2 just before loading into a 12% NU-PAGE gel, MOPS buffer containing NuPAGE antioxidant. For PAGE under native conditions, 0.25 µg Ixolaris dried without SDS was applied to a 12% gel. Gels were silver stained according to manufacture's instructions.

Binding of Ixolaris to Factor X, Factor Xa and Factor VIIa. Ixolaris (20 nM) was preincubated with Factor X (20 nM), Factor Xa (20 nM), or Factor VIIa (20 nM) in 5 mM HEPES, pH 7.4, for 10 minutes. The sample was loaded into a 8% precast PAGE and proteins were then transferred to PVDF membrane in 10 mM CAPS, 10% methanol, pH 11. Primary antibody (polyclonal antibody anti-Factor X, 10 µg/mL, or MoAb anti-Factor VII, 5 µg/mL) was incubated for 1 hour in TBS-T (Tris-buffered saline, with 0.05% Tween and 5% non-fat milk). After three 10-minute washes with TBS-T, the membranes were incubated for 30 minutes with rabbit anti-goat AP-coupled secondary antibody (1:20,000 in TBS-T) for detection of Factor X and Factor Xa, or with anti-mouse AP-coupled secondary antibody (1:10,000 in TBS-T) for detection of Factor VIIa. After membrane washing, Western Blue Stabilized substrate for AP (Promega) was added. Reactions were stopped by addition of water.

Kinetic assay of Factor Xa production by Factor VIIa/TF. This assay was performed as described by Lindhout et al (Lindhout, T. et al. 1995 *Thromb Haemost* 74:910–915). Ixolaris was incubated with Factor X, followed by addition of Factor VIIa/TF (1 nM/0.2 pM) previously incubated at 37° C. in buffer containing 50 mM Hepes, 0.1 M NaCl, 5 mM $CaCl_2$, 0.5% BSA, pH 7.4 (Buffer A). Chromogenic substrate (S2222, 250 µM) hydrolysis was detected using a Versamax microplate ELISA reader (Molecular Devices, Sunnyvale, Calif.) equipped with a microplate mixer and heating system (Francischetti, I. M. B. et al. 1999 *Biochemistry* 3:16674–16685). The total volume of the reactions was 200 µl. Care was taken to ensure that substrate was less than 20% hydrolyzed. Reactions were continuously recorded at 405 nm for 1 hour at 37° C. To have an estimation of Factor Xa production at each time point, data was transformed as Δ absorbance (Δ A405/min) as described (Hamamoto, T. et al. 1993 *J Biol Chem* 268:8704–8710) using Excel 2000 software (MicroSoft Excel Analysis Tools, Seattle, Wash.). Factor Xa concentrations were interpolated from a standard curve relating Δ A405/min and known Factor Xa concentrations (Hamamoto, T. et al. 1993 *J Biol Chem* 268: 8704–8710). Amidolytic activity by Factor VIIa/TF alone upon S2222 alone was not detected. In some experiments, data were plotted as Vs/Vo against Ixolaris concentration, where Vs is the velocity of substrate hydrolysis in the presence of inhibitor and Vo in its absence (Williams, J. W., and Morrison J. F. 1979 *Methods Enzymol* 63:437–467; Cha, S. 1975 *Biochem Pharmacol* 24:2177–2185). Enzymes, Ixolaris, and chromogenic substrate were diluted in a Buffer A. Specific assay conditions are described in the figure legends.

Preparation of DEGR-FX and des-Gla-DEGR-Xa. This procedure was performed as described by Husten et al. (Husten, E. J. et al 1987 *J Biol Chem* 262:12953–12961), with modifications. DEGR (40 µM) was added to des-Gla-Factor Xa (2 µM) in 100 mM Tris, 100 mM NaCl, and incubated overnight at room temperature. The mixture was extensively dialyzed against 1 liter TBS (3 times), and recovered to test for amidolytic activity that was not detectable after 1-hour incubation of des-Gla-DEGR-Factor Xa (40 nM) with S2222 (1 mM) at 37° C. Factor X (2 µM) was incubated with DEGR, and dialyzed as described above. DEGR-Factor X was devoid of coagulant activity and exhibited no amidolytic activity following incubation with Factor VIIa/TF. DEGR-Factor X or DEGR-Factor Xa (10 nM) did not interfere with the amidolytic activity of FVIIa/TF (1 nM/1 nM) upon S2288, indicating that complete removal of free DEGR was achieved by extensive dialysis.

Factor VIIa/TF amidolytic activity. Ixolaris was incubated for 15 minutes at 37° C. with Factor VIIa/TF (1 nM/1 nM) (previously incubated for 15 min at 37° C.) followed by addition of S2288 (1 mM) (Hamamoto, T. et al. 1993 *J Biol Chem* 268:8704–8710). Substrate hydrolysis was followed at 405 nm, at 37° C. In some experiments, reactions were initiated with Ixolaris or Ixolaris/scaffold that was added to a mixture containing Factor VIIa/TF and S2288.

Activation of Factor IX. This procedure was performed as described by Komiyama et al. (Komiyama, Y. et al. 1990 *Biochemistry* 29:9418–9425). Briefly, Factor VIIa (1 nM)/TF (1 nM) was incubated with Ixolaris for 15 min at 37° C. followed by addition of Factor IX (1.4 µM). In some experiments, Ixolaris was previously incubated with DEGR-FX or DEGR-FXa for 15 min at 37° C., before addition of Factor VIIa/TF. After 15 minutes, Factor IX (1.4 µM) was added and reactions continued for 40 minutes at 37° C. Reactions were stopped by addition of Laemmly buffer, and boiling for 5 min. Proteins were separated by 4–12% NU/PAGE with MES buffer. All reactants were incubated in 50 mM Hepes, 100 mM NaCl, 5mM $CaCl_2$, 0.01% BSA. Factor IX (1.4 µM) was devoid of amidolytic activity after 1 hour incubation with S2222 (250 µM), indicating that Factor Xa was not a contaminant of the preparation. Under identical experimental conditions, Factor Xa could be detected at concentration as low as 20 pM. To test whether Factor IX was contaminated with Factor X, Factor IX (1.4 µM) was incubated with Factor VIIa/TF (4 nM/1 pM) and S2222 and no substrate hydrolysis could be detected. Control experiments showed that 50 pM Factor X incubated with FVIIa/TF was followed by substrate hydrolysis. This result indicated that Factor IX was not contaminated with detectable concentration of Factor X. Bands were analyzed by densitometry (SigmaScan software) and the area calculated for quantification of Factor IX activation.

Human umbilical vein endothelial cells (HUVEC) culture, and generation of FXa by HUVEC. This procedure was performed as described by Orthner et al (Orthner, C. et al. 1995 Blood 86:436–443). Primary culture of HUVEC, harvested from umbilical veins was purchased from Clonetics (San Diego, Calif.). After trypsinization cells were grown to confluence in 96-well plates in 200 µl EBM-2 medium in a humidified incubator at 37° C. with 5% $CO_2$. On the day of experiment EBM-2 was replaced by 200 µl fresh EBM-2, and LPS (10 µg/ml) was added for 4 hours to induce TF expression. Subsequently, cells were rinsed three times with HEPES-buffer (10 mM HEPES, 135 mM NaCl, 4 mM KCl, 1 mM $MgCl_2$, 4 mM $CaCl_2$, 11 mM D-glucose, and 0.5% BSA). HEPES-buffer was removed and a mixture of 180 µl containing Factor X (200 nM) and Ixolaris (0–8 nM) previously incubated together at 37° C. for 15 min was added to the cells. This step was followed immediately by addition of Factor VIIa (1 nM) to start reactions. After 30 min, 100 µl was removed and added to 100 µl of S2222 (500 µM) diluted in Buffer A. Absorbance reading at 405 nm (substrate hydrolysis) was followed for 1 h and Factor Xa concentration was estimated by a standard curve, using known concentrations of Factor Xa. Appropriate controls were run in parallel.

Prothrombin time. This procedure was performed using thromboMAX with Calcium reagent (Sigma) following manufacturer's instructions. Ixolaris (0–10 nM) was incubated with pre-warmed (37° C.) plasma (100 µl), followed by addition of pre-warmed thromboplastin reagent (200 µl). Tubes were shaken and the time necessary for clot formations was detected by visual inspection.

Specificity of Ixolaris. Ixolaris (32 nM, final concentration) was preincubated for 15 minutes at 37° C. with the enzymes listed in Table 1, followed by addition of the appropriate chromogenic substrate as indicated in Table 1.

Statistical analysis, curve fitting, and data handling. Data are presented as the mean±SE, using SigmaPlot Graphing software, statistical mode (Jandel Scientific).

While the present invention has been described in some detail for purposes of clarity and understanding, one skilled in the art will appreciate that various changes in form and detail can be made without departing from the true scope of the invention. All references referred to above are hereby incorporated by reference.

Appendix A

Table I

Table I shows Ixolaris carboxy truncations.

In this table "X" may represent an amino group, including but not limited to carbobenzoxyl, dansyl, or T-butyloxycarbonyl; an acetyl group; a 9-fluorenylmethoxy-carbonyl (FMOC); a macromolecular carrier group including but not limited to lipid-fatty acid conjugates, polyethylene glycol, or carbohydrates.

Additionally, in this table "Z" may represent a carboxyl group; an amino group; a T-butyloxycarbonyl group; a macromolecular carrier group including but not limited to lipid-fatty acid conjugates, polyethylene glycol, or carbohydrates.

TABLE I

Carboxy Truncations

| | |
|---|---|
| X-AER-Z | (SEQ ID NO 1) |
| X-AERV-Z | (SEQ ID NO 2) |
| X-AERVS-Z | (SEQ ID NO 3) |

TABLE I-continued

Carboxy Truncations

| Sequence | SEQ ID |
|---|---|
| X-AERVSE-Z | (SEQ ID NO 4) |
| X-AERVSEM-Z | (SEQ ID NO 5) |
| X-AERVSEMD-Z | (SEQ ID NO 6) |
| X-AERVSEMDI-Z | (SEQ ID NO 7) |
| X-AERVSEMDIY-Z | (SEQ ID NO 8) |
| X-AERVSEMDIYE-Z | (SEQ ID NO 9) |
| X-AERVSEMDIYEF-Z | (SEQ ID NO 10) |
| X-AERVSEMDIYEFE-Z | (SEQ ID NO 11) |
| X-AERVSEMDIYEFES-Z | (SEQ ID NO 12) |
| X-AERVSEMDIYEFESW-Z | (SEQ ID NO 13) |
| X-AERVSEMDIYEFESWV-Z | (SEQ ID NO 14) |
| X-AERVSEMDIYEFESWVS-Z | (SEQ ID NO 15) |
| X-AERVSEMDIYEFESWVSC-Z | (SEQ ID NO 16) |
| X-AERVSEMDIYEFESWVSCL-Z | (SEQ ID NO 17) |
| X-AERVSEMDIYEFESWVSCLD-Z | (SEQ ID NO 18) |
| X-AERVSEMDIYEFESWVSCLDP-Z | (SEQ ID NO 19) |
| X-AERVSEMDIYEFESWVSCLDPE-Z | (SEQ ID NO 20) |
| X-AERVSEMDIYEFESWVSCLDPEQ-Z | (SEQ ID NO 21) |
| X-AERVSEMDIYEFESWVSCLDPEQV-Z | (SEQ ID NO 22) |
| X-AERVSEMDIYEFESWVSCLDPEQVT-Z | (SEQ ID NO 23) |
| X-AERVSEMDIYEFESWVSCLDPEQVTC-Z | (SEQ ID NO 24) |
| X-AERVSEMDIYEFESWVSCLDPEQVTCE-Z | (SEQ ID NO 25) |
| X-AERVSEMDIYEFESWVSCLDPEQVTCES-Z | (SEQ ID NO 26) |
| X-AERVSEMDIYEFESWVSCLDPEQVTCESQ-Z | (SEQ ID NO 27) |
| X-AERVSEMDIYEFESWVSCLDPEQVTCESQE-Z | (SEQ ID NO 28) |
| X-AERVSEMDIYEFESWVSCLDPEQVTCESQEG-Z | (SEQ ID NO 29) |
| X-AERVSEMDIYEFESWVSCLDPEQVTCESQEGT-Z | (SEQ ID NO 30) |
| X-AERVSEMDIYEFESWVSCLDPEQVTCESQEGTH-Z | (SEQ ID NO 31) |
| X-AERVSEMDIYEFESWVSCLDPEQVTCESQEGTHA-Z | (SEQ ID NO 32) |
| X-AERVSEMDIYEFESWVSCLDPEQVTCESQEGTHAS-Z | (SEQ ID NO 33) |
| X-AERVSEMDIYEFESWVSCLDPEQVTCESQEGTHASY-Z | (SEQ ID NO 34) |
| X-AERVSEMDIYEFESWVSCLDPEQVTCESQEGTHASYN-Z | (SEQ ID NO 35) |
| X-AERVSEMDIYEFESWVSCLDPEQVTCESQEGTHASYNR-Z | (SEQ ID NO 36) |
| X-AERVSEMDIYEFESWVSCLDPEQVTCESQEGTHASYNRK-Z | (SEQ ID NO 37) |
| X-AERVSEMDIYEFESWVSCLDPEQVTCESQEGTHASYNRKT-Z | (SEQ ID NO 38) |
| X-AERVSEMDIYEFESWVSCLDPEQVTCESQEGTHASYNRKTG-Z | (SEQ ID NO 39) |
| X-AERVSEMDIYEFESWVSCLDPEQVTCESQEGTHASYNRKTGQ-Z | (SEQ ID NO 40) |
| X-AERVSEMDIYEFESWVSCLDPEQVTCESQEGTHASYNRKTGQC-Z | (SEQ ID NO 41) |
| X-AERVSEMDIYEFESWVSCLDPEQVTCESQEGTHASYNRKTGQCE-Z | (SEQ ID NO 42) |

TABLE I-continued

Carboxy Truncations

| | |
|---|---|
| X-AERVSEMDIYEFESWVSCLDPEQVTCESQEGTHASYNRKTGQCEE-Z | (SEQ ID NO 43) |
| X-AERVSEMDIYEFESWVSCLDPEQVTCESQEGTHASYNRKTGQCEEQ-Z | (SEQ ID NO 44) |
| X-AERVSEMDIYEFESWVSCLDPEQVTCESQEGTHASYNRKTGQCEEQK-Z | (SEQ ID NO 45) |
| X-AERVSEMDIYEEESWVSCLDPEQVTCESQEGTHASYNRKTGQCEEQKG-Z | (SEQ ID NO 46) |
| X-AERVSEMDIYEFESWVSCLDPEQVTCESQEGTHASYNRKTGQCEEQKGT-Z | (SEQ ID NO 47) |
| X-AERVSEMDIYEEESWVSCLDPEQVTCESQEGTHASYNRKTGQCEEQKGTE-Z | (SEQ ID NO 48) |
| X-AERVSEMDIYEFESWVSCLDPEQVTCESQEGTHASYNRKTGQCEEQKGTEC-Z | (SEQ ID NO 49) |
| X-AERVSEMDIYEFESWVSCLDPEQVTCESQEGTHASYNRKTGQCEEQKGTECG-Z | (SEQ ID NO 50) |
| X-AERVSEMDIYEFESWVSCLDPEQVTCESQEGTHASYNRKTGQCEEQKGTECGG-Z | (SEQ ID NO 51) |
| X-AERVSEMDIYEFESWVSCLDPEQVTCESQEGTHASYNRKTGQCEEQKGTECGGG-Z | (SEQ ID NO 52) |
| X-AERVSEMDIYEFESWVSCLDPEQVTCESQEGTHASYNRKTGQCEEQKGTECGGGE-Z | (SEQ ID NO 53) |
| X-AERVSEMDIYEFESWVSCLDPEQVTCESQEGTHASYNRKTGQCEEQKGTECGGGEN-Z | (SEQ ID NO 54) |
| X-AERVSEMDIYEFESWVSCLDPEQVTCESQEGTHASYNRKTGQCEEQKGTECGGGENH-Z | (SEQ ID NO 55) |
| X-AERVSEMDIYEFESWVSCLDPEQVTCESQEGTHASYNRKTGQCEEQKGTECGGGENHF-Z | (SEQ ID NO 56) |
| X-AERVSEMDIYEFESWVSCLDPEQVTCESQEGTHASYNRKTGQCEEQKGTECGGGENHFE-Z | (SEQ ID NO 57) |
| X-AERVSEMDIYEFESWVSCLDPEQVTCESQEGTHASYNRKTGQCEEQKGTECGGGENHFET-Z | (SEQ ID NO 58) |
| X-AERVSEMDIYEFESWVSCLDPEQVTCESQEGTHASYNRKTGQCEEQKGTECGGGENHFETL-Z | (SEQ ID NO 59) |
| X-AERVSEMDIYEFESWVSCLDPEQVTCESQEGTHASYNRKTGQCEEQKGTECGGGENHFETLL-Z | (SEQ ID NO 60) |
| X-AERVSEMDIYEFESWVSCLDPEQVTCESQEGTHASYNRKTGQCEEQKGTECGGGENHFETLLK-Z | (SEQ ID NO 61) |
| X-AERVSEMDIYEFESWVSCLDPEQVTCESQEGThASYNRKTGQCEEQKGTECGGGENHFETLLKC-Z | (SEQ ID NO 62) |
| X-AERVSEMDIYEFESWVSCLDPEQVTCESQEGTHASYNRKTGQCEEQKGTECGGGENHFETLLKCN-Z | (SEQ ID NO 63) |
| X-AERVSEMDIYEFESWVSCLDPEQVTCESQEGTHASYNRKTGQCEEQKGTECGGGENHFETLLKCNE-Z | (SEQ ID NO 64) |
| X-AERVSEMDIYEFESWVSCLDPEQVTCESQEGTHASYNRKTGQCEEQKGTECGGGENHFETLLKCNES-Z | (SEQ ID NO 65) |
| X-AERVSEMDIYEFESWVSCLDPEQVTCESQEGTHASYNRKTGQCEEQKGTECGGGENHFETLLKCNESC-Z | (SEQ ID NO 66) |
| X-AERVSEMDIYEFESWVSCLDPEQVTCESQEGTHASYNRKTGQCEEQKGTECGGGENHFETLLKCNESCN-Z | (SEQ ID NO 67) |
| X-AERVSEMDIYEFESWVSCLDPEQVTCESQEGTHASYNRKTGQCEEQKGTECGGGENHFETLLKCNESCND-Z | (SEQ ID NO 68) |
| X-AERVSEMDIYEFESWVSCLDPEQVTCESQEGTHASYNRKTGQCEEQKGTECGGGENHFETLLKCNESCNDA-Z | (SEQ ID NO 69) |
| X-AERVSEMDIYEFESWVSCLDPEQVTCESQEGTHASYNRKTGQCEEQKGTECGGGENHFETLLKCNESCNDAP-Z | (SEQ ID NO 70) |
| X-AERVSEMDIYEFESWVSCLDPEQVTCESQEGTHASYNRKTGQCEEQKGTECGGGENHFETLLKCNESCNDAPK-Z | (SEQ ID NO 71) |
| X-AERVSEMDIYEFESWVSCLDPEQVTCESQEGTHASYNRKTGQCEEQKGTECGGGENHFETLLKCNESCNDAPKP-Z | (SEQ ID NO 72) |
| X-AERVSEMDIYEFESWVSCLDPEQVTCESQEGTHASYNRKTGQCEEQKGTECGGGENHFETLLKCNESCNDAPKPP-Z | (SEQ ID NO 73) |
| X-AERVSEMDIYEFESWVSCLDPEQVTCESQEGTHASYNRKTGQCEEQKGTECGGGENHFETLLKCNESCNDAPKPPC-Z | (SEQ ID NO 74) |
| X-AERVSEMDIYEFESWVSCLDPEQVTCESQEGTHASYNRKTGQCEEQKGTECGGGENHFETLLKCNESCNDAPKPPCS-Z | (SEQ ID NO 75) |
| X-AERVSEMDIYEFESWVSCLDPEQVTCESQEGTHASYNRKTGQCEEQKGTECGGGENHFETLLKCNESCNDAPKPPCSL-Z | (SEQ ID NO 76) |
| X-AERVSEMDIYEFESWVSCLDPEQVTCESQEGTHASYNRKTGQCEEQKGTECGGGENHFETLLKCNESCNDAPKPPCSLE-Z | (SEQ ID NO 77) |
| X-AERVSEMDIYEFESWVSCLDPEQVTCESQEGTHASYNRKTGQCEEQKGTECGGGENHFETLLKCNESCNDAPKPPCSLEV-Z | (SEQ ID NO 78) |
| X-AERVSEMDIYEFESWVSCLDPEQVTCESQEGTHASYNRKTGQCEEQKGTECGGGENHFETLLKCNESCNDAPKPPCSLEVD-Z | (SEQ ID NO 79) |
| X-AERVSEMDIYEFESWVSCLDPEQVTCESQEGTHASYNRKTGQCEEQKGTECGGGENHFETLLKCNESCNDAPKPPCSLEVDY-Z | (SEQ ID NO 80) |

TABLE I-continued

Carboxy Truncations

| | |
|---|---|
| X-AERVSEMDIYEFESWVSCLDPEQVTCESQEGTHASYNRKTGQCEEQKGTECGGGENHFETLLKCNESCNDAPKPPCSLEVDYG-Z | (SEQ ID NO 81) |
| X-AERVSEMDIYEFESWVSCLDPEQVTCESQEGTHASYNRKTGQCEEQKGTECGGGENHFETLLKCNESCNDAPKPPCSLEVDYGV-Z | (SEQ ID NO 82) |
| X-AERVSEMDIYEFESWVSCLDPEQVTCESQEGTHASYNRKTGQCEEQKGTECGGGENHFETLLKCNESCNDAPKPPCSLEVDYGVG-Z | (SEQ ID NO 83) |
| X-AERVSEMDIYEFESWVSCLDPEQVTCESQEGTHASYNRKTGQCEEQKGTECGGGENHFETLLKCNESCNDAPKPPCSLEVDYGVGR-Z | (SEQ ID NO 84) |
| X-AERVSEMDIYEFESWVSCLDPEQVTCESQEGTHASYNRKTGQCEEQKGTECGGGENHFETLLKCNESCNDAPKPPCSLEVDYGVGRA-Z | (SEQ ID NO 85) |
| X-AERVSEMDIYEFESWVSCLDPEQVTCESQEGTHASYNRKTGQCEEQKGTECGGGENHFETLLKCNESCNDAPKPPCSLEVDYGVGRAN-Z | (SEQ ID NO 86) |
| X-AERVSEMDIYEFESWVSCLDPEQVTCESQEGTHASYNRKTGQCEEQKGTECGGGENHFETLLKCNESCNDAPKPPCSLEVDYGVGRANI-Z | (SEQ ID NO 87) |
| X-AERVSEMDIYEFESWVSCLDPEQVTCESQEGTHASYNRKTGQCEEQKGTECGGGENHFETLLKCNESCNDAPKPPCSLEVDYGVGRANIP-Z | (SEQ ID NO 88) |
| X-AERVSEMDIYEFESWVSCLDPEQVTCESQEGTHASYNRKTGQCEEQKGTECGGGENHFETLLKCNESCNDAPKPPCSLEVDYGVGRANIPR-Z | (SEQ ID NO 89) |
| X-AERVSEMDIYEFESWVSCLDPEQVTCESQEGTHASYNRKTGQCEEQKGTECGGGENHFETLLKCNESCNDAPKPPCSLEVDYGVGRANIPRW-Z | (SEQ ID NO 90) |
| X-AERVSEMDIYEFESWVSCLDPEQVTCESQEGTHASYNRKTGQCEEQKGTECGGGENHFETLLKCNESCNDAPKPPCSLEVDYGVGRANIPRWY-Z | (SEQ ID NO 91) |
| X-AERVSEMDIYEFESWVSCLDPEQVTCESQEGTHASYNRKTGQCEEQKGTECGGGENHFETLLKCNESCNDAPKPPCSLEVDYGVGRANIPRWYY-Z | (SEQ ID NO 92) |
| X-AERVSEMDIYEFESWVSCLDPEQVTCESQEGTHASYNRKTGQCEEQKGTECGGGENHFETLLKCNESCNDAPKPPCSLEVDYGVGRANIPRWYYD-Z | (SEQ ID NO 93) |
| X-AERVSEMDIYEFESWVSCLDPEQVTCESQEGTHASYNRKTGQCEEQKGTECGGGENHFETLLKCNESCNDAPKPPCSLEVDYGVGRANIPRWYYDT-Z | (SEQ ID NO 94) |
| X-AERVSEMDIYEFESWVSCLDPEQVTCESQEGTHASYNRKTGQCEEQKGTECGGGENHFETLLKCNESCNDAPKPPCSLEVDYGVGRANIPRWYYDTN-Z | (SEQ ID NO 95) |
| X-AERVSEMDIYEFESWVSCLDPEQVTCESQEGTHASYNRKTGQCEEQKGTECGGGENHFETLLKCNESCNDAPKPPCSLEVDYGVGRANIPRWYYDTNN-Z | (SEQ ID NO 96) |
| X-AERVSEMDIYEFESWVSCLDPEQVTCESQEGTHASYNRKTGQCEEQKGTECGGGENHFETLLKCNESCNDAPKPPCSLEVDYGVGRANIPRWYYDTNNA-Z | (SEQ ID NO 97) |
| X-AERVSEMDIYEFESWVSCLDPEQVTCESQEGTHASYNRKTGQCEEQKGTECGGGENHFETLLKCNESCNDAPKPPCSLEVDYGVGRANIPRWYYDTNNAT-Z | (SEQ ID NO 98) |
| X-AERVSEMDIYEFESWVSCLDPEQVTCESQEGTHASYNRKTGQCEEQKGTECGGGENHFETLLKCNESCNDAPKPPCSLEVDYGVGRANIPRWYYDTNNATC-Z | (SEQ ID NO 99) |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 100) |

TABLE I-continued

| Carboxy Truncations | |
|---|---|
| VGRANIPRWYYDTNNATCE-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 101) |
| VGRANIPRWYYDTNNATCEM-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 102) |
| VGRANIPRWYYDTNNATCEMF-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 103) |
| VGRANIPRWYYDTNNATCEMFT-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 104) |
| VGRANIPRWYYDTNNATCEMFTY-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 105) |
| VGRANIPRWYYDTNNATCEMFTYG-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 106) |
| VGRANIPRWYYDTNNATCEMFTYGG-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 107) |
| VGRANIPRWYYDTNNATCEMFTYGGI-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 108) |
| VGRANIPRWYYDTNNATCEMFTYGGIT-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 109) |
| VGRANIPRWYYDTNNATCEMFTYGGITG-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 110) |
| VGRANIPRWYYDTNNATCEMFTYGGITGN-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 111) |
| VGRANIPRWYYDTNNATCEMFTYGGITGNK-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 112) |
| VGRANIPRWYYDTNNATCEMFTYGGITGNKN-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 113) |
| VGRANIPRWYYDTNNATCEMFTYGGITGNKNN-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 114) |
| VGRANIPRWYYDTNNATCEMFTYGGITGNKNNF-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 115) |
| VGRANIPRWYYDTNNATCEMFTYGGITGNKNNFE-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 116) |
| VGRANIPRWYYDTNNATCEMFTYGGITGNKNNFES-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 117) |
| VGRANIPRWYYDTNNATCEMFTYGGITGNKNNFESE-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 118) |
| VGRANIPRWYYDTNNATCEMFTYGGITGNKNNFESEE-Z | |
| X-AERVSEMDIYEFESWVSCLDPEQVTCESQEGTHASYNRKTGQCEEQKGTECGGGENHFETLLKCNESCNDAPKPPCSLEVDYG | (SEQ ID NO 119) |

TABLE I-continued

Carboxy Truncations

VGRANIPRWYYDTNNATCEMFTYGGITGNKNNFESEEE-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 120)

VGRANIPRWYYDTNNATCEMFTYGGITGNKNNFESEEEC-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 121)

VGRANIPRWYYDTNNATCEMFTYGGITGNKNNFESEEECK-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 122)

VGRANIPRWYYDTNNATCEMFTYGGITGNKNNFESEEECKE-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 123)

VGRANIPRWYYDTNNATCEMFTYGGITGNKNNFESEEECKET-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 124)

VGRANIPRWYYDTNNATCEMFTYGGITGNKNNFESEEECKETC-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 125)

VGRANIPRWYYDTNNATCEMFTYGGITGNKNNFESEEECKETCK-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 126)

VGRANIPRWYYDTNNATCEMFTYGGITGNKNNFESEEECKETCKG-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 127)

VGRANIPRWYYDTNNATCEMFTYGGITGNKNNFESEEECKETCKGF-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 128)

VGRANIPRWYYDTNNATCEMFTYGGITGNKNNFESEEECKETCKGFS-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 129)

VGRANIPRWYYDTNNATCEMFTYGGITGNKNNFESEEECKETCKGFSL-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 130)

VGRANIPRWYYDTNNATCEMFTYGGITGNKNNFESEEECKETCKGFSLL-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 131)

VGRANIPRWYYDTNNATCEMFTYGGITGNKNNFESEEECKETCKGFSLLK-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 132)

VGRANIPRWYYDTNNATCEMFTYGGITGNKNNFESEEECKETCKGFSLLKK-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 133)

VGRANIPRWYYDTNNATCEMFTYGGITGNKNNFESEEECKETCKGFSLLKKV-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 134)

VGRANIPRWYYDTNNATCEMFTYGGITGNKNNFESEEECKETCKGFSLLKKVN-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 135)

VGRANIPRWYYDTNNATCEMFTYGGITGNKNNFESEEECKETCKGFSLLKKVNV-Z

X-AERVSEMDIYEFESWVSCLDPEQVTCESQEGTHASYNRKTGQCEEQKGTECGGGENHFETLLKCNESCNDAPKPPCSLEVDYG (SEQ ID NO 136)

VGRANIPRWYYDTNNATCEMFTYGGITGNKNNFESEEECKETCKGFSLLKKVNVT-Z

TABLE I-continued

Carboxy Truncations

X-AERVSEMDIYEFESWVSCLDPEQVTCESQEGTHASYNRKTGQCEEQKGTECGGGENHFETLLKCNESCNDAPKPPCSLEVDYG     (SEQ ID NO 137)
VGRANIPRWYYDTNNATCEMFTYGGITGNKNNFESEEECKETCKGFSLLKKVNVTI-Z

X-AERVSEMDIYEFESWVSCLDPEQVTCESQEGTHASYNRKTGQCEEQKGTECGGGENHFETLLKCNESCNDAPKPPCSLEVDYG     (SEQ ID NO 138)
VGRANIPRWYYDTNNATCEMFTYGGITGNKNNFESEEECKETCKGFSLLKKVNVTIN-Z

Appendix B

Table II

Table II shows Ixolaris amino truncations.

In this table "X" may represent an amino group, a hydrophobic group, including but not limited to carbobenzoxyl, dansyl, or T-butyloxycarbonyl; an acetyl group; a 9-fluorenylmethoxy-carbonyl (FMOC); a macromolecular carrier group including but not limited to lipid-fatty acid conjugates, polyethylene glycol, or carbohydrates.

Additionally, in this table "Z" may represent a carboxyl group; an amino group; a T-butyloxycarbonyl group; a macromolecular carrier group including but not limited to lipid-fatty acid conjugates, polyethylene glycol, or carbohydrates.

TABLE II

Amino Truncations

X-TIN-Z (SEQ ID NO 139)
X-VTIN-Z (SEQ ID NO 140)
X-NVTIN-Z (SEQ ID NO 141)
X-VNVTIN-Z (SEQ ID NO 142)
X-KVNVTIN-Z (SEQ ID NO 143)
X-KKVNVTIN-Z (SEQ ID NO 144)
X-LKKVNVTIN-Z (SEQ ID NO 145)
X-LLKKVNVTIN-Z (SEQ ID NO 146)
X-SLLKKVNVTIN-Z (SEQ ID NO 147)
X-FSLLKKVNVTIN-Z (SEQ ID NO 148)
X-GFSLLKKVNVTIN-Z (SEQ ID NO 149)
X-KGFSLLKKVNVTIN-Z (SEQ ID NO 150)
X-CKGFSLLKKVNVTIN-Z (SEQ ID NO 151)
X-TCKGFSLLKKVNVTIN-Z (SEQ ID NO 152)
X-ETCKGFSLLKKVNVTIN-Z (SEQ ID NO 153)
X-KETCKGFSLLKKVNVTIN-Z (SEQ ID NO 154)
X-CKETCKGFSLLKKVNVTIN-Z (SEQ ID NO 155)
X-ECKETCKGFSLLKKVNVTIN-Z (SEQ ID NO 156)
X-EECKETCKGFSLLKKVNVTIN-Z (SEQ ID NO 157)
X-EEECKETCKGFSLLKKVNVTIN-Z (SEQ ID NO 158)
X-SEEECKETCKGFSLLKKVNVTIN-Z (SEQ ID NO 159)
X-ESEEECKETCKGFSLLKKVNVTIN-Z (SEQ ID NO 160)
X-FESEEECKETCKGFSLLKKVNVTIN-Z (SEQ ID NO 161)
X-NFESEEECKETCKGFSLLKKVNVTIN-Z (SEQ ID NO 162)
X-NNFESEEECKETCKGFSLLKKVNVTIN-Z (SEQ ID NO 163)
X-KNNFESEEECKETCKGFSLLKKVNVTIN-Z (SEQ ID NO 164)

TABLE II-continued

Amino Truncations

X-NKNNFESEEECKETCKGFSLLKKVNVTIN-Z (SEQ ID NO 165)
X-GNKNNFESEEECKETCKGFSLLKKVNVTIN-Z (SEQ ID NO 166)
X-TGNKNNFESEEECKETCKGFSLLKKVNVTIN-Z (SEQ ID NO 167)
X-ITGNKNNFESEEECKETCKGFSLLKKVNVTIN-Z (SEQ ID NO 168)
X-GITGNKNNFESEEECKETCKGFSLLKKVNVTIN-Z (SEQ ID NO 169)
X-GGITGNKNNFESEEECKETCKGFSLLKKVNVTIN-Z (SEQ ID NO 170)
X-YGGITGNKNNFESEEECKETCKGFSLLKKVNVTIN-Z (SEQ ID NO 171)
X-TYGGITGNKNNFESEEECKETCKGFSLLKKVNVTIN-Z (SEQ ID NO 172)
X-FTYGGITGNKNNFESEEECKETCKGFSLLKKVNVTIN-Z (SEQ ID NO 173)
X-MFTYGGITGNKNNFESEEECKETCKGFSLLKKVNVTIN-Z (SEQ ID NO 174)
X-EMFTYGGITGNKNNFESEEECKETCKGFSLLKKVNVTIN-Z (SEQ ID NO 175)
X-CEMFTYGGITGNKNNFESEEECKETCKGFSLLKKVNVTIN-Z (SEQ ID NO 176)
X-TCEMFTYGGITGNKNNFESEEECKETCKGFSLLKKVNVTIN-Z (SEQ ID NO 177)
X-ATCEMFTYGGITGNKNNFESEEECKETCKGFSLLKKVNVTIN-Z (SEQ ID NO 178)
X-NATCEMFTYGGITGNKNNFESEEECKETCKGFSLLKKVNVTIN-Z (SEQ ID NO 179)
X-NNATCEMFTYGGITGNKNNFESEEECKETCKGFSLLKKVNVTIN-Z (SEQ ID NO 180)
X-TNNATCEMFTYGGITGNKNNFESEEECKETCKGFSLLKKVNVTIN-Z (SEQ ID NO 181)
X-DTNNATCEMFTYGGITGNKNNFESEEECKETCKGFSLLKKVNVTIN-Z (SEQ ID NO 182)
X-YDTNNATCEMFTYGGITGNKNNFESEEECKETCKGFSLLKKVNVTIN-Z (SEQ ID NO 183)
X-YYDTNNATCEMFTYGGITGNKNNEESEEECKETCKGFSLLKKVNVTIN-Z (SEQ ID NO 184)
X-WYYDTNNATCEMFTYGGITGNKNNFESEEECKETCKGFSLLKKVNVTIN-Z (SEQ ID NO 185)
X-RWYYDTNNATCEMFTYGGITGNKNNFESEEECKETCKGFSLLKKVNVTIN-Z (SEQ ID NO 186)
X-PRWYYDTNNATCEMFTYGGITGNKNNFESEEECKETCKGFSLLKKVNVTIN-Z (SEQ ID NO 187)
X-IPRWYYDTNNATCEMFTYGGITGNKNNFESEEECKETCKGFSLLKKVNVTIN-Z (SEQ ID NO 188)
X-NIPRWYYDTNNATCEMFTYGGITGNKNNFESEEECKETCKGFSLLKKVNVTIN-Z (SEQ ID NO 189)
X-ANIPRWYYDTNNATCEMFTYGGITGNKNNFESEEECKETCKGFSLLKKVNVTIN-Z (SEQ ID NO 190)
X-RANIPRWYYDTNNATCEMFTYGGITGNKNNFESEEECKETCKGFSLLKKVNVTIN-Z (SEQ ID NO 191)
X-GRANIPRWYYDTNNATCEMFTYGGITGNKNNFESEEECKETCKGFSLLKKVNVTIN-Z (SEQ ID NO 192)
X-VGRANIPRWYYDTNNATCEMFTYGGITGNKNNFESEEECKETCKGFSLLKKVNVTIN-Z (SEQ ID NO 193)
X-GVGRANIPRWYYDTNNATCEMFTYGGITGNKNNFESEEECKETCKGFSLLKKVNVTIN-Z (SEQ ID NO 194)
X-YGVGRANIPRWYYDTNNATCEMFTYGGITGNKNNFESEEECKETCKGFSLLKKVNVTIN-Z (SEQ ID NO 195)
X-DYGVGRANIPRWYYDTNNATCEMFTYGGITGNKNNFESEEECKETCKGFSLLKKVNVTIN-Z (SEQ ID NO 196)
X-VDYGVGRANIPRWYYDTNNATCEMFTYGGITGNKNNFESEEECKETCKGFSLLKKVNVTIN-Z (SEQ ID NO 197)
X-EVDYGVGRANIPRWYYDTNNATCEMFTYGGITGNKNNFESEEECKETCKGFSLLKKVNVTIN-Z (SEQ ID NO 198)
X-LEVDYGVGRANIPRWYYDTNNATCEMFTYGGITGNKNNFESEEECKETCKGFSLLKKVNVTIN-Z (SEQ ID NO 199)
X-SLEVDYGVGRANIPRWYYDTNNATCEMFTYGGITGNKNNFESEEECKETCKGFSLLKKVNVTIN-Z (SEQ ID NO 200)
X-CSLEVDYGVGRANIPRWYYDTNNATCEMFTYGGITGNKNNFESEEECKETCKGFSLLKKVNVTIN-Z (SEQ ID NO 201)
X-PCSLEVDYGVGRANIPRWYYDTNNATCEMFTYGGITGNKNNFESEEECKETCKGFSLLKKVNVTIN-Z (SEQ ID NO 202)

TABLE II-continued

Amino Truncations

X-PPCSLEVDYGVGRANIPRWYYDTNNATCEMFTYGGITGNKNNFESEEECKETCKGFSLLKKVNVTIN-Z (SEQ ID NO 203)

X-KPPCSLEVDYGVGRANIPRWYYDTNNATCEMFTYGGITGNKNNFESEEECKETCKGFSLLKKVNVTIN-Z (SEQ ID NO 204)

X-PKPPCSLEVDYGVGRANIPRWYYDTNNATCEMFTYGGITGNKNNFESEEECKETCKGFSLLKKVNVTIN-Z (SEQ ID NO 205)

X-APKPPCSLEVDYGVGRANIPRWYYDTNNATCEMFTYGGITGNKNNFESEEECKETCKGFSLLKKVNVTIN-Z (SEQ ID NO 206)

X-DAPKPPCSLEVDYGVGRANIPRWYYDTNNATCEMFTYGGITGNKNNFESEEECKETCKGFSLLKKVNVTIN-Z (SEQ ID NO 207)

X-NDAPKPPCSLEVDYGVGRANIPRWYYDTNNATCEMFTYGGITGNKNNFESEEECKETCKGFSLLKKVNVTIN-Z (SEQ ID NO 208)

X-CNDAPKPPCSLEVDYGVGRANIPRWYYDTNNATCEMFTYGGITGNKNNFESEEECKETCKGFSLLKKVNVTIN-Z (SEQ ID NO 209)

X-SCNDAPKPPCSLEVDYGVGRANIPRWYYDTNNATCEMFTYGGITGNKNNFESEEECKETCKGFSLLKKVNVTIN-Z (SEQ ID NO 210)

X-ESCNDAPKPPCSLEVDYGVGRANIPRWYYDTNNATCEMFTYGGITGNKNNFESEEECKETCKGFSLLKKVNVTIN-Z (SEQ ID NO 211)

X-NESCNDAPKPPCSLEVDYGVGRANIPRWYYDTNNATCEMFTYGGITGNKNNFESEEECKETCKGFSLLKKVNVTIN-Z (SEQ ID NO 212)

X-CNESCNDAPKPPCSLEVDYGVGRANIPRWYYDTNNATCEMFTYGGITGNKNNFESEEECKETCKGFSLLKKVNVTIN-Z (SEQ ID NO 213)

X-KCNESCNDAPKPPCSLEVDYGVGRANIPRWYYDTNNATCEMFTYGGITGNKNNFESEEECKETCKGFSLLKKVNVTIN-Z (SEQ ID NO 214)

X-LKCNESCNDAPKPPCSLEVDYGVGRANIPRWYYDTNNATCEMFTYGGITGNKNNFESEEECKETCKGFSLLKKVNVTIN-Z (SEQ ID NO 215)

X-LLKCNESCNDAPKPPCSLEVDYGVGRANIPRWYYDTNNATCEMFTYGGITGNKNNFESEEECKETCKGFSLLKKVNVTIN-Z (SEQ ID NO 216)

X-TLLKCNESCNDAPKPPCSLEVDYGVGRANIPRWYYDTNNATCEMFTYGGITGNKNNFESEEECKETCKGFSLLKKVNVTIN-Z (SEQ ID NO 217)

X-ETLLKCNESCNDAPKPPCSLEVDYGVGRANIPRWYYDTNNATCEMFTYGGITGNKNNFESEEECKETCKGFSLLKKVNVTIN-Z (SEQ ID NO 218)

X-FETLLKCNESCNDAPKPPCSLEVDYGVGRANIPRWYYDTNNATCEMFTYGGITGNKNNFESEEECKETCKGFSLLKKVNVTIN-Z (SEQ ID NO 219)

X-HFETLLKCNESCNDAPKPPCSLEVDYGVGRANIPRWYYDTNNATCEMFTYGGITGNKNNFESEEECKETCKGFSLLKKVNVTIN-Z (SEQ ID NO 220)

X-NHFETLLKCNESCNDAPKPPCSLEVDYGVGRANIPRWYYDTNNATCEMFTYGGITGNKNNFESEEECKETCKGFSLLKKVNVTIN-Z (SEQ ID NO 221)

X-ENHFETLLKCNESCNDAPKPPCSLEVDYGVGRANIPRWYYDTNNATCEMFTYGGITGNKNNFESEEECKETCKGFSLLKKVNVTIN-Z (SEQ ID NO 222)

X-GENHFETLLKCNESCNDAPKPPCSLEVDYGVGRANIPRWYYDTNNATCEMFTYGGITGNKNNFESEEECKETCKGFSLLKKVNVTIN-Z (SEQ ID NO 223)

X-GGENHFETLLKCNESCNDAPKPPCSLEVDYGVGRANIPRWYYDTNNATCEMFTYGGITGNKNNFESEEECKETCKGFSLLKKVNVTIN-Z (SEQ ID NO 224)

X-GGGENHFETLLKCNESCNDAPKPPCSLEVDYGVGRANIPRWYYDTNNATCEMFTYGGITGNKNNFESEEECKETCKGFSLLKKVNVTIN-Z (SEQ ID NO 225)

X-CGGGENHFETLLKCNESCNDAPKPPCSLEVDYGVGRANIPRWYYDTNNATCEMFTYGGITGNKNNFESEEECKETCKGFSLLKKVNVTIN-Z (SEQ ID NO 226)

X-ECGGGENHFETLLKCNESCNDAPKPPCSLEVDYGVGRANIPRWYYDTNNATCEMFTYGGITGNKNNFESEEECKETCKGFSLLKKVNVTIN-Z (SEQ ID NO 227)

X-TECGGGENHFETLLKCNESCNDAPKPPCSLEVDYGVGRANIPRWYYDTNNATCEMFTYGGITGNKNNFESEEECKETCKGFSLLKKVNVTIN-Z (SEQ ID NO 228)

X-GTECGGGENHFETLLKCNESCNDAPKPPCSLEVDYGVGRANIPRWYYDTNNATCEMFTYGGITGNKNNFESEEECKETCKGFSLLKKVNVTIN-Z (SEQ ID NO 229)

X-KGTECGGGENHFETLLKCNESCNDAPKPPCSLEVDYGVGRANIPRWYYDTNNATCEMFTYGGITGNKNNFESEEECKETCKGFS (SEQ ID NO 230)

TABLE II-continued

Amino Truncations

```
                                                                                   LLKKVNVTIN-Z
X-QKGTECGGGENHFETLLKCNESCNDAPKPPCSLEVDYGVGRANIPRWYYDTNNATCEMFTYGGITGNKNNFESEEECKETCKGF  (SEQ ID NO 231)

SLLKKVNVTIN-Z
X-EQKGTECGGGENHFETLLKCNESCNDAPKPPCSLEVDYGVGRANIPRWYYDTNNATCEMFTYGGITGNKNNFESEEECKETCKG   (SEQ ID NO 232)

FSLLKKVNVTIN-Z
X-EEQKGTECGGGENHFETLLKCNESCNDAPKPPCSLEVDYGVGRANIPRWYYDTNNATCEMFTYGGITGNKNNFESEEECKETCK    (SEQ ID NO 233)

GFSLLKKVNVTIN-Z
X-CEEQKGTECGGGENHFETLLKCNESCNDAPKPPCSLEVDYGVGRANIPRWYYDTNNATCEMFTYGGITGNKNNFESEEECKETC     (SEQ ID NO 234)

KGFSLLKKVNVTIN-Z
X-QCEEQKGTECGGGENHFETLLKCNESCNDAPKPPCSLEVDYGVGRANIPRWYYDTNNATCEMFTYGGITGNKNNFESEEECKET      (SEQ ID NO 235)

CKGFSLLKKVNVTIN-Z
X-GQCEEQKGTECGGGENHFETLLKCNESCNDAPKPPCSLEVDYGVGRANIPRWYYDTNNATCEMFTYGGITGNKNNFESEEECKE       (SEQ ID NO 236)

TCKGFSLLKKVNVTIN-Z
X-TGQCEEQKGTECGGGENHFETLLKCNESCNDAPKPPCSLEVDYGVGRANIPRWYYDTNNATCEMFTYGGITGNKNNEESEEECK        (SEQ ID NO 237)

ETCKGFSLLKKVNVTIN-Z
X-KTGQCEEQKGTECGGGENHFETLLKCNESCNDAPKPPCSLEVDYGVGRANIPRWYYDTNNATCEMFTYGGITGNKNNFESEEEC         (SEQ ID NO 238)

KETCKGFSLLKKVNVTIN-Z
X-RKTGQCEEQKGTECGGGENHFETLLKCNESCNDAPKPPCSLEVDYGVGRANIPRWYYDTNNATCEMFTYGGITGNKNNFESEEE          (SEQ ID NO 239)

CKETCKGFSLLKKVNVTIN-Z
X-NRKTGQCEEQKGTECGGGENHFETLLKCNESCNDAPKPPCSLEVDYGVGRANIPRWYYDTNNATCEMFTYGGITGNKNNFESEE           (SEQ ID NO 240)

ECKETCKGFSLLKKVNVTIN-Z
X-YNRKTGQCEEQKGTECGGGENHFETLLKCNESCNDAPKPPCSLEVDYGVGRANIPRWYYDTNNATCEMETYGGITGNKNNFESE            (SEQ ID NO 241)

EECKETCKGFSLLKKVNVTIN-Z
X-SYNRKTGQCEEQKGTECGGGENHFETLLKCNESCNDAPKPPCSLEVDYGVGRANIPRWYYDTNNATCEMETYGGITGNKNNFES             (SEQ ID NO 242)

EEECKETCKGFSLLKKVNVTIN-Z
X-ASYNRKTGQCEEQKGTECGGGENHFETLLKCNESCNDAPKPPCSLEVDYGVGRANIPRWYYDTNNATCEMFTYGGITGNKNNFE              (SEQ ID NO 243)

SEEECKETCKGFSLLKKVNVTIN-Z
X-HASYNRKTGQCEEQKGTECGGGENHFETLLKCNESCNDAPKPPCSLEVDYGVGRANIPRWYYDTNNATCEMFTYGGITGNKNNF               (SEQ ID NO 244)

ESEEECKETCKGFSLLKKVNVTIN-Z
X-THASYNRKTGQCEEQKGTECGGGENHFETLLKCNESCNDAPKPPCSLEVDYGVGRANIPRWYYDTNNATCEMFTYGGITGNKNN                (SEQ ID NO 245)

FESEEECKETCKGFSLLKKVNVTIN-Z
X-GTHASYNRKTGQCEEQKGTECGGGENHFETLLKCNESCNDAPKPPCSLEVDYGVGRANIPRWYYDTNNATCEMFTYGGITGNKN                 (SEQ ID NO 246)

NFESEEECKETCKGFSLLKKVNVTIN-Z
X-EGTHASYNRKTGQCEEQKGTECGGGENHFETLLKCNESCNDAPKPPCSLEVDYGVGRANIPRWYYDTNNATCEMFTYGGITGNK                  (SEQ ID NO 247)

NNFESEEECKETCKGFSLLKKVNVTIN-Z
X-QEGTHASYNRKTGQCEEQKGTECGGGENHFETLLKCNESCNDAPKPPCSLEVDYGVGRANIPRWYYDTNNATCEMFTYGGITGN                   (SEQ ID NO 248)

KNNFESEEECKETCKGFSLLKKVNVTIN-Z
X-SQEGTHASYNRKTGQCEEQKGTECGGGENHFETLLKCNESCNDAPKPPCSLEVDYGVGRANIPRWYYDTNNATCEMFTYGGITG                    (SEQ ID NO 249)
```

TABLE II-continued

Amino Truncations

```
                                 NKNNFESEEECKECTCKGFSLLKKVNVTIN-Z
X-ESQEGTHASYNRKTGQCEEQKGTECGGGENHFETLLKCNESCNDAPKPPCSLEVDYGVGRANIPRWYYDTNNATCEMFTYGGIT    (SEQ ID NO 250)
                                 GNKNNFESEEECKECTCKGFSLLKKVNVTIN-Z
X-CESQEGTHASYNRKTGQCEEQKGTECGGGENHFETLLKCNESCNDAPKPPCSLEVDYGVGRANIPRWYYDTNNATCEMFTYGGI     (SEQ ID NO 251)
                                 TGNKNNFESEEECKECTCKGFSLLKKVNVTIN-Z
X-TCESQEGTHASYNRKTGQCEEQKGTECGGGENHFETLLKCNESCNDAPKPPCSLEVDYGVGRANIPRWYYDTNNATCEMFTYGG     (SEQ ID NO 252)
                                 ITGNKNNFESEEECKECTCKGFSLLKKVNVTIN-Z
X-VTCESQEGTHASYNRKTGQCEEQKGTECGGGENHFETLLKCNESCNDAPKPPCSLEVDYGVGRANIPRWYYDTNNATCEMFTYG     (SEQ ID NO 253)
                                 GITGNKNNFESEEECKECTCKGFSLLKKVNVTIN-Z
X-QVTCESQEGTHASYNRKTGQCEEQKGTECGGGENHFETLLKCNESCNDAPKPPCSLEVDYGVGRANIPRWYYDTNNATCEMFTY     (SEQ ID NO 254)
                                 GGITGNKNNFESEEECKECTCKGFSLLKKVNVTIN-Z
X-EQVTCESQEGTHASYNRKTGQCEEQKGTECGGGENHFETLLKCNESCNDAPKPPCSLEVDYGVGRANIPRWYYDTNNATCEMFT     (SEQ ID NO 255)
                                 YGGITGNKNNFESEEECKECTCKGFSLLKKVNVTIN-Z
X-PEQVTCESQEGTHASYNRKTGQCEEQKGTECGGGENHFETLLKCNESCNDAPKPPCSLEVDYGVGRANIPRWYYDTNNATCEMF     (SEQ ID NO 256)
                                 TYGGITGNKNNFESEEECKECTCKGFSLLKKVNVTIN-Z
X-DPEQVTCESQEGTHASYNRKTGQCEEQKGTECGGGENHFETLLKCNESCNDAPKPPCSLEVDYGVGRANIPRWYYDTNNATCEM     (SEQ ID NO 257)
                                 FTYGGITGNKNNFESEEECKECTCKGFSLLKKVNVTIN-Z
X-LDPEQVTCESQEGTHASYNRKTGQCEEQKGTECGGGENHFETLLKCNESCNDAPKPPCSLEVDYGVGRANIPRWYYDTNNATCE     (SEQ ID NO 258)
                                 MFTYGGITGNKNNFESEEECKECTCKGFSLLKKVNVTIN-Z
X-CLDPEQVTCESQEGTHASYNRKTGQCEEQKGTECGGGENHFETLLKCNESCNDAPKPPCSLEVDYGVGRANIPRWYYDTNNATC     (SEQ ID NO 259)
                                 EMFTYGGITGNKNNFESEEECKECTCKGFSLLKKVNVTIN-Z
X-SCLDPEQVTCESQEGTHASYNRKTGQCEEQKGTECGQGENHFETLLKCNESCNDAPKPPCSLEVDYGVGRANIPRWYYDTNNAT     (SEQ ID NO 260)
                                 CEMFTYGGITGNKNNFESEEECKECTCKGFSLLKKVNVTIN-Z
X-VSCLDPEQVTCESQEGTHASYNRKTGQCEEQKGTECGGGENHFETLLKCNESCNDAPKPPCSLEVDYGVGRANIPRWYYDTNNA    (SEQ ID NO 261)
                                 TCEMFTYGGITGNKNNFESEEECKECTCKGFSLLKKVNVTIN-Z
X-WVSCLDPEQVTCESQEGTHASYNRKTGQCEEQKGTECGGGENHFETLLKCNESCNDAPKPPCSLEVDYGVGRANIPRWYYDTNN    (SEQ ID NO 262)
                                 ATCEMFTYGGITGNKNNFESEEECKECTCKGFSLLKKVNVTIN-Z
X-SWVSCLDPEQVTCESQEGTHASYNRKTGQCEEQKGTECGGGENHFETLLKGNESCNDAPKPPCSLEVDYGVGRANIPRWYYDTN    (SEQ ID NO 263)
                                 NATCEMFTYGGITGNKNNFESEEECKECTCKGFSLLKKVNVTIN-Z
X-ESWVSCLDPEQVTCESQEGTHASYNRKTGQCEEQKGTECGGGENHFETLLKCNESCNDAPKPPCSLEVDYGVGRANIPRWYYDT    (SEQ ID NO 264)
                                 NNATCEMFTYGGITGNKNNFESEEECKECTCKGFSLLKKVNVTIN-Z
X-FESWVSCLDPEQVTCESQEGTHASYNRKTGQCEEQKGTECGGGENHFETLLKCNESCNDAPKPPCSLEVDYGVGRANIPRWYYD    (SEQ ID NO 265)
                                 TNNATCEMFTYGGITGNKNNFESEEECKECTCKGFSLLKKVNVTIN-Z
X-EFESWVSCLDPEQVTCESQEGTHASYNRKTGQCEEQKGTECGGGENHFETLLKCNESCNDAPKPPCSLEVDYGVGRANTPRWYY    (SEQ ID NO 266)
                                 DTNNATCEMFTYGGITGNKNNEESEEECKECTCKGFSLLKKVNVTIN-Z
X-YEFESWVSCLDPEQVTCESQEGTHASYNRKTGQCEEQKGTECGGGENHFETLLKCNESCNDAPKPPCSLEVDYGVGRANIPRWY    (SEQ ID NO 267)
                                 YDTNNATCEMFTYGGITGNKNNFESEEECKECTCKGFSLLKKVNVTIN-Z
X-IYEFESWVSCLDPEQVTCESQEGTHASYNRKTGQCEEQKGTECGGGENHFETLLKCNESCNDAPKPPCSLEVDYGVGRANIPRW    (SEQ ID NO 268)
                                 YYDTNNATCEMFTYGGITGNKNNFESEEECKECTCKGFSLLKKVNVTIN-Z
```

TABLE II-continued

Amino Truncations

X-DIYEFESWVSCLDPEQVTCESQEGTHASYNRKTGQCEEQKGTECGGGENHFETLLKCNESCNDAPKPPCSLEVDYGVGRANIPR (SEQ ID NO 269)
WYYDTNNATCEMFTYGGITGNKNNFESEEECKECTCKGFSLLKKVNVTIN-Z

X-MDIYEFESWVSCLDPEQVTCESQEGTHASYNRKTGQCEEQKGTECGGGENHFETLLKCNESCNDAPKPPCSLEVDYGVGRANIP (SEQ ID NO 270)
RWYYDTNNATCEMFTYGGITGNKNNFESEEECKECTCKGFSLLKKVNVTIN-Z

X-EMDIYEFESWVSCLDPEQVTCESQEGTHASYNRKTGQCEEQKGTECGGGENHFETLLKCNESCNDAPKPPCSLEVDYGVGRANI (SEQ ID NO 271)
PRWYYDTNNATCEMFTYGGITGNKNNFESEEECKECTCKGFSLLKKVNVTIN-Z

X-SEMDIYEFESWVSCLDPEQVTCESQEGTHASYNRKTGQCEEQKGTECGGGENHFETLLKCNESCNDAPKPPCSLEVDYGVGRAN (SEQ ID NO 272)
IPRWYYDTNNATCEMFTYGGITGNKNNFESEEECKECTCKGFSLLKKVNVTIN-Z

X-VSEMDIYEEESWVSCLDPEQVTCESQEGTHASYNRKTGQCEEQKGTECGGGENHFETLLKCNESCNDAPKPPCSLEVDYGVGRA (SEQ ID NO 273)
NIPRWYYDTNNATCEMFTYGGITGNKNNFESEEECKECTCKGFSLLKKVNVTIN-Z

X-RVSEMDIYEFESWVSCLDPEQVTCESQEGTHASYNRKTGQCEEQKGTECGGGENHFETLLKCNESCNDAPKPPCSLEVDYGVGR (SEQ ID NO 274)
ANIPRWYYDTNNATCEMFTYGGITGNKNNEESEEECKECTCKGFSLLKKVNVTIN-Z

X-ERVSEMDIYEFESWVSCLDPEQVTCESQEGTHASYNRKTGQCEEQKGTECGGGENHFETLLKCNESCNDAPKPPCSLEVDYGVG (SEQ ID NO 275)
RANIPRWYYDTNNATCEMFTYGGITGNKNNFESEEECKECTCKGFSLLKKVNVTIN-Z

X-AERVSEMDIYEFESWVSCLDPEQVTCESQEGTHASYNRKTGQCEEQKGTECGGGENHFETLLKCNESCNDAPKPPCSLEVDYGV (SEQ ID NO 138)
GRANIPRWYYDTNNATCEMFTYGGITGNKNNFESEEECKECTCKGFSLLKKVNVTIN-Z

What is claimed is:

1. A purified composition comprising a DNA, or its complement, said DNA encoding an Ixolaris protein comprising SEQ ID NO: 138.

2. A purified composition comprising a cDNA, or its complement, said cDNA encoding an Ixolaris protein comprising SEQ ID NO: 138.

3. A purified composition comprising a DNA, or its complement, said DNA encoding an Ixolaris protein having anticoagulant activity and said DNA hybridizing to the DNA sequence set forth in SEQ ID NO: 470 under high stringency conditions defined as hybridization to filter-bound DNA in 0.5 M NaHPO$_4$, 7m% sodium dodecyl sulfate (SDS), 1 mM EDTA at 65° C., and washing in 0.1 times SSC/0.1% SDS at 68° C.

4. A purified composition comprising a DNA, or its complement, said DNA encoding an Ixolaris protein having anticoagulant activity and said protein comprising an Ixolaris Kunitz domain comprising amino acids 18 to 68 of SEQ ID NO: 138, and an Ixolaris Kunitz domain comprising amino acids 76 to 126 of SEQ ID NO: 138.

5. A vector comprising the purified composition of any of claims 1 to 4.

6. A host cell comprising the vector of claim 5.

7. In an array of DNA immobilized on a substrate, the improvement comprising the inclusion in said array of the DNA of claim 3 or its complement.

* * * * *

UNITED STATES PATENT AND TRADEMARK OFFICE
CERTIFICATE OF CORRECTION

| | | |
|---|---|---|
| PATENT NO. | : 7,078,508 B2 | Page 1 of 1 |
| APPLICATION NO. | : 10/408166 | |
| DATED | : July 18, 2006 | |
| INVENTOR(S) | : Francischetti et al. | |

It is certified that error appears in the above-identified patent and that said Letters Patent is hereby corrected as shown below:

In Col. 305, Line 35 (approx.), Claim 3, delete "7m%" and insert -- 7% --.

Signed and Sealed this

Twentieth Day of February, 2007

JON W. DUDAS
*Director of the United States Patent and Trademark Office*